United States Patent
Verdine et al.

(10) Patent No.: US 8,592,377 B2
(45) Date of Patent: Nov. 26, 2013

(54) STITCHED POLYPEPTIDES

(75) Inventors: Gregory L. Verdine, Newton, MA (US); Young-Woo Kim, Belmont, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 699 days.

(21) Appl. No.: 12/593,384

(22) PCT Filed: Mar. 28, 2008

(86) PCT No.: PCT/US2008/058575
§ 371 (c)(1),
(2), (4) Date: Mar. 5, 2010

(87) PCT Pub. No.: WO2008/121767
PCT Pub. Date: Oct. 9, 2008

(65) Prior Publication Data
US 2010/0184645 A1    Jul. 22, 2010

Related U.S. Application Data

(60) Provisional application No. 60/908,566, filed on Mar. 28, 2007.

(51) Int. Cl.
*A61K 38/12* (2006.01)
*C07K 7/54* (2006.01)
*C07K 5/12* (2006.01)

(52) U.S. Cl.
USPC ........................................................ 514/21.1

(58) Field of Classification Search
None
See application file for complete search history.

(56) References Cited

U.S. PATENT DOCUMENTS

| | | | |
|---|---|---|---|
| 4,270,537 A | 6/1981 | Romaine | |
| 4,596,556 A | 6/1986 | Morrow et al. | |
| 4,730,006 A | 3/1988 | Bohme et al. | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,015,235 A | 5/1991 | Crossman | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,312,335 A | 5/1994 | McKinnon et al. | |
| 5,328,483 A | 7/1994 | Jacoby | |
| 5,334,144 A | 8/1994 | Alchas et al. | |
| 5,339,163 A | 8/1994 | Homma et al. | |
| 5,364,851 A | 11/1994 | Joran | |
| 5,383,851 A | 1/1995 | McKinnon et al. | |
| 5,417,662 A | 5/1995 | Hjertman et al. | |
| 5,446,128 A | 8/1995 | Kahn | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,622,852 A | 4/1997 | Korsmeyer | |
| 5,649,912 A | 7/1997 | Peterson | |
| 5,663,316 A | 9/1997 | Xudong | |
| 5,704,911 A | 1/1998 | Parsons | |
| 5,708,136 A | 1/1998 | Burrell et al. | |
| 5,750,767 A | 5/1998 | Carpino et al. | |
| 5,811,515 A | 9/1998 | Grubbs et al. | |
| 5,824,483 A | 10/1998 | Houston, Jr. et al. | |
| 5,834,209 A | 11/1998 | Korsmeyer | |
| 5,856,445 A | 1/1999 | Korsmeyer | |
| 5,874,529 A | 2/1999 | Gilon et al. | |
| 5,893,397 A | 4/1999 | Peterson et al. | |
| 5,922,863 A | 7/1999 | Grubbs et al. | |
| 5,955,593 A | 9/1999 | Korsmeyer | |
| 5,965,703 A | 10/1999 | Horne et al. | |
| 5,993,412 A | 11/1999 | Deily et al. | |
| 5,998,583 A | 12/1999 | Korsmeyer | |
| 6,051,554 A | 4/2000 | Hornik et al. | |
| 6,153,391 A | 11/2000 | Picksley et al. | |
| 6,184,344 B1 | 2/2001 | Kent et al. | |
| 6,271,198 B1 | 8/2001 | Braisted et al. | |
| 6,326,354 B1 | 12/2001 | Gross et al. | |
| 6,610,657 B1 | 8/2003 | Goueli | |
| 6,613,874 B1 | 9/2003 | Mazur et al. | |
| 6,703,382 B2 | 3/2004 | Wang et al. | |
| 6,713,280 B1 | 3/2004 | Huang et al. | |
| 6,849,428 B1 | 2/2005 | Evans et al. | |
| 6,875,594 B2 | 4/2005 | Muir et al. | |
| 7,064,193 B1 | 6/2006 | Cory et al. | |
| 7,083,983 B2 | 8/2006 | Lane et al. | |
| 7,084,244 B2 | 8/2006 | Gilon et al. | |
| 7,183,059 B2 | 2/2007 | Verdine et al. | |
| 7,192,713 B1 | 3/2007 | Verdine et al. | |
| 7,202,332 B2 | 4/2007 | Arora et al. | |
| 7,247,700 B2 | 7/2007 | Korsmeyer et al. | |
| 7,538,190 B2 | 5/2009 | Robinson et al. | |
| 7,705,118 B2 | 4/2010 | Arora et al. | |
| 7,723,469 B2 | 5/2010 | Walensky et al. | |
| 7,745,573 B2 | 6/2010 | Robinson et al. | |
| 7,786,072 B2 | 8/2010 | Verdine et al. | |
| 8,324,428 B2 | 12/2012 | Verdine et al. | |
| 2004/0038901 A1 | 2/2004 | Basler et al. | |
| 2004/0067503 A1 | 4/2004 | Tan et al. | |
| 2004/0171809 A1 | 9/2004 | Korsmeyer et al. | |
| 2005/0250680 A1 | 11/2005 | Walensky et al. | |
| 2006/0008848 A1 | 1/2006 | Verdine et al. | |
| 2006/0014675 A1 | 1/2006 | Arora et al. | |

(Continued)

FOREIGN PATENT DOCUMENTS

| WO | WO 96/34878 A1 | 11/1996 |
|---|---|---|
| WO | WO 97/13537 A1 | 4/1997 |

(Continued)

OTHER PUBLICATIONS

International Search Report and Written Opinion for PCT/US2008/058575 mailed Nov. 17, 2008.

(Continued)

*Primary Examiner* — Noble Jarrell
(74) *Attorney, Agent, or Firm* — Wolf, Greenfield & Sacks, P.C.; C. Hunter Baker

(57) ABSTRACT

The present invention provides inventive stitched polypeptides, pharmaceutical compositions thereof, and methods of making and using inventive stitched polypeptides.

33 Claims, 42 Drawing Sheets

(56) References Cited

U.S. PATENT DOCUMENTS

| | | |
|---|---|---|
| 2008/0262200 A1 | 10/2008 | Nash |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2009/0326192 A1 | 12/2009 | Nash et al. |
| 2010/0081611 A1 | 4/2010 | Bradner et al. |
| 2010/0168388 A1 | 7/2010 | Bernal et al. |
| 2010/0184628 A1 | 7/2010 | Nash |
| 2010/0216688 A1 | 8/2010 | Nash et al. |
| 2010/0234563 A1 | 9/2010 | Arora et al. |
| 2010/0298201 A1 | 11/2010 | Nash et al. |
| 2011/0028753 A1 | 2/2011 | Verdine et al. |
| 2011/0144303 A1 | 6/2011 | Nash et al. |
| 2011/0144306 A1 | 6/2011 | Verdine et al. |
| 2011/0223149 A1 | 9/2011 | Nash et al. |
| 2011/0263815 A1 | 10/2011 | Nash |
| 2012/0082636 A1 | 4/2012 | Walensky et al. |
| 2012/0172311 A1 | 7/2012 | Nash et al. |
| 2012/0190818 A1 | 7/2012 | Nash |
| 2012/0270800 A1* | 10/2012 | Verdine et al. ........... 514/19.4 |
| 2013/0005943 A1 | 1/2013 | Arora et al. |

FOREIGN PATENT DOCUMENTS

| | | |
|---|---|---|
| WO | WO 97/37705 A1 | 10/1997 |
| WO | WO 99/34850 A1 | 7/1999 |
| WO | WO 00/06187 A2 | 2/2000 |
| WO | WO 02/064790 A2 | 8/2002 |
| WO | WO 03/106491 A2 | 12/2003 |
| WO | WO 2004/041275 A1 | 5/2004 |
| WO | WO 2004/058804 A1 | 7/2004 |
| WO | WO 2005/040202 A2 | 5/2005 |
| WO | WO 2005/040202 A3 | 5/2005 |
| WO | WO 2005/044839 A2 | 5/2005 |
| WO | WO 2005/090388 A1 | 9/2005 |
| WO | WO 2005/118620 A2 | 12/2005 |
| WO | WO 2005/118620 A3 | 12/2005 |
| WO | WO 2005/118634 A2 | 12/2005 |
| WO | WO 2006/103666 A2 | 10/2006 |
| WO | WO 2007/141533 A2 | 12/2007 |
| WO | WO 2008/061192 A2 | 5/2008 |
| WO | WO 2008/095063 A1 | 8/2008 |
| WO | WO 2008/121767 A2 | 10/2008 |
| WO | WO 2010/011313 A2 | 1/2010 |
| WO | WO 2011/008260 A2 | 1/2011 |
| WO | WO 2012/040459 A2 | 3/2012 |
| WO | WO 2012/174423 A1 | 12/2012 |

OTHER PUBLICATIONS

Adhikary et al., Transcriptional regulation and transformation by Myc proteins. Nat Rev Mol Cell Biol. Aug. 2005;6(8):635-45.

Aman et al., cDNA cloning and characterization of the human interleukin 13 receptor alpha chain. J Biol Chem. Nov. 15, 1996;271(46):29265-70.

Andrews et al., Kinetic analysis of the interleukin-13 receptor complex. J Biol Chem. Nov. 29, 2002;277(48):46073-8. Epub Sep. 26, 2002.

Babine et al., Molecular Recognition of Proteinminus signLigand Complexes: Applications to Drug Design. Chem Rev. Aug. 5, 1997;97(5):1359-1472.

Banerjee et al., Structure of a DNA glycosylase searching for lesions. Science. Feb. 24, 2006;311(5764):1153-7.

Banerjee et al., Structure of a repair enzyme interrogating undamaged DNA elucidates recognition of damaged DNA. Nature. Mar. 31, 2005;434(7033):612-8.

Barker et al., Mining the Wnt pathway for cancer therapeutics. Nat Rev Drug Discov. Dec. 2006;5(12):997-1014.

Belokon et al., Improved procedures for the synthesis of (S)-2-[N-(N'-benzyl-prolyl)amino]benzophenone (BPB) and Ni(II) complexes of Schiff's bases derived from BPB and amino acids. Tetrahedron: Asymmetry. 1998;9:4249-52.

Berge et al., Pharmaceutical salts. J Pharm Sci. Jan. 1977;66(1):1-19.

Bernal et al., Reactivation of the p53 tumor suppressor pathway by a stapled p53 peptide. J Am Chem Soc. Mar. 7, 2007;129(9):2456-7. Epub Feb. 7, 2007.

Bierzynski et al., A salt bridge stabilizes the helix formed by isolated C-peptide of Rnase A. Proc Natl Acad Sci U S A. Apr. 1982;79(8):2470-4.

Blackwell et al., Highly Efficient Synthesis of Covalently Cross-Linked Peptide Helices by Ring-Closing Metathesis. Angew Chem Int Ed. 1994;37(23):3281-84.

Blackwell et al., Ring-closing metathesis of olefinic peptides: design, synthesis, and structural characterization of macrocyclic helical peptides. J Org Chem. Aug. 10, 2001;66(16):5291-302.

Bode et al., Chemoselective amide ligations by decarboxylative condensations of N-alkylhydroxylamines and alpha-ketoacids. Angew Chem Int Ed Engl. Feb. 13, 2006;45(8):1248-52.

Bracken et al., Synthesis and Nuclear Magnetic Resonance Structure Determination of an $\alpha$-Helical, Bicyclic, Lactam-Bridged Hexapeptide. J Am Chem Soc. 1994;116:6431-32.

Brusselle et al., Allergen-induced airway inflammation and bronchial responsiveness in wild-type and interleukin-4-deficient mice. Am J Respir Cell Mol Biol. Mar. 1995;12(3):254-9.

Chiaramonte et al., Studies of murine schistosomiasis reveal interleukin-13 blockade as a treatment for established and progressive liver fibrosis. Hepatology. Aug. 2001;34(2):273-82.

Cohn et al., Cutting Edge: IL-4-independent induction of airway hyperresponsiveness by Th2, but not Th1, cells. J Immunol. Oct. 15, 1998;161(8):3813-6.

Cole et al., Transcription-independent functions of MYC: regulation of translation and DNA replication. Nat Rev Mol Cell Biol. Oct. 2008;9(10):810-5. Epub Aug. 13, 2008.

Dawson et al., Synthesis of proteins by native chemical ligation. Science. Nov. 4, 1994;266(5186):776-9.

De Guzman et al., Structural basis for cooperative transcription factor binding to the CBP coactivator. J Mol Biol. Feb. 3, 2006;355(5):1005-13. Epub Oct. 5, 2005.

Debinski et al., Retargeting interleukin 13 for radioimmunodetection and radioimmunotherapy of human high-grade gliomas. Clin Cancer Res. Oct. 1999;5(10 Suppl):3143s-3147s.

Denmark et al., Cyclopropanation with Diazomethane and Bis(oxazoline)palladium(II) Complexes. J Org Chem. May 16, 1997;62(10):3375-3389.

Doron et al., Probiotics: their role in the treatment and prevention of disease. Expert Rev Anti Infect Ther. 2006;4:261-75.

Eisenmesser et al., Solution structure of interleukin-13 and insights into receptor engagement. J Mol Biol. Jun. 29, 2001;310(1):231-41.

Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.

Erlanson et al., The leucine zipper domain controls the orientation of AP-1 in the NFAT.AP-1.DNA complex. Chem Biol. Dec. 1996;3(12):981-91.

Favrin et al., Two-state folding over a weak free-energy barrier. Biophys J. Sep. 2003;85(3):1457-65.

Fischback et al., Specific biochemical inactivation of oncogenic Ras proteins by nucleoside diphosphate kinase. Cancer Res. Jul. 15, 2003;63(14):4089-94.

Fischer et al., The HIV-1 Rev activation domain is a nuclear export signal that accesses an export pathway used by specific cellular RNAs. Cell. Aug. 11, 1995;82(3):475-83.

Fromme et al., Structural basis for removal of adenine mispaired with 8-oxoguanine by MutY adenine DNA glycosylase. Nature. Feb. 12, 2004;427(6975):652-6.

Furstner et al., Alkyne Metathesis: Development of a Novel Molybdenum-Based Catalyst System and Its Application to the Total Synthesis of Epothilone A and C. Chem Euro J. 2001;7(24):5299-5317.

Furstner et al., Mo[N(t-Bu)(AR)]$_3$ Complexes as Catalyst Precursors: In Situ Activation and Application to Metathesis Reactions of Alkynes and Diynes. J Am Chem Soc. 1999;121:9453-54.

Furstner et al., Nozaki—Hiyama—Kishi Reactions Catalytic in Chromium. J Am Chem Soc. 1996;118:12349-57.

(56) References Cited

OTHER PUBLICATIONS

Gallivan et al., A neutral, water-soluble olefin metathesis catalyst based on an *N*-heterocyclic carbene ligand. Tetrahedron Letters. 2005;46:2577-80.
Gante, Peptidomimetics—Tailored Enzyme Inhibitors. J Angew Chem Int Ed Engl. 1994;33:1699-1720.
Gerber-Lemaire et al., Glycosylation pathways as drug targets for cancer: glycosidase inhibitors. Mini Rev Med Chem. Sep. 2006;6(9):1043-52.
Giannis et al., Peptidomimetics for Receptor Ligands—Discovery, Development, and Medical Perspectives. Angew Chem Int Ed Engl. 1993;32:1244-67.
Görlich et al., Transport between the cell nucleus and the cytoplasm. Annu Rev Cell Dev Biol. 1999;15:607-60.
Grubbs et al., Ring-Closing Metathesis and Related Processes in Organic Synthesis. Acc Chem Res. 1995;28:446-52.
Grünig et al., Requirement for IL-13 independently of IL-4 in experimental asthma. Science. Dec. 18, 1998;282(5397):2261-3.
Harper et al., Efficacy of a bivalent L1 virus-like particle vaccine in prevention of infection with human papillomavirus types 16 and 18 in young women: a randomized controlled trial. Lancet. Nov. 13-19, 2004;364(9447):1757-65.
Hipfner et al., Connecting proliferation and apoptosis in development and disease. Nat Rev Mol Cell Biol. Oct. 2004;5(10):805-15.
Holford et al., Adding 'splice' to protein engineering. Structure. Aug. 15, 1998;6(8):951-6.
Kelly-Welch et al., Interleukin-4 and Interleukin-13 Signaling Connections Maps. Science. 2003;300:1527-28.
Kim et al., Stereochemical effects of all-hydrocarbon tethers in i,i+4 stapled peptides. Bioorg Med Chem Lett. May 1, 2009;19(9):2533-6. Epub Mar. 13, 2009.
Kimmerlin et al., '100 years of peptide synthesis': ligation methods for peptide and protein synthesis with applications to beta-peptide assemblies. J Pept Res. Feb. 2005;65(2):229-60.
Knackmuss et al., Specific inhibition of interleukin-13 activity by a recombinant human single-chain immunoglobulin domain directed against the IL-13 receptor alpha1 chain. Biol Chem. Mar. 2007;388(3):325-30.
Kouzarides, Acetylation: A regulatory modification to rival phosphorylation? EMBO J. Mar. 15, 2000;19(6):1176-9.
Kutchukian et al., All-atom model for stabilization of alpha-helical structure in peptides by hydrocarbon staples. J Am Chem Soc. Apr. 8, 2009;131(13):4622-7.
Laporte et al., Molecular and structural basis of cytokine receptor pleiotropy in the interleukin-4/13 system. Cell. Jan. 25, 2008;132(2):259-72.
Le Geuzennec et al., Molecular determinants of the interaction of Mad with the PAH2 domain of mSin3. J Biol Chem. Jun. 11, 2004;279(24):25823-9. Epub Mar. 26, 2004.
Leduc et al., Helix-stabilized cyclic peptides as selective inhibitors of steroid receptor-coactivator interactions. Proc Natl Acad Sci USA. 2003;100(20):11273-78.
Liskamp, Conformationally restricted amino acids and dipeptides, (non)peptidomimetics and secondary structure mimetics. Recl Travl Chim Pays-Bas. 1994;113:1-19.
Liu et al., Chemical Ligation Approach to Form a Peptide Bond between Unprotected Peptide Segments. Concept and Model Study. J Am Chem Soc. 1994;116(10):4149-53.
Losey et al., Crystal structure of *Staphylococcus aureus* tRNA adenosine deaminase TadA in complex with RNA. Nat Struct Mol Biol. Feb. 2006;13(2):153-9. Epub Jan. 15, 2006.
MacMillan, Evolving strategies for protein synthesis converge on native chemical ligation. Angew Chem Int Ed Engl. Nov. 27, 2006;45(46):7668-72.
Miloux et al., Cloning of the human IL-13R alpha1 chain and reconstitution with the IL4R alpha of a functional IL-4/IL-13 receptor complex. FEBS Lett. Jan. 20, 1997;401(2-3):163-6.
Moy et al., Solution structure of human IL-13 and implication for receptor binding. J Mol Biol. Jun. 29, 2001;310(1):219-30.
Muir et al., Expressed protein ligation: A general method for protein engineering. Proc Natl Acad Sci U S A. Jun. 9, 1998;95(12):6705-10.
Muir, Semisynthesis of proteins by expressed protein ligation. Annu Rev Biochem. 2003;72:249-89. Epub Feb. 27, 2003.
Nair et al., X-ray structures of Myc-Max and Mad-Max recognizing DNA. Molecular bases of regulation by proto-oncogenic transcription factors. Cell. Jan. 24, 2003;112(2):193-205.
Nilsson et al., Staudinger ligation: A peptide from a thioester and azide. Org Lett. Jun. 29, 2000;2(13):1939-41.
Node et al., Hard Acid and Soft Nucleophile Systems. 3. Dealkylation of Esters with Aluminum Halide-Thiol and Aluminum Halide-Sulfide Stustems. J Org Chem. 1981;46:1991-93.
Pakotiprapha et al., Crystal structure of *Bacillus stearothermophilus* UvrA provides insight into ATP-modulated dimerization, UvrB interaction, and DNA binding. Mol Cell. Jan. 18, 2008;29(1):122-33. Epub Dec. 27, 2007.
Phelan et al., A General Method for Constraining Short Peptides to an α-Helical Conformation. J Am Chem Soc. 1997;119(3):455-60.
Qiu et al., Convenient, Large-Scale Asymmetric Synthesis of Enantiomerically Pure *trans*-Cinnamylglycine and -α-Alanine. Tetrahedron. 2000;56:2577-82.
Rawlinson et al., CRM1-mediated nuclear export of dengue virus RNA polymerase NS5 modulates interleukin-8 induction and virus production. J Biol Chem. Jun. 5, 2009;284(23):15589-97. Epub Mar. 18, 2009.
Roos et al., Synthesis of α-Substituted α-Amino Acids via Cationic Intermediates. J Org Chem. 1993;58:3259-68.
Sampietro et al., Crystal structure of a beta-catenin/BCL9/Tcf4 complex. Mol Cell. Oct. 20, 2006;24(2):293-300.
Saxon et al., Cell surface engineering by a modified Staudinger reaction. Science. Mar. 17, 2000;287(5460):2007-10.
Schafmiester et al., An All-Hydrocarbon Cross-Linking System for Enhancing the Helicity and Metabolic Stability of Peptides. J Am Chem Soc. 2000;122:5891-92.
Scheffzek et al., The Ras-RasGAP complex: structural basis for GTPase activation and its loss in oncogenic Ras mutants. Science. Jul. 18, 1997;277(5324):333-8.
Scholtz et al., The mechanism of alpha-helix formation by peptides. Annu Rev Biophys Biomol Struct. 1992;21:95-118.
Schrock et al., Tungsten(VI) Neopentylidyne Complexes. Organometallics. 1982;1:1645-51.
Shair, A closer view of an oncoprotein-tumor suppressor interaction. Chem Biol. Nov. 1997;4(11):791-4.
Soucek et al., Modelling Myc inhibition as a cancer therapy. Nature. Oct. 2, 2008;455(7213):679-83. Epub Aug. 17, 2008.
Still et al., Semianalytical Treatment of Solvation for Molecular Mechanics and Dynamics. J Am Chem Soc. 1990;112:6127-29.
Thompson et al., Mutants of interleukin 13 with altered reactivity toward interleukin 13 receptors. J Biol Chem. Oct. 15, 1999;274(42):29944-50.
Vaickus et al., Immune markers in hematologic malignancies. Crit Rev Oncol Hematol. Dec. 1991;11(4):267-97.
Venancio et al., Reconstructing the ubiquitin network: cross-talk with other systems and identification of novel functions. Genome Biol. 2009;10(3):R33. Epub Mar. 30, 2009.
Verdine et al., The challenge of drugging undruggable targets in cancer: lessons learned from targeting BCL-2 family members. Clin Cancer Res. Dec. 15, 2007;13(24):7264-70.
Walensky et al., A stapled BID BH3 helix directly binds and activates BAX. Mol Cell. Oct. 20, 2006;24(2):199-210.
Walensky et al., Activation of apoptosis in vivo by a hydrocarbon-stapled BH3 helix. Science. Sep. 3, 2004;305(5689):1466-70.
Walter et al., Critical role for IL-13 in the development of allergen-induced airway hyperreactivity. J Immunol. Oct. 15, 2001;167(8):4668-75.
Wang et al., Inhibition of p53 degradation by Mdm2 acetylation. FEBS Lett. Mar. 12, 2004;561(1-3):195-201.
Wilen et al., Strategies in Optical Resolution. Tetrahedron. 1977;33:2725-36.
Wills-Karp et al., Interleukin-13: central mediator of allergic asthma. Science. Dec. 18, 1998;282(5397):2258-61.
Wills-Karp, Interleukin-13 in asthma pathogenesis. Immunol Rev. Dec. 2004;202:175-90.

(56) References Cited

OTHER PUBLICATIONS

Wills-Karp, The gene encoding interleukin-13: A susceptibility locus for asthma and related traits. Respir Res. 2000;1(1):19-23. Epub Jul. 17, 2000.

Yang et al., Synthesis and helical structure of lactam bridged BH3 peptides derived from proapoptotic Bcl-2 family proteins. Bioorg Med Chem Lett. 2004;14:1403-06.

Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.

Zhou et al., Identification of Ubiquitin Target Proteins Using Cell-Based Arrays. J Proteome Res. 2007;6:4397-4406.

Zor et al., Solution of the KIX domain CBP bound to the transactivation domain of c-Myb. J Mol. Biol. Mar. 26, 2004;337(3):521-34.

Invitation to Pay Additional Fees for PCT/US2009/004260 mailed Mar. 19, 2010.

Bang et al., Total chemical synthesis of crambin. J Am Chem Soc. Feb. 11, 2004;126(5):1377-83.

International Preliminary Report on Patentability for PCT/US2010/001952, Jan. 26, 2012.

Extended European Search Report for EP 12159110.1, mailed Jul. 20, 2012.

Invitation to Pay Additional Fees for PCT/US2011/052755 mailed Feb. 16, 2012.

International Search Report and Written Opinion for PCT/US2011/052755, mailed Apr. 25, 2012.

Office Communication, mailed Feb. 9, 2012, for U.S. Appl. No. 12/420,816.

Office Communication, mailed Oct. 18, 2011, for U.S. Appl. No. 12/796,212.

[No Author Listed] Designing Custom Peptide. from SIGMA Genosys, pp. 1-2. Accessed Jul. 27, 2012.

Berendsen et al., A glimpse of the Holy Grail? Science. Oct. 23, 1998;282(5389):642-3.

Bradley et al., Limits of cooperativity in a structurally modular protein: response of the Notch ankyrin domain to analogous alanine substitutions in each repeat. J Mol Biol. Nov. 22, 2002;324(2):373-86.

Greenlee et al., A General Synthesis of α-vinyl-α-amino acids. Tetrahedron Letters. 1978;42:3999-40002.

Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.

Kazmaier, Sythesis of Quaternary Amino Acids Containing β, γ- as well as γ,δ-Unsaturated Side Chains via Chelate-Enolate Claisen Rearrangement. Tetrahedron Letters. 1996;37(30):5351-4.

McNamara et al., Peptides constrained by an aliphatic linkage between two C(alpha) sites: design, synthesis, and unexpected conformational properties of an i,(i + 4)-linked peptide. J Org Chem. Jun. 29, 2001;66(13):4585-94

Ngo et al., Computational complexity, protein structure prediction, and the levinthal paradox. In: The Protein Folding Problem and Tertiary Structure Prediction. K. Mem, Jr., et al. Eds. 1994:433-506.

Rudinger, Characteristics of the amino acids as components of a peptide hormone sequence. In:Peptide Hormones. J.A. Parsons, ed. University Park Press. Jun. 1976:1-7.

Schinzel et al., The phosphate recognition site of Escherichia coli maltodextrin phosphorylase. FEBS Lett. Jul. 29, 1991;286(1-2):125-8.

Schmiedeberg et al., Reversible backbone protection enables combinatorial solid-phase ring-closing metathesis reaction (RCM) in peptides. Org Lett. Jan. 10, 2002;4(1):59-62.

Tanaka, Design and synthesis of non-proteinogenic amino acids and secondary structures of their peptides. Yakugaku Zasshi. Oct. 2006:126(10):931-44. Japanese.

Voet et al., Biochemistry. Second Edition. John Wiley & Sons, Inc. 1995:235-241.

Invitation to Pay Additional Fees, mailed Oct. 29, 2010, for PCT/US2010/001952.

International Search Report and Written Opinion for PCT/US2010/001952 mailed Feb. 2, 2011.

International Search Report and Written Opinion for PCT/US2009/004260 mailed Oct. 15, 2010.

International Preliminary Report on Patentability for PCT/US2009/004260 mailed Feb. 3, 2011.

U.S. Appl. No. 61/385,405, Verdine et al., Sep. 22, 2010.

International Preliminary Report on Patentability for PCT/US2008/058575 mailed Oct. 8, 2009.

Office Communication, mailed Feb. 17, 2011, for U.S. Appl. No. 12/796,212.

Andrews et al., Forming Stable Helical Peptides Using Natural and Artificial Amino Acids. Tetrahedron. 1999;55:11711-43.

Armstrong et al., X = Y-ZH Systems as potential 1,3-dipoles. 5. Intramolecular cycloadditions of imines of a-amino acid esters. Tetrahedron. 1985;41(17):3547-58.

Attisano et al., TGFbeta and Wnt pathway cross-talk. Cancer Metastasis Rev. Jan.-Jun. 2004;23(1-2):53-61.

Barandon et al., Reduction of infarct size and prevention of cardiac rupture in transgenic mice overexpressing FrzA. Circulation. Nov. 4, 2003;108(18):2282-9. Epub Oct. 27, 2003.

Beloken et al., Chiral Complexes of Ni(II), Cu(II) and Cu(I) as Reagents, Catalysts and Receptors for Asymmetric Syntheses and Chiral Recognition of Amino Acids. Prue & Appl Chem. 1992;64(12):1917-24.

Bennett et al., Regulation of osteoblastogenesis and bone mass by Wnt10b. Proc Natl Acad Sci U S A. Mar. 1, 2005;102(9):3324-9. Epub Feb. 22, 2005.

Biagini et al., Cross-metathesis of Unsaturated α-amino Acid Derivatives. J Chem Soc Perkin Trans. 1998;1:2485-99.

Boyden et al., High bone density due to a mutation in LDL-receptor-related protein 5. N Engl J Med. May 16, 2002;346(20):1513-21.

Brubaker et al., Solution structure of the interacting domains of the Mad-Sin3 complex: implications for recruitment of a chromatin-modifying complex. Cell. Nov. 10, 2000;103(4):655-65.

Burger et al., Synthesis of a-(trifluoromethyl)-substituted a-amino acids. Part 7. An efficient syntheses for a-trifluromethyl-substituted w-carboxy a-amino acids. Chemiker-Zeitung. 1990;114(3):101-04. German.

Caricasole et al., The Wnt pathway, cell-cycle activation and beta-amyloid: novel therapeutic strategies in Alzheimer's disease? Trends Pharmacol Sci. May 2003;24(5):233-8.

Chen et al., Small molecule-mediated disruption of Wnt-dependent signaling in tissue regeneration and cancer. Nat Chem Biol. Feb. 2009;5(2):100-7. Epub Jan. 4, 2009.

Cheon et al., beta-Catenin stabilization dysregulates mesenchymal cell proliferation, motility, and invasiveness and causes aggressive fibromatosis and hyperplastic cutaneous wounds. Proc Natl Acad Sci U S A. May 14, 2002;99(10):6973-8. Epub Apr. 30, 2002.

Christodoulides et al., WNT10B mutations in human obesity. Diabetologia. Apr. 2006;49(4):678-84. Epub Feb. 14, 2006.

Clark et al., Supramolecular Design by Covalent Capture. Design of a Peptide Cylinder via Hydrogen-Bond-Promoted Intermolecular Olefun Metathesis. J Am Chem Soc. 1995;117:12364-65.

Clevers, Wnt/beta-catenin signaling in development and disease. Cell. Nov. 3, 2006;127(3):469-80.

Cong et al., A protein knockdown strategy to study the function of beta-catenin in tumorigenesis. BCM Mol. Biol. Sep. 29, 2003;4:10.

Cossu et al., Wnt signaling and the activation of myogenesis in mammals. EMBO J. Dec. 15, 1999;18(24):6867-72.

Cusack et al., 2,4,6-Tri-isopropylbenzenesulphonyl Hydrazide: A Convenient Source of Di-imide. Tetrahedron. 1976;32:2157-62.

Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.

Fuchs et al., Socializing with the neighbors: stem cells and their niche. Cell. Mar. 19, 2004;116(6):769-78.

Gat et al., De Novo hair follicle morphogenesis and hair tumors in mice expressing a truncated beta-catenin in skin. Cell. Nov. 25, 1998;95(5):605-14.

Gavathiotis et al., BAX activation is initiated at a novel interaction site. Nature. Oct. 23, 2008;455(7216):1076-81.

(56) References Cited

OTHER PUBLICATIONS

Gong et al., LDL receptor-related protein 5 (LRP5) affects bone accrual and eye development. Cell. Nov. 16, 2001;107(4):513-23.
Goodson et al., Potential Growth Antagonists. I. Hydantoins and Disubstituted Glycines. J Org Chem. 1960;25:1920-24.
Goun et al., Molecular transporters: synthesis of oligoguanidinium transporters and their application to drug delivery and real-time imaging. Chembiochem. Oct. 2006;(10):1497-515.
Greenfield et al., Computed circular dichroism spectra for the evaluation of protein conformation. Biochemistry. Oct. 1969;8(10):4108-16.
Guinn et al., Synthesis and characterization of polyamides containing unnatural amino acids. Biopolymers. May 1995;35(5):503-12.
Hartmann et al., Dual roles of Wnt signaling during chondrogenesis in the chicken limb. Development. Jul. 2000;127(14):3141-59.
Hartmann, A Wnt canon orchestrating osteoblastogenesis. Trends Cell Biol. Mar. 2006;16(3):151-8. Epub Feb. 7, 2006.
Henchey et al., Contemporary strategies for the stabilization of peptides in the α-helical conformation. Curr Opin Chem Biol. 2008;12:692-97.
Hoang et al., Dickkopf 3 inhibits invasion and motility of Saos-2 osteosarcoma cells by modulating the Wnt-beta-catenin pathway. Cancer Res. Apr. 15, 2004;64(8):2734-9.
Huang et al., Tankyrase inhibition stabilizes axin and antagonizes Wnt signalling. Nature. Oct. 1, 2009;461(7264):614-20. Epub Sep. 16, 2009.
Jackson et al., General Approach to the Synthesis of Short α-Helical Peptides. J Am Chem Soc. 1991;113:9391-93.
Jamieson et al., Granulocyte-macrophage progenitors as candidate leukemic stem cells in blast-crisis CML. N Engl J Med. Aug. 12, 2004;351(7):657-67.
Jordan et al., Wnt4 overexpression disrupts normal testicular vasculature and inhibits testosterone synthesis by repressing steroidogenic factor 1/beta-catenin synergy. Proc Natl Acad Sci U S A. Sep. 16, 2003;100(19):10866-71. Epub Aug. 29, 2003.
Karwoski et al., Lysinonorleucine cross-link formation in alpha amino heptenoic acid-substituted peptide derivatives. Biopolymers. 1978;17(5):1119-27.
Katoh et al., Cross-talk of WNT and FGF signaling pathways at GSK3beta to regulate beta-catenin and SNAIL signaling cascades. Cancer Biol Ther. Sep. 2006;5(9):1059-64. Epub Sep. 4, 2006.
Katsu et al., The human frizzled-3 (FZD3) gene on chromosome 8p21, a receptor gene for Wnt ligands, is associated with the susceptibility to schizophrenia. Neurosci Lett. Dec. 15, 2003;353(1):53-6.
Kaul et al., Stereochemical control of peptide folding. Bioorg Med Chem. Jan. 1999;7(1):105-17.
Kinzler et al., Identification of FAP locus genes from chromosome 5q21. Science. Aug. 9, 1991;253(5020):661-5.
Kinzler et al., Lessons from hereditary colorectal cancer. Cell. Oct. 18, 1996;87(2):159-70.
Kondo et al., Frizzled 4 gene (FZD4) mutations in patients with familial exudative vitreoretinopathy with variable expressivity. Br J Ophthalmol. Oct. 2003;87(10):1291-5.
Korcsmaros et al., Uniformly curated signaling pathways reveal tissue-specific cross-talks and support drug target discovery. Bioinformatics. Aug. 15, 2010;26(16):2042-50. Epub Jun. 11, 2010.
Korinek et al., Depletion of epithelial stem-cell compartments in the small intestine of mice lacking Tcf-4. Nat Genet. Aug. 1998;19(4):379-83.
Kotha et al., Modification of constrained peptides by ring-closing metathesis reaction. Bioorg Med Chem Lett. Jun. 4, 2001;11(11):1421-3.
Kozlovsky et al., GSK-3 and the neurodevelopmental hypothesis of schizophrenia. Eur Neurodevelopment hypothesis of schizophrenia. Eur Neuropsychopharmacol. Feb. 2002;12(1):13-25.
Kussie et al., Structure of the MDM2 oncoprotein bound to the p53 tumor suppressor Transactivation domain. Science. Nov. 8, 1996;274(5289):948-53.
Lacombe et al., Reduction of Olefins on Solid Support Using Diimide. Tetranderon Lett. 1998;39:6785-86.

Lammi et al., Mutations in AXIN2 cause familial tooth agenesis and predispose to colorectal cancer. Am J Hum Genet. May 2004;74(5):1043-50. Epub Mar. 23, 2004.
Laughlin et al., Functional variants within the secreted frizzled-related protein 3 gene are associated with hip osteoarthritis in females. Proc Natl Acad Sci U S A. Jun. 29, 2004;101(26):9757-62. Epub Jun. 21, 2004.
Le Geuzennec et al., Molecular characterization of Sin3 PAH-domain interactor specificity and identification of PAH partners. Nucleic Acids Res. 2006;34(14):3929-37. Epub Aug. 12, 2006.
Liang et al., Wnt5a inhibits B cell proliferation and functions as a tumor suppressor in hematopoietic tissue. Cancer Cell. Nov. 2003;4(5):349-60.
Little et al., A Mutation in the LDL Receptor-Related Protein 5 Gene Results in the Autosomal Dominant High-Bone-Mass Trait. Am J Hum Genet. 2002;70:11-19.
Liu et al., Targeted degradation of beta-catenin by chimeric F-box fusion proteins. Biochem Biophys Res Commun. Jan. 23, 2004;313(4):1023-9.
Lo et al., Phosphorylation by the beta-catenin/MAPK complex promotes 14-3-3-mediated nuclear export of TCF/POP-1 in signal-responsive cells in C. elegans. Cell. Apr. 2, 2004;117(1):95-106.
Logan et al., The Wnt signaling pathway in development and disease. Annu Rev Cell Dev Biol 2004;20:781-810.
Loughlin et al., Functional variants within the secreted frizzled-related protein 3 gene are associated with hip osteoarthritis in females. Proc Natl Acad Sci U S A. Jun. 29, 2004;101(26):9757-62. Epub Jun. 21, 2004.
Luo et al., Wnt signaling and hunian diseases: what are the therapeutic implications? Lab Invest. Feb. 2007;87(2):97-103. Epub Jun. 8, 2007.
Luu et al, Wnt/beta-catenin signaling pathway as a novel cancer drug target. Curr Cancer Drug Targets. Dec. 2004;4(8):653-71.
Miyaoka et al., Increased expression of Wnt-1 in schizophrenic brains. Schizophr Res. Jul. 27, 1999;38(1):1-6.
Moellering et al., Direct inhibition of the NOTCH transcription factor complex. Nature. Nov. 12, 2009;462(7270):182-8.
Moon et al., Wnt and beta-catenin signalling: diseases and therapies. Nat Rev Genet. Sep. 2004;5(9):689-699.
Morin, beta-catenin signaling and cancer. Bioessays. Dec. 1999;21(12):1021-30.
Mudher et al., Alzheimer's disease—do tauists and baptists finally shake hands? Trends Neurosci. Jan. 2002;25(1):22-6.
Myung et al., The ubiquitin-proteasome pathway and proteasome inhibitors. Med Res Rev. Jul. 2001;21(4):245-73.
Nakashima et al., Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.
Niemann et al., Homozygous WNT3 mutation causes tetra-amelia in a large consanguineous family. Am J Hum Genet. Mar. 2004;74(3):558-63. Epub Feb. 5, 2004.
Nishisho et al., Mutations of chromosome 5q21 genes in FAP and colorectal cancer patients. Science. Aug. 9, 1991;253(5020):665-9.
Okamura et al., Redundant regulation of T cell differentiation and TCRalpha gene expression by the transcription factors LEF-1 and TCF-1. Immunity. Jan. 1998;8(1):11-20.
Olson et al, Sizing up the heart: development redux in disease. Genes Dev. Aug. 15, 2003;17(16):1937-56. Epub Jul. 31, 2003.
Perantoni, Renal development: perspectives on a Wnt-dependent process. Semin Cell Dev Biol. Aug. 2003;14(4):201-8.
Polakis, The oncogenic activation of beta-catenin. Curr Opin Genet Dev. Feb. 1999;9(1):15-21.
Reya et al., Wnt signalling in stem cells and cancer. Nature. Apr. 14, 2005;434(7035):843-50.
Rich et al., Synthesis of the cytostatic cyclic tetrapeptide, chlamydocin. Tetranderon Letts. 1983;24(48):5305-08.
Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-1 promoter is a target of the beta-catenin/T-cell factor pathway. J Biol Chem. Aug. 16, 2002;277(33):29577-83. Epub Jun. 4, 2002.

(56) References Cited

OTHER PUBLICATIONS

Ross et al., Inhibition of adipogenesis by Wnt signaling. Science. Aug. 11, 2000;289(5481):950-3.
Satoh et al., AXIN1 mutations in hepatocellular carcinomas, and growth suppression in cancer cells by virus-mediated transfer of AXIN1. Nat Genet. Mar. 2000;24(3):245-50.
Sattler et al., Structure of Bcl-xL-Bak peptide complex: recognition between regulators of apoptosis. Science. Feb. 14, 1997;275(5302):983-6.
Si et al., CCNI/Cyr61 is regulated by the canonical Wnt signal and plays an important role in Wnt3A-induced osteoblast differentiation of mesenchymal stem cells. Mol Cell Biol. Apr. 2006;26(8):2955-64.
Su et al, Eradication of pathogenic beta-catenin by Skp1/Cullin/F box ubiquitination machinery. Proc Natl Acad Sci U S A. Oct. 28, 2003;100(22):12729-34. Epub Oct. 16, 2003.
Takeda et al., Human sebaceous tumors harbor inactivating mutations in LEF1. Nat Med. Apr. 2006;12(4):395-7. Epub Mar. 26, 2006.
Tian et al., The role of the Wnt-signaling antagonist DKK1 in the development of osteolytic lesions in multiple myeloma. N. Engl J Med. Dec. 25, 2003;349(26):2483-94.
Toomes et al, Mutations in LRP5 or FZD4 underlie the common familial exudative vitreoretinopathy locus on chromosome 11q. Am J Hum Genet. Apr. 2004;74(4):721-30. Epub Mar. 11, 2004.
Torrance et al., Combinatorial chemoprevention of intestinal neoplasia. Nat Med. Sep. 2000;6(9):1024-8.
Tsuji et al., Antiproliferative activity of REIC/Dkk-3 and its significant down-regulation in non-small lung carcinomas. Biochem Biophys Res Commun. Nov. 23, 2001;289(1):257-63.
Van Genderen et al., Development of several organs that require inductive epithelial-mesenchymal interactions is impaired in LEF-1-deficient mice. Genes Dev. Nov. 15, 1994;8(22):2691-703.
Van Gijn et al., The wnt-frizzled cascade in cardiovascular disease. Cardiovasc Res. Jul. 2002;55(1):16-24.
Varallo et al., Beta-catenin expression in Dupuytren's disease: potential role for cell-matrix interactions in modulating beta-catenin levels in vivo and in vitro. Oncogene. Jun. 12, 2003;22(24):3680-4.
Verma et al., Small interfering RNAs directed against beta-catenin inhibit the in vitro and in vivo growth of colon cancer cells. Clin Cancer Res. Apr. 2003;9(4):1291-300.
Williams et al., Asymmetric Synthesis of Monosubstituted and α,α-Disubstituted α-Amino Acids via Diastereoselective Glycine Enolate Alkylations. J Am Chem Soc. 1991;113:9276-86.
Xi et al., Use of DNA and peptide nucleic acid molecular beacons for detection and quantification of rRNA in solution and in whole cells. Appl Environ Microbiol. Sep. 2003;69(9):5673-8.
Xing et al., Crystal structure of a beta-catenin/axin complex suggests a mechanism for the beta-catenin destruction complex. Genes Dev. Nov. 15, 2003;17(22):2753-64. Epub Nov. 4, 2003.
Yu et al., The role of Axin2 in calvarial morphogenesis and craniosynostosis. Development. Apr. 2005;132(8):1995-2005.
Zhou et al., Lymphoid enhancer factor 1 directs hair follicle patterning and epithelial cell fate. Genes Dev. Mar. 15, 1995;9(6):700-13.
Zhou et al., Tyrosine kinase inhibitor STI-571/Gleevec down-regulates the beta-catenin signaling activity. Cancer Lett. Apr. 25, 2003;193(2):161-70.
Extended European Search Report for EP 09800675.2, mailed Dec. 6, 2012.
Extended European Search Report for EP 12159110.1, mailed Sep. 27, 2012.
International Search Report and Written Opinion for PCT/US2012/042738, mailed Oct. 18, 2012.
International Search Report and Written Opinion for PCT/US2008/052580, mailed May 16, 2008.
Notice of Allowance, mailed Aug. 6, 2012, in U.S. Appl. No. 12/796,212.
Agola et al., Rab GTPases as regulators of endocytosis, targets of disease and therapeutic opportunities. Clin Genet. Oct. 2011;80(4):305-318.
Altschul et al., Basic local alignment search tool. J Mol Biol. Oct. 5, 1990;215(3):403-10.

Blundell et al., Atomic positions in rhombohedral 2-zinc insulin crystals. Nature. Jun. 25, 1971;231(5304):506-11
Brandt et al., Dimeric fragment of the insulin receptor alpha-subunit binds insulin with full holoreceptor affinity. J Biol Chem. Apr. 13, 2001;276(15):12378-84. Epub Jan. 12, 2001.
Carillo et al., The Multiple Sequence Alignment Problem in Biology. SIAM J Applied Math. 1988;48:1073-82.
Carlson et al., Specificity landscapes of DNA binding molecules elucidate biological function. Proc Natl Acad Sci U S A. Mar. 9, 2010;107(10):4544-9. doi: 10.1073/pnas.0914023107. Epub Feb. 22, 2010.
Chen et al., Determination of the helix and beta form of proteins in aqueous solution by circular dichroism. Biochemistry. Jul. 30, 1974;13(16):3350-9.
Cheng et al., Emerging role of RAB GTPases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Chia et al., Emerging roles for Rab family GTPases in human cancer. Biochim Biophys Acta. Apr. 2009;1795(2):110-6.
De Meyts et al., Insulin interactions with its receptors: experimental evidence for negative cooperativity. Biochem Biophys Res Commun. Nov. 1, 1973;55(1):154-61.
De Meyts, The structural basis of insulin and insulin-like growth factor-I receptor binding and negative co-operativity, and its relevance to mitogenic versus metabolic signalling. Diabetologia. Sep. 1994;37Suppl 2:S135-48.
Devereux et al., A comprehensive set of sequence analysis programs for the VAX. Nucleic Acids Res. Jan. 11, 1984;12(1 Pt 1):387-95.
Evans et al., The Rise of Azide-Alkyne 1,3-Dipolar 'Click' Cycloaddition and its Application to Polymer Science and Surface Modification. Australian Journal of Chemistry. 2007;60:384-95.
Fisher et al., Myc/Max and other helix-loop-helix/leucine zipper proteins bend DNA toward the minor groove. Proc Natl Acad Sci U S A. Dec. 15, 1992;89(24):11779-83.
Harris et al., Synthesis of proline-modified analogues of the neuroprotective agent glycyl-l-prolyl-glutamic Acid (GPE). Tetrahedron. 2005;61:10018-35.
Hellman et al., Electrophoretic mobility shift assay (EMSA) for detecting protein-nucleic acid interactions. Nat Protoc. 2007;2(8):1849-61.
Huang et al., How insulin binds: The B-chain alpha-helix contacts the L1 beta-helix of the insulin receptor. J Mol Biol. Aug. 6, 2004;341(2):529-50.
Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.
Junutula et al., Molecular characterization of Rab11 interactions with members of the family of Rab11-interacting proteins. J Biol Chem. Aug. 6, 2004;279(32):33430-7. Epub Jun. 1, 2004.
Kim et al., Synthesis of all-hydrocarbon stapled α-helical peptides by ring-closing olefin metathesis. Nat Protoc. Jun. 2011;6(6):761-71. doi: 10.1038/nprot.2011.324. Epub May 12, 2011.
Kohler et al., DNA specificity enhanced by sequential binding of protein monomers. Proc Natl Acad Sci U S A. Oct. 12, 1999;96(21):11735-9.
Kolb et al., Click Chemistry: Diverse Chemical Function from a Few Good Reactions. Angew Chem Int Ed Engl. Jun. 1, 2001;40(11):2004-2021.
Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.
Kristensen et al., Functional reconstitution of insulin receptor binding site from non-binding receptor fragments. J Biol Chem. May 24, 2002;277(21):18340-5. Epub Mar. 18, 2002.
Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.

(56) References Cited

OTHER PUBLICATIONS

Lou et al., The first three domains of the insulin receptor differ structurally from the insulin-like growth factor 1 receptor in the regions governing ligand specificity. Proc Natl Acad Sci U S A. Aug. 15, 2006;103(33):12429-34. Epub Aug. 7, 2006.

Luscher et al., The basic region/helix-loop-helix/leucine zipper domain of Myc proto-oncoproteins: function and regulation. Oncogene. May 13, 1999;18(19):2955-66.

Marshall et al., Back to the future: ribonuclease A. Biopolymers. 2008;90(3):259-77.

McKern et al., Structure of the insulin receptor ectodomain reveals a folded-over conformation. Nature. Sep. 14, 2006;443(7108):218-21. Epub Sep. 6, 2006.

Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.

Meyers et al., Formation of mutually exclusive Rab11 complexes with members of the family of Rab11-interacting proteins regulates Rab11 endocytic targeting and function. J Biol Chem. Dec. 13, 2002;277(50):49003-10. Epub Oct. 9, 2002.

Mynarcik et al., Alanine-scanning mutagenesis of a C-terminal ligand binding domain of the insulin receptor alpha subunit. J Biol Chem. Feb. 2, 1996;271(5):2439-42.

Mynarcik et al., Identification of common ligand binding determinants of the insulin and insulin-like growth factor 1 receptors. Insights into mechanisms of ligand binding. J Biol Chem. Jul. 25, 1997;272(30):18650-5.

Picksley et al., Immunochemical analysis of the interaction of p53 with MDM2;—fine mapping of the MDM2 binding site on p53 using synthetic peptides. Oncogene. Sep. 1994;9(9):2523-9.

Pillutla et al., Peptides identify the critical hotspots involved in the biological activation of the insulin receptor. J Biol Chem. Jun. 21, 2002;277(25):22590-4. Epub Apr. 18, 2002.

Schäffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.

Schäffer et al., Assembly of high-affinity insulin receptor agonists and antagonists from peptide building blocks. Proc Natl Acad Sci U S A. Apr. 15, 2003;100(8):4435-9. Epub Apr. 8, 2003.

Seabra et al., Rab GTPases, intracellular traffic and disease. Trends Mol Med. Jan. 2002;8(1):23-30.

Shiba et al., Structural basis for Rab11-dependent membrane recruitment of a family of Rab11-interacting protein 3 (FIP3)/Arfophilin-1. Proc Natl Acad Sci U S A. Oct. 17, 2006;103(42):15416-21. Epub Oct. 9, 2006.

Siddle et al., Specificity in ligand binding and intracellular signalling by insulin and insulin-like growth factor receptors. Biochem Soc Trans. Aug. 2001;29(Pt 4):513-25.

Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.

Smith et al., Structural resolution of a tandem hormone-binding element in the insulin receptor and its implications for design of peptide agonists. Proc Natl Acad Sci U S A. Apr. 13, 2010;107(15):6771-6. doi: 10.1073/pnas.1001813107. Epub Mar. 26, 2010.

Stein et al., Rab proteins and endocytic trafficking: potential targets for therapeutic intervention. Adv Drug Deliv Rev. Nov. 14, 2003;55(11):1421-37.

Stenmark et al., The Rab GTPase family. Genome Biol. 2001;2(5):3007.1-3007.7.

Stueanaes et al., Beta-adrenoceptor stimulation potentiates insulin-stimulated PKB phosphorylation in rat cardiomyocytes via cAMP and Pka. Br J Pharmacol. May 2010;160(1):116-29. doi: 10.1111/j.1476-5381.2010.00677.x.

Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.

Tornøe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.

Uesugi et al., The alpha-helical FXXPhiPhi motif in p53: TAF interaction and discrimination by MDM2. Proc Natl Acad Sci U S A. Dec. 21, 1999;96(26):14801-6.

Wang, 4-Alkyl-2-trichloromethyloxazolidin-5-ones: Valuable Precursors to Enantiomerically Pure C- and N-Protected α-Alkyl Prolines. Synlett. 1999;1:33-36.

Wei et al., Disorder and structure in the Rab11 binding domain of Rab11 family interacting protein 2. Biochemistry. Jan. 27, 2009;48(3):549-57. doi: 10.1021/bi8020197.

Wilen, Tables of Resolving Agents and Optical Resolutions. E.L. Eliel, ed. Universtify of Notre Dame Press, Notre Dame, IN. 1972:268-98.

Wilson et al., The FIP3-Rab11 protein complex regulates recycling endosome targeting to the cleavage furrow during late cytokinesis. Mol Biol Cell. Feb. 2005;16(2):849-60. Epub Dec. 15, 2004.

Zimm et al., Theory of the Phase Transition between Helix and Random Coil in Polypeptide Chains. J Chem Phys. 1959;31:526-35.

* cited by examiner

Figure 16

Stabilized α-Helix of BID BH3 Domain

% Cytochrome c release at 400 nM dose in wild type (WT) & BAX/BAK double knockout (DKO) mitochondria

| | 82 87 90 94 98 101 | | $BCL-X_L$ binding $K_D$ |
|---|---|---|---|
| SAHBa 23-mer (1) | EDIIR NIAR HLA $S_5$ VGD $S_5$ N_D R SIW | SAHBa 23-mer (30) | 39 nM |
| SAHBa 18-mer (2) | NIAR HLA $S_5$ VGD $S_5$ N_D R SIW | SAHBa 18-mer (31) | 63 nM |
| SAHBa stitched 22-mer (3) | EDIIR NIA $S_5$ HLA $B_5$ VGD W N_D $S_8$ SI | SAHBa stitched 22-mer (32) | 59 nM |
| SAHBa stitched 17-mer (4) | NIA $S_5$ HLA $B_5$ VGD W N_D $S_8$ SI | SAHBa stitched 17-mer (33) | 49 nM |
| SAHBa stitched 15-mer (5) | NIA $S_5$ HLA $B_5$ VGD W N_D $S_8$ | SAHBa stitched 15-mer (34) | 150 nM |

STITCHED POLYPEPTIDES

PRIORITY INFORMATION

The present application is a national stage filing under 35 U.S.C. §371 of international PCT application, PCT/US2008/058575, filed Mar. 28, 2008, which claims priority under 35 U.S.C. §119(e) to U.S. provisional patent application, U.S. Ser. No. 60/908,566, filed Mar. 28, 2007, the entire contents of each of which is hereby incorporated by reference.

BACKGROUND OF THE INVENTION

The important biological roles that peptides and polypeptides play as hormones, enzyme inhibitors, substrates, neurotransmitters, and neuromediators has led to the widespread use of peptides or peptide mimetics in medicinal chemistry as therapeutic agents. The peptide's bioactive conformation, combining structural elements such as alpha helices, beta sheets, turns, and/or loops, is important as it allows for selective biological recognition of receptors or enzymes, thereby influencing cell-cell communication and/or controlling vital cell functions, such as metabolism, immune defense, and reproduction (Babine et al., Chem. Rev. (1997) 97:1359). The alpha-helix is one of the major structural components of peptides. However, alpha-helical peptides have a propensity for unraveling and forming random coils, which are, in most cases, biologically less active, or even inactive, and are highly susceptible to proteolytic degradation.

Many research groups have developed strategies for the design and synthesis of more robust peptides as therapeutics. For example, one strategy has been to incorporate more robust functionalities into the peptide chain while still maintaining the peptide's unique conformation and secondary structure (see, for example, Gante, J. Angew. Chem. Int. Ed. Engl. (1994) 33:1699-1720; R. M. J. Liskamp, Recl. Tray. Chim. Pays-Bas 1994, 113, 1; Giannis, T. Kolter, Angew. Chem. Int. Ed. Engl. 1993, 32, 1244; P. D. Bailey, Peptide Chemistry, Wiley, New York, 1990, p. 182; and references cited therein). Another approach has been to stabilize the peptide via covalent cross-links (see, for example, Phelan et al. 1997 J. Am. Chem. Soc. 119:455; Leuc et al. 2003 Proc. Nat'l. Acad. Sci. USA 100:11273; Bracken et al., 1994 J. Am. Chem. Soc. 116:6432; Yan et al. 2004 Bioorg. Med. Chem. 14:1403). However, the majority of the reported methodologies involve use of polar and/or labile crosslinking groups.

SUMMARY OF THE INVENTION

"Peptide stapling" is a term coined from a synthetic methodology wherein two olefin-containing sidechains present in a polypeptide chain are covalently joined (e.g., "stapled together") using a ring-closing metathesis (RCM) reaction to form a cross-linked ring (see, the cover art for J. Org. Chem. (2001) vol. 66, issue 16 describing metathesis-based crosslinking of alpha-helical peptides; Blackwell et al.; Angew Chem. Int. Ed. (1994) 37:3281). However, the term "peptide stapling," as used herein, encompasses the joining of two double bond-containing sidechains, two triple bond-containing sidechains, or one double bond-containing and one triple bond-containing side chain, which may be present in a polypeptide chain, using any number of reaction conditions and/or catalysts to facilitate such a reaction, to provide a singly "stapled" polypeptide. Additionally, the term "peptide stitching," as used herein, refers to multiple and tandem "stapling" events in a single polypeptide chain to provide a "stitched" (multiply stapled) polypeptide.

Stapling of a peptide using all-hydrocarbon cross-link has been shown to help maintain its native conformation and/or secondary structure, particularly under physiologically relevant conditions (see Schafmiester, et al., J. Am. Chem. Soc. (2000) 122:5891-5892; Walensky et al., Science (2004) 305: 1466-1470). For example, stapling a polypeptide by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding uncrosslinked (e.g., "unstitched" or "unstapled") peptide. Such constraints have been applied to the apoptosis-inducing BID-BH3 alpha-helix, resulting in a higher suppression of malignant growth of leukemia in an animal model compared to the unstitched polypeptide; see Walensky et al., Science (2004) 305:1466-1470; U.S. Patent Application Publication No. 2005/02506890; and U.S. Patent Application Publication No. 2006/0008848, each of which is incorporated herein by reference.

Novel stitched polypeptides and their "unstitched" precursors are the focus of the present invention. The present invention provides novel stitched and "unstitched" polypeptides, and methods for their preparation and use. The present invention also provides pharmaceutical compositions, including pharmaceutical compositions for oral administration, comprising an inventive stitched polypeptide and a pharmaceutically acceptable excipient. In certain embodiments, the present invention provides novel alpha-helical stitched polypeptides. In certain embodiments, the inventive alpha-helical polypeptides retain their alpha-helical structure under physiological conditions, such as in the body of a subject (e.g., in the gastrointestinal tract; in the bloodstream).

Thus, in certain embodiments, the present invention provides an "unstitched" substantially alpha-helical polypeptide of the formula:

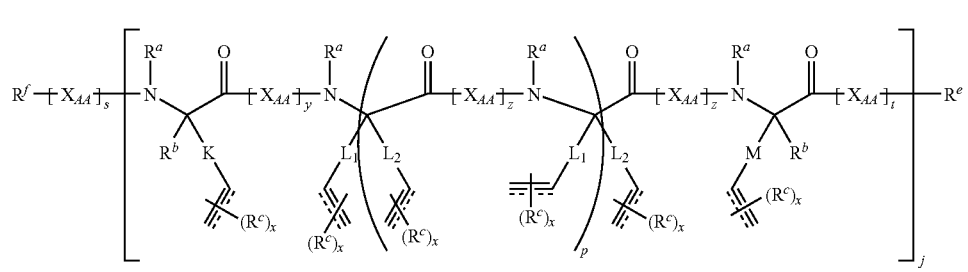

wherein:

each instance of K, $L_1$, $L_2$, and M, is, independently, a bond, cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or $R^a$ is a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^c$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, $-R^E$, $-OR^E$, $-N(R^E)_2$, or $-SR^E$, wherein each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino or thiol protecting group; or two $R^E$ groups together form a substituted or unsubstituted 5- to 6-membered heterocyclic or heteroaromatic ring;

each instance of $R^f$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;

each instance of $X_{AA}$ is, independently, a natural or unnatural amino acid;

each instance of x is, independently, an integer between 0 to 3;

y and z are, independently, an integer between 2 to 6;

j is, independently, an integer between 1 to 10;

p is an integer between 0 to 10;

each instance of s and t is, independently, an integer between 0 and 100; and wherein ===== corresponds to a double or triple bond.

The amino acid sequence of the peptide may be substantially similar to or homologous to a known bioactive peptide.

In certain embodiments, the present invention provides a "stitched" substantially alpha-helical polypeptide of the formula:

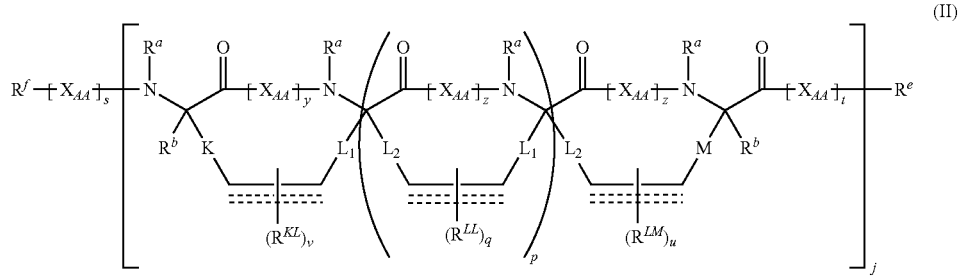

(II)

wherein

K, $L_1$, $L_2$, M, $R^a$, $R^b$, $R^e$, $R^f$, s, t, y, z, j, p, and $X_{AA}$ are as defined herein;

each instance of $R^{KL}$, $R^{LL}$, and $R^{LM}$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; or two adjacent $R^{LM}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of u, v, and q, is, independently, an integer between 0 to 4; and

===== corresponds to a single, double, or triple bond.

In certain embodiments, the present invention also provides substantially alpha-helical polypeptides of the formulae:

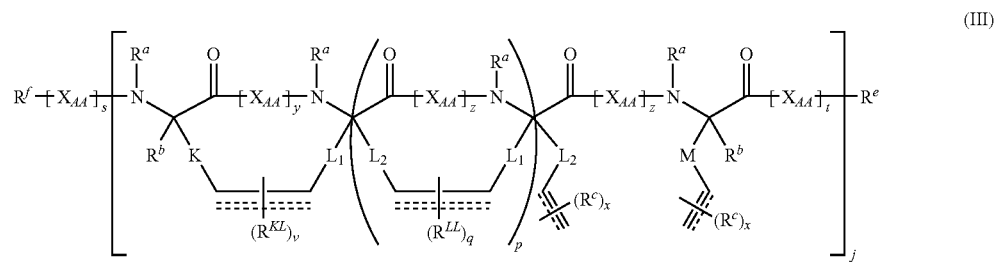

(III)

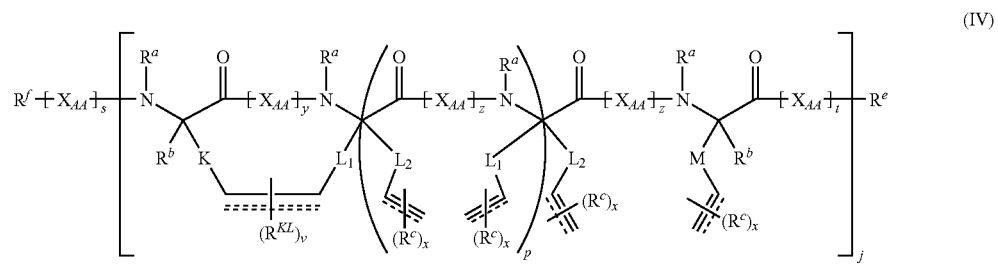

(IV)

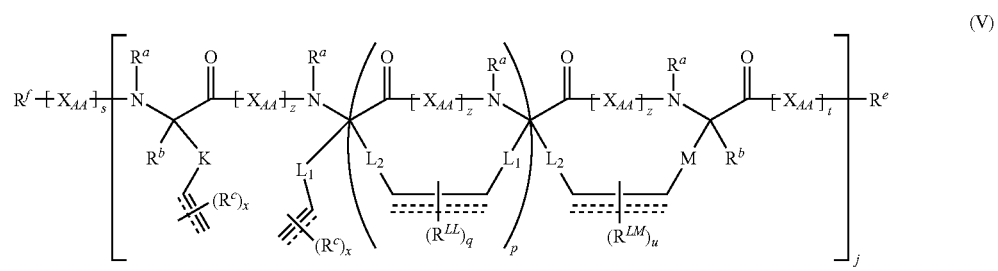

(V)

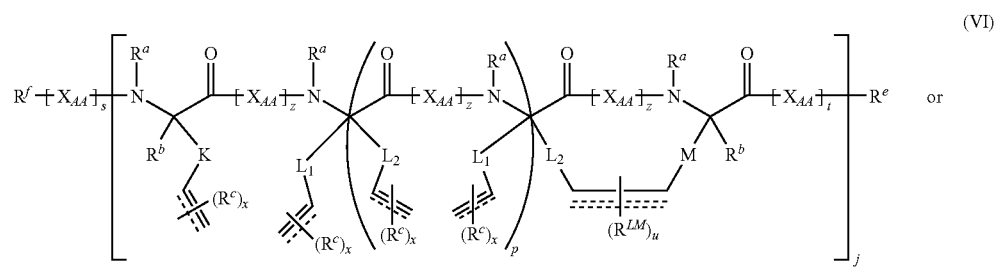

(VI) or

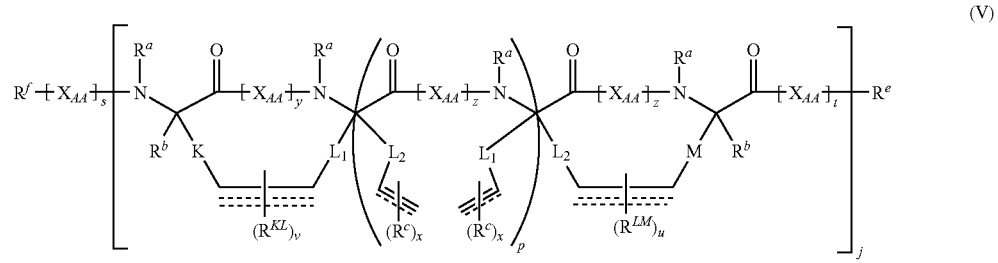

(V)

wherein K, L$_1$, L$_2$, M, R$^a$, R$^b$, R$^e$, R$^f$, R$^c$, R$^{KL}$, R$^{LL}$, R$^{LM}$, S, t, x, y, z, j, p, v, u, q, X$_{AA}$, ═══ and ══ are defined herein.

The present invention is also directed to a method of making a substantially alpha-helical polypeptide, said method comprising the steps of:

(i) providing a bis-amino acid of the formula (A):

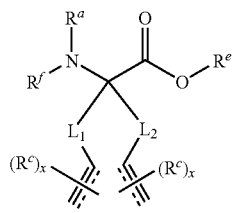

wherein L$_1$, L$_2$, R$^a$, R$^e$, R$^f$, R$^c$, x, and ══ are defined herein;

(ii) providing an amino acid of the formula (B):

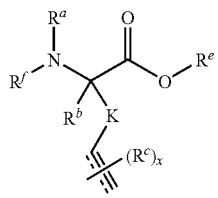

wherein K, R$^a$, R$^b$, R$^e$, R$^f$, R$^c$, x, and ══ are defined herein;

(iii) providing an amino acid of the formula (C):

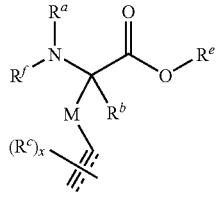

wherein M, R$^a$, R$^b$, R$^e$, R$^f$, R$^c$, x, and ══ are defined herein;

(iv) providing at least one additional amino acid; and (v) reacting said amino acids of formulae (A), (B), and (C) with at least one amino acid of step (iv) to provide a polypeptide of formula (I).

In certain embodiments, the above method further comprises making a substantially alpha-helical polypeptide of formulae (II) to (VII) by (vi) treating the polypeptide of step (v) with a catalyst. In certain embodiments, the catalyst is a ring closing metathesis catalyst.

The present invention also provides a bis-amino acid having the formula:

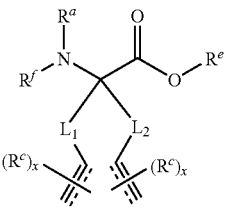

wherein L$_1$, L$_2$, R$^a$, R$^e$, R$^f$, R$^c$, x, and ══ are defined herein.

Furthermore, the present invention provides a pharmaceutical composition comprising a substantially alpha-helical inventive polypeptide and a pharmaceutically acceptable excipient.

In certain embodiments, the pharmaceutical composition is suitable for oral administration. In certain embodiments, the pharmaceutical composition is suitable for IV administration.

The present invention is also directed to a method of treating a disease, disorder, or condition in a subject by administering a therapeutically effective amount of a substantially alpha-helical polypeptide formulae (II) to (VII) to a subject in need thereof.

This application refers to various issued patent, published patent applications, journal articles, and other publications, all of which are incorporated herein by reference.

The details of one or more embodiments of the invention are set forth herein. Other features, objects, and advantages of the invention will be apparent from the description, the figures, the examples, and the claims.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The compounds of the present invention (e.g., amino acids, and unstitched, partially stitched, and stitched peptides and polypeptides) may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, IN 1972).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substitutents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

As used herein, substituent names which end in the suffix "-ene" refer to a biradical derived from the removal of two hydrogen atoms from the substitutent. Thus, for example, acyl is acylene; alkyl is alkylene; alkenyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

The term "acyl," as used herein, refers to a group having the general formula —C(=O)R$^A$, —C(=O)OR$^A$, —C(=O)—O—C(=O)R$^A$, —C(=O)SR$^A$, —C(=O)N(R$^A$)$_2$, —C(=S)R$^A$, —C(=S)N(R$^A$)$_2$, and —C(=S)S(R$^A$), —C(=NR$^A$)R$^A$, —C(=NR$^A$)OR$^A$, —C(=NR$^A$)SR$^A$, and —C(=NR$^A$)N(R$^A$)$_2$, wherein R$^A$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^A$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^i$), wherein R$^i$ is an optionally substituted acyl group, as defined herein, and the oxygen moiety is directly attached to the parent molecule.

The term "acylene," as used herein, refers to an acyl group having the general formulae: —R$^O$—(C=X$^1$)—R$^O$—, —R$^O$—X$^2$(C=X$^1$)—R$^O$—, or —R$^O$—X$^2$(C=X$^1$)X$^3$—R$^O$—, where X$^1$, X$^2$, and X$^3$ is, independently, oxygen, sulfur, or NR$^r$, wherein R$^r$ is hydrogen or aliphatic, and R$^O$ is an optionally substituted alkylene, alkenylene, alkynylene, heteroalkylene, heteroalkenylene, or heteroalkynylene group, as defined herein. Exemplary acylene groups wherein R$^O$ is alkylene includes —(CH$_2$)$_T$—O(C=O)—(CH$_2$)$_T$—; —(CH$_2$)$_T$—NR$^r$(C=O)—(CH$_2$)$_T$—; —(CH$_2$)$_T$—O(C=NR$^r$)—(CH$_2$)$_T$—; —(CH$_2$)$_T$—NR$^r$(C=NR$^r$)—(CH$_2$)$_T$—; —(CH$_2$)$_T$—(C=O)—(CH$_2$)$_T$—; —(CH$_2$)$_T$—(C=NR$^r$)—(CH$_2$)$_T$—; —(CH$_2$)$_T$—S(C=S)—(CH$_2$)$_T$—; —(CH$_2$)$_T$—NR$^r$(C=S)—(CH$_2$)$_T$—; —(CH$_2$)$_T$—S(C=NR$^r$)—(CH$_2$)$_T$—; —(CH$_2$)$_T$—O(C=S)—(CH$_2$)$_T$—; —(CH$_2$)$_T$—(C=S)—(CH$_2$)$_T$—; or —(CH$_2$)$_T$—S(C=O)—(CH$_2$)$_T$—, and the like, which may bear one or more substituents; and wherein each instance of xx is, independently, an integer between 0 to 20. Acylene groups may be cyclic or acyclic, branched or unbranched, substituted or unsubstituted. Acylene substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet another embodiments, the alkenyl group contains 2-carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl(propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula (—$NH_2$). A "substituted amino" refers either to a mono-substituted amine (—$NHR^h$) of a disubstituted amine (—$NR^h_2$), wherein the $R^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the di-substituted amino group (—$NR^h_2$) form a 5- to 6-membered heterocyclic ring.

The term "aliphaticamino," refers to a "substituted amino" of the formula (—$NR^h_2$), wherein $R^h$ is, independently, a hydrogen or an optionally substituted aliphatic group, as defined herein, and the amino moiety is directly attached to the parent molecule.

The term "aliphaticoxy," refers to a "substituted hydroxyl" of the formula (—$OR^i$), wherein $R^i$ is an optionally substituted aliphatic group, as defined herein, and the oxygen moiety is directly attached to the parent molecule.

The term "alkyloxy" refers to a "substituted hydroxyl" of the formula (—$OR^i$), wherein $R^i$ is an optionally substituted alkyl group, as defined herein, and the oxygen moiety is directly attached to the parent molecule.

The term "alkylthioxy" refers to a "substituted thiol" of the formula (—$SR^r$), wherein $R^r$ is an optionally substituted alkyl group, as defined herein, and the sulfur moiety is directly attached to the parent molecule.

The term "alkylamino" refers to a "substituted amino" of the formula (—$NR^h_2$), wherein $R^h$ is, independently, a hydrogen or an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). Additionally, arylene groups may be incorporated as a linker group into an alkylene, alkenylene, alkynylene, heteroalkylene, heteroalkenylene, or heteroalkynylene group, as defined herein.

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—$OR^i$), wherein $R^i$ is an optionally substituted aryl group, as defined herein, and the oxygen moiety is directly attached to the parent molecule.

The term "arylamino," refers to a "substituted amino" of the formula (—$NR^h_2$), wherein $R^h$ is, independently, a hydrogen or an optionally substituted aryl group, as defined herein, and the nitrogen moiety is directly attached to the parent molecule.

The term "arylthioxy" refers to a "substituted thiol" of the formula (—$SR^r$), wherein $R^r$ is an optionally substituted aryl group, as defined herein, and the sulfur moiety is directly attached to the parent molecule.

The term "azido," as used herein, refers to a group of the formula (—$N_3$). An "optionally substituted azido" refers to a group of the formula (—$N_3R^r$), wherein $R^r$ can be any substitutent (other than hydrogen). Substituents include, but are not limited to, any of the substituents described herein, that result in the formation of a stable moiety (e.g., a suitable amino protecting group; (e.g., aliphatic, alkyl, alkenyl, alkynyl, heteroaliphatic, heterocyclic, aryl, heteroaryl, acyl, cyano, amino, nitro, hydroxyl, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted).

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaliphaticamino" refers to a "substituted amino" of the formula ($-NR^h{}_2$), wherein $R^h$ is, independently, a hydrogen or an optionally substituted heteroaliphatic group, as defined herein, and the nitrogen moiety is directly attached to the parent molecule.

The term "heteroaliphaticoxy" refers to a "substituted hydroxyl" of the formula ($-OR^i$), wherein $R^i$ is an optionally substituted heteroaliphatic group, as defined herein, and the oxygen moiety is directly attached to the parent molecule.

The term "heteroaliphaticthioxy" refers to a "substituted thiol" of the formula ($-SR^r$), wherein $R^r$ is an optionally substituted heteroaliphatic group, as defined herein, and the sulfur moiety is directly attached to the parent molecule.

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkenyl," as used herein, refers to an alkenyl moiety, as defined herein, which contain one or more oxygen, sulfur, nitrogen, phosphorus, or silicon atoms, e.g., in place of carbon atoms. 1

The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heteroalkylamino" refers to a "substituted amino" of the formula ($-NR^h{}_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula ($-OR^i$), wherein $R^i$ is an optionally substituted heteroalkyl group, as defined herein, and the oxygen moiety is directly attached to the parent molecule.

The term "heteroalkylthioxy" refers to a "substituted thiol" of the formula ($-SR^r$), wherein $R^r$ is an optionally substituted heteroalkyl group, as defined herein, and the sulfur moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the ($-NR^h_2$), wherein $R^h$ is, independently, a hydrogen or an optionally substituted heteroaryl group, as defined herein, and the nitrogen moiety is directly attached to the parent molecule.

The term "heteroaryloxy" refers to a "substituted hydroxyl" of the formula ($-OR^i$), wherein $R^i$ is an optionally substituted heteroaryl group, as defined herein, and the oxygen moiety is directly attached to the parent molecule.

The term "heteroarylthioxy" refers to a "substituted thiol" of the formula ($-SR^r$), wherein $R^r$ is an optionally substituted heteroaryl group, as defined herein, and the sulfur moiety is directly attached to the parent molecule.

The term "hydroxy," or "hydroxyl," as used herein, refers to a group of the formula ($-OH$). A "substituted hydroxyl" refers to a group of the formula ($-OR^i$), wherein $R^i$ can be any substitutent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula ($=NR^r$), wherein $R^r$ corresponds to hydrogen or any substitutent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted).

The term "isocyano," as used herein, refers to a group of the formula ($-NC$).

The term "nitro," as used herein, refers to a group of the formula ($-NO_2$).

The term "oxo," as used herein, refers to a group of the formula ($=O$).

As used herein, the term "resin" refers to a resin useful for solid phase synthesis. Solid phase synthesis is a well-known synthetic technique; see generally, Atherton, E., Sheppard, R. C. *Solid Phase Peptide Synthesis: A Practical Approach*, IRL Press, Oxford, England, 1989, and Stewart J. M., Young, J. D. *Solid Phase Peptide Synthesis*, 2nd edition, Pierce Chemical Company, Rockford, 1984, the entire contents of each of which are hereby incorporated herein by reference. Exemplary resins which may be employed by the present invention include, but are not limited to:

(1) alkenyl resins (e.g., REM resin, vinyl sulfone polymer-bound resin, vinyl-polystyrene resin);

(2) amine functionalized resins (e.g., amidine resin, N-(4-Benzyloxybenzyl)hydroxylamine polymer bound, (aminomethyl)polystyrene, polymer bound (R)-(+)-a-methylbenzylamine, 2-Chlorotrityl Knorr resin, 2-N-Fmoc-Aminodibenzocyclohepta-1,4-diene, polymer-bound resin, 4-[4-(1-Fmoc-aminoethyl)-2-methoxy-5-nitrophenoxy] butyramidomethyl-polystyrene resin, 4-Benzyloxybenzylamine, polymer-bound, 4-Carboxybenzenesulfonamide, polymer-bound, Bis(tert-butoxycarbonyl)thiopseudourea, polymer-bound, Dimethylaminomethyl-polystyrene, Fmoc-3-amino-3-(2-nitrophenyl)propionic acid, polymer-bound, N-Methyl aminomethylated polystyrene, PAL resin, Sieber amide resin, tert-Butyl N-(2-mercaptoethyl)carbamate, polymer-bound, Triphenylchloromethane-4-carboxamide polymer bound);

(3) benzhydrylamine (BHA) resins (e.g., 2-Chlorobenzhydryl chloride, polymer-bound, HMPB-benzhydrylamine polymer bound, 4-Methylbenzhydrol, polymer-bound, Benzhydryl chloride, polymer-bound, Benzhydrylamine polymer-bound);

(4) Br-functionalized resins (e.g., 4-(Benzyloxy)benzyl bromide polymer bound, 4-Bromopolystyrene, Brominated PPOA resin, Brominated Wang resin, Bromoacetal, polymer-bound, Bromopolystyrene, HypoGel® 200 Br, Polystyrene A-Br for peptide synthesis, Selenium bromide, polymer-bound, TentaGel HL-Br, TentaGel MB-Br, TentaGel S—Br, TentaGel S—Br);

(5) Chloromethyl resins (e.g., 5-[4-(Chloromethyl)phenyl]pentyl]styrene, polymer-bound, 4-(Benzyloxy)benzyl chloride polymer bound, 4-Methoxybenzhydryl chloride, polymer-bound);

(6) CHO-functionalized resins (e.g., (4-Formyl-3-methoxyphenoxymethyl)polystyrene, (4-Formyl-3-methoxyphenoxymethyl)polystyrene, 3-Benzyloxybenzaldehyde, polymer-bound, 4-Benzyloxy-2,6-dimethoxybenzaldehyde, polymer-bound, Formylpolystyrene, HypoGel® 200 CHO, Indole resin, Polystyrene A-CH(OEt)$_2$, TentaGel HL-CH(OEt)$_2$);

(7) Cl-functionalized resins (e.g., Benzoyl chloride polymer bound, (Chloromethyl)polystyrene, Merrifield's resin);

(8) CO$_2$H functionalized resins (e.g., Carboxyethylpolystyrene, HypoGel® 200 COOH, Polystyrene AM-COOH, TentaGel HL-COOH, TentaGel MB-COOH, TentaGel S—COOH);

(9) Hypo-Gel resins (e.g., HypoGel® 200 FMP, HypoGel® 200 PHB, HypoGel® 200 Trt-OH, HypoGel® 200 HMB);

(10) I-functionalized resins (e.g., 4-Iodophenol, polymer-bound, Iodopolystyrene); Janda-Jels™ (JandaJel$^a$ Rink amide, JandaJel-NH$_2$, JandaJel-Cl, JandaJel-4-Mercaptophenol, JandaJel-OH, JandaJel-1-(3-Dimethylaminopropyl)-3-ethylcarbodiimide, JandaJel-1,3,4,6,7,8-hexahydro-2H-pyrimido-[1,2-a]pyrimidine, JandaJel-morpholine, JandaJel-polypyridine, JandaJel-Triphenylphosphine, JandaJel-Wang);

(11) MBHA resins (3[4'-(Hydroxymethyl)phenoxy]propionic acid-4-methylbenzhydrylamine resin, 4-(Hydroxymethyl)phenoxyacetic acid polymer-bound to MBHA resin, HMBA-4-methylbenzhydrylamine polymer bound, 4-Methylbenzhydrylamine hydrochloride polymer bound Capacity (amine));

(12) NH$_2$ functionalized resins ((Aminomethyl)polystyrene, (Aminomethyl)polystyrene, HypoGel® 200 NH$_2$, Polystyrene AM-NH$_2$, Polystyrene Microspheres 2-aminoethylated, Polystyrol Microspheres 2-bromoethylated, Polystyrol Microspheres 2-hydroxyethylated, TentaGel HL-NH$_2$, Tentagel M Br, Tentagel M NH$_2$, Tentagel M OH, TentaGel MB-NH$_2$, TentaGel S—NH$_2$, TentaGel S—NH$_2$);

(13) OH-functionalized resins (e.g., 4-Hydroxymethylbenzoic acid, polymer-bound, Hydroxymethyl Resins, OH-functionalized Wang Resins);

(14) oxime resins (e.g., 4-Chlorobenzophenone oxime polymer bound, Benzophenone oxime polymer bound, 4-Methoxybenzophenone oxime polymer bound);

(15) PEG resins (e.g., ethylene glycol polymer bound);

(16) Boc-/Blz peptide synthesis resins (e.g., Boc-Lys(Boc)-Lys[Boc-Lys(Boc)]-Cys(Acm)-b-Ala-O-PAM resin, Boc-Lys(Fmoc)-Lys[Boc-Lys(Fmoc)]-b-Ala-O-Pam resin, Boc-Lys(Boc)-Lys[Boc-Lys(Boc)]-Lys {Boc-Lys(Boc)-Lys[Boc-Lys(Boc)]}-b-Ala-O-PAM resin, Boc-Lys(Fmoc)-Lys[Boc-Lys(Fmoc)]-Lys {Boc-Lys(Fmoc)-Lys[Boc-Lys(Fmoc)]}-b-Ala-O-PAM resin, Boc-Lys(Boc)-Lys[Boc-Lys(Boc)]-Lys {Boc-Lys(Boc)-Lys[Boc-Lys(Boc)]}-Cys(Acm)-b-Ala-O-PAM resin, Preloaded PAM resins);

(17) Fmoc-/t-Bu peptide synthesis resins (e.g., Fmoc-Lys(Fmoc)-Lys[Fmoc-Lys(Fmoc)]-b-Ala-O-Wang resin, Fmoc-Lys(Fmoc)-Lys[Fmoc-Lys(Fmoc)]-Lys{Fmoc-Lys(Fmoc)-Lys[Fmoc-Lys(Fmoc)]}-b-Ala-O-Wang resin, Preloaded TentaGel® S Trityl Resins, Preloaded TentaGel® Resins, Preloaded Trityl Resins, Preloaded Wang Resins, Trityl Resins Preloaded with Amino Alcohols);

(19) thiol-functionalized resins (e.g., HypoGel® 200 S-Trt, Polystyrene AM-S-Trityl, TentaGel HL-S-Trityl, TentaGel MB-S-Trityl, TentaGel S—S-Trityl); and

(20) Wang resins (e.g., Fmoc-Ala-Wang resin, Fmoc-Arg(Pbf)-Wang resin, Fmoc-Arg(Pmc)-Wang resin, Fmoc-Asn(Trt)-Wang resin, Fmoc-Asp(OtBu)-Wang resin, Fmoc-Cys(Acm)-Wang resin, Fmoc-Cys(StBu)-Wang resin, Fmoc-Cys(Trt) Wang resin, Fmoc-Gln(Trt)-Wang resin, Fmoc-Glu(OtBu)-Wang resin, Fmoc-Gly-Wang resin, Fmoc-H is(Trt)-Wang resin, Fmoc-Ile-Wang resin, Fmoc-Leu-Wang resin, Fmoc-Lys(Boc)-Wang resin, Fmoc-Met-Wang resin, Fmoc-D-Met-Wang resin, Fmoc-Phe-Wang resin, Fmoc-Pro-Wang resin, Fmoc-Ser(tBu)-Wang resin, Fmoc-Ser(Trt)-Wang resin, Fmoc-Thr(tBu)-Wang resin, Fmoc-Trp(Boc) Wang resin, Fmoc-Trp-Wang resin, Fmoc-Tyr(tBu)-Wang resin, Fmoc-Val-Wang resin).

The term "stable moiety," as used herein, preferably refers to a moiety which possess stability sufficient to allow manufacture, and which maintains its integrity for a sufficient period of time to be useful for the purposes detailed herein.

A "suitable amino-protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable carboxylic acid protecting group," or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxyl protecting group" as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "suitable thiol protecting group," as used herein, are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of suitable ester groups include formates, acetates, proprionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "thio," or "thiol," as used herein, refers to a group of the formula (—SH). A "substituted thiol" refers to a group of the formula (—SR$^r$), wherein R$^r$ can be any substituent that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "thiooxo," as used herein, refers to a group of the formula (=S).

As used herein, a "pharmaceutically acceptable form thereof" includes any pharmaceutically acceptable salts, prodrugs, tautomers, isomers, and/or polymorphs of a compound of the present invention, as defined below and herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. In recent years several types of bioreversible derivatives have been exploited for utilization in designing prodrugs. Using esters as a prodrug type for compounds containing a carboxyl or hydroxyl functionality is known in the art as described, for example, in "The Organic Chemistry of Drug Design and Drug Interaction" Richard Silverman, published by Academic Press (1992).

As used herein, the term "tautomer" includes two or more interconvertible compounds resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972).

As used herein, "polymorph" refers to a crystalline inventive compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

The term "amino acid" refers to a molecule containing both an amino group and a carboxyl group. Amino acids include alpha-amino acids and beta-amino acids, the structures of which are depicted below. In certain embodiments, an amino acid is an alpha amino acid.

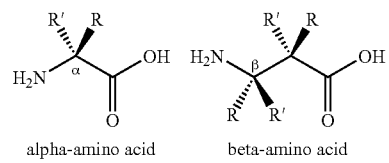

alpha-amino acid    beta-amino acid

Suitable amino acids include, without limitation, natural alpha-amino acids such as D- and L-isomers of the 20 common naturally occurring alpha-amino acids found in peptides (e.g., A, R, N, C, D, Q, E, G, H, I, L, K, M, F, P, S, T, W, Y, V, as provided in Table 1 depicted below), unnatural alpha-amino acids (as depicted in Tables 2 and 3 below), natural beta-amino acids (e.g., beta-alanine), and unnatural beta-amino acids.

Amino acids used in the construction of peptides of the present invention may be prepared by organic synthesis, or obtained by other routes, such as, for example, degradation of or isolation from a natural source. In certain embodiments of the present invention, the formula —[$X_{AA}$]— corresponds to the natural and/or unnatural amino acids having the following formulae:

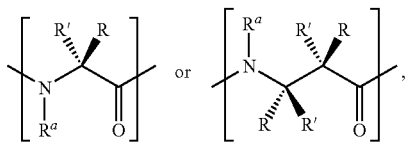

wherein R and R' correspond a suitable amino acid side chain, as defined below and herein, and $R^a$ is as defined below and herein.

TABLE 1

| Exemplary natural alpha-amino acids | Suitable amino acid side chains | |
|---|---|---|
| | R | R' |
| L-Alanine (A) | —$CH_3$ | —H |
| L-Arginine (R) | —$CH_2CH_2CH_2$—NHC(=NH)$NH_2$ | —H |
| L-Asparagine (N) | —$CH_2C$(=O)$NH_2$ | —H |
| L-Aspartic acid (D) | —$CH_2CO_2H$ | —H |
| L-Cysteine (C) | —$CH_2SH$ | —H |
| L-Glutamic acid (E) | —$CH_2CH_2CO_2H$ | —H |
| L-Glutamine (Q) | —$CH_2CH_2C$(=O)$NH_2$ | —H |
| Glycine (G) | —H | —H |
| L-Histidine (H) | —$CH_2$-2-(1H-imidazole) | —H |
| L-Isoleucine (I) | -sec-butyl | —H |
| L-Leucine (L) | -iso-butyl | —H |
| L-Lysine (K) | —$CH_2CH_2CH_2CH_2NH_2$ | —H |
| L-Methionine (M) | —$CH_2CH_2SCH_3$ | —H |
| L-Phenylalanine (F) | —$CH_2Ph$ | —H |
| L-Proline (P) | -2-(pyrrolidine) | —H |
| L-Serine (S) | —$CH_2OH$ | —H |
| L-Threonine (T) | —$CH_2CH(OH)(CH_3)$ | —H |
| L-Tryptophan (W) | —$CH_2$-3-(1H-indole) | —H |
| L-Tyrosine (Y) | —$CH_2$-(p-hydroxyphenyl) | —H |
| L-Valine (V) | -isopropyl | —H |

TABLE 2

| Exemplary unnatural alpha-amino acids | Suitable amino acid side chains | |
|---|---|---|
| | R | R' |
| D-Alanine | —H | —$CH_3$ |
| D-Arginine | —H | —$CH_2CH_2CH_2$—NHC(=NH)$NH_2$ |
| D-Asparagine | —H | —$CH_2$C(=O)$NH_2$ |
| D-Aspartic acid | —H | —$CH_2CO_2H$ |
| D-Cysteine | —H | —$CH_2SH$ |
| D-Glutamic acid | —H | —$CH_2CH_2CO_2H$ |
| D-Glutamine | —H | —$CH_2CH_2$C(=O)$NH_2$ |
| D-Histidine | —H | —$CH_2$-2-(1H-imidazole) |
| D-Isoleucine | —H | -sec-butyl |
| D-Leucine | —H | -iso-butyl |
| D-Lysine | —H | —$CH_2CH_2CH_2CH_2NH_2$ |
| D-Methionine | —H | —$CH_2CH_2SCH_3$ |
| D-Phenylalanine | —H | —$CH_2Ph$ |
| D-Proline | —H | -2-(pyrrolidine) |
| D-Serine | —H | —$CH_2OH$ |
| D-Threonine | —H | —$CH_2CH(OH)(CH_3)$ |
| D-Tryptophan | —H | —$CH_2$-3-(1H-indole) |
| D-Tyrosine | —H | —$CH_2$-(p-hydroxyphenyl) |
| D-Valine | —H | -isopropyl |
| Di-vinyl | —CH=$CH_2$ | —CH=$CH_2$ |

TABLE 2-continued

| Exemplary unnatural alpha-amino acids | R and R' are equal to: | |
|---|---|---|
| α-methyl-Alanine (Aib) | —$CH_3$ | —$CH_3$ |
| α-methyl-Arginine | —$CH_3$ | —$CH_2CH_2CH_2$—NHC(=NH)$NH_2$ |
| α-methyl-Asparagine | —$CH_3$ | —$CH_2$C(=O)$NH_2$ |
| α-methyl-Aspartic acid | —$CH_3$ | —$CH_2CO_2H$ |
| α-methyl-Cysteine | —$CH_3$ | —$CH_2SH$ |
| α-methyl-Glutamic acid | —$CH_3$ | —$CH_2CH_2CO_2H$ |
| α-methyl-Glutamine | —$CH_3$ | —$CH_2CH_2$C(=O)$NH_2$ |
| α-methyl-Histidine | —$CH_3$ | —$CH_2$-2-(1H-imidazole) |
| α-methyl-Isoleucine | —$CH_3$ | -sec-butyl |
| α-methyl-Leucine | —$CH_3$ | -iso-butyl |
| α-methyl-Lysine | —$CH_3$ | —$CH_2CH_2CH_2CH_2NH_2$ |
| α-methyl-Methionine | —$CH_3$ | —$CH_2CH_2SCH_3$ |
| α-methyl-Phenylalanine | —$CH_3$ | —$CH_2Ph$ |
| α-methyl-Proline | —$CH_3$ | -2-(pyrrolidine) |
| α-methyl-Serine | —$CH_3$ | —$CH_2OH$ |
| α-methyl-Threonine | —$CH_3$ | —$CH_2CH(OH)(CH_3)$ |
| α-methyl-Tryptophan | —$CH_3$ | —$CH_2$-3-(1H-indole) |
| α-methyl-Tyrosine | —$CH_3$ | —$CH_2$-(p-hydroxyphenyl) |
| α-methyl-Valine | —$CH_3$ | -isopropyl |
| Di-vinyl | —CH=$CH_2$ | —CH=$CH_2$ |
| Norleucine | —H | —$CH_2CH_2CH_2CH_3$ |

TABLE 3

| Exemplary unnatural alpha-amino acids | Suitable amino acid side chains R and R' is equal to hydrogen or —$CH_3$, and: |
|---|---|
| Terminally unsaturated alpha-amino acids and bis alpha-amino acids (e.g., modified cysteine, modified lysine, modified tryptophan, modified serine, modified threonine, modified proline, modified histidine, modified alanine, and the like). | —$(CH_2)_g$—S—$(CH_2)_g$CH=$CH_2$, —$(CH_2)_g$—O—$(CH_2)_g$CH=$CH_2$, —$(CH_2)_g$—NH—$(CH_2)_g$CH=$CH_2$, —$(CH_2)_g$—(C=O)—S—$(CH_2)_g$CH=$CH_2$, —$(CH_2)_g$—(C=O)—O—$(CH_2)_g$CH=$CH_2$, —$(CH_2)_g$—(C=O)—NH—$(CH_2)_g$CH=$CH_2$, —$CH_2CH_2CH_2CH_2$—NH—$(CH_2)_g$CH=$CH_2$, —$(C_6H_5)$-p-O—$(CH_2)_g$CH=$CH_2$, —CH($CH_3$)—O—$(CH_2)_g$CH=$CH_2$, —$CH_2$CH(—O—CH=$CH_2$)($CH_3$), -histidine-N(($CH_2)_g$CH=$CH_2$), -tryptophan-N(($CH_2)_g$CH=$CH_2$), and —$(CH_2)_{g+1}$(CH=$CH_2$), wherein: each instance of g is, independently, 0 to 10. |

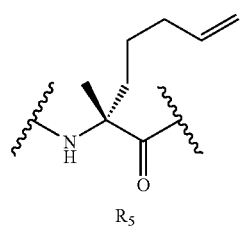 [SMILES: *N[C@](C)(CCCC=C)C(*)=O]

$R_5$

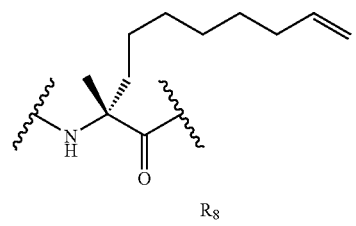 [SMILES: *N[C@](C)(CCCCCCC=C)C(*)=O]

$R_8$

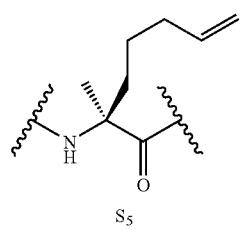 [SMILES: *N[C@@](C)(CCCC=C)C(*)=O ; "S5"]

$S_5$

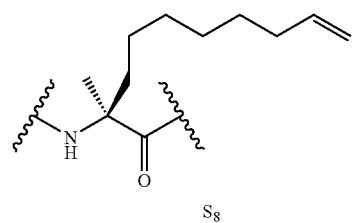 [SMILES: *N[C@@](C)(CCCCCCC=C)C(*)=O ; "S8"]

$S_8$

TABLE 3-continued

| Exemplary unnatural alpha-amino acids | Suitable amino acid side chains R and R' is equal to hydrogen or —CH$_3$, and: |
| --- | --- |

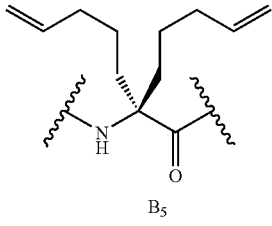

B$_5$

There are many known unnatural amino acids any of which may be included in the peptides of the present invention. See for example, S. Hunt, *The Non-Protein Amino Acids: In Chemistry and Biochemistry of the Amino Acids*, edited by G. C. Barrett, Chapman and Hall, 1985. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C(=O)C$_6$H$_5$; —CF$_3$; —CN; -halo; —NO$_2$; CH$_3$), and statine. Additionally, the amino acids suitable for use in the present invention may be derivatized to include amino acid residues that are hydroxylated, phosphorylated, sulfonated, acylated, and glycosylated, to name a few.

The term "amino acid side chain" refers to a group attached to the alpha- or beta-carbon of an amino acid. A "suitable amino acid side chain" includes, but is not limited to, any of the suitable amino acid side chains as defined above, and as provided in Tables 1 to 3.

For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted. Terminally unsaturated amino acid side chains include, but are not limited to, side chains as depicted in Table 3.

A "peptide" or "polypeptide" comprises a polymer of amino acid residues linked together by peptide (amide) bonds. The term(s), as used herein, refers to proteins, polypeptides, and peptide of any size, structure, or function.

Typically, a peptide or polypeptide will be at least three amino acids long. A peptide or polypeptide may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof. As used herein "dipeptide" refers to two covalently linked amino acids.

The Following Definitions are More General Terms Used Throughout the Present Application:

The term "subject," as used herein, refers to any animal. In certain embodiments, the subject is a mammal. In certain embodiments, the term "subject", as used herein, refers to a human (e.g., a man, a woman, or a child).

The terms "administer," "administering," or "administration," as used herein refers to implanting, absorbing, ingesting, injecting, or inhaling, the inventive polypeptide or compound.

The terms "treat" or "treating," as used herein, refers to partially or completely alleviating, inhibiting, ameliorating, and/or relieving the disease or condition from which the subject is suffering.

The terms "effective amount" and "therapeutically effective amount," as used herein, refer to the amount or concentration of a biologically active agent conjugated to an inventive polypeptide of the presently claimed invention, or amount or concentration of an inventive polypeptide, that, when administered to a subject, is effective to at least partially treat a condition from which the subject is suffering.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

As used herein, a "biologically active agent" or "therapeutically active agent" refers to any substance used as a medicine for treatment, prevention, delay, reduction or amelioration of a disease, condition, or disorder, and refers to a substance that is useful for therapy, including prophylactic and therapeutic treatment. A biologically active agent also includes a compound that increases the effect or effectiveness of another compound, for example, by enhancing potency or reducing adverse effects of the other compound.

In certain embodiments, a biologically active agent is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, antipyretic, birth control agent, hormone, prostaglandin, progestational agent, anti-glaucoma agent, ophthalmic agent, anticholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), or inhibitors/intercalators of DNA, RNA, protein-protein interactions, protein-receptor interactions, etc.

Exemplary biologically active agents include, but are not limited to, small organic molecules such as drug compounds, peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the biologically active agent is a cell. Exemplary cells include immune system cells (e.g., mast, lymphocyte, plasma cell, macrophage, dendritic cell, neutrophils, eosinophils), connective tissue cells (e.g., blood cells, erythrocytes, leucocytes, megakaryocytes, fibroblasts, osteoclasts), stem cells (e.g., embryonic stem cells, adult stem cells), bone cells, glial cells, pancreatic cells, kidney cells, nerve cells, skin cells, liver cells, muscle cells, adipocytes, Schwann cells, Langerhans cells, as well as (micro)-tissues such as the Islets of Langerhans.

In certain embodiments, the biologically active agent is a small organic molecule. In certain embodiments, a small organic molecule is non-peptidic. In certain embodiments, a small organic molecule is non-oligomeric. In certain embodiments, a small organic molecule is a natural product or a natural product-like compound having a partial structure (e.g., a substructure) based on the full structure of a natural product. Exemplary natural products include steroids, penicillins, prostaglandins, venoms, toxins, morphine, paclitaxel (Taxol), morphine, cocaine, digitalis, quinine, tubocurarine, nicotine, muscarine, artemisinin, cephalosporins, tetracyclines, aminoglycosides, rifamycins, chloramphenicol, asperlicin, lovastatin, ciclosporin, curacin A, eleutherobin, discodermolide, bryostatins, dolostatins, cephalostatins, antibiotic peptides, epibatidine, α-bungarotoxin, tetrodotoxin, teprotide, and neurotoxins from *Clostridium botulinum*. In certain embodiments, a small organic molecule is a drug approved by the Food and Drugs Administration as provided in the Code of Federal Regulations (CFR).

As used herein, a "label" refers to a moiety that has at least one element, isotope, or functional group incorporated into the moiety which enables detection of the inventive polypeptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). It will be appreciated that the label may be attached to the inventive polypeptide at any position that does not interfere with the biological activity or characteristic of the inventive polypeptide that is being detected.

In general, a label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label FITC); d) a label which has one or more photoaffinity moieties; and e) a label which has a ligand moiety with one or more known binding partners (such as biotin-streptavidin, FK506-FKBP, etc.). Any of these type of labels as described above may also be referred to as "diagnostic agents" as defined herein.

In certain embodiments, such as in the identification of a biological target, label comprises a radioactive isotope, preferably an isotope which emits detectable particles, such as β particles. In certain embodiments, the label comprises one or more photoaffinity moieties for the direct elucidation of intermolecular interactions in biological systems. A variety of known photophores can be employed, most relying on photoconversion of diazo compounds, azides, or diazirines to nitrenes or carbenes (see, Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

In certain embodiments, the label comprises one or more fluorescent moieties. In certain embodiments, the label is the fluorescent label FITC. In certain embodiments, the label comprises a ligand moiety with one or more known binding partners. In certain embodiments, the label comprises the ligand moiety biotin.

As used herein, a "diagnostic agent" refers to imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F. Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and *Handbook of Fluorescent Probes and Research Products*, Molecular Probes, 9$^{th}$ edition, 2002).

BRIEF DESCRIPTION OF THE DRAWINGS

FIG. 16. The alpha-helix of BID BH3 domain (SAHBa) as reported in Walensky et al. *Science* (2004) 305:1466, was stabilized by stapling, as reported herein, and subjected to the cytochrome C release assay, as reported therein. One of the tandem RCM products, peptide 34, which is shorter than SAHBa by 8 residues, showed similar potency in cytochrome C releasing effect, likely via a pro-apoptotic BAX/BAK pathway. The peptide 34 showed lower binding affinity for anti-apoptotic protein BCL-XL, suggesting this peptide might have higher specificity for BAX protein than SAHBa does.

DETAILED DESCRIPTION OF CERTAIN EMBODIMENTS OF THE INVENTION

Figure 1:
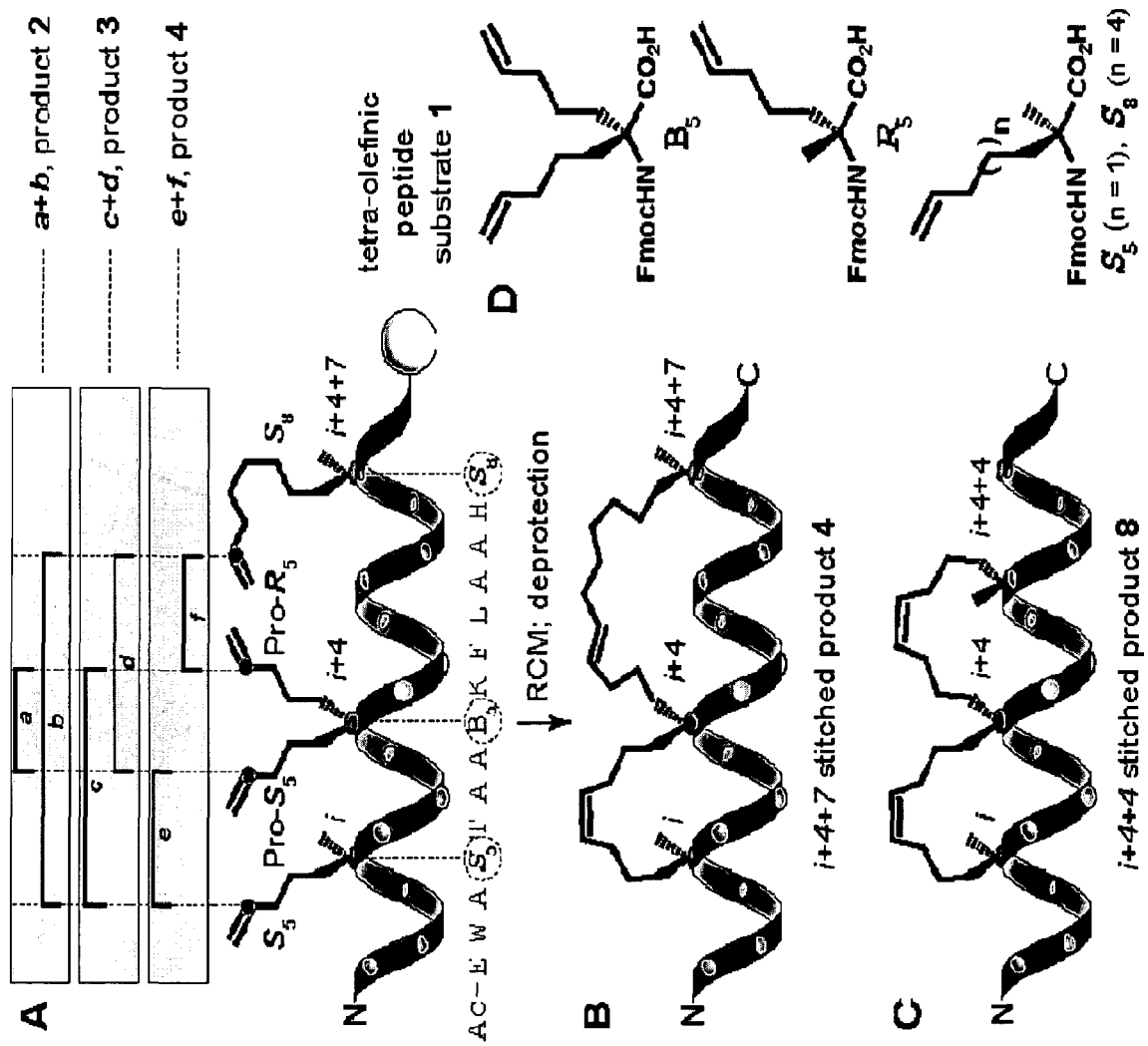
FIG. 1. Synthesis of stitched α-helical peptides by tandem ring-closing olefin metathesis. (A) Schematic structure of a α-helical tetra-olefinic peptide designed to undergo tandem-RCM. Three regioisomeric tandem-RCM pathways are possible (a+b, c+d, and e+f); these would yield products 2, 3, and 4, respectively. (B) Schematic structure of the sole product, the stitched peptide 4. The stereochemical configuration of the spiro carbon (red dot) and the N-terminal olefin were established by modeling; that of the C-terminal olefin was not unambiguously established but is expected to be trans. (C) Schematic structure of the product of an i+4+4 crosslinking reaction, the stitched peptide 8. The stereochemical configuration of the spiro carbon (red dot) and the olefins were established by modeling. (D) Olefin-bearing amino acids used in this study. (A-D) Blue groups face forward in these views; red backward.

The present invention provides novel polypeptides comprising (i) at least two amino acids, each comprising at least one terminally unsaturated amino acid sidechain, and (ii) at least one amino acid comprising at least two terminally unsaturated amino acid side chains. Such polypeptides may be reacted under suitable conditions to form inventive stabilized "stitched" polypeptides. In certain embodiments, these multiple "staples," or cross-links, which comprise the "stitch" are used to stabilize the polypeptides secondary structure (e.g., an alpha helix).

The present invention also provides pharmaceutical compositions comprising an inventive stitched polypeptide. Furthermore, the present invention provides methods of making and using inventive stitched polypeptides.

Inventive stitched polypeptides, as described herein, may be useful wherever such stabilized secondary structural motifs are advantageous, for example, as a therapeutic agent, as a biological probe, or as a drug delivery agent. The inventive peptides may function as modulators of protein-protein, protein-ligand, or protein-receptor binding interactions. In certain embodiments, these inventive stitched polypeptides are useful in the treatment of proliferative, neurological, immunological, endocrinologic, cardiovascular, hematologic, and/or inflammatory diseases, disorders, and/or conditions, and conditions characterized by premature or unwanted cell death.

Exemplary secondary structural motifs of polypeptides and proteins include, but are not limited to, an alpha-helix, alpha-L, $3_{10}$ helix, $\pi$ helix, and type II helices (e.g., left-handed helices). In certain embodiments, the predominant secondary structural motif of the inventive polypeptide is an alpha helix.

In one aspect, the present invention provides an "unstitched" polypeptide of the formula (I):

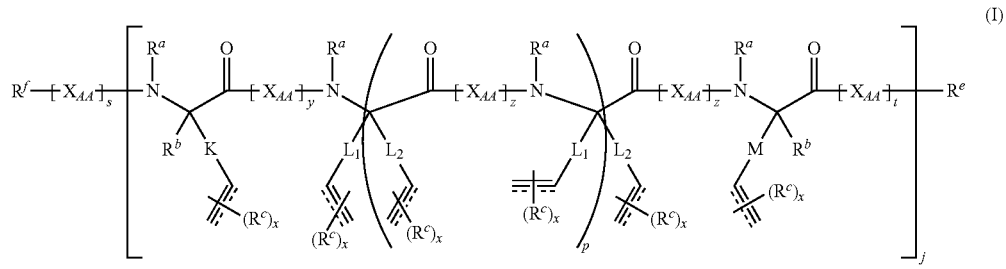

wherein:

each instance of K, $L_1$, $L_2$, and M, is, independently, a bond, cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or $R^a$ is a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^c$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, $-R^E$, $-OR^E$, $-N(R^E)_2$, or $-SR^E$, wherein each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups together form a substituted or unsubstituted 5- to 6-membered heterocyclic or heteroaromatic ring;

each instance of $R^f$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;

each instance of $X_{AA}$ is, independently, a natural or unnatural amino acid;

each instance of x is, independently, an integer between 0 to 3;

each instance of y and z is, independently, an integer between 2 to 6;

each instance of j is, independently, an integer between 1 to 10;

each instance of p is, independently, an integer between 0 to 10;

each instance of s and t is, independently, an integer between 0 and 100;

each instance of u, v, and q, is, independently, an integer between 0 to 4;

and wherein:

═════ corresponds to a double or triple bond.

As is understood by one skilled in the art, $R^f$ corresponds to the N-terminus and $R^e$ corresponds to the C-terminus of the peptide chain.

Under suitable reaction conditions, a "stitched" polypeptide of the formulae (II) is generated from a polypeptide of formula (I):

heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^c$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, $-R^E$, $-OR^E$, $-N(R^E)_2$, or $-SR^E$, wherein each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups together form a substituted or unsubstituted 5- to 6-membered heterocyclic or heteroaromatic ring;

each instance of $R^f$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsub-

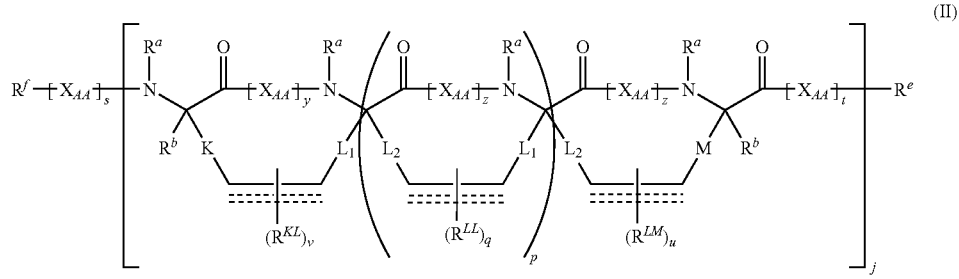

wherein:

each instance of K, $L_1$, $L_2$, and M, is, independently, a bond, cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or $R^a$ is a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted stituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; substituted or unsubstituted acyl; or $R^f$ and $R^a$ together form a substituted or unsubstituted 5- to 6-membered heterocyclic or heteroaromatic ring;

each instance of $R^{KL}$, $R^{LL}$, and $R^{LM}$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; or two adjacent $R^{LM}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of x is, independently, an integer between 0 to 3;

each instance of y and z is, independently, an integer between 2 to 6;

each instance of j is, independently, an integer between 1 to 10;

each instance of p is, independently, an integer between 0 to 10;

each instance of s and t is, independently, an integer between 0 and 100;

each instance of u, v, and q, is, independently, an integer between 0 to 4;

and wherein:

═══ corresponds to a double or triple bond; and

┄┄┄ corresponds to a single, double, or triple bond.

As will be appreciated by one of skill in the art, a partially "stitched" polypeptide of the formulae (III) to (VII) may also be generated from a polypeptide of formula (I) under suitable reaction conditions:

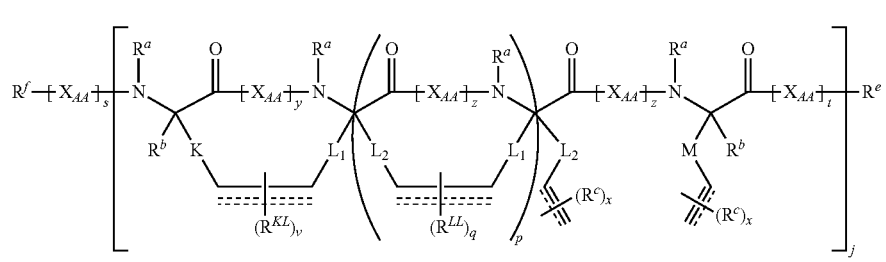

(III)

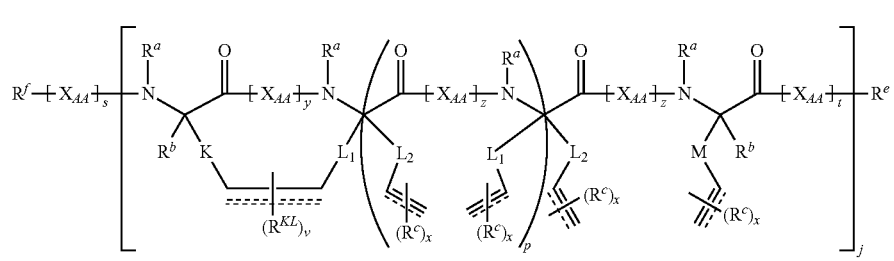

(IV)

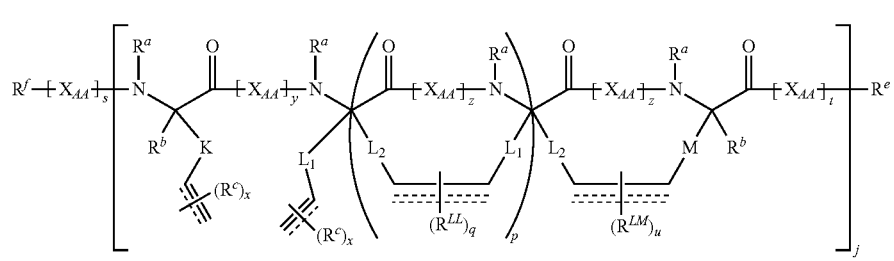

(V)

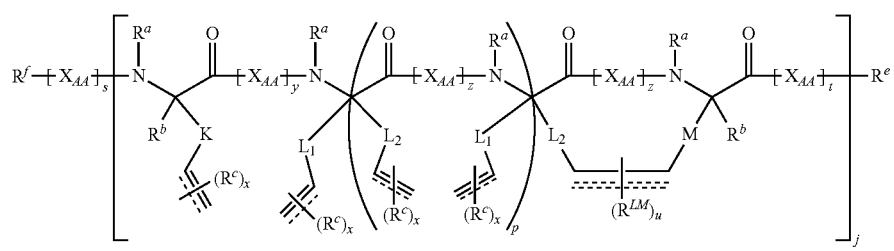

(VI) or

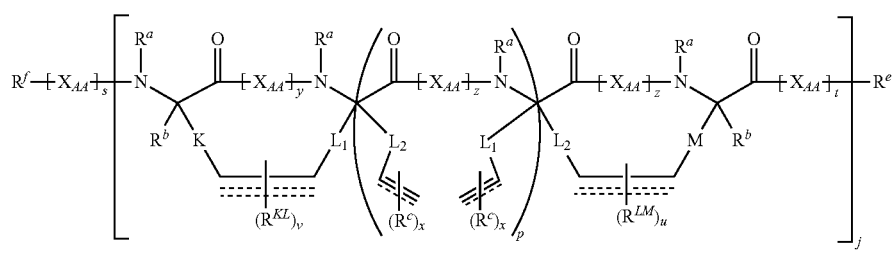

(VII)

wherein:

each instance of K, $L_1$, $L_2$, and M, is, independently, a bond, cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or $R^a$ is a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^c$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, $-R^E$, $-OR^E$, $-N(R^E)_2$, or $-SR^E$, wherein each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups together form a substituted or unsubstituted 5- to 6-membered heterocyclic or heteroaromatic ring;

each instance of $R^f$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;

each instance of $R^{KL}$, $R^{LL}$, and $R^{LM}$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; or two adjacent $R^{LM}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of x is, independently, an integer between 0 to 3;

each instance of y and z is, independently, an integer between 2 to 6;

each instance of j is, independently, an integer between 1 to 10;

each instance of p is, independently, an integer between 0 to 10;

each instance of s and t is, independently, an integer between 0 and 100;

each instance of u, v, and q, is, independently, an integer between 0 to 4;

and wherein:

══════ corresponds to a double or triple bond; and

══════ corresponds to a single, double, or triple bond.

In certain embodiments, ══════ corresponds to a double bond.

In certain embodiments, ══════ corresponds to a triple bond.

In certain embodiments, ══════ corresponds to a single bond.

In certain embodiments, ══════ corresponds to a double bond.

In certain embodiments, ══════ corresponds to a triple bond.

In certain embodiments, the polypeptide of the above formulae (I), (II), (III), (IV), (V), (VI), or (VII) is an alpha-helical polypeptide. In certain embodiments, the polypeptide of the above formulae (I), (II), (III), (IV), (V), (VI), or (VII) is a substantially alpha-helical polypeptide. As used herein, the phrase "substantially alpha-helical" refers to a polypeptide adopting, on average, backbone ($\phi$, $\psi$) dihedral angles in a range from about (−90°, −15°) to about (−35°, −70°). Alternatively, the phrase "substantially alpha-helical" refers to a polypeptide adopting dihedral angles such that the $\psi$ dihedral angle of one residue and the $\phi$ dihedral angle of the next residue sums, on average, about −80° to about −125°. In certain embodiments, the inventive polypeptide adopts dihedral angles such that the $\psi$ dihedral angle of one residue and the p dihedral angle of the next residue sums, on average, about −100° to about −110°. In certain embodiments, the inventive polypeptide adopts dihedral angles such that the $\psi$ dihedral angle of one residue and the $\phi$ dihedral angle of the next residue sums, on average, about −105°. Furthermore, the phrase "substantially alpha-helical" may also refer to a polypeptide having at least 50%, 60%, 70%, 80%, 90%, or 95% of the amino acids provided in the polypeptide chain in an alpha-helical conformation, or with dihedral angles as specified above and herein. Confirmation of a polypeptide's alpha-helical secondary structure may be ascertained by well-known analytical techniques, such as x-ray crystallography, electron crystallography, fiber diffraction, fluorescence anisotropy, circular dichroism (CD), and nuclear magnetic resonance spectroscopy.

In certain embodiments, the present invention provides a polypeptide of the formulae:

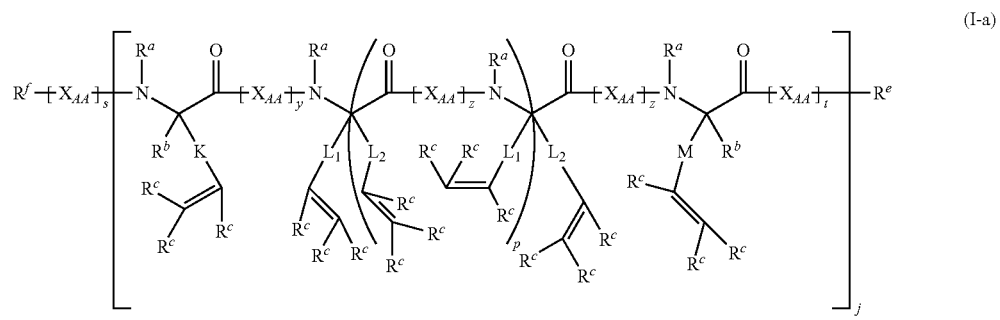

(I-a)

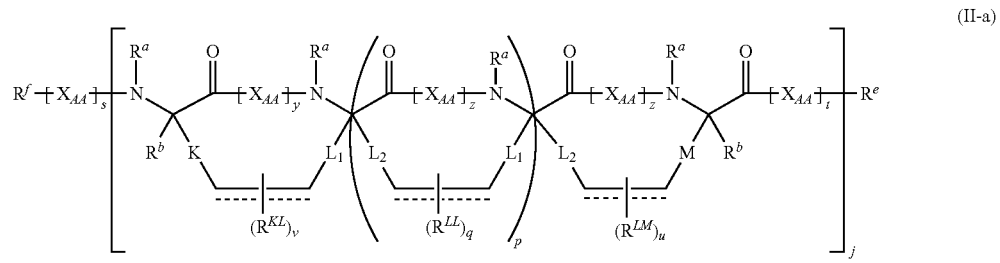

(II-a)

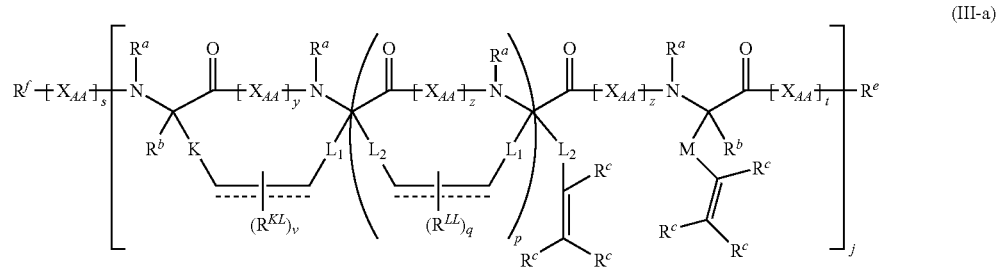

(III-a)

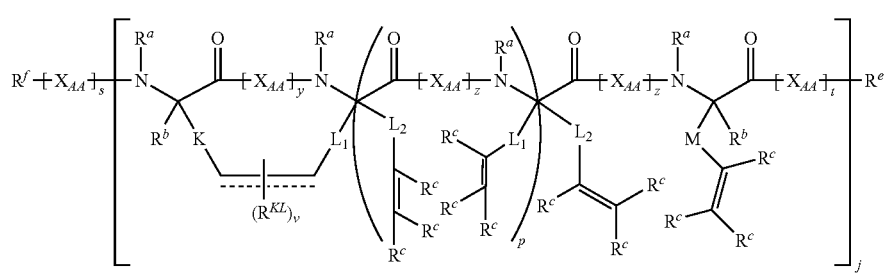
(IV-a)

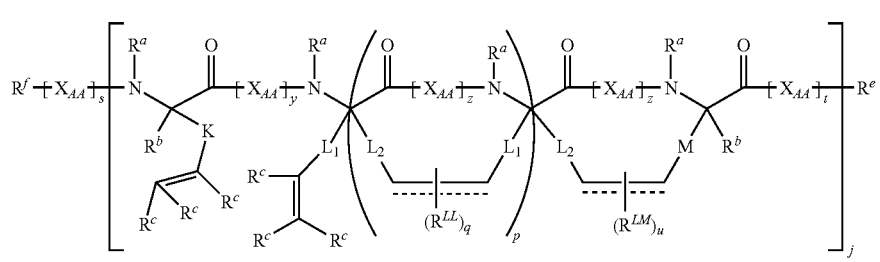
(V-a)

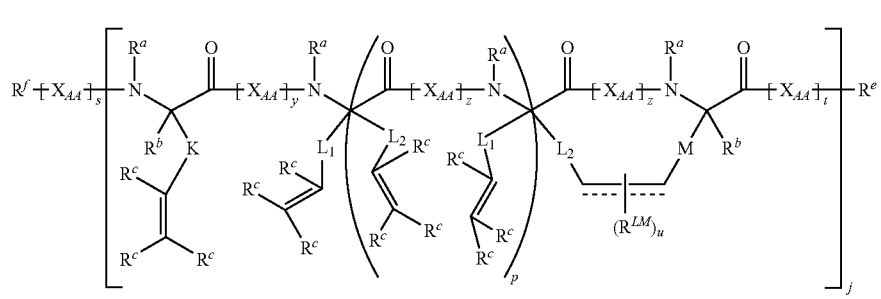
(VI-a)

or

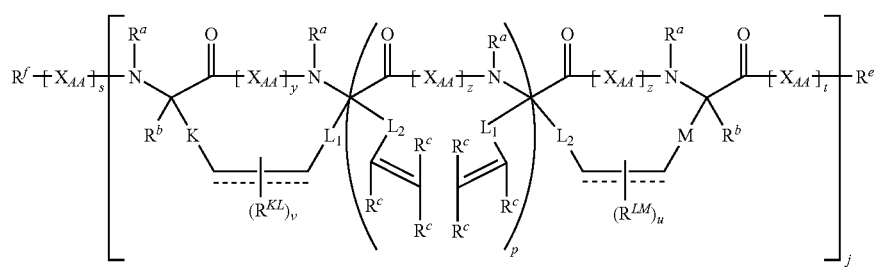
(VII-a)

wherein K, M, $L_1$, $L_2$, $R^a$, $R^b$, $R^c$, $R^e$, $R^f$, $X_{AA}$, $R^{KL}$, $R^{LL}$, $R^{LM}$, S, t, j, p, y, z, v, u, q, are as defined and described above and herein;

wherein ---------- corresponds to a single or double bond; and wherein u, v and q are, independently, 0, 1, 2, 3, or 4.

In certain embodiments, all ---------- corresponds to a single bond, and u, v and q are, independently, 0, 1, 2, 3, or 4.

In certain embodiments, all ---------- corresponds to a double bond, u, v and q are, independently, 0, 1, or 2.

In certain embodiments, the present invention provides a polypeptide of the formulae:

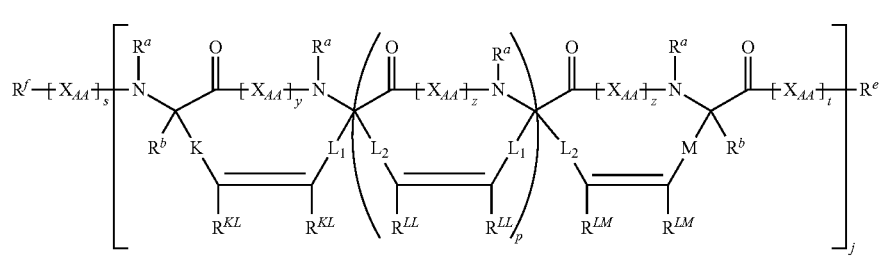
(II-b)

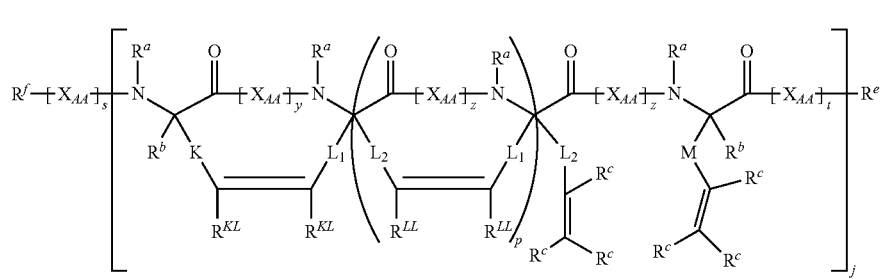
(III-b)
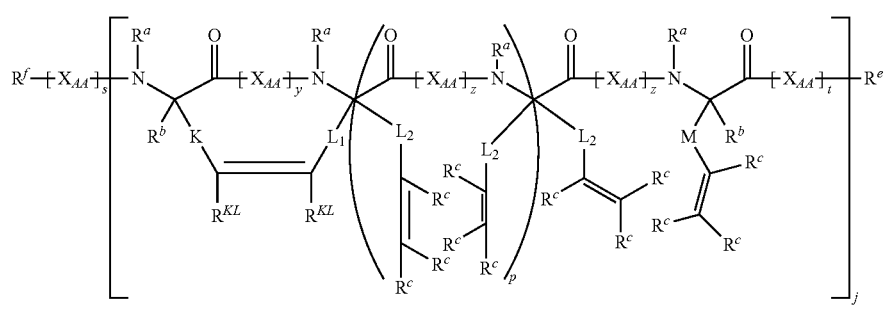
(IV-b)
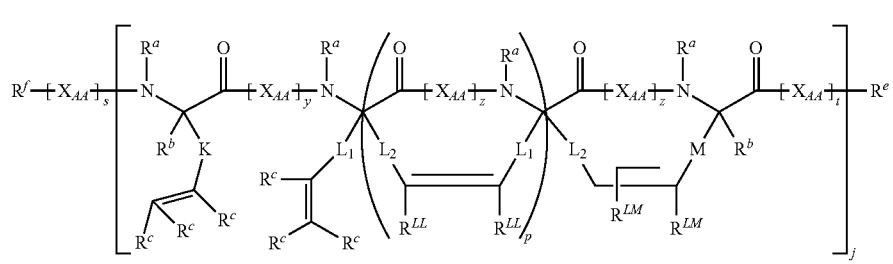
(V-b)
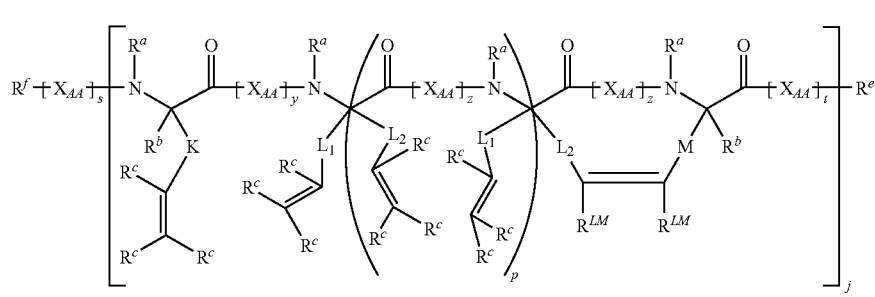
(VI-b)
or
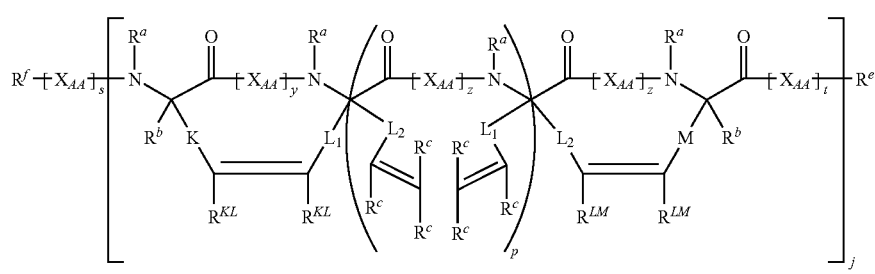
(VII-b)
wherein K, M, $L_1$, $L_2$, $R^a$, $R^b$, $R^c$, $R^e$, $R^f$, $X_{AA}$, $R^{KL}$, $R^{LL}$, $R^{LM}$, s, t, j, p, y, and z are as defined and described above and herein.
In certain embodiments, the present invention provides a polypeptide of the formulae:

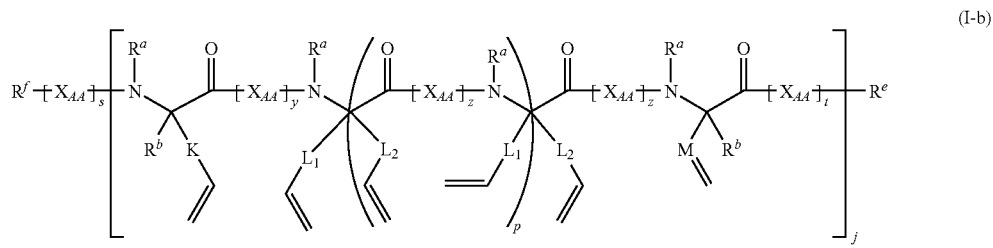
(I-b)
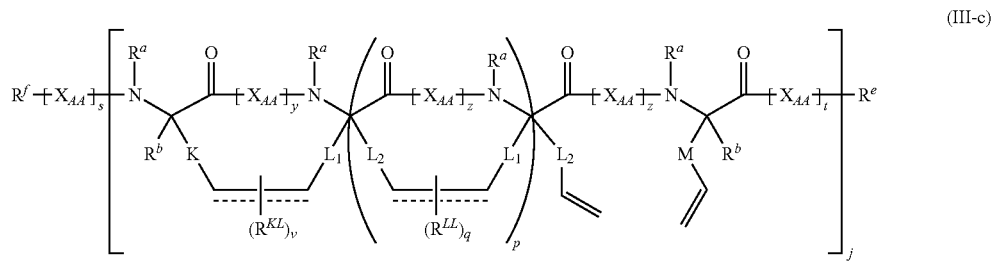
(III-c)
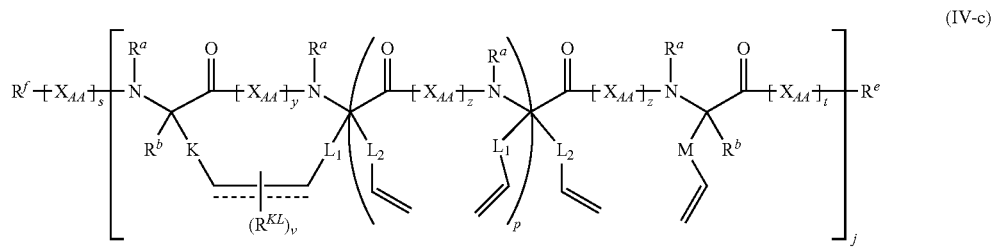
(IV-c)
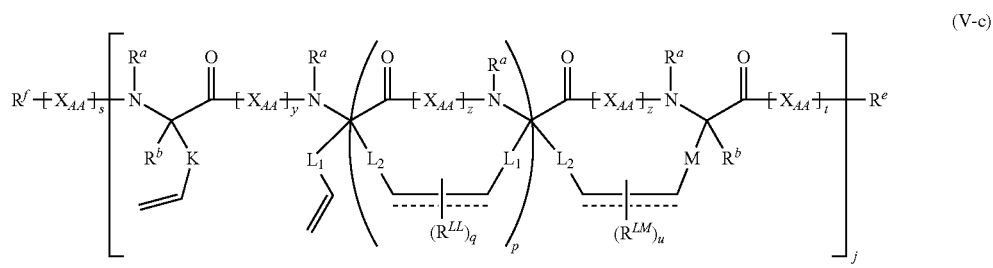
(V-c)
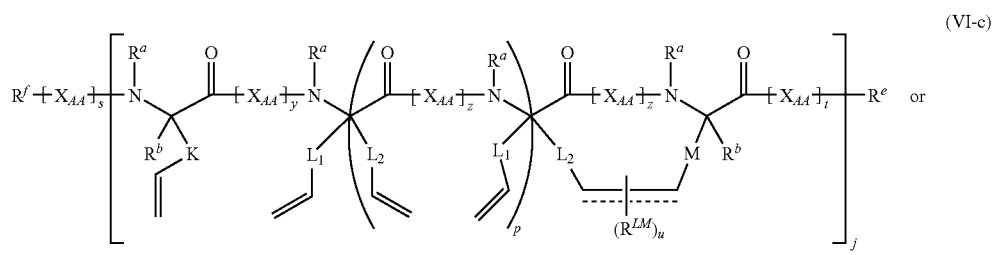
(VI-c) or
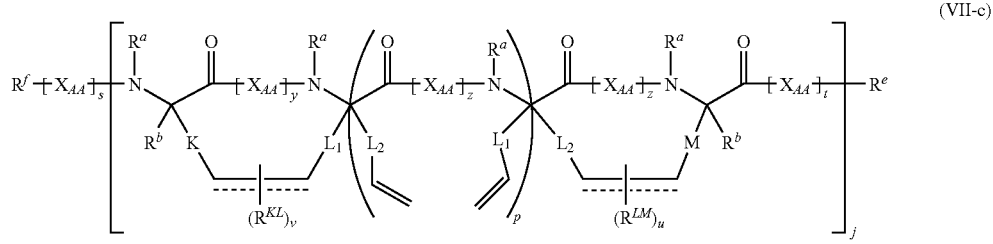
(VII-c)
wherein K, M, $L_1$, $L_2$, $R^a$, $R^b$, $R^c$, $R^e$, $R^f$, $X_{AA}$, $R^{KL}$, $R^{LL}$, $R^{LM}$, s, t, j, p, y, and z are as defined and described above and herein.
In certain embodiments, the present invention provides a polypeptide of the formulae:

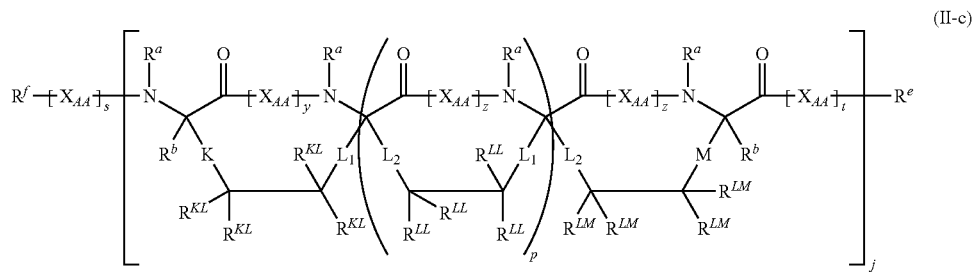

(II-c)

wherein K, M, L$_1$, L$_2$, R$^a$, R$^b$, R$^c$, R$^e$, R$^f$, X$_{AA}$, R$^{KL}$, R$^{LL}$, R$^{LM}$, s, t, j, p, y, and z are as defined and described above and herein.

In certain embodiments, each instance of K, L$_1$, L$_2$, and M, independently, corresponds to a bond, cyclic or acyclic, branched or unbranched, substituted or unsubstituted C$_{1-20}$ alkylene; cyclic or acyclic, branched or unbranched, substituted or unsubstituted C$_{1-20}$ alkenylene; cyclic or acyclic, branched or unbranched, substituted or unsubstituted C$_{1-20}$ alkynylene; cyclic or acyclic, branched or unbranched, substituted or unsubstituted C$_{1-20}$ heteroalkylene; cyclic or acyclic, branched or unbranched, substituted or unsubstituted C$_{1-20}$ heteroalkenylene; cyclic or acyclic, branched or unbranched, substituted or unsubstituted C$_{1-20}$ heteroalkynylene; substituted or unsubstituted C$_{1-20}$ arylene; substituted or unsubstituted C$_{1-20}$ heteroarylene; or substituted or unsubstituted C$_{1-20}$ acylene; cyclic or acyclic, branched or unbranched, substituted or unsubstituted C$_{1-15}$ alkylene; cyclic or acyclic, branched or unbranched, substituted or unsubstituted C$_{1-15}$ alkenylene; cyclic or acyclic, branched or unbranched, substituted or unsubstituted C$_{1-15}$ alkynylene; cyclic or acyclic, branched or unbranched, substituted or unsubstituted C$_{1-15}$ heteroalkylene; cyclic or acyclic, branched or unbranched, substituted or unsubstituted C$_{1-15}$ heteroalkenylene; cyclic or acyclic, branched or unbranched, substituted or unsubstituted C$_{1-15}$ heteroalkynylene; substituted or unsubstituted C$_{1-15}$ arylene; substituted or unsubstituted C$_{1-15}$ heteroarylene; or substituted or unsubstituted C$_{1-15}$ acylene; cyclic or acyclic, branched or unbranched, substituted or unsubstituted C$_{1-10}$ alkylene; cyclic or acyclic, branched or unbranched, substituted or unsubstituted C$_{1-10}$ alkenylene; cyclic or acyclic, branched or unbranched, substituted or unsubstituted C$_{1-10}$ alkynylene; cyclic or acyclic, branched or unbranched, substituted or unsubstituted C$_{1-10}$ heteroalkylene; cyclic or acyclic, branched or unbranched, substituted or unsubstituted C$_{1-10}$ heteroalkenylene; cyclic or acyclic, branched or unbranched, substituted or unsubstituted C$_{1-10}$ heteroalkynylene; substituted or unsubstituted C$_{1-10}$ arylene; substituted or unsubstituted C$_{1-10}$ heteroarylene; or substituted or unsubstituted C$_{1-10}$ acylene; cyclic or acyclic, branched or unbranched, substituted or unsubstituted C$_{1-8}$ alkylene; cyclic or acyclic, branched or unbranched, substituted or unsubstituted C$_{1-8}$ alkenylene; cyclic or acyclic, branched or unbranched, substituted or unsubstituted C$_{1-8}$ alkynylene; cyclic or acyclic, branched or unbranched, substituted or unsubstituted C$_{1-8}$ heteroalkylene; cyclic or acyclic, branched or unbranched, substituted or unsubstituted C$_{1-8}$ heteroalkenylene; cyclic or acyclic, branched or unbranched, substituted or unsubstituted C$_{1-8}$ heteroalkynylene; substituted or unsubstituted C$_{1-8}$ arylene; substituted or unsubstituted C$_{1-8}$ heteroarylene; or substituted or unsubstituted C$_{1-8}$ acylene; cyclic or acyclic, branched or unbranched, substituted or unsubstituted C$_{1-5}$ alkylene; cyclic or acyclic, branched or unbranched, substituted or unsubstituted C$_{1-5}$ alkenylene; cyclic or acyclic, branched or unbranched, substituted or unsubstituted C$_{1-5}$ alkynylene; cyclic or acyclic, branched or unbranched, substituted or unsubstituted C$_{1-5}$ heteroalkylene; cyclic or acyclic, branched or unbranched, substituted or unsubstituted C$_{1-5}$ heteroalkenylene; cyclic or acyclic, branched or unbranched, substituted or unsubstituted C$_{1-5}$ heteroalkynylene; substituted or unsubstituted C$_{1-5}$ arylene; substituted or unsubstituted C$_{1-5}$ heteroarylene; or substituted or unsubstituted C$_{1-5}$ acylene.

In certain embodiments, K is acyclic. In certain embodiments, K is unbranched. In certain embodiments, K is unsubstituted. In certain embodiments, K is a bond. In certain embodiments, K is not a bond.

In certain embodiments, M is acyclic. In certain embodiments, M is unbranched. In certain embodiments, M is unsubstituted. In certain embodiments, M is a bond. In certain embodiments, M is not a bond.

In certain embodiments, L$_1$ is acyclic. In certain embodiments, L$_1$ is unbranched. In certain embodiments, L$_1$ is unsubstituted. In certain embodiments, L$_1$ is a bond. In certain embodiments, L$_1$ is not a bond.

In certain embodiments, L$_2$ is acyclic. In certain embodiments, L$_2$ is unbranched. In certain embodiments, L$_2$ is unsubstituted. In certain embodiments, L$_2$ is a bond. In certain embodiments, L$_2$ is not a bond.

In certain embodiments, L$_1$ and L$_2$ are the same. In certain embodiments, L$_1$ and L$_2$ are different. In certain embodiments, when L$_1$ is a bond, L$_2$ is not a bond, or when L$_2$ is a bond, L$_1$ is not a bond. In certain embodiments, a polypeptide of any of the above formulae wherein L$_1$ and L$_2$ are both bonds is specifically excluded.

In certain embodiments, K and M are the same. In certain embodiments, K and M are different.

In certain embodiments, K and L$_1$ are the same. In certain embodiments, K and L$_1$ are different. In certain embodiments, K and L$_2$ are the same. In certain embodiments, K and L$_2$ are different.

In certain embodiments, M and L$_1$ are the same. In certain embodiments, M and L$_1$ are different. In certain embodiments, M and L$_2$ are the same. In certain embodiments, M and L$_2$ are different.

In certain embodiments, all of K, L$_1$, L$_2$, and M are the same. In certain embodiments, all of K, L$_1$, L$_2$, and M are different.

In certain embodiments, each instance of K, L$_1$, L$_2$, and M, independently, corresponds to the formulae: —(CH$_2$)$_{g+1}$—; —(CH$_2$)$_g$S—(CH$_2$)$_g$—; —(CH$_2$)$_g$—(C═O)—S—(CH$_2$)$_g$—; —(CH$_2$)$_g$—O—(CH$_2$)$_g$—; —(CH$_2$)$_g$—(C═O)—O—(CH$_2$)$_g$—; —(CH$_2$)$_g$—NH—(CH$_2$)$_g$—; —(CH$_2$)$_g$(C═O)—NH—(CH$_2$)$_g$—; —(CH$_2$)$_g$CH(CH$_3$)—O—(CH$_2$)$_g$—;

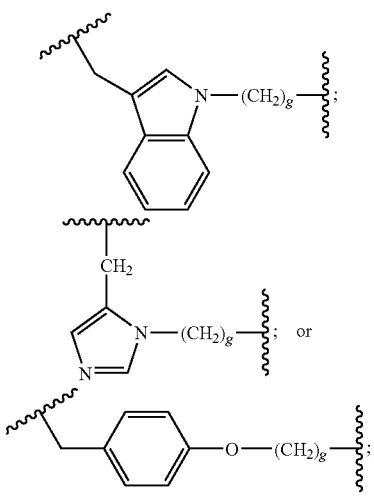

wherein each instance of g is, independently, 0 to 10, inclusive.

In certain embodiments, each instance of K, $L_1$, $L_2$, and M, independently, corresponds to the formulae —$(CH_2)_{g+1}$—, and g is 0, 1, 2, 3, 4, 5, or 6.

In certain embodiments, —$[X_{AA}]$— corresponds to the formulae:

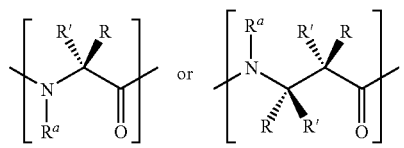

wherein:

each instance of R and R' are, independently, hydrogen, or a suitable amino acid side chain as defined herein, and $R^a$ is as previously defined above and herein.

Suitable amino acid side chains include, but are not limited to, both natural and unnatural amino acid side chains as provided in Tables 1 to 3, and as described herein. In certain embodiments, each instance of $X_{AA}$ is an alpha amino acid, corresponding to the formula (α). In certain embodiments, each instance of $X_{AA}$ is a natural L-amino acid, as provided in Table 1. In certain embodiments, each instance of $X_{AA}$ is, independently, a natural L-amino acid as provided in Table 1, or an unnatural D-amino acid as provided in Table 2.

The group $R^e$ corresponds to the C-terminus of the peptide chain, and corresponds to the variables —$R^E$, —$OR^E$, —$N(R^E)_2$, or —$SR^E$, wherein $R^E$ is as defined above and herein. For example, if —$[X_{AA}]$— corresponds to an alpha amino acid of formula:

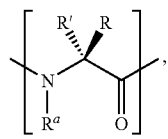

it follows that, in certain embodiments, —$[X_{AA}]_t$—$R^e$ corresponds to the formulae:

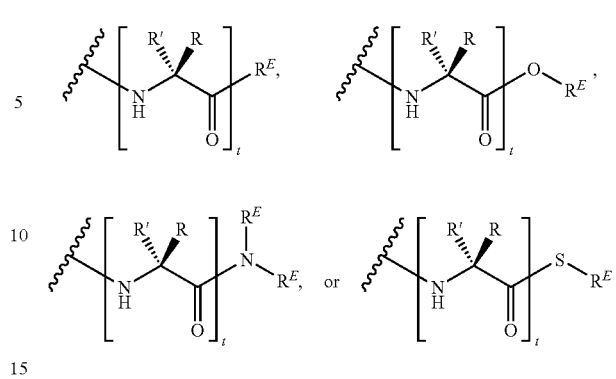

wherein each instance of $R^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; or a suitable hydroxyl, amino, or thiol protecting group; and two $R^E$ groups taken together may optionally form a substituted or unsubstituted 5- to 6-membered heterocyclic or heteroaromatic ring.

In certain embodiments, $R^e$ is —$OR^E$, and $R^E$ is hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; or a suitable hydroxyl protecting group.

In certain embodiments, $R^e$ is —$SR^E$, and $R^E$ is hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; or a suitable thiol protecting group.

In certain embodiments, $R^e$ is —$N(R^E)_2$, and each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; or two $R^E$ groups together form a substituted or unsubstituted 5- to 6-membered heterocyclic or heteroaromatic ring.

The group $R^f$ corresponds to the N-terminus of the peptide chain. For example, if —$[X_{AA}]$— corresponds to an alpha amino acid of formula:

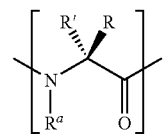

it follows that, in certain embodiments, $R^f$—$[X_{AA}]_s$— corresponds to the formulae:

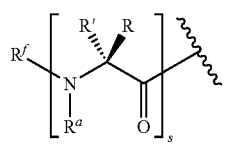

wherein R and R' are defined as above and herein; and wherein $R^r$ is hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring.

In certain embodiments, $R^f$ is hydrogen. In certain embodiments, $R^f$ is $C_{1-6}$ alkyl. In certain embodiments, $R^f$ is —$CH_3$. In certain embodiments, $R^f$ is a suitable amino protecting group. In certain embodiments, $R^f$ is -Boc. In certain embodiments, $R^f$ is -Fmoc. In certain embodiments, $R^f$ is acyl. In certain embodiments, $R^f$ is —(C=O)$CH_3$.

In certain embodiments, $R^f$ is a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene.

Exemplary labels include, but are not limited to FITC and biotin:

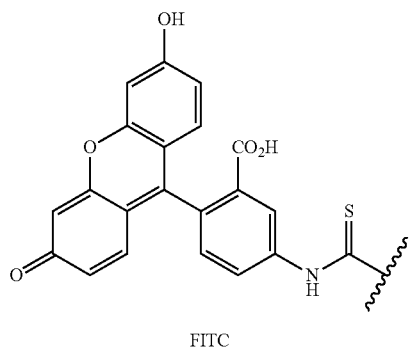

FITC

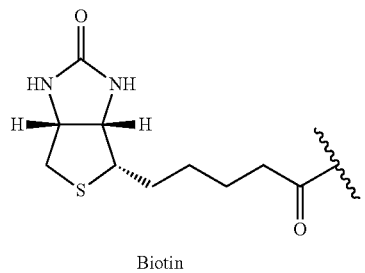

Biotin

In certain embodiments, the label is directly joined to the inventive polypeptide (i.e., through a bond).

In certain embodiments, the label is indirectly joined to the inventive polypeptide (i.e., through a linker).

In certain embodiments, the linker is a cyclic or acyclic, branched or unbranched, substituted or unsubstituted alkylene. In certain embodiments, the linker is a cyclic or acyclic, branched or unbranched, substituted or unsubstituted alkenylene. In certain embodiments, the linker is a cyclic or acyclic, branched or unbranched, substituted or unsubstituted alkynylene. In certain embodiments, the linker is a cyclic or acyclic, branched or unbranched, substituted or unsubstituted heteroalkylene. In certain embodiments, the linker is a cyclic or acyclic, branched or unbranched, substituted or unsubstituted heteroalkenylene. In certain embodiments, the linker is a cyclic or acyclic, branched or unbranched, substituted or unsubstituted heteroalkynylene. In certain embodiments, the linker is a substituted or unsubstituted arylene. In certain embodiments, the linker is a substituted or unsubstituted heteroarylene. In certain embodiments, the linker is a substituted or unsubstituted acylene.

For example, in certain embodiments, the linker is cyclic or acyclic, branched or unbranched, substituted or unsubstituted heteroalkylene selected from:

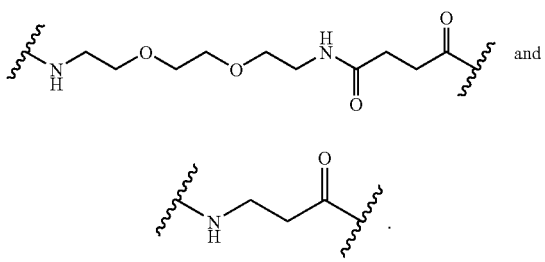

In certain embodiments, $R^a$ is hydrogen. In certain embodiments, $R^a$ is $C_{1-6}$ alkyl. In certain embodiments, $R^a$ is —$CH_3$. In certain embodiments, $R^a$ is acyl. In certain embodiments, $R^a$ is —(C=O)$CH_3$.

In certain embodiments, each instance of $R^b$ is, independently, hydrogen or cyclic or acyclic, branched or unbranched, substituted or unsubstituted aliphatic. In certain embodiments, $R^b$ is hydrogen or —$CH_3$. In certain embodiments, $R^b$ is —$CH_3$.

In certain embodiments, each instance of $R^c$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl. In certain embodiments, each instance of $R^c$, is, independently, hydrogen; or cyclic or acyclic, branched or unbranched, substituted or unsubstituted aliphatic. In certain embodiments, each instance of $R^c$ is, independently, hydrogen or cyclic or acyclic, branched or unbranched, substituted or unsubstituted alkyl. In certain embodiments, $R^b$ is hydrogen or —$CH_3$. In certain embodiments, each instance of $R^c$ is hydrogen.

In certain embodiments, each instance of $R^{KL}$, $R^{LL}$, and $R^{LM}$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; or nitro.

In certain embodiments, each instance of $R^{KL}$, $R^{LL}$, and $R^{LM}$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro.

In certain embodiments, p is 0. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, p is 10.

The variables y and z indicate how many amino acids, defined by the variable [$X_{AA}$], there are between amino acids containing terminally unsaturated amino acid side chain(s), as provided in polypeptides of formulae (I) to (VII). For example, as depicted below for a polypeptide of formula (I), wherein p is 0 (hereafter designated as formula (I-c)), wherein the variables K, M, $L_1$, $L_2$, $R^a$, $R^b$, $R^c$, $R^e$, $R^f$, $X_{AA}$, s, t, j, y, and z are as defined and described above and herein, and wherein i represents one site of an alpha,alpha-disubstituted (terminally unsaturated amino acid side chain) amino acid, variable y provides information as to the position of the amino acid containing a terminally unsaturated side chain on the N-terminal side of i, such as the positions i−3, i−4, i−6, and i−7, and z provides information as to the position of the amino acid containing a terminally unsaturated side chain on the C-terminal side of i, such as the positions i+3, i+4, i+6, and i+7. Table 3 correlates these specific locations of i relative to the variables y and z for formula (I-c).

TABLE 3

| | i−7 | i−6 | i−4 | i−3 | i | i+3 | i+4 | i+6 | i+7 |
|---|---|---|---|---|---|---|---|---|---|
| y | 6 | 5 | 3 | 2 | | | | | |
| z | | | | | | 2 | 3 | 5 | 6 |

In certain embodiments, each instance of y and z are, independently, 2, 3, 5, or 6.

In certain embodiments, both y and z are 2. In certain embodiments, both y and z are 3. In certain embodiments, both y and z are 5. In certain embodiments, both y and z are 6.

In certain embodiments, y is 2 and z is 3. In certain embodiments, y is 2 and z is 5. In certain embodiments, y is 2 and z is 6.

In certain embodiments, y is 3 and z is 2. In certain embodiments, y is 3 and z is 5. In certain embodiments, y is 3 and z is 6.

In certain embodiments, y is 5 and z is 2. In certain embodiments, y is 5 and z is 3. In certain embodiments, y is 5 and z is 6.

In certain embodiments, y is 6 and z is 2. In certain embodiments, y is 6 and z is 3. In certain embodiments, y is 6 and z is 5.

In certain embodiments, the present invention also provides intermediates used in the synthesis of inventive polypeptides. For example, the present invention provides bis-amino acids of formula:

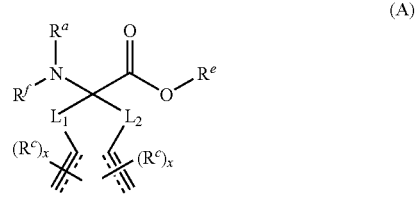

(A)

wherein $L_1$, $L_2$, $R^a$, $R^c$, $R^e$, $R^f$, x, and ═══ are as defined and described above and herein.

In certain embodiments, a bis amino acid of formula (A) has the formula:

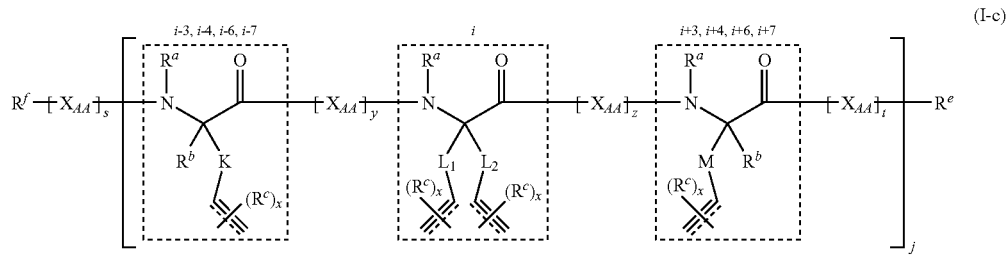

(I-c)

(A-1)

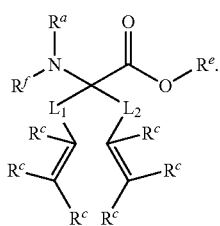

wherein $L_1$, $L_2$, $R^a$, $R^c$, $R^e$, and $R^f$ are as defined and described above and herein.

In certain embodiments, a bis amino acid of formula (A) has the formula:

(A-2)

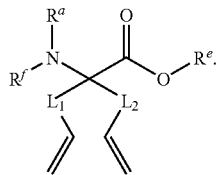

wherein $L_1$, $L_2$, $R^a$, $R^e$, and $R^f$ are as defined and described above and herein.

Exemplary amino acids of formula (A) include, but are not limited to, those as depicted below, wherein $R^a$, $R^f$, and $R^e$ are defined above and herein. In certain embodiments, $R^a$ is hydrogen, and $R^f$ is a suitable amino protecting group. In certain embodiments, $R^a$ is hydrogen, and $R^f$ is -Boc or -Fmoc. In certain embodiments, both $R^a$ and $R^f$ are suitable amino protecting groups. In certain embodiments, both $R^a$ and $R^f$ are hydrogen. In certain embodiments, $R^e$ is hydrogen.

Exemplary Amino Acids of Formula (A).

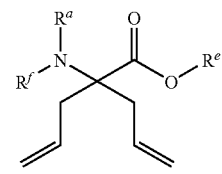

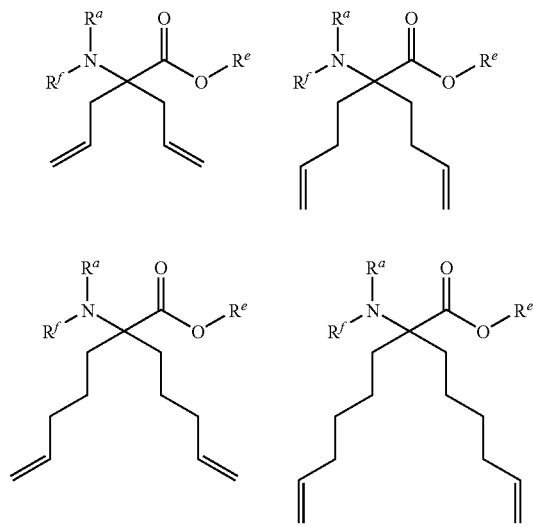

-continued

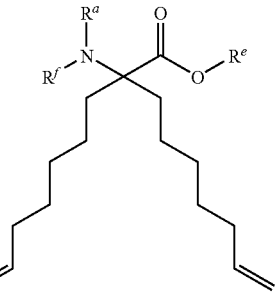

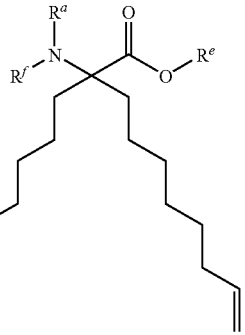

Methods of Synthesis

The present invention is also directed to methods of synthesizing stitched and unstitched inventive polypeptides.

The synthesis of an inventive polypeptide first involves the selection of a desired sequence and number of amino acids and amino acid analogues. As one of ordinary skill in the art will realize, the number, stereochemistry, and type of amino acid structures (natural or non-natural) selected will depend upon the size of the polypeptide to be prepared, the ability of the particular amino acids to generate a desired structural motif (e.g., an alpha-helix), and any particular motifs that are desirable to mimic (for example, a p53 donor helical peptide).

Once the amino acids are selected, synthesis of the inventive polypeptide can be achieved using standard deprotection and coupling reactions. Formation of peptide bonds and polypeptide synthesis are techniques well-known to one skilled in the art, and encompass both solid phase and solution phase methods; see generally, Bodanszky and Bodanszky, *The Practice of Peptide Synthesis*, Springer-Verlag, Berlin, 1984; Atherton and Sheppard, *Solid Phase Peptide Synthesis: A Practical Approach*, IRL Press at Oxford University Press Oxford, England, 1989, and Stewart and Young, *Solid phase Peptide Synthesis*, 2nd edition, Pierce Chemical Company, Rockford, 1984, the entire contents of each of which are incorporated herein by reference. In both solution phase and solid phase techniques, the choice of the protecting groups must be considered, as well as the specific coupling techniques to be utilized. For a detailed discussion of peptide synthesis techniques for solution phase and solid phase reactions, see, *Bioorganic chemistry: Peptides and Proteins*, Hecht, Oxford University Press, New York: 1998, the entire contents of which are incorporated herein by reference.

In certain embodiments, the method comprises a solution phase synthesis of an inventive polypeptide. Solution phase synthesis, as mentioned above, is a well-known technique for the construction of polypeptides. An exemplary solution phase synthesis comprises the steps of: (1) providing an amino acid protected at the N-terminus with a suitable amino protecting group; (2) providing an amino acid protected at the C-terminus with a suitable carboxylic acid protecting group;

(3) coupling the N-protected amino acid to the C-protected amino acid; (4) deprotecting the product of the coupling reaction; and (5) repeating steps (3) to (4) until a desired polypeptide is obtained, wherein at least two of the amino acids coupled at any of the above steps each comprise at least one terminally unsaturated amino acid sidechain, and at least one α,α-disubstituted amino acid comprises two terminally unsaturated amino acid side chains. During the course of the above synthesis, various parameters can be varied, including, but not limited to placement of amino acids with terminally unsaturated side chains, stereochemistry of amino acids, terminally unsaturated side chain length and functionality, and amino acid residues utilized.

In certain embodiments, the method comprises a solid phase synthesis of an inventive polypeptide. Solid phase synthesis, as mentioned above, is a well-known technique for the construction of polypeptides. An exemplary solid phase synthesis comprises the steps of: (1) providing a resin-bound amino acid; (2) deprotecting the resin bound amino acid; (3) coupling an amino acid to the deprotected resin-bound amino acid; (4) repeating steps (3) until a desired peptide is obtained, wherein at least two of the amino acids coupled at any of the above steps each comprise at least one terminally unsaturated amino acid sidechain, and at least one α,α-disubstituted amino acid comprises two terminally unsaturated amino acid side chains. During the course of the above synthesis, various parameters can be varied, including, but not limited to placement of amino acids with terminally unsaturated side chains, stereochemistry of amino acids, terminally unsaturated side chain length and functionality, and amino acid residues utilized.

After a desired polypeptide is synthesized using an appropriate technique, the polypeptide is contacted with a specific catalyst to promote "stitching" of the polypeptide. For example, the resin-bound polypeptide may be contacted with a catalyst to promote "stitching," or may first be cleaved from the resin, and then contacted with a catalyst to promote "stitching."

Thus, in one aspect, the present invention is directed to a method of making a polypeptide of formulae (I), (I-a), (I-b), or (I-c) comprising the steps of:

(i) providing a bis-amino acid of the formula:

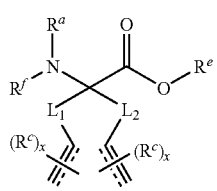

(A)

(ii) providing an amino acid of the formula:

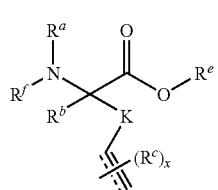

(B)

(iii) providing an amino acid of the formula:

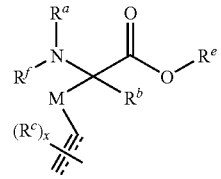

(C)

wherein the variables K, $L_1$, $L_2$, M, $R^a$, $R^b$, $R^c$, $R^e$, $R^f$, x, and ═══ are defined herein;

(iv) providing at least one additional amino acid; and (v) coupling said amino acids of formulae (A), (B), and (C) with at least one amino acid of step (iv) under suitable conditions to provide a polypeptide of formulae (I), (I-a), (I-b), or (I-c).

As used herein, the phrase "providing at least one additional amino acid" refers to providing at least one natural or unnatural amino acid structurally different than a compound of formulae (A), (B), or (C). The above synthetic method may employ any and all known amino acids in order to generate a polypeptide of any one of formulae (I) to (VII), and subsets thereof. In certain embodiments, the amino acids employable by the above synthetic method are defined and described herein.

In certain embodiments, step (iv) provides at least two additional (i.e., structurally different) amino acids. In certain embodiments, step (iv) provides at least three additional amino acids. In certain embodiments, step (iv) provides at least four additional amino acids. In certain embodiments, step (iv) provides at least five additional amino acids.

In certain embodiments, step (iv) further includes providing a peptide which will be incorporated into the inventive polypeptide. In certain embodiments, step (iv) further includes providing a peptide comprising at least 2 amino acids. In certain embodiments, step (iv) further includes providing a peptide comprising at least 3 amino acids. In certain embodiments, step (iv) further includes providing a peptide comprising at least 4 amino acids. In certain embodiments, step (iv) further includes providing a peptide comprising at least 5 amino acids.

In certain embodiments, the at least one type of additional amino acid of step (iv) corresponds to the formulae:

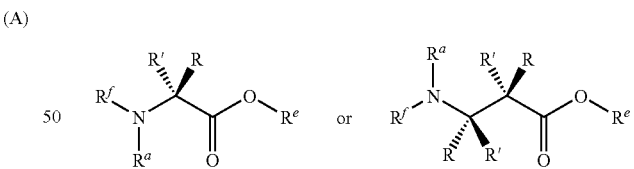

wherein R', R, $R^a$, $R^e$, and $R^f$ are defined above and herein.

Different amino acids have different propensities for forming different secondary structures. For example, methionine (M), alanine (A), leucine (L), glutamate (E), and lysine (K) all have especially high alpha-helix forming propensities. In contrast, proline (P) and glycine (G) are alpha-helix disruptors. Thus, in certain embodiments, the at least one amino acid of step (iv) refers to a group selected from alanine, arginine, asparagine, aspartic acid, cysteine, glutamic acid, glutamine, histidine, isoleucine, leucine, lysine, methionine, phenylalanine, serine, threonine, tryptophan, tyrosine, and valine.

In certain embodiments, the above reaction of step (iv) further comprises the use of a coupling reagent. Exemplary coupling reagents include, but are not limited to, benzotriazol-1-yloxy-tris(dimethylamino)-phosphonium hexafluorophosphate (BOP), benzotriazole-1-yl-oxy-tris-pyrrolidino-phosphonium hexafluorophosphate (PyBOP), bromo-tris-pyrrolidino phosphonium hexafluorophosphate (PyBroP), 1-ethyl-3-(3-dimethyllaminopropyl) carbodiimide (EDC), N,N'-carbonyldiimidazole (CDI), 3-(diethoxyphosphoryloxy)-1,2,3-benzotriazin-4(3H)-one (DEPBT), 1-hydroxy-7-azabenzotriazole (HOAt), 1-hydroxy-7-benzotriazole (HOBt), 2-(7-aza-1H-benzotriazole-1-yl)-1,1,3,3-tetramethyluronium hexafluorophosphate (HATU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium hexafluorophosphate (HBTU), O-(7-azabenzotriazole-1-yl)-N,N,N',N'-tetramethyluronium tetrafluoroborate (TATU), 2-(1H-benzotriazole-1-yl)-1,1,3,3-tetramethyluronium tetrafluoroborate (TBTU), N,N,N',N'-tetramethyl-O-(3,4-dihydro-4-oxo-1,2,3-benzotriazin-3-yl) uranium tetrafluoroborate (TDBTU), and O—(N-succinimidyl)-1,1,3,3-tetramethyl uranium tetrafluoroborate (TSTU)).

In certain embodiments, the above reaction of step (iv) further comprises a suitable base. Suitable bases include, but are not limited to, potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene (DBU), N-methylmorpholine, diisopropylethylamine (DIPEA), tetramethylethylenediamine (TMEDA), pyridine (Py), 1,4-diazabicyclo[2.2.2]octane (DABCO), N,N-dimethylamino pyridine (DMAP), or triethylamine (NEt$_3$).

In certain embodiments, the reaction of step (iv) is carried out in a suitable medium. A suitable medium is a solvent or a solvent mixture that, in combination with the combined reacting partners and reagents, facilitates the progress of the reaction therebetween. A suitable solvent may solubilize one or more of the reaction components, or, alternatively, the suitable solvent may facilitate the suspension of one or more of the reaction components; see generally, *March's Advanced Organic Chemistry: Reactions*, Mechanisms, and Structure, M. B. Smith and J. March, 5$^{th}$ Edition, John Wiley & Sons, 2001, and *Comprehensive Organic Transformations*, R. C. Larock, 2$^{nd}$ Edition, John Wiley & Sons, 1999, the entire contents of each of which are incorporated herein by reference. Suitable solvents for include ethers, halogenated hydrocarbons, aromatic solvents, polar aprotic solvents, or mixtures thereof. In other embodiments, the solvent is diethyl ether, dioxane, tetrahydrofuran (THF), dichloromethane (DCM), dichloroethane (DCE), acetonitrile (ACN), chloroform, toluene, benzene, dimethylformamide (DMF), dimethylacetamide (DMA), dimethylsulfoxide (DMSO), N-methylpyrrolidinone (NMP), or mixtures thereof.

In other embodiments, the reaction of step (iv) is conducted at suitable temperature, such as between about 0° C. and about 100° C.

The present invention is also directed to a method of making a polypeptide of formulae (II), (III), (IV), (V), (VI), or (VII), or any subsets thereof, comprising the steps of:

(i) providing a bis-amino acid of the formula:

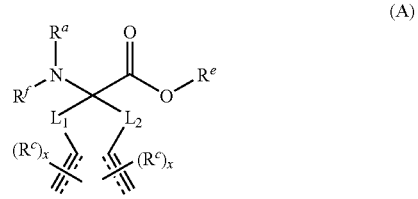

(A)

(ii) providing an amino acid of the formula:

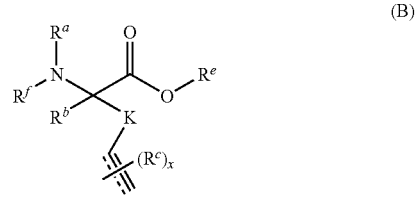

(B)

(iii) providing an amino acid of the formula:

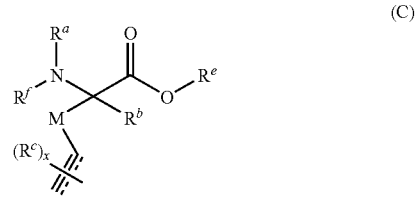

(C)

wherein K, L$_1$, L$_2$, M, R$^a$, R$^b$, R$^c$, R$^e$, R$^f$, x, and ═══ are defined above and herein;

(iv) providing at least one additional amino acid;

(v) coupling said amino acids of formulae (A), (B), and (C) with at least one additional amino acid of step (iv) to provide a polypeptide of formulae (I), (I-a), or (I-b); and (vi) treating the polypeptide of step (v) with a catalyst.

In certain embodiments, the reaction of step (iv) comprises a suitable coupling reagent, a suitable base, a suitable medium, and/or is conducted at a suitable temperature.

One of ordinary skill in the art will realize that a variety of catalysts can be utilized in step (vi) of the above method. Selection of a particular catalyst will vary with the reaction conditions utilized and the functional groups present in the particular peptide. In certain embodiments, the catalyst of step (vi) is a ring closing metathesis (RCM) catalyst. In certain embodiments, the RCM catalyst is a tungsten (W), molybdenum (Mo), or ruthenium (Ru) catalyst. In certain embodiments, the RCM catalyst is a ruthenium catalyst. Suitable RCM catalysts employable by the above synthetic method include catalysts are as depicted below, and as described in see Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

In certain embodiments, the RCM catalyst is a Schrock catalyst. In certain embodiments, the Schrock catalyst is selected from any of the following:

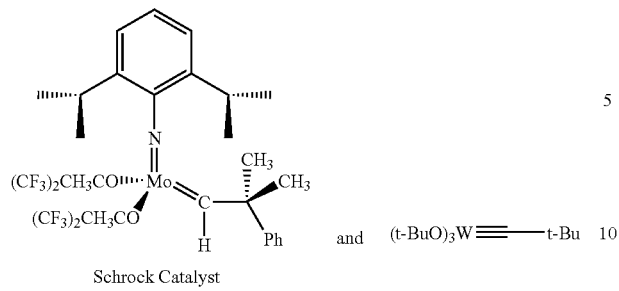

Schrock Catalyst and 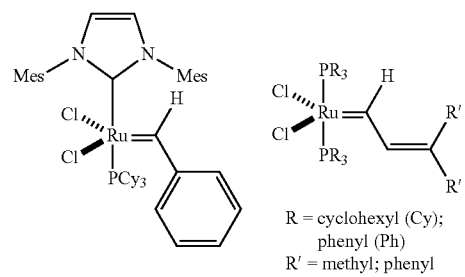

In certain embodiments, the RCM catalyst is a Grubbs catalyst. In certain embodiments, the Grubbs catalyst is selected from any of the following:

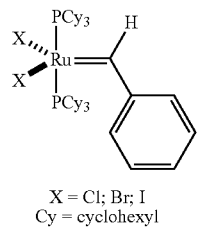

X = Cl; Br; I
Cy = cyclohexyl

Benzylidenebis-(tricyclohexylphosphine)-dichlororuthenium (X=Cl)

Benzylidenebis-(tricyclohexylphosphine)-dibromoruthenium (X=Br)

Benzylidenebis-(tricyclohexylphosphine)-diiodoruthenium (X=I);

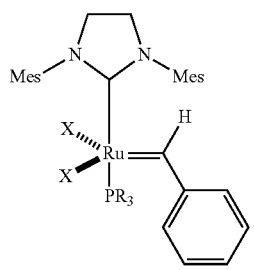

X = Cl; Br; I
R = cyclohexyl (Cy); phenyl (Ph); benzyl (Bn)

1,3-(Bis(mesityl)-2-imidazolidinylidene)dichloro-(phenylmethylene) (tricyclohexyl-phosphine)ruthenium (X=Cl; R=cyclohexyl)

1,3-(Bis(mesityl)-2-imidazolidinylidene)dibromo-(phenylmethylene) (tricyclohexyl-phosphine)ruthenium (X=Br; R=cyclohexyl)

1,3-(Bis(mesityl)-2-imidazolidinylidene)diiodo-(phenylmethylene) (tricyclohexyl-phosphine)ruthenium (X=I; R=cyclohexyl)

1,3-(Bis(mesityl)-2-imidazolidinylidene)dichloro-(phenylmethylene) (triphenylphosphine)ruthenium (X=Cl; R=phenyl)

1,3-(Bis(mesityl)-2-imidazolidinylidene)dichloro-(phenylmethylene) (tribenzylphosphine)ruthenium (X=Cl; R=benzyl);

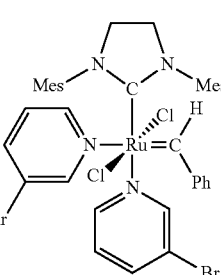

R = cyclohexyl (Cy); phenyl (Ph)
R' = methyl; phenyl

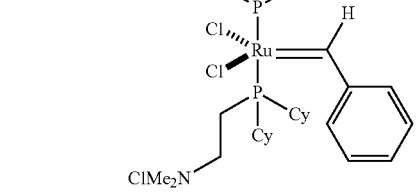

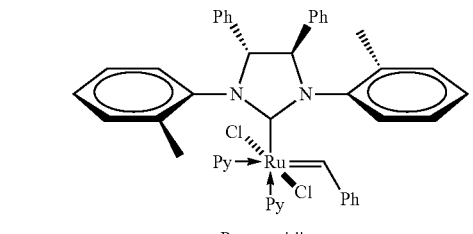

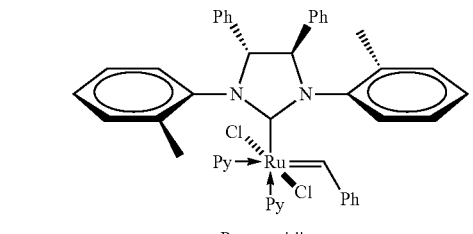

Py = pyridine
Ph = phenyl

In certain embodiments, the RCM catalyst is a Grubbs-Hoveyda catalyst. In certain embodiments, the Grubbs-Hoveyda catalyst is selected from any of the following:

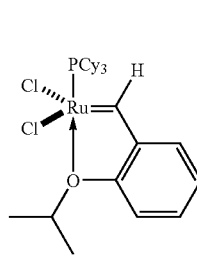 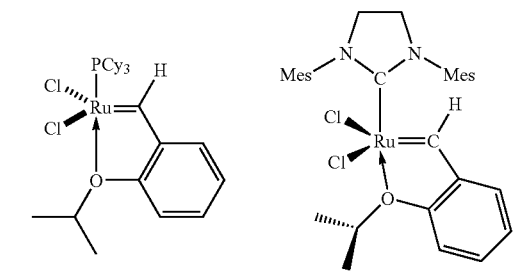

In certain embodiments, the RCM catalyst is selected from any of the following:

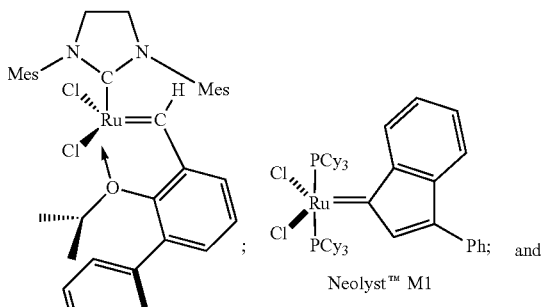

Blechart Catalyst

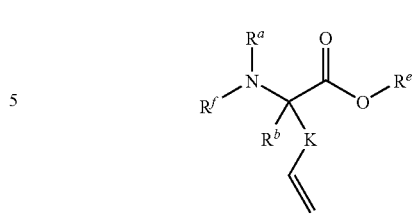 and

Neolyst™ M1

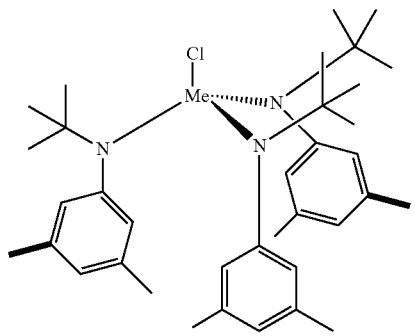

Furstner Catalyst

It will also be appreciated, that in addition to RCM catalysts, other reagents capable of promoting carbon-carbon bond formation can also be utilized. For example, other reactions that can be utilized, include, but are not limited to palladium coupling reactions, transition metal catalyzed cross coupling reactions, pinacol couplings (terminal aldehydes), hydrozirconation (terminal alkynes), nucleophilic addition reactions, and NHK (Nozaki-Hiyama-Kishi (Furstner et al., *J. Am. Chem. Soc.* 1996, 118, 12349)) coupling reactions. Thus, the appropriate reactive moieties are first incorporated into desired amino acids or unnatural amino acids, and then the peptide is subjected to reaction conditions to effect "stitching" and subsequent stabilization of a desired secondary structure.

In certain embodiments, a compound of formula (B) has the formula:

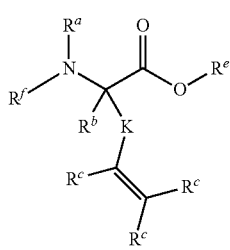

(B-1)

wherein K, $R^a$, $R^c$, $R^e$, and $R^f$ are defined above and herein.

In certain embodiments, a compound of formula (B) has the formula:

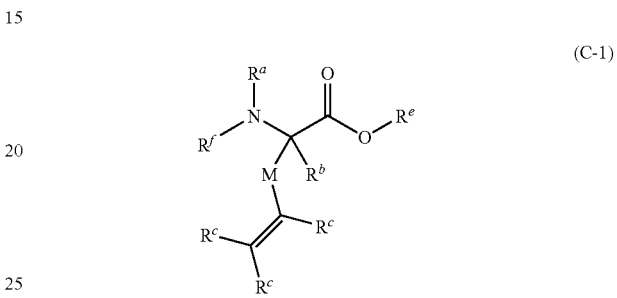

(B-2)

wherein K, $R^a$, $R^c$, $R^e$, and $R^f$ are defined above and herein.

In certain embodiments, a compound of formula (C) has the formula:

(C-1)

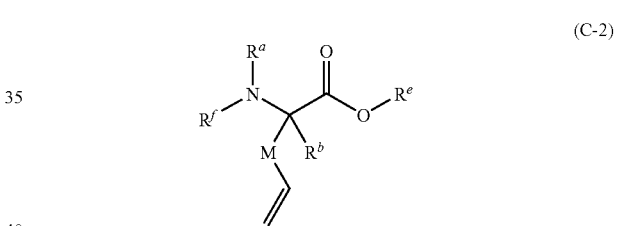

wherein M, $R^a$, $R^c$, $R^e$, and $R^f$ are defined above and herein.

In certain embodiments, a compound of formula (C) has the formula:

(C-2)

wherein M, $R^a$, $R^c$, $R^e$, and $R^f$ are defined above and herein.

Exemplary Amino Acids of Formulae (B) and (C) (Corresponding to Amino Acids with one terminally unsaturated side chain) include, but are not limited to, those as depicted below, wherein $R^a$, $R^f$, and $R^e$ are defined above and herein. In certain embodiments, $R^a$ is hydrogen, and $R^f$ is -Boc or -Fmoc. In certain embodiments, both $R^a$ and $R^f$ are hydrogen. In certain embodiments, $R^e$ is hydrogen.

In certain embodiments, an amino acid of formula (B) is an R-configurated amino acids. In certain embodiments, an R-configurated amino acid of formula (B) is a D-amino acid. In certain embodiments, an amino acid of formula (B) is an S-configurated amino acids. In certain embodiments, an S-configurated amino acid of formula (B) is an L-amino acid. In certain embodiments, an amino acid of formula (B) is racemic. In certain embodiments, amino acids of formula (B) are a mixture of D- and L-amino acids.

In certain embodiments, an amino acid of formula (C) is an R-configurated amino acid. In certain embodiments, an R-configurated amino acid of formula (C) is a D-amino acid. In certain embodiments, an amino acid of formula (C) is an S-configurated amino acid. In certain embodiments, an S-configurated amino acid of formula (C) is an L-amino acid. In certain embodiments, an amino acid of formula (C) is racemic. In certain embodiments, amino acids of formula (C) are a mixture of D- and L-amino acids.

Exemplary Amino Acids of Formulae (B) and (C)

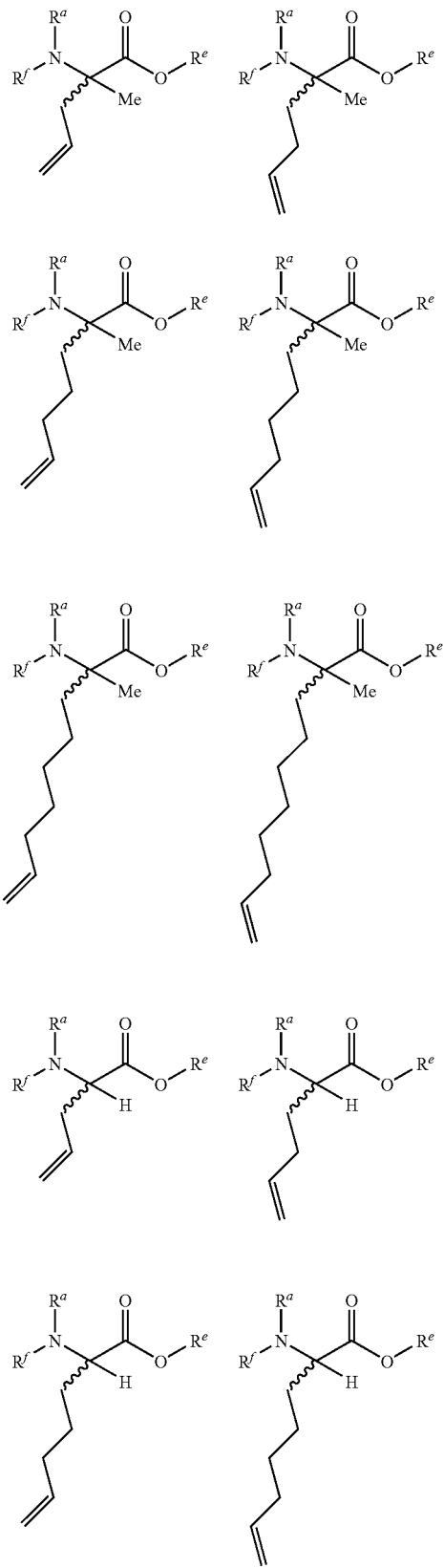

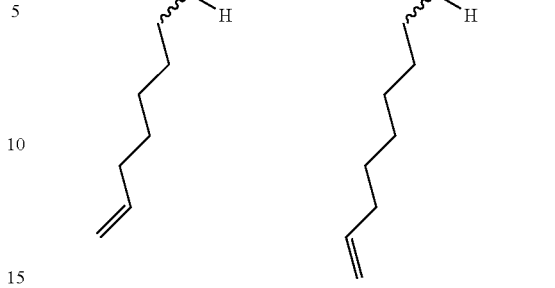

In another aspect, the present invention provides a method of synthesizing an inventive polypeptide comprising the steps of:

(1) providing a selected number of amino acids comprising (i) at least two amino acids, each comprising at least one terminally unsaturated amino acid sidechain, and (ii) at least one α,α-disubstituted amino acid comprising two terminally unsaturated amino acid side chains;

(2) coupling the selected number of amino acids together to generate a first peptide; and (3) treating the first peptide with a suitable catalyst to provide a stitched peptide.

In certain embodiments, divinyl amino acid as "an α,α-disubstituted amino acid comprising two terminally unsaturated amino acid side chains" is specifically excluded.

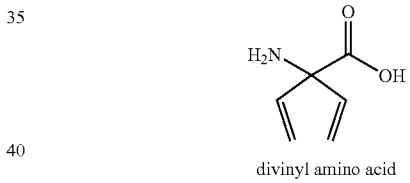

divinyl amino acid

In certain embodiments, each terminally unsaturated amino acid sidechain is reactive toward ring closing metathesis. In certain embodiments, the suitable catalyst is a ring metathesis catalyst. In certain embodiments, the ring closing metathesis catalyst may generate at least two cross-linked rings by the above method. Depending upon the nature of the selected amino acids and their specific location in the peptide chain, stitched peptides of the present invention may comprise at least 2, 3, 4, 5, 6, or 7, cross-links, and may comprise one or more constitutional/structural isomers (i.e., compounds with the same molecular weight but having different connectivity). For example, as depicted in the following Scheme, in certain embodiments, tandem "stitching" of a polypeptide of formula (I-c), as described above and herein, provides three possible stitched products designated herein as (II-d), (VIII), and (IX), wherein K, M, L$_1$, L$_2$, R$^a$, R$^b$, R$^c$, R$^e$, R$^f$, X$_{AA}$, R$^{KL}$, R$^{LL}$, R$^{LM}$, s, t, j, p, y, z, u, q, and v, are as defined herein.

In certain embodiments, the above synthetic method generates one stitched product as a preferred product. As used herein a "preferred product" refers to one constitutional isomer present as the major constituent in a mixture of isomers. In certain embodiments, a "preferred product" refers to one constitutional isomer present as a component in at least about 50%, 55%, 60%, 65%, 70%, 75%, 80%, 85%, 90%, 95%, 98%, or 99%, of an isomeric mixture. In certain embodiments, the preferred product corresponds to a compound of formula (II-d).

In certain embodiments, nested (e.g., formula (VIII)) or overlapping (e.g., formula (IX)) cross-linked products are minor products. In certain embodiments, nested (e.g., formula (VIII)) or overlapping (e.g., formula (IX)) cross-linked products are not generated from the reaction.

Tandem "Stitching" of a Polypeptide of Formula (I-c)

(2) coupling the selected number of amino acids together to generate a first peptide; and (3) treating the first peptide with a suitable catalyst.

The above modifications to the synthetic method are provided as examples only, and are not intended to limit the scope or intent of the present invention. The present invention contemplates any and all types of modifications in order to provide at least 2, 3, 4, 5, 6, or 7, cross-linked staples into the above described polypeptides.

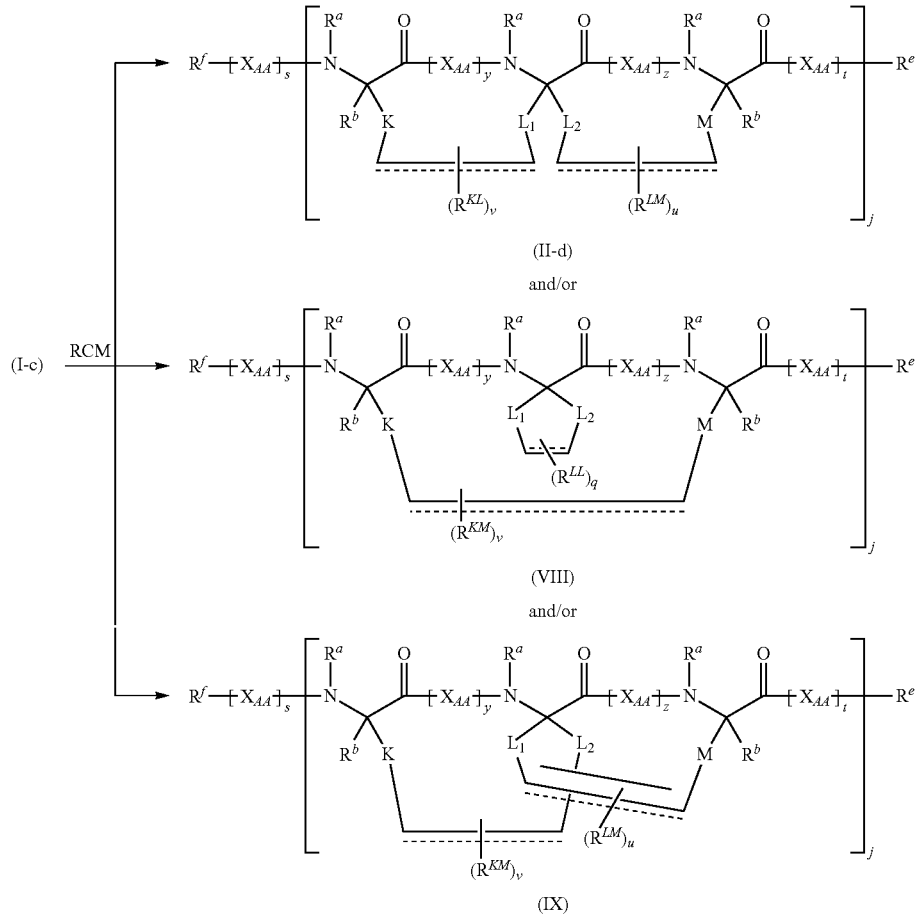

The above synthetic method may be further modified to include at least three cross-linking staples by:

(1) providing a selected number of natural or unnatural amino acids, wherein said number comprises: (i) at least four amino acids, each comprising at least one terminally unsaturated amino acid sidechain, and (ii) at least one α,α-disubstituted amino acid comprising two terminally unsaturated amino acid side chains;

(2) coupling the selected number of amino acids together to generate a first peptide; and (3) treating the first peptide with a suitable catalyst.

Additionally, the above synthetic method may be modified to include at least three cross-linking staples by:

(1) providing a selected number of natural or unnatural amino acids, wherein said number comprises: (i) at least two amino acids, each comprising at least one terminally unsaturated amino acid sidechain, and (ii) at least two α,α-disubstituted amino acids, each comprising two terminally unsaturated amino acid side chains;

The above amino acids comprising one to two terminally unsaturated amino acid sidechains are so incorporated into the polypeptide chain in order to provide proximal terminally unsaturated sidechains. These proximal terminally unsaturated sidechains may be in the same plane as, or same side of the polypeptide chain as, each other in any given conformation of the polypeptide. Upon treatment with a suitable catalyst, these proximal side chains react with each other via "stapling" to provide a stitched, conformationally stabilized, polypeptide. In certain embodiments, the proximal terminally unsaturated sidechains are arranged such that the resulting "staple" does not interfere with the biological/therapeutic activity of the stitched inventive polypeptide.

Additional Synthetic Modifications

After "stitching" of an inventive polypeptide, as described above, the method may further comprise additional synthetic modification(s). Any chemical or biological modification may be made. In certain embodiments, such modifications include reduction, oxidation, and nucleophilic or electrophilic additions to a functional group (e.g., a double bond provided from a metathesis reaction) of the cross-link to provide a synthetically modified stitched polypeptide. Other modifications may include conjugation of a stitched polypeptide, or a synthetically modified stitched polypeptide, with a biologically active agent, label or diagnostic agent anywhere on the stitched polypeptide scaffold, e.g., such as at the N-terminus of the stitched polypeptide, the C-terminus of the stitched polypeptide, on an amino acid side chain of the stitched polypeptide, or at one or more modified or unmodified stitched sites (i.e., to a staple). Such modification may be useful in delivery of the peptide or biologically active agent to a cell, tissue, or organ. Such modifications may allow for targeting to a particular type of cell or tissue.

Thus, in certain embodiments, the above synthetic method further comprises:
(vii) treating the polypeptide of step (vi) with a suitably reactive agent under suitable conditions to provide a synthetically modified stitched polypeptide.

One of ordinary skill in the art will appreciate that a wide variety of reactions, conditions, and "suitably reactive agent(s)" may be employed to promote such a transformation, therefore, a wide variety of reactions, conditions, and reactive agents are envisioned; see generally, *March's Advanced Organic Chemistry: Reactions, Mechanisms, and Structure*, M. B. Smith and J. March, 5$^{th}$ Edition, John Wiley & Sons, 2001; *Advance Organic Chemistry, Part B: Reactions and Synthesis*, Carey and Sundberg, 3$^{rd}$ Edition, Plenum Press, New York, 1993; and *Comprehensive Organic Transformations*, R. C. Larock, 2$^{nd}$ Edition, John Wiley & Sons, 1999, the entirety of each of which is hereby incorporated herein by reference. Exemplary "suitably reactive agents" may be any agent reactive with a multiple bond (e.g., a double or triple bond). In certain embodiments, suitably reactive agents are able to react with a double bond or triple bond, for example, via a hydrogenation, osmylation, hydroxylation (mono- or di-), amination, halogenation, cycloaddition (e.g., cyclopropanation, aziridination, epoxidation), oxy-mercuration, and/or a hydroboronation reaction, to provide a functionalized single bond or double bond. As one of ordinary skill in the art will clearly recognize, these above-described transformations will introduce functionalities compatible with the particular stabilized structures and the desired biological interactions; such functionalities include, but are not limited to, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted amino; substituted or unsubstituted thiol, halo; cyano; nitro; azido; imino; oxo; and thiooxo.

In another aspect, in certain embodiments, the above method further comprises
(vii) treating the polypeptide of step (vi) with a suitably reactive agent to provide a synthetically modified stitched polypeptide, and
(viii) treating the modified stitched polypeptide of step (vii) with a biologically active agent to provide a modified stitched polypeptide conjugated to a biologically-active agent.

Furthermore, in another aspect, in certain embodiments, the above method comprises:
(vii) treating a stitched peptide of step (vi) with a biologically active agent to provide a stitched peptide conjugated to a biologically-active agent.

In another aspect, in certain embodiments, the above method further comprises
(vii) treating the polypeptide of step (vi) with a suitable reagent to provide a synthetically modified stitched polypeptide, and
(viii) treating the modified stitched polypeptide of step (vii) with a diagnostic agent to provide a modified stitched polypeptide conjugated to a diagnostic agent.

Furthermore, in another aspect, in certain embodiments, the above method comprises:
(vii) treating a stitched peptide of step (vi) with a diagnostic agent to provide a stitched peptide conjugated to a diagnostic agent.

Conjugation of an agent (e.g., a label, a diagnostic agent, a biologically active agent) to the inventive polypeptide may be achieved in a variety of different ways. The agent may be covalently conjugated, directly or indirectly, to the polypeptide at the site of stapling, or to the N-terminus or the C-terminus of the polypeptide chain. Alternatively, the agent may be noncovalently conjugated, directly or indirectly, to the polypeptide at the site of stapling, or to the N-terminus or the C-terminus of the polypeptide chain. Indirect covalent conjugation is by means of one or more covalent bonds. Indirect noncovalent conjugation is by means of one or more noncovalent bonds. Conjugation may also be via a combination of non-covalent and covalent forces/bonds. The agent may also be conjugated through a covalent or non-covalent linking group.

Any suitable bond may be used in the conjugation of a biologically active agent and/or diagnostic agent to the inventive polypeptide present invention. Such bonds include amide linkages, ester linkages, disulfide linkages, carbon-carbon bonds, carbamate, carbonate, urea, hydrazide, and the like. In some embodiments, the bond is cleavable under physiological conditions (e.g., enzymatically cleavable, cleavable with a high or low pH, with heat, light, ultrasound, x-ray, etc). However, in some embodiments, the bond is not cleavable.

Combinatorial Synthesis of Novel Stabilized Structures

It will also be appreciated by one of ordinary skill in the art that the synthetic method as described above can also be applied to combinatorial synthesis of inventive polypeptides. Although combinatorial synthesis techniques can be applied in solution, it is more typical that combinatorial techniques are performed on the solid phase using split-and-pool techniques. During the course of the combinatorial synthesis, various parameters can be varied, including, but not limited to placement of amino acids with terminally unsaturated side chains, stereochemistry of amino acids, terminally unsaturated side chain length and functionality, and amino acid residues utilized.

The present invention, in one aspect, provides methods for the synthesis of libraries of novel inventive polypeptides, as described above, comprising (1) providing a collection of resin-bound amino acids; (2) deprotecting each of said resin bound amino acids; (3) separating said collection of deprotected resin bound amino acids into n equal portions, wherein n represents the number of different types of amino acids to be coupled; (4) coupling of each of n types of amino acids to the deprotected amino acid; (5) combining each of the n portions together; and (6) repeating steps (2)-(5) until a desired polypeptide is obtained, wherein at least two of the amino acids coupled at any of the above steps each comprise at least one terminally unsaturated amino acid sidechain, and at least one α,α-disubstituted amino acid comprises two terminally unsaturated amino acid side chains. After a desired polypeptide is synthesized, the resin-bound polypeptide may be contacted with a catalyst to promote "stitching," or may first be cleaved from the resin, and then contacted with a catalyst to promote "stitching."

It will be appreciated by one of ordinary skill in the art that the libraries of compounds having stabilized secondary structures can be further diversified at specific functional moieties after the desired stabilized structures are formed. For example, free or latent amino acid functionalities may be diversified, or alternatively or additionally, free or latent functionality present on the cross-linkers may be diversified. In particularly preferred embodiments, in but one example, the hydrophilicity of stabilized structures may be increased by the introduction of hydroxyl moieties. As one of ordinary skill in the art will realize, the diversification reactions will be selected to introduce functionalities compatible with the particular stabilized structures and the desired biological interactions, and these functionalities include, but are not limited to hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted amino; substituted or unsubstituted thiol, halo; cyano; nitro; azido; imino; oxo; and thiooxo.

Methods of Use

The present invention provides a method of treating a disease, disorder, or condition comprising administering to a subject diagnosed with or having susceptibility to the disease, disorder, or condition, a therapeutically effective amount of an inventive polypeptide, or pharmaceutically acceptable form thereof. Exemplary diseases, disorders, or conditions which may be treated by administration of an inventive polypeptide comprise proliferative, neurological, immunological, endocrinologic, cardiovascular, hematologic, and inflammatory diseases, disorders, or conditions, and conditions characterized by premature or unwanted cell death.

As used herein a proliferative disease, condition, or disorder includes, but is not limited to, cancer, hematopoietic neoplastic disorders, proliferative breast disease, proliferative disorders of the lung, proliferative disorders of the colon, proliferative disorders of the liver, and proliferative disorders of the ovary.

Examples of cancers treatable by the above method include carcinoma, sarcoma, or metastatic disorders, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma, Examples of hematopoietic neoplastic disorders treatable by the above method includes diseases involving hyperplastic/neoplastic cells of hematopoietic origin, e.g., arising from myeloid, lymphoid or erythroid lineages, or precursor cells thereof. In certain embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of proliferative breast disease treatable by the above method includes epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of proliferative disorders of the lung treatable by the above method include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of proliferative disorders of the colon treatable by the above method include, but are not limited to, non-neoplastic polyps, adenomas, familial syndromes, colorectal carcinogenesis, colorectal carcinoma, and carcinoid tumors.

Examples of proliferative disorders of the liver treatable by the above method include, but are not limited to, nodular hyperplasias, adenomas, and malignant tumors, including primary carcinoma of the liver and metastatic tumors.

Examples of proliferative disorders of the ovary treatable by the above method include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The polypeptides described herein can also be used to treat, prevent or diagnose conditions characterised by overactive cell death or cellular death due to physiologic insult etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, myelodysplasia. The polypeptides of the invention that act to decrease apoptosis can be used to treat disorders associated with an undesirable level of cell death. Thus, the anti-apoptotic peptides of the invention can be used to treat disorders such as those that lead to cell death associated with viral infection, e.g., infection associated with infection with human immunodeficiency virus (HIV).

A wide variety of neurological diseases are characterized by the gradual loss of specific sets of neurons, and the anti-apoptotic peptides can be used in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. The anti-apoptotic peptides of the invention can be used to treat all such disorders associated with undesirable cell death.

Some examples of neurologic disorders that can be treated with the polypeptides described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a Prion-mediated disease, Huntington's Disease, Pick's Disease, Amyotrophic Lateral Sclerosis (ALS), Parkinson's Disease, and Lewy Body Disease.

Some examples of endocrinologic disorders that can be treated with the polypeptides described herein include but are not limited to diabetes, hypothyroidism, hypopituitarism, hypoparathyroidism, hypogonadism, fertility disorders, etc.

Some examples of immunologic disorders that can be treated with the polypeptides described herein include but are not limited to organ transplant rejection, arthritis, lupus, IBD, Crohn's disease, asthma, multiple sclerosis, diabetes, Graft versus host diseases, autoimmune diseases, psoriasis, rheumatoid arthritis, etc.

Examples of cardiovascular disorders that can be treated or prevented with the polypeptides of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices.

The inventive stitched polypeptides may serve to treat the above-described diseases, disorders, or conditions, by disrupting native protein-protein, protein-ligand, and/or protein-receptor interactions. For example, many biologically important protein/protein interactions, such as p53/MDM2 and Bcl-X1/Bak, are mediated by one protein donating a helix into a cleft of its helix-accepting partner. The interaction of p53 and MDM2 and mutations in the p53 gene have been identified in virtually half of all reported cancer cases (see, Shair *Chem. & Biol.* 1997, 4, 791, the entire contents of which are incorporated herein by reference). As stresses are imposed on a cell, p53 is believed to orchestrate a response that leads to either cell-cycle arrest and DNA repair, or programmed cell death. As well as mutations in the p53 gene that alter the function of the p53 protein directly, p53 can be altered by changes in MDM2. The MDM2 protein has been shown to bind to p53 and disrupt transcriptional activation by associating with the transactivation domain of p53. For example, an 11 amino-acid peptide derived from the transactivation domain of p53 forms an amphipathic alpha-helix of 2.5 turns that inserts into the MDM2 crevice.

Thus, in certain embodiments, an inventive polypeptide is an alpha helical polypeptide that is capable of binding tightly to a helix acceptor and disrupting native protein/protein interactions. These structures may then be screened using high throughput techniques to identify optimal small molecule peptides. In certain embodiments, an inventive polypeptide is an alpha helical p53 polypeptide capable of binding to the *Xenopus* MDM2 protein. The novel structures that disrupt the MDM2 interaction might be useful for many applications, including, but not limited to, control of soft tissue sarcomas (which overexpresses MDM2 in the presence of wild type p53). These cancers may be held in check with small molecules that could intercept MDM2, thereby preventing suppression of p53. Additionally, small molecules disrupters of MDM2-p53 interactions could be used as adjuvant therapy to help control and modulate the extent of the p53 dependent apoptosis response in conventional chemotherapy.

In certain embodiments, the inventive polypeptide is homologous to a known alpha helical peptide. In certain embodiments, the inventive polypeptide is at least 80%, 85%, 90%, or 95% homologous to a known alpha helical peptide.

In addition, the inventive polypeptides may be useful in the area of materials science. For example, molecules such as lipids and other polymeric molecules may be attached to the terminal peptide moieties and thus generate potentially important biomaterials.

In addition to the above-mentioned uses, the inventive polypeptides may be used for studies in bioinorganic chemistry or in catalysis, either as a ligand for a transition metal capable of mimicking an important biological environment, or by acting in concert with a particular transition metal catalyst to effect a desired chemical reaction.

Pharmaceutical Compositions

The present invention provides pharmaceutical compositions comprising an inventive stitched polypeptide, or pharmaceutically acceptable form thereof, and a pharmaceutically acceptable carrier. Such pharmaceutical compositions may optionally comprise one or more additional biologically-active substances. In accordance with some embodiments, a method of administering a pharmaceutical composition comprising inventive compositions to a subject in need thereof is provided. In some embodiments, inventive compositions are administered to humans. For the purposes of the present invention, the phrase "active ingredient" generally refers to an inventive polypeptide, as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* 21$^{st}$ Edition, A. R. Gennaro, (Lippincott, Williams & Wilkins, Baltimore, Md., 2006) discloses various carriers used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a conjugate of this invention may include ointments, pastes, creams, lotions, gels, powders, solutions, sprays, inhalants and/or patches. Generally, the active component is admixed under sterile conditions with a pharmaceutically acceptable carrier and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Administration

In some embodiments, a therapeutically effective amount of an inventive pharmaceutical composition is delivered to a patient and/or organism prior to, simultaneously with, and/or after diagnosis with a disease, disorder, and/or condition. In some embodiments, a therapeutic amount of an inventive composition is delivered to a patient and/or organism prior to, simultaneously with, and/or after onset of symptoms of a disease, disorder, and/or condition. In some embodiments, the amount of inventive conjugate is sufficient to treat, alleviate, ameliorate, relieve, delay onset of, inhibit progression of, reduce severity of, and/or reduce incidence of one or more symptoms or features of the disease, disorder, and/or condition.

The compositions, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. The compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions of the present invention may be administered by any route. In some embodiments, the pharmaceutical compositions of the present invention are administered variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

In certain embodiments, the conjugates of the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In some embodiments, the present invention encompasses "therapeutic cocktails" comprising inventive polypeptides. In some embodiments, the inventive polypeptide comprises a single species which can bind to multiple targets. In some embodiments, different inventive polypeptides comprise different targeting moiety species, and all of the different targeting moiety species can bind to the same target. In some embodiments, different inventive polypeptides comprise different targeting moiety species, and all of the different targeting moiety species can bind to different targets. In some embodiments, such different targets may be associated with the same cell type. In some embodiments, such different targets may be associated with different cell types.

It will be appreciated that inventive polypeptides and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive conjugate useful for detecting tumors may be administered concurrently with another agent useful for detecting tumors), or they may achieve different effects (e.g., control of any adverse effects).

Pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive polypeptide may be administered concurrently with another biologically active agent used to treat the same disorder), and/or they may achieve different effects (e.g., control of any adverse effects). In some embodiments, polypeptides of the invention are administered with a second biologically active agent that is approved by the U.S. Food and Drug Administration.

In will further be appreciated that biologically active agents utilized in this combination may be administered together in a single composition or administered separately in different compositions.

In general, it is expected that biologically active agents utilized in combination be utilized at levels that do not exceed the levels at which they are utilized individually. In some embodiments, the levels utilized in combination will be lower than those utilized individually.

In some embodiments, inventive pharmaceutical compositions may be administered in combination with any biologically active agent or therapeutic regimen that is useful to treat, alleviate, ameliorate, relieve, delay onset of, inhibit progression of, reduce severity of, and/or reduce incidence of one or more symptoms or features of cancer. For example, inventive compositions may be administered in combination with traditional cancer therapies including, but not limited to, surgery, chemotherapy, radiation therapy, hormonal therapy, immunotherapy, complementary or alternative therapy, and any combination of these therapies.

In some embodiments, inventive compositions are administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g. chemotherapy, radiation therapy, hormonal therapy, immunotherapy, complementary or alternative therapy) may be employed.

In some embodiments, inventive compositions are administered in combination with radiation therapy. Radiation therapy (also known as radiotherapy, X-ray therapy, or irradiation) is the use of ionizing radiation to kill cancer cells and shrink tumors. Radiation therapy may be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g. a target organ, tissue, and/or cell) by damaging their genetic material, preventing tumor cells from growing and dividing. In general, radiation therapy attempts to damage as many tumor cells as possible while limiting harm to nearby healthy tissue. Hence, it is often administered in multiple doses, allowing healthy tissue to recover between fractions.

In some embodiments, inventive compositions are administered in combination with immunotherapy. Immunotherapy is the use of immune mechanisms against tumors which can be used in various forms of cancer, such as breast cancer (e.g. trastuzumab/Herceptin®), leukemia (e.g. gemtuzumab ozogamicin/Mylotarg®), and non-Hodgkin's lymphoma (e.g. rituximab/Rituxan®). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines.

In some embodiments, vaccines can be administered to prevent and/or delay the onset of cancer. In some embodiments, cancer vaccines prevent and/or delay the onset of cancer by preventing infection by oncogenic infectious agents. In some embodiments, cancer vaccines prevent and/or delay the onset of cancer by mounting an immune response against cancer-specific epitopes. To give but one example of a cancer vaccine, an experimental vaccine for HPV types 16 and 18 was shown to be 100% successful at preventing infection with these types of HPV and, thus, are able to prevent the majority of cervical cancer cases (Harper et al., 2004, *Lancet*, 364:1757).

In some embodiments, inventive compositions are administered in combination with complementary and alternative medicine treatments. Some exemplary complementary measures include, but are not limited to, botanical medicine (e.g. use of mistletoe extract combined with traditional chemotherapy for the treatment of solid tumors); acupuncture for managing chemotherapy-associated nausea and vomiting and in controlling pain associated with surgery; prayer; psychological approaches (e.g. "imaging" or meditation) to aid in pain relief or improve mood. Some exemplary alternative measures include, but are not limited to, diet and other lifestyle changes (e.g. plant-based diet, the grape diet, and the cabbage diet).

In some embodiments, inventive compositions are administered in combination with any of the traditional cancer treatments described herein, which are often associated with unpleasant, uncomfortable, and/or dangerous side effects. For example, chronic pain often results from continued tissue damage due to the cancer itself or due to the treatment (i.e., surgery, radiation, chemotherapy). Alternatively or additionally, such therapies are often associated with hair loss, nausea, vomiting, diarrhea, constipation, anemia, malnutrition, depression of immune system, infection, sepsis, hemorrhage, secondary neoplasms, cardiotoxicity, hepatotoxicity, nephrotoxicity, ototoxicity, etc. Thus, inventive compositions which are administered in combination with any of the traditional cancer treatments described herein may be also be administered in combination with any therapeutic agent or therapeutic regimen that is useful to treat, alleviate, ameliorate, relieve, delay onset of, inhibit progression of, reduce severity of, and/or reduce incidence of one or more side effects of cancer treatment. To give but a few examples, pain can be treated with opioids and/or analgesics (e.g. morphine, oxycodone, antiemetics, etc.); nausea and vomiting can be treated with $5\text{-}HT_3$ inhibitors (e.g. dolasetron/Anzemet®, granisetron/Kytril®, ondansetron/Zofran®, palonsetron/Aloxi®) and/or substance P inhibitors (e.g. aprepitant/Emend®); immunosuppression can be treated with a blood transfusion; infection and/or sepsis can be treated with antibiotics (e.g. penicillins, tetracyclines, cephalosporins, sulfonamides, aminoglycosides, etc.); and so forth.

In some embodiments, inventive compositions may be administered and/or inventive diagnostic methods may be performed in combination with any therapeutic agent or therapeutic regimen that is useful to diagnose one or more symptoms or features of cancer (e.g. detect the presence of and/or locate a tumor). In some embodiments, inventive conjugates may be used in combination with one or more other diagnostic agents. To give but one example, conjugates used to detect tumors may be administered in combination with other agents useful in the detection of tumors. For example, inventive conjugates may be administered in combination with traditional tissue biopsy followed by immunohistochemical staining and serological tests (e.g. prostate serum antigen test). Alternatively or additionally, inventive conjugates may be administered in combination with a contrasting agent for use in computed tomography (CT) scans and/or MRI.

Kits

The invention provides a variety of kits comprising one or more of the polypeptides of the invention. For example, the invention provides a kit comprising an inventive polypeptide and instructions for use. A kit may comprise multiple different polypeptides. A kit may comprise any of a number of additional components or reagents in any combination. All of the various combinations are not set forth explicitly but each combination is included in the scope of the invention.

According to certain embodiments of the invention, a kit may include, for example, (i) one or more inventive polypeptides and one or more particular biologically active agents to be delivered; (ii) instructions for administering the conjugate to a subject in need thereof.

Kits typically include instructions which may, for example, comprise protocols and/or describe conditions for production of inventive polypeptides, administration of inventive polypeptides to a subject in need thereof, design of novel inventive polypeptides, etc. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, etc., may be enclosed. An identifier, e.g., a bar code, radio frequency identification (ID) tag, etc., may be present in or on the kit or in or one or more of the vessels or containers included in the kit. An identifier can be used, e.g., to uniquely identify the kit for purposes of quality control, inventory control, tracking, movement between workstations, etc.

EXEMPLIFICATION

The present invention will be more specifically illustrated by the following examples. However, it should be understood that the present invention is not limited by these examples in any manner.

Example 1

Stitching Alpha-Helical Peptides by Tandem Ring-Closing Metathesis

For the bis-olefinic amino acid that provides the spiro junction of the stitched peptide, we chose bis-pentenylglycine ($B_5$) (FIG. 1D). Studies with single hydrocarbon staples had established that five-carbon chain length in $B_5$ to be optimal at the C-terminal end of the i,i+4 staple, when S-configurated and combined with an N-terminal $S_5$ residue; and at the N-terminal end of the i,i+7 staple, when R-configurated and combined with a C-terminal $S_8$ residue. (Schafmeister et al. *J. Am. Chem. Soc.* (2000) 122:5891-5892). Peptides containing an N-terminal $S_5$ (i), central $B_5$ (i+4) and C-terminal $S_8$ (i+4+7) bear four terminal olefins, which are equivalent electronically but differentiated regiochemically by virtue of their attachment to the peptide framework.

Considering only intramolecular reaction pathways, tandem-RCM could produce three regioisomeric products, 2, 3 and 4 (FIG. 1A). Of particular concern was the possibility that the two olefins in $B_5$ might preferentially react with each other during RCM (reaction a), because the resulting 9-membered ring would be smaller than either of those produced by inter-residue RCM.

To investigate all the possible reaction pathways, we turned to model studies examining each in isolation using the sequence of the C-peptide of RNase A (Bierzynski, A.; Kim, P. S.; Baldwin, R. L. *Proc. Acad. Sci. U.S.A.* 1982, 79, 2470-2474). A model peptide designed to test reaction a by incorporating only $B_5$, was a poor substrate for RCM (Table 5, entry II), probably owing to ring strain in the transition state leading to the cyclononenyl product A literature search failed to produce any reported example of RCM leading to cyclononenyl product. The ethyl ester of Fmoc amino acid $B_5$ also failed to form the cyclononenyl product under similar conditions; instead, a dimeric 18-membered metathesis product was formed as the exclusive product (Scheme 2).

TABLE 5

Sequences of Peptide Substrates and Percent Conversions for Metathesis Reaction.

| | Substrate sequence[a] | SEQ ID No. | Rxn modeled | % conversion[b] 2 h | +2 h[c] |
|---|---|---|---|---|---|
| I | Ac-EWAETAAAKFLAAHA, | 9 SEQ ID 1 | | — | — |
| II | Ac-EWAETAAB$_5$KFLAAHA | SEQ ID 2 | a | <2[d] | <2[d] |
| III | Ac-EWAS$_5$TAAAKFLAAHS$_8$ | SEQ ID 3 | b | <2[d] | <2[d] |
| IV | Ac-EWAS$_5$TAAR$_5$KFLAAHA | SEQ ID 4 | c | <2[d] | <2[d] |
| V | Ac-EWAETAAS$_5$KFLAAHS$_8$ | SEQ ID 5 | d | 48 | — |
| VI | Ac-EWAS$_5$TAAS$_5$KFLAAHA | SEQ ID 6 | e | >98 | — |
| VII | Ac-EWAETAAR$_5$KFLAAHS$_8$ | SEQ ID 7 | f | >98 | — |
| VIII | Ac-EWAS$_5$TAAS$_5$KFLAAH*[e] | SEQ ID 8 | | (product 6) >98 | — |
| IX | Ac-EWA*TAAR$_5$KFLAAHS$_8$[e] | SEQ ID 9 | | (product 5) >98 | — |
| X | Ac-EWAS$_5$TAAB$_5$KFLAAHS$_8$ | SEQ ID 10 | | (product 4[f]) >98 | — |
| XI | Ac-EWAS$_5$TAAB$_5$KFLR$_5$AHA | SEQ ID 11 | | (product 8[f]) >98 | — |

[a]Metathesis was performed on solid support with the fully protected peptide using 20 mol % Grubbs catalyst[4b] in dichloroethane.
[b]Percent conversion [product/(product/(product + starting material)] as determined by reversed-phase HPLC following cleavage from resin.
[c]Product yield following a second 2-hour metathesis reaction using fresh catalyst.
[d]RCM product was not detected.
[e]Asterisk represents alpha-aminoisobutyric acid (Aib), which was incorporated to mimic the helix-stabilizing effect of the alpha, alpha-disubstituted amino acids $S_5$ and $S_8$.
[f]Double RCM product.

A peptide configured to test reaction b also failed to yield appreciable amounts of product (entry III, Table 5). These results having thus indicated that the a+b tandem-RCM pathway is disfavored, the two remaining alternatives were c+d and e+f In model peptides, reaction c failed and d gave only modest yields (entries IV and V, respectively). On the other hand, both reactions e and f proceeded efficiently (entries VI and VII, respectively), as expected from previous studies (see Schafmeister, C. E.; Po, J.; Verdine, G. L. *J. Am. Chem. Soc.* 2000, 122, 5891-5892). The exquisite selectivity of RCM in these peptides is clearly evident from comparison of entry VI with IV, in which inversion of a single stereogenic center causes a nearly quantitative reaction to fail.

Of the six mono-RCM reactions, by far the two most efficient ones were e and f. Should this preferential reactivity be retained with a peptide containing all four olefinic tethers required to introduce a stitched helix, then the e+f pathway might be favored enough to provide product 4 cleanly. To test this, we synthesized peptide 1 and subjected it to RCM under the same conditions as used in the component reactions, then deprotected the peptide and analyzed the products by LCMS. A single product peak accounted for 90% of the product mixture, with the remainder being unreacted starting material. This product had the molecular mass expected of the product of tandem metathesis (i.e., 1 minus 2 mol equivalents of ethylene). Edman degradation revealed that only the olefin-containing amino acids had been altered in the RCM reaction. By subjecting resin-bound 1 to a second round of RCM, we were able to increase the product conversion to greater than 98%. The results of the mono-RCM reactions had suggested 4 to be the most likely structure for the tandem-RCM product, and this assignment was confirmed by computational analysis of the two possible stitched products, 3 and 4; Molecular modeling indicated that the lowest energy double bond isomer of product 4 is lower in energy than the most stable isomer of 3 by ~15 kcal/mol. This is in part due to three syn-pentane interactions that arise in product 3. Computational analysis further indicated a ~2.5 kcal/mol preference for the i,i+4 olefin to be configurated cis; the i,i+7 olefin has no such configurational bias, and therefore the intrinsic preference of the catalyst to produce trans olefins probably dominates.

Figure 2A:
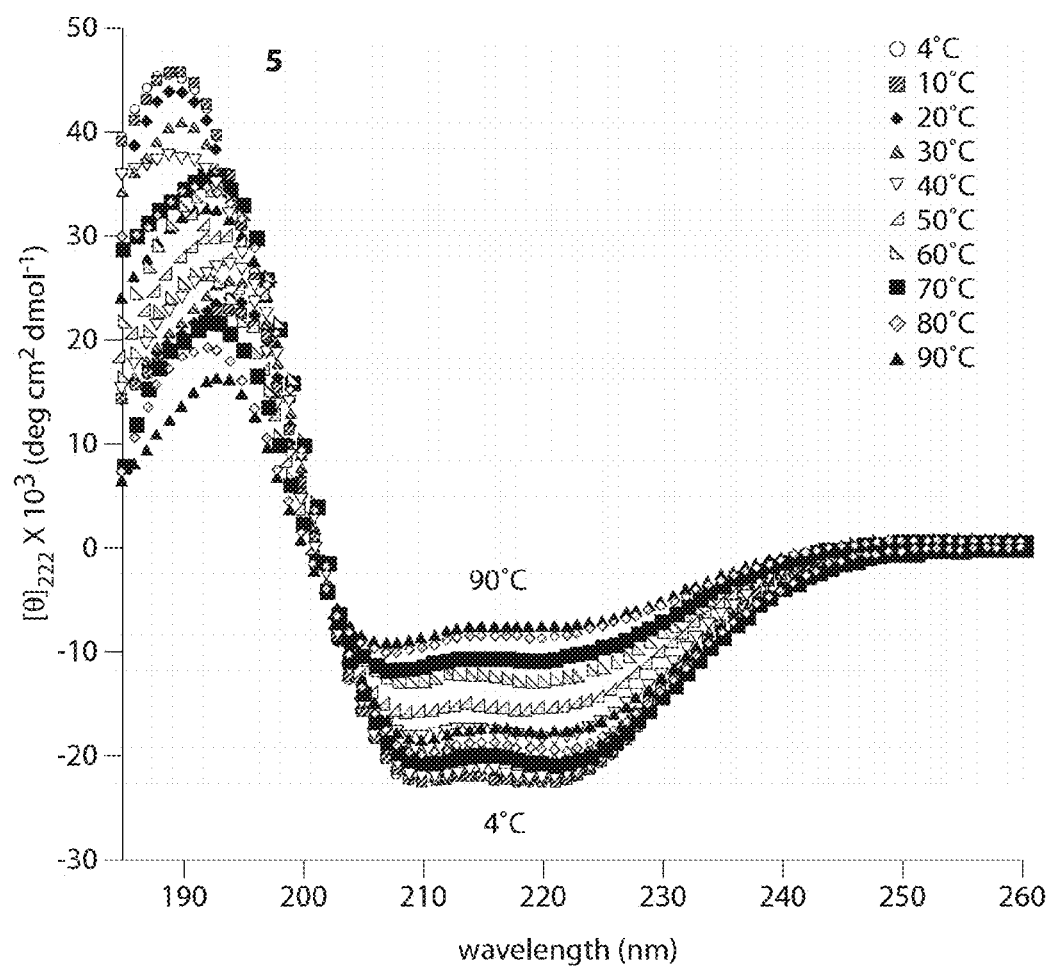
FIGS. 2A-2C. Temperature-dependent circular dichroism spectra of (A) 5, and (B) 4. Inset: thermal melting curves and $T_m$. (C) Comparison of the rates of trypsin digestion of 4 versus 5.
Figure 2B:
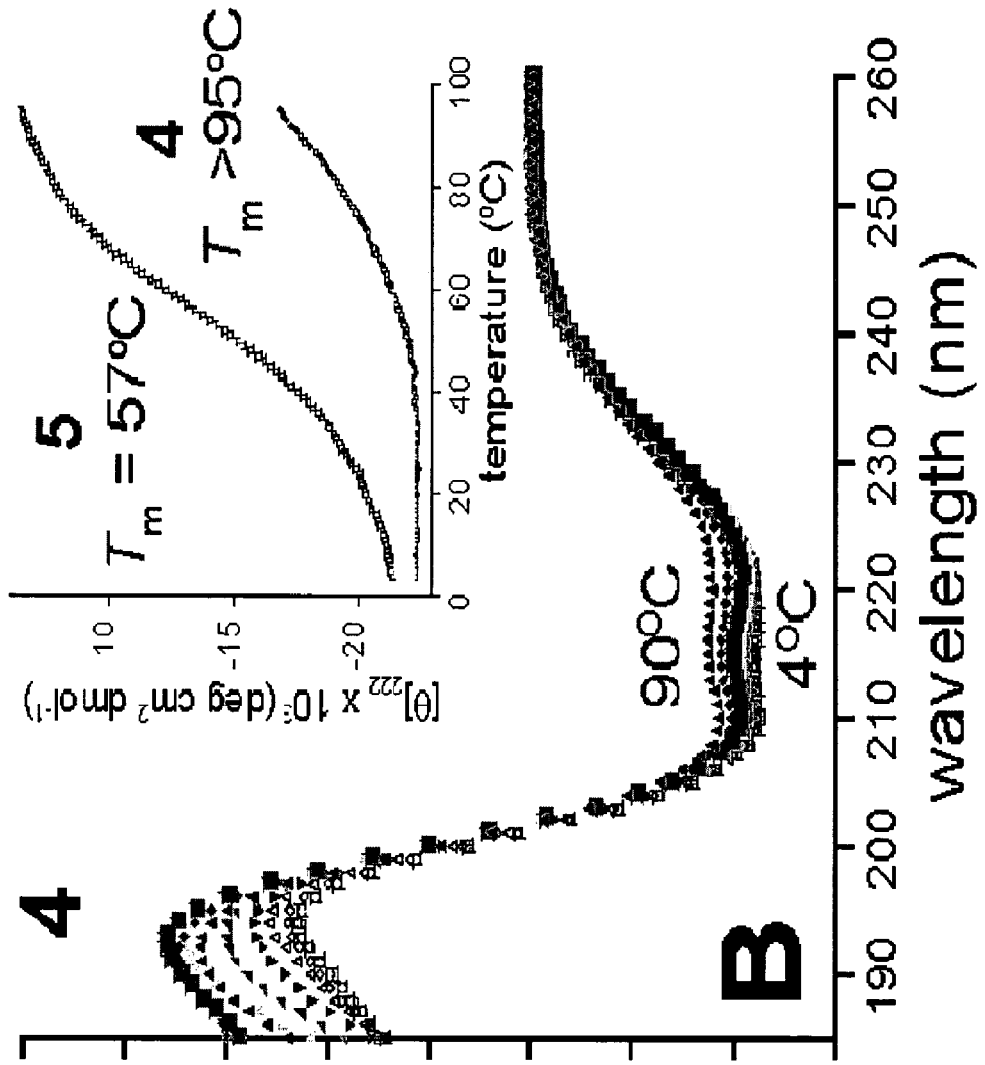
Figure 2C:
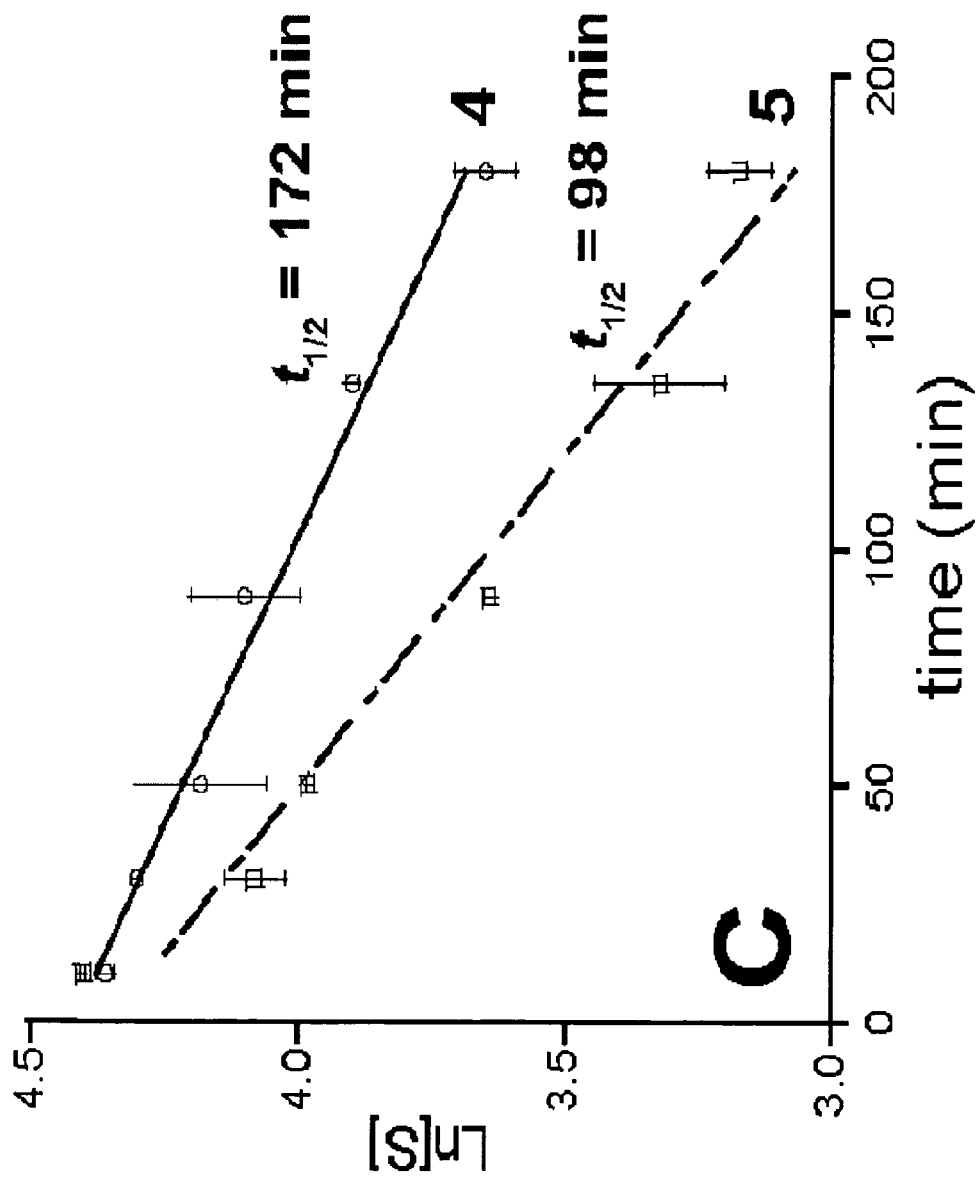
Figure 3A:
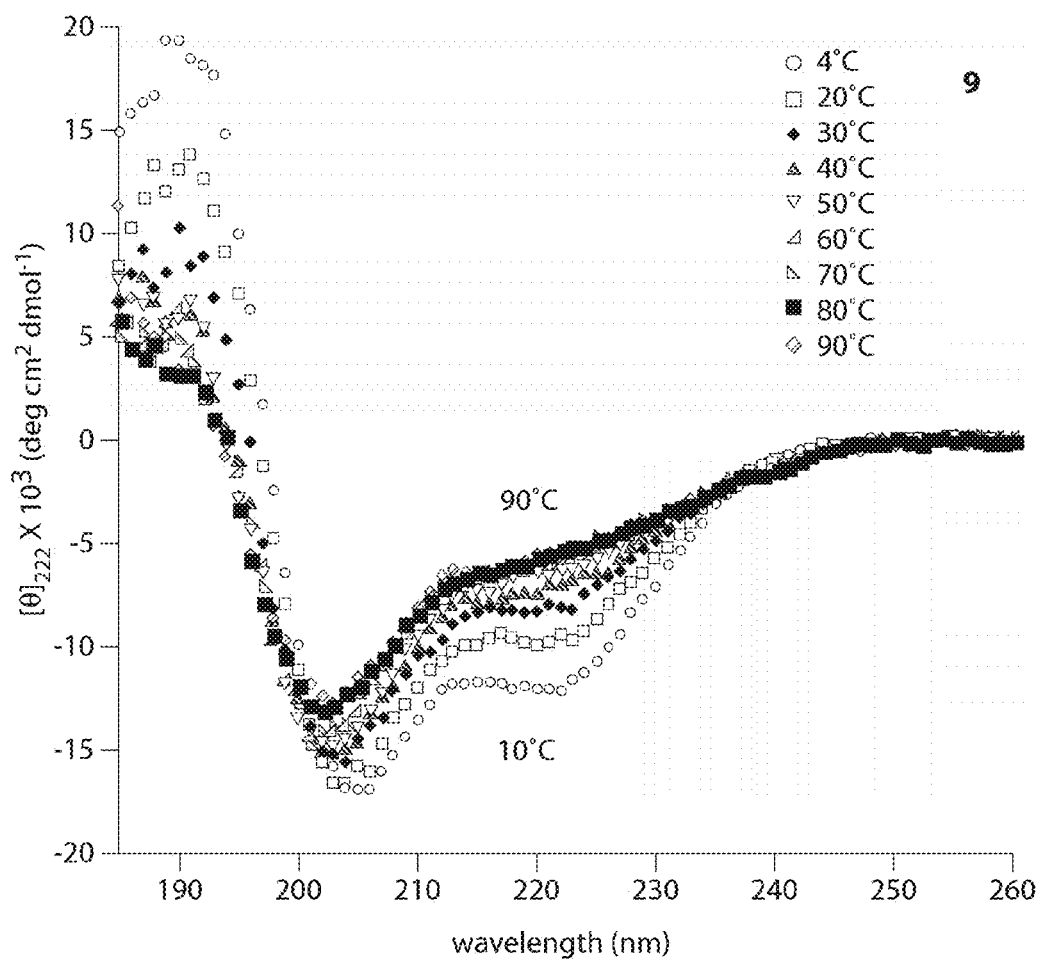
FIGS. 3A-3C. Temperature-dependent circular dichroism spectra of (A) peptide 9 (97 M), (B) 6 (98 M), (C) 8 (94 M).
Figure 3B:
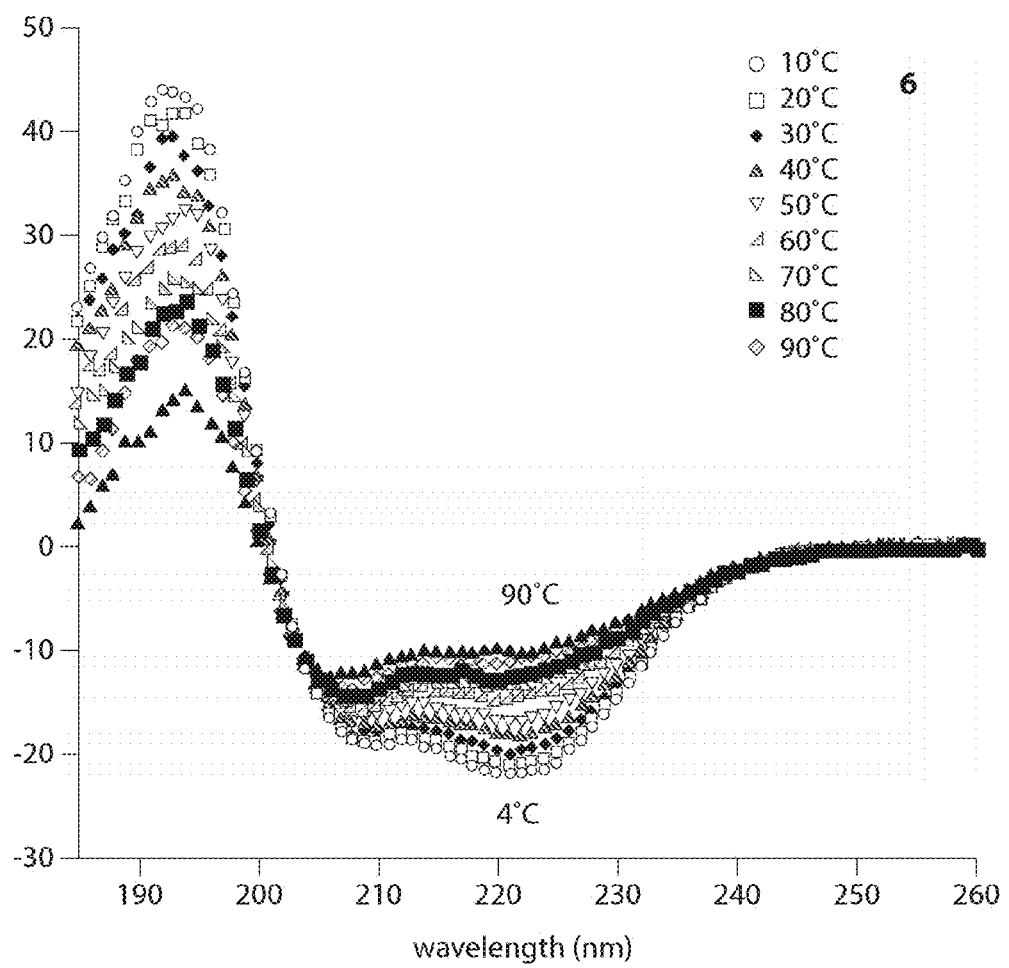
Figure 3C:
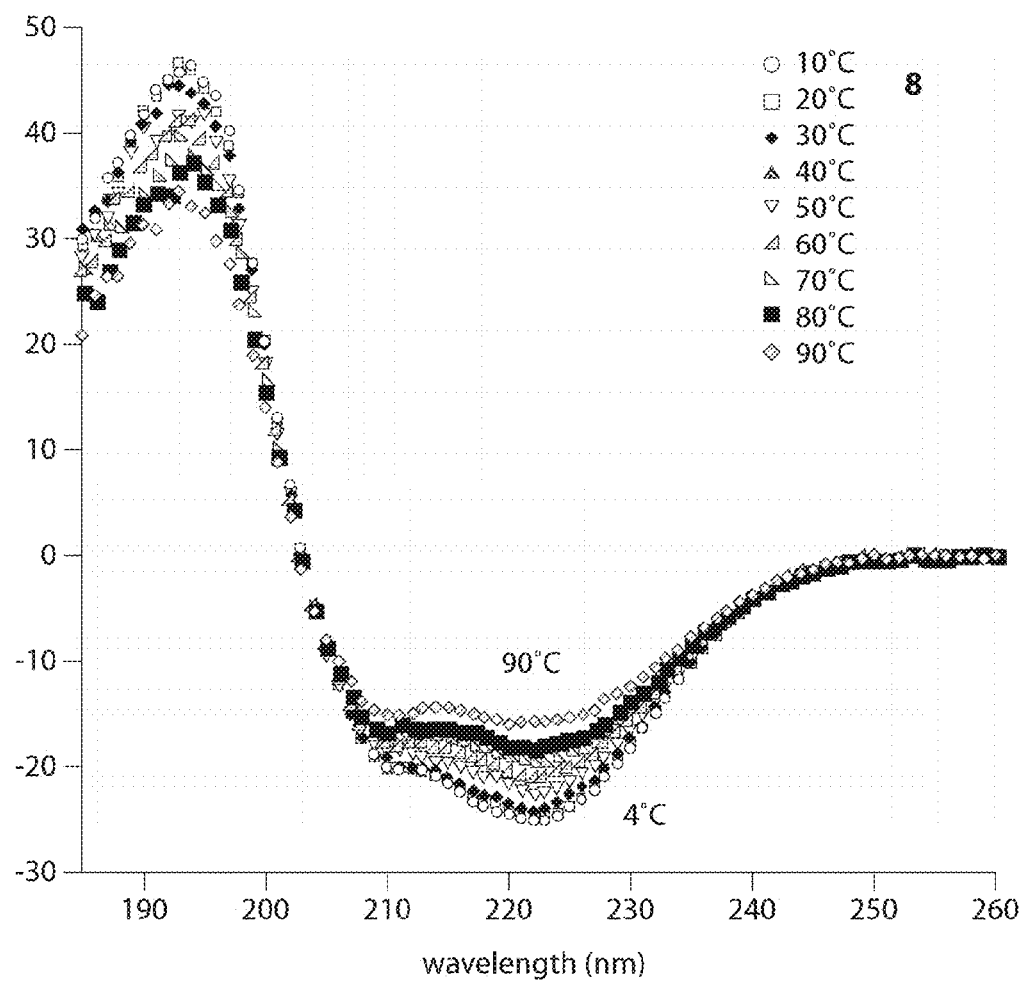
Figure 4:
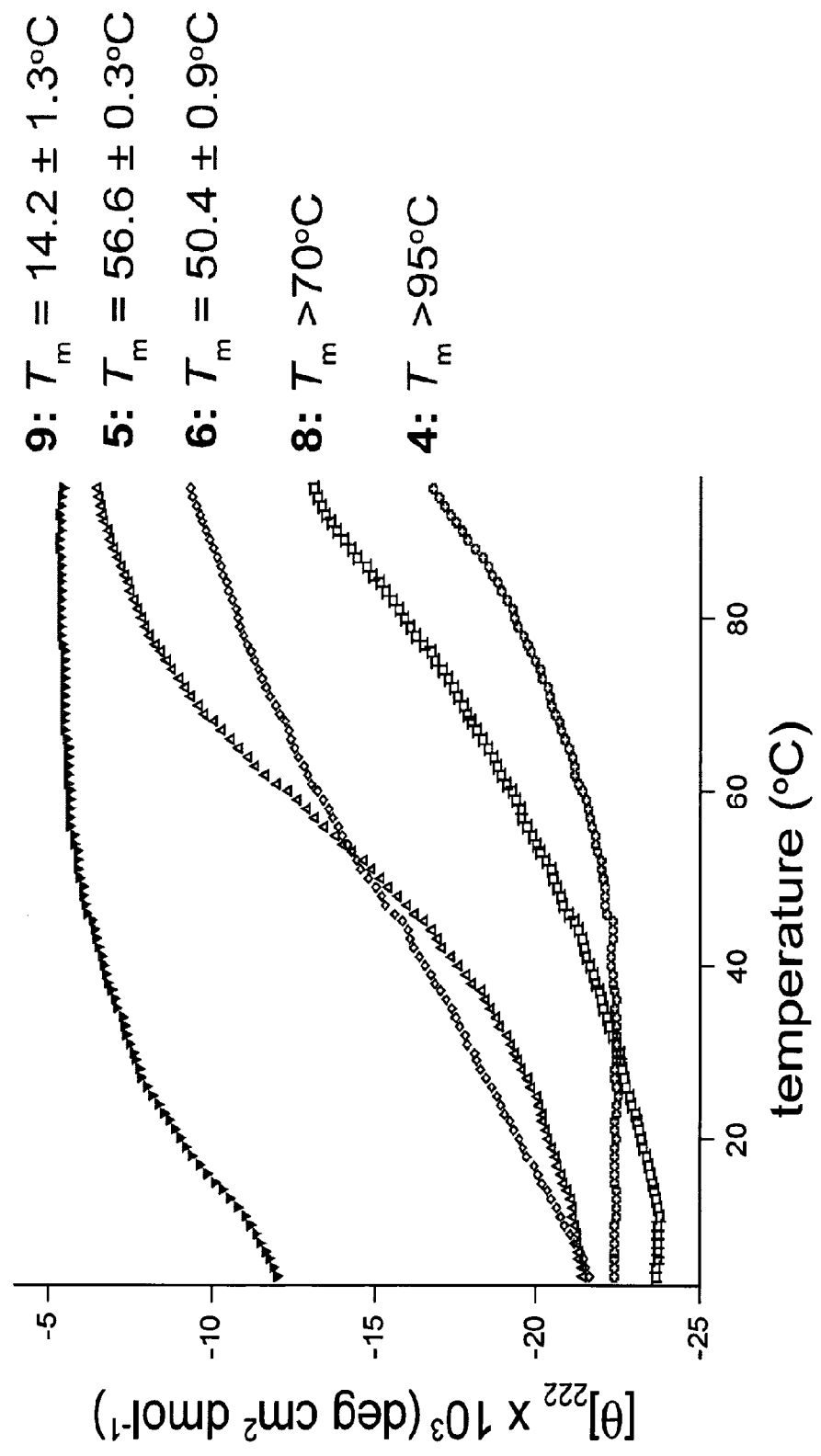
FIG. 4. Thermal melting curves and $T_m$.
Figure 5:
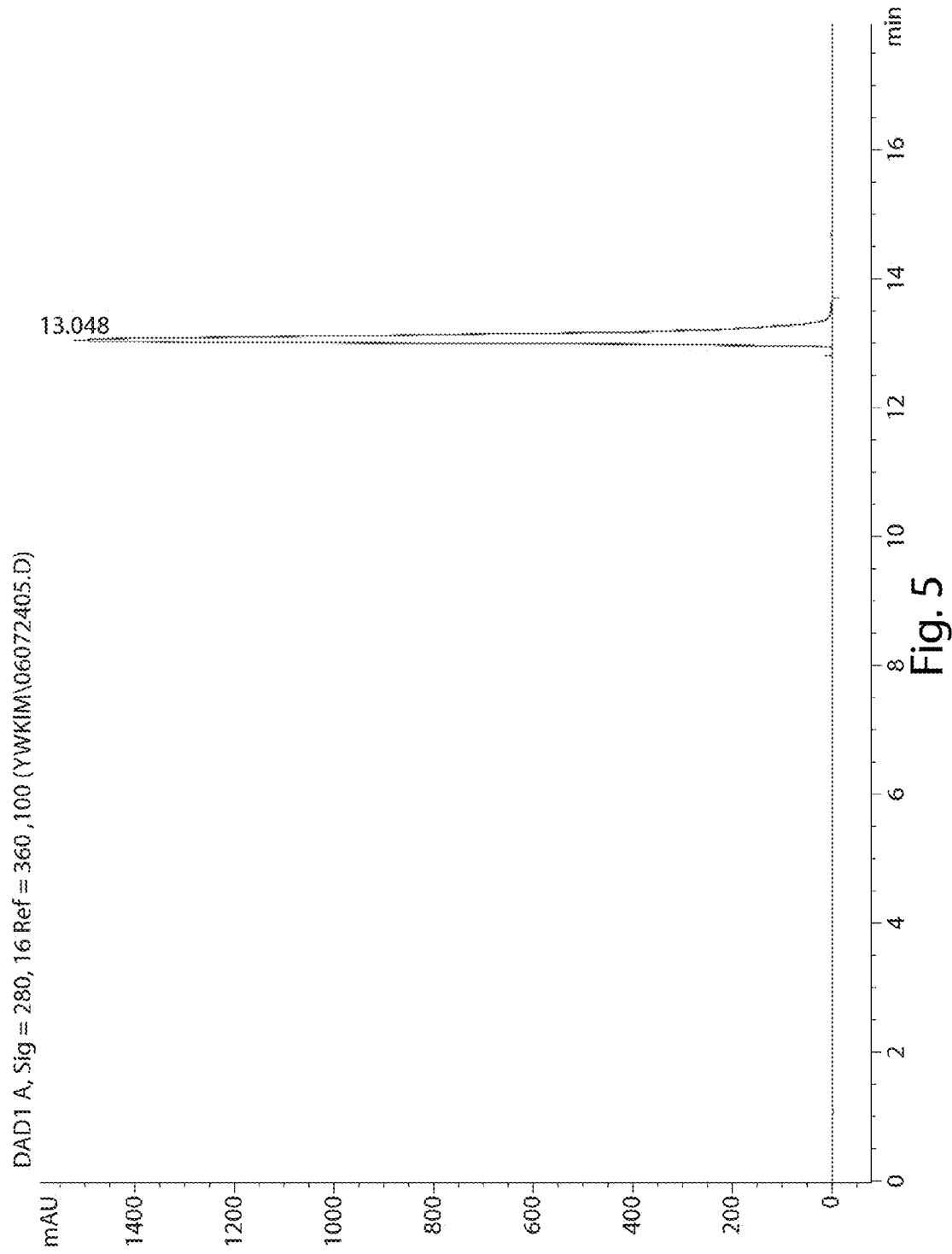
FIG. 5. HPLC chromatogram of purified peptide 9. 10-64% B for 0-12 min; 64-10% B for 1215 min; 10% B for 15-18 min on an Agilent $C_{18}$ reverse phase column (3.5×150 mm); A: 0.1% TFA in $H_2O$, B: acetonitrile; flow rate: 0.5 mL/min.
Figure 6:
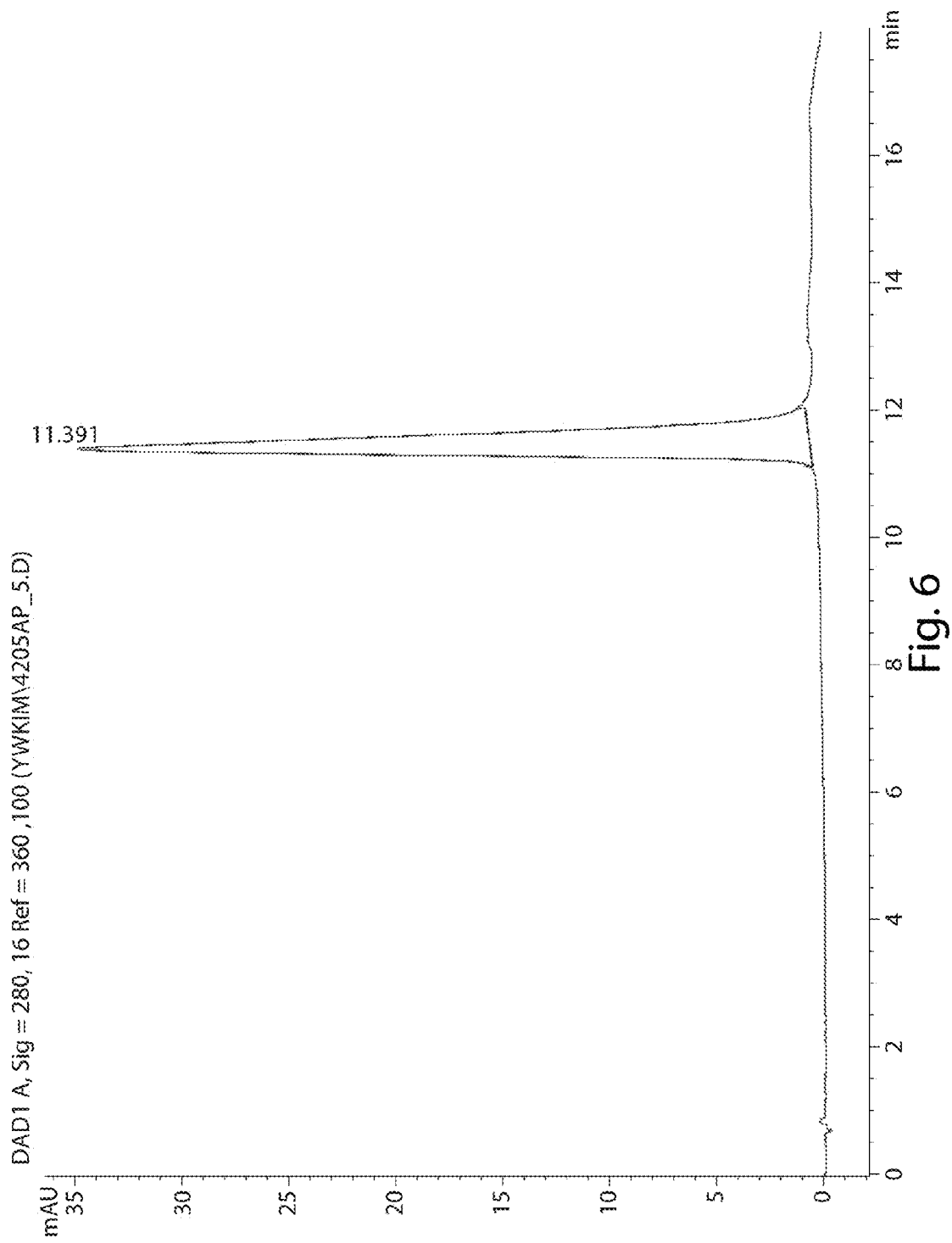
FIG. 6. HPLC chromatogram of purified peptide 4. 50-85% B for 0-14 min; 85-50% for 14-18 min on an Agilent $C_{18}$ reverse phase column (3.5×150 mm); A: 0.1% TFA in $H_2O$, B: acetonitrile; flow rate: 0.5 mL/min.
Figure 7:
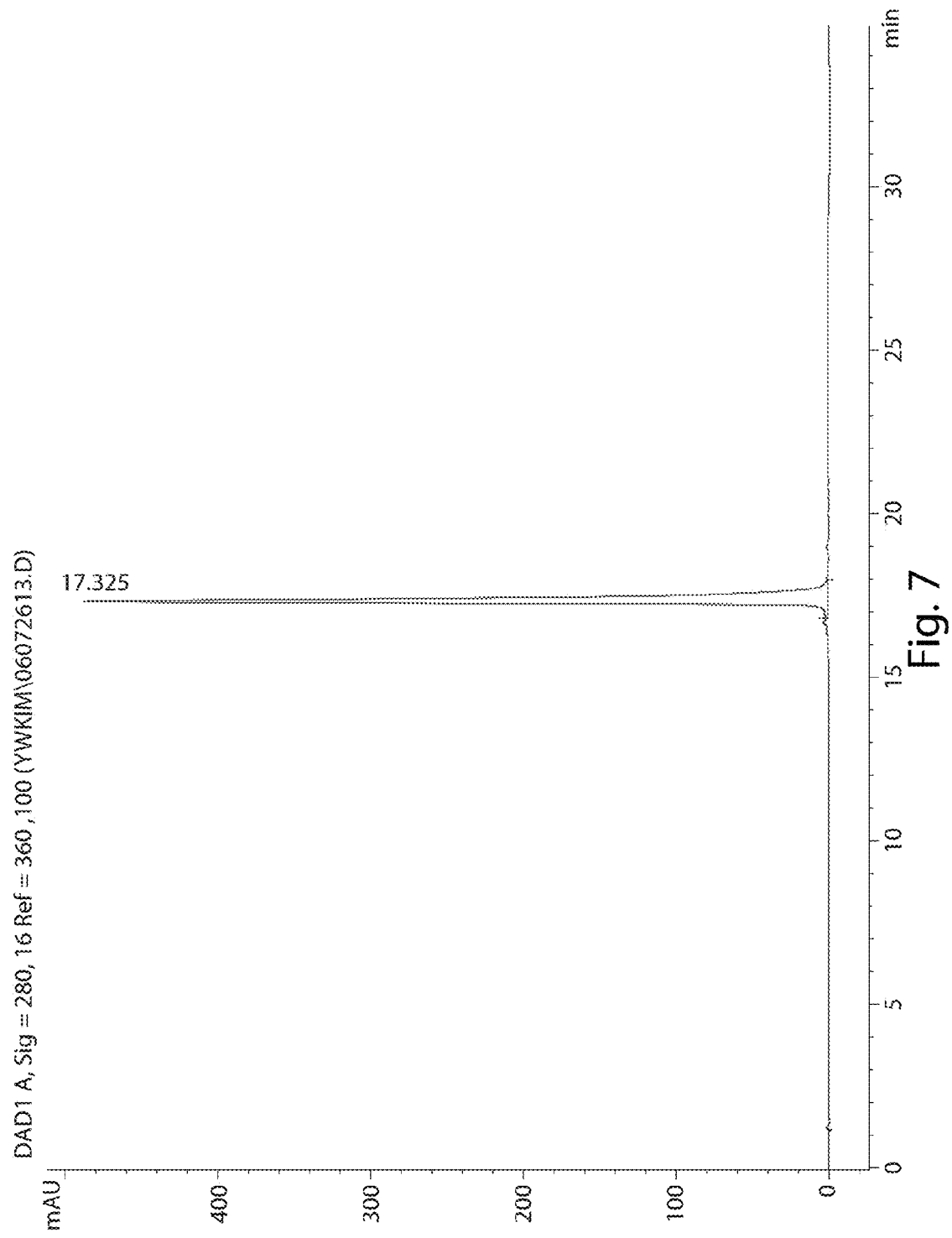
FIG. 7. HPLC chromatogram of purified peptide 6. 10-100% B for 0-20 min; 100% B for 20-25 min; 100-10% B for 25-30 min 10% B for 30-35 min on an Agilent $C_{18}$ reverse phase column (3.5×150 mm); A: 0.1% TFA in $H_2O$, B: acetonitrile; flow rate: 0.5 mL/min.
Figure 8:
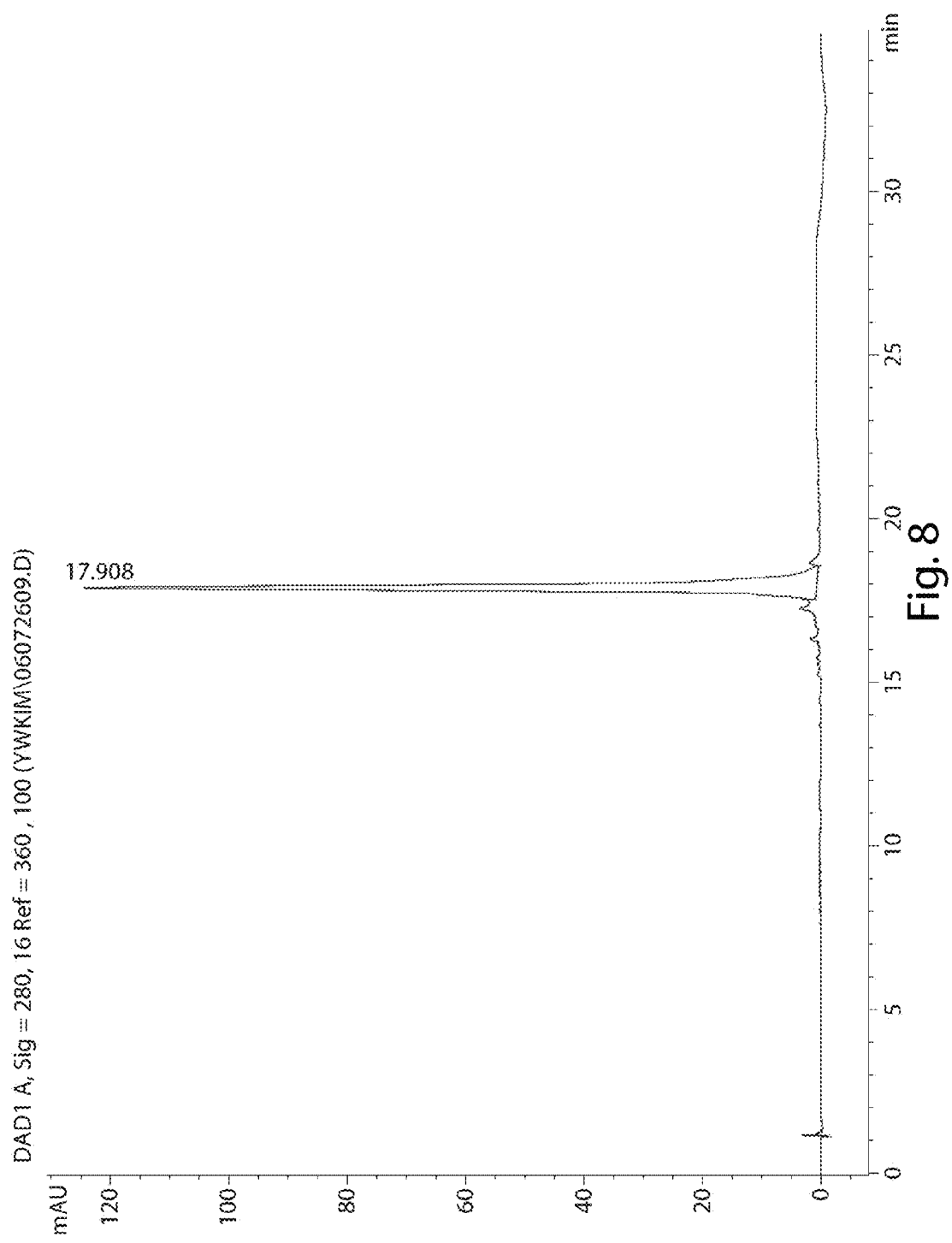
FIG. 8. HPLC chromatogram of purified peptide 5. 10-100% B for 0-20 min; 100% B for 20-25 min; 100-10% B for 25-30 min 10% B for 30-35 min on an Agilent $C_{18}$ reverse phase column (3.5×150 mm); A: 0.1% TFA in $H_2O$, B: acetonitrile; flow rate: 0.5 mL/min.
Figure 9:
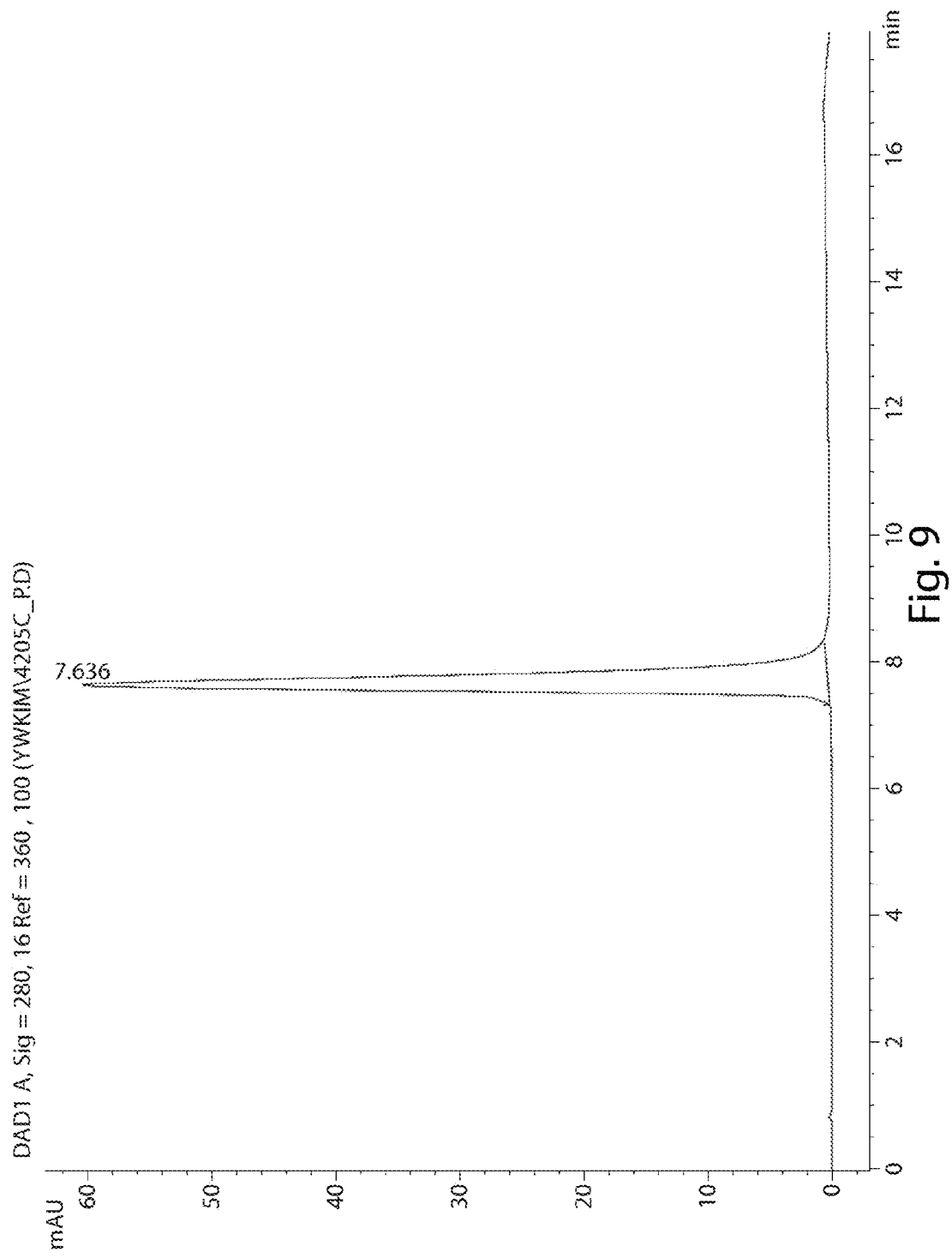
FIG. 9. HPLC chromatogram of purified peptide 8. 50-85% B for 0-14 min; 85-50% for 14-18 min on an Agilent $C_{18}$ reverse phase column (3.5×150 mm); A: 0.1% TFA in $H_2O$, B: acetonitrile; flow rate: 0.5 mL/min.
Figure 10:
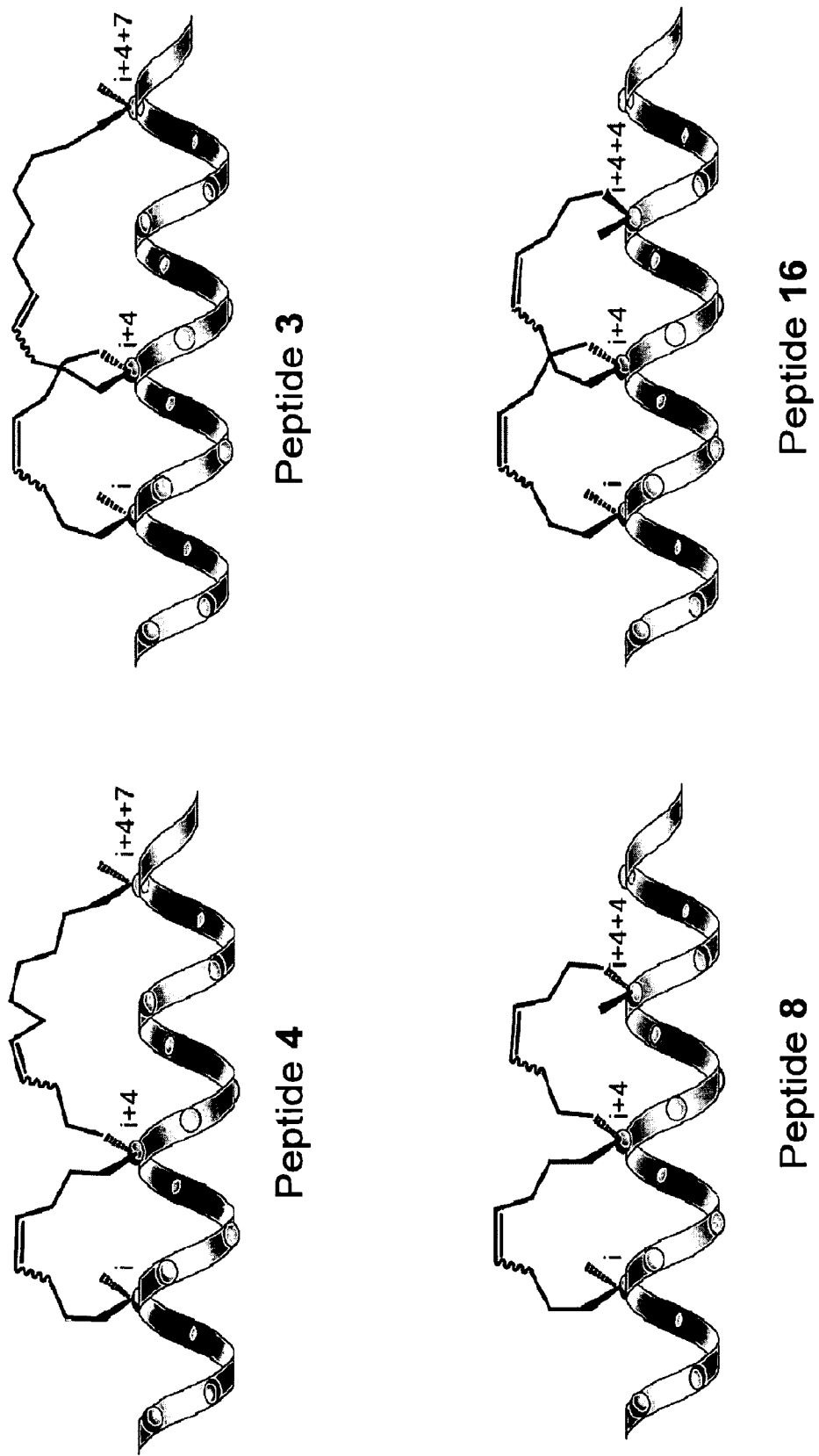
FIG. 10. Schematic structures of peptides 3, 4, 8, and 16.

Circular dichroism (CD) measurements were performed to determine the effects of stitching on the conformational preferences and thermal stability of the peptides. Stitched peptide 4 displayed the characteristic CD signature of alpha-helices, but was less affected by increasing temperature than single-stapled peptides 5 and 6 (FIGS. 2A, 2B, and 3B). Indeed, whereas 5 underwent a cooperative melting transition at 57° C., 4 retained more than 50% of its alpha-helicity even at 95° C. (see FIG. 4 for additional melting data). The greater helix stability of peptide 4 than 5 was accompanied by enhanced resistance to tryptic digestion; even in the presence of a vast molar excess of trypsin, the stitched peptide 4 exhibited a half-life of nearly three hours (172 min, FIG. 2C).

To investigate the possibility of forming stitched peptides having the i+4+4 constitution, we again applied the half-site rules to design peptide 7 (Table 1, entry XI). This substrate also underwent efficient RCM leading to a doubly crosslinked product. Computational analysis indicated that both olefins in the stitched product 8 (FIG. 1C) would have to be cis-configurated in order to form a stable alpha-helix. Though 8 clearly exhibited helical character greater than the stapled peptide 5 and less than that of the i+4+7 stitched peptide 4, the apparently complex melting behavior of 8 precluded accurate $T_m$ determination.

Experiment General.

Commercially available solvents and reagents were used as received unless otherwise indicated. Tetrahydrofuran (THF) was distilled from sodium metal in the presence of benzophenone under dry nitrogen. Dichloromethane ($CH_2Cl_2$) was distilled from calcium hydride under dry nitrogen. Reactions involving moisture-sensitive reagents were carried out under an inert atmosphere of dry argon. All glassware was dried prior to use, and all liquid transfers were performed using dry syringes and needles. All NMR spectra were recorded on a Varian Mercury 400 model spectrometer. Chemical shifts (δ) for $^1H$ and $^{13}C$ NMR spectra are reported in ppm relative to residual solvent protons or carbons, respectively. High resolution ESI mass spectra were obtained using a LCT mass spectrometer (Micromass Inc., Beverly, Mass.). Peptides were purified by reverse-phase HPLC with a 9.4×250 mm Agilent $C_{18}$ reverse phase column using an Agilent 1100 series HPLC. Analysis of the purified peptides was performed on an Agilent 1100 series LC/MSD electrospray trap with a 3.5×150 mm Agilent $C_{18}$ reverse phase column.

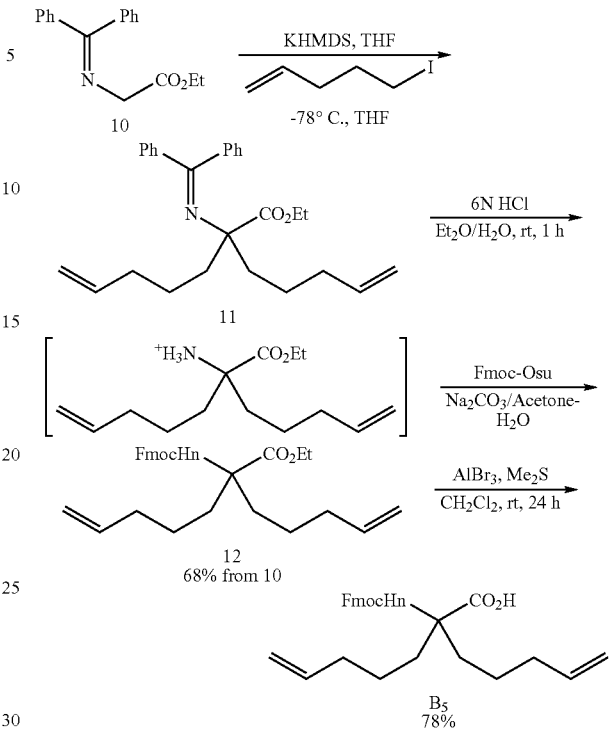

Scheme 1. Synthesis of Fmoc-protected bis-pentenyl glycine $B_5$

Ethyl 2-(diphenylmethyleneamino)-2-(pent-4-enyl)hept-6-enoate (11)

A procedure previously described for dialkylation of N-(diphenylmethylene)glycine ethyl ester was used after modifications (see Denmark, S. E.; Stavenger, R. A.; Faucher, A.-M.; Edwards, J. P. *J. Org. Chem.* 1997, 62, 3375-3389): To a stirred solution of N-(diphenylmethylene)glycine ethyl ester 10 (13.63 g, 51 mmol) in THF (250 mL) was added a solution of KHMDS (11.2 g, 56.1 mmol, 1.1 equiv.) in THF (56 mL) via a cannula at −78° C. over 15 min. After stirring at −78° C. for 1 h, the resulting orange-colored solution was treated with 5-iodo-1-pentene (12 g, 61.2 mmol, 1.2 equiv.). The reaction mixture was allowed to warm to room temperature and stirred for 2 h. The resulting suspension was cooled to −40° C. and another solution of KHMDS (15.3 g, 76.5 mmol, 1.5 equiv.) in THF (77 mL) was added via a cannula over 15 min and stirred for 1 h. 5-iodo-1-pentene (16 g, 81.6 mmol, 1.6 equiv.) was then quickly added to the burgundy-colored mixture, and the reaction was left to warm to room temperature overnight (16 h). The reaction was quenched by addition of saturated $NH_4Cl$ solution in water (100 mL). The organics were extracted with ethyl acetate (2×150 mL), washed with $Na_2S_2O_3$ solution and then with brine. The organic layer was dried over $MgSO_4$, filtered, and concentrated under reduced pressure. The resulting residue was dried in vacuo overnight and used for the next reaction without further purification: $^1$H-NMR (400 MHz, $CDCl_3$) δ 7.83-7.12 (m, 10H), 5.80 (m, 2H), 5.02 (dd, J=17.2, 1.6 Hz, 2H), 4.96 (dd, J=10.4, 1.6 Hz, 2H), 3.74 (q, J=6.8 Hz, 2H), 2.05 (dd, J=14.0, 7.2 Hz, 4H), 1.92 (m, 4H), 1.45 (m, 4H), 1.13 (t, J=6.8 Hz, 3H); $^{13}$C-NMR (100 MHz, $CDCl_3$) δ 174.8, 166.0, 141.3, 138.9, 128.5, 128.2, 127.9, 115.0, 69.2, 60.5, 37.5, 34.4, 23.3, 14.2; HRMS (ESI) m/z for $C_{27}H_{34}NO_2$ [M+H]$^+$ calcd 404.2589. found 404.2577.

Ethyl 2-(((9H-fluoren-9-yl)methoxy)carbonylamino)-2-(pent-4-enyl)hept-6-enoate (12)

To a stirred solution of crude ethyl 2-(diphenylmethyleneamino)-2-(pent-4-enyl)hept-6-enoate 11 (18.2 g, 45.1 mmol) in ethyl ether (200 mL) was added a 6N solution of hydrochloric acid (45 mL) at 0° C. over 45 min and the resulting mixture was stirred for another 15 min. The organics were extracted in ethyl ether (2×100 mL), and the combined etherial layer was concentrated. The residue was dissolved in acetone (75 mL), to which a solution of N-(9-fluorenylmethoxycarbonyloxy)succinimide (16 g, 47.5 mmol, 1.05 equiv.) in acetone (75 mL) and a solution of sodium carbonate (19.1 g, 180.4 mmol, 4.0 equiv.) in water (150 mL) were consecutively added. The resulting mixture was stirred at room temperature for 16 h. The product was extracted with ethyl acetate (2×150 mL) and the combined organic layer was dried over MgSO$_4$, filtered, and concentrated under reduced pressure. The resulting residue was purified by silica gel column chromatography (eluting with 7% ethyl acetate in n-hexanes) to give 12 as a white solid: $^1$H-NMR (400 MHz, CDCl$_3$) δ 7.77 (d, J=7.2 Hz, 2H), 7.62 (d, J=8.0 Hz, 2H), 7.40 (t, J=7.2 Hz, 2H), 7.32 (dt, J=7.2, 0.8 Hz, 2H), 5.90 (br s, 1H), 5.75 (m, 2H), 4.99 (d, J=17.6 Hz, 2H), 4.95 (d, J=11.2 Hz, 2H), 4.39 (d, J=6.8 Hz, 2H), 4.25 (m, 3H), 2.35 (dt, J=12.8, 4.0 Hz, 2H), 2.02 (m, 4H), 1.76 (dt, J=12.8, 4.0 Hz, 2H) 1.39 (m, 2H), 1.30 (t, J=7.2 Hz, 3H), 1.06 (m, 2H); $^{13}$C-NMR (100 MHz, CDCl$_3$) δ 174.2, 154.0, 144.2, 141.6, 138.5, 127.9, 127.3, 125.3, 120.2, 115.1, 66.3, 64.2, 62.1, 47.6, 35.3, 33.6, 23.6, 14.5; HRMS (ESI) m/z for $C_{29}H_{36}NO_4$ [M+H]$^+$ calcd 462.2644. found 462.2637.

2-(((9H-Fluoren-9-yl)methoxy)carbonylamino)-2-(pent-4-enyl)hept-6-enoic acid (B$_5$)

A procedure previously described for dealkylation of esters was used after modifications (see Node et al., *J. Org. Chem.* 1981, 46, 1991): To a stirred solution of aluminum bromide (22.4 g, 84.0 mmol, 3.0 equiv.) in methyl sulfide (90 mL) was slowly added a solution of ethyl 2-(((9H-fluoren-9-yl)methoxy)carbonylamino)-2-(pent-4-enyl)hept-6-enoate 12 (12.7 g, 27.5 mmol) in dichloromethane (90 mL) at 0° C. over 15 min. The resulting mixture was allowed to warm to room temperature and stirred for 24 h. The reaction mixture was poured into water and acidified with a diluted HCl. The product was extracted with dichloromethane (2×100 mL) and the combined organic layer was washed with brine, dried over MgSO$_4$, and concentrated under reduced pressure. The residual yellowish solid was purified by silica gel column chromatography (eluting with 7% methanol in dichloromethane) to give B$_5$ as a white solid: $^1$H-NMR (400 MHz, CDCl$_3$) δ 9.94 (bs, 1H), 7.78 (d, J=7.6 Hz, 2H), 7.61 (d, J=7.6 Hz, 2H), 7.41 (t, J=7.6 Hz, 2H), 7.33 (dt, J=7.6, 0.8 Hz, 2H), 5.75 (m, 2H), 5.00 (d, J=18.8 Hz, 2H), 4.96 (d, J=11.6 Hz, 2H), 4.42 (d, J=6.8 Hz, 2H), 4.23 (t, J=6.8 Hz, 1H), 2.34 (dt, J=12.8, 3.6 Hz, 2H), 2.04 (m, 4H), 1.82 (dt, J=12.8, 3.6 Hz, 2H) 1.40 (m, 2H), 1.17 (m, 2H); $^{13}$C-NMR (100 MHz, CDCl$_3$) δ 179.2, 154.2, 144.1, 141.6, 138.3, 128.0, 127.3, 125.2, 120.3, 115.2, 66.5, 64.1, 47.5, 35.2, 33.6, 23.5; HRMS (ESI) m/z for $C_{27}H_{31}NO_4$ [M+H]$^+$ calcd 434.2331. found 434.2334.

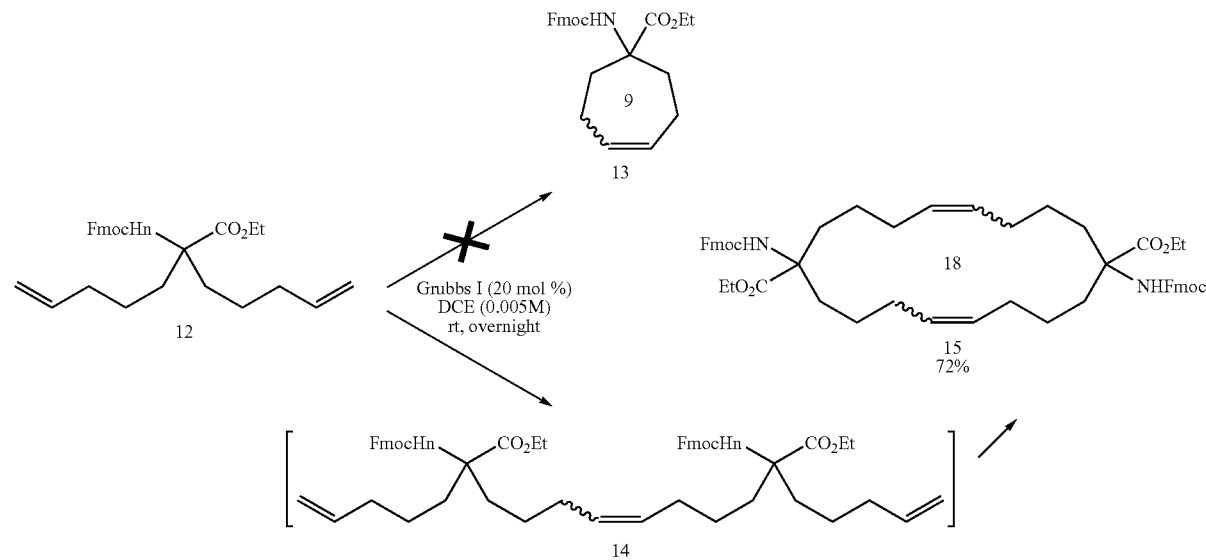

Scheme 2. Metathesis of Fmoc-protected bis-pentenyl glycine ethyl ester 12

Ring closing metathesis of Fmoc-protected bis-pentenyl glycine ethyl ester 12

A solution of Fmoc-protected bis-pentenyl glycine ethyl ester 12 (116 mg, 0.25 mmol) in 1,2-dichloroethane (degassed, 50 mL for 0.005M) was stirred in the presence of Grubbs catalyst 1$^{st}$ generation (41 mg, 0.05 mmol, 20 mol %) at room temperature. After 19 hours, LC/MS data from the reaction mixture showed that only 5% of unreacted starting material was left and that at least five different isomers of dimeric cyclized product 15 were formed. Presence of monomeric cyclized product 13 was not detected. Intermediate 14 was not detected, indicating the second metathesis (intramolecular RCM) might have proceeded rapidly. After the solvent was removed under reduced pressure, the products were purified by silica gel column chromatography (eluting with 12.5% ethyl acetate in n-hexanes) as a white foam: $^1$H-NMR (400 MHz, CDCl$_3$) δ 7.78-7.75 (m, 4H), 7.65-7.61 (m, 4H), 7.42-7.37 (m, 4H), 7.34-7.29 (m, 4H), 6.01 (br s, 0.6H), 5.95 (br s, 0.3H), 5.92 (br s, 1.1H), 5.19-5.11 (m, 4H), 4.39 (d, J=7.2 Hz, 4H), 2.47-2.41 (m, 2H), 2.26-2.20 (m, 4H), 2.06-1.66 (m, 10H), 1.54-1.31 (m, 10H), 1.04-0.76 (m, 4H); HRMS (ESI) m/z for C$_{54}$H$_{66}$N$_3$O$_8$ [M+NH$_4$]$^+$ calcd 884.4850. found 884.4857.

Peptide Synthesis.

The peptides were prepared using Fmoc chemistry on Rink Amide MBHA resin (NovaBiochem) with a loading capacity of 0.66 mmol/g. The dry resin was swelled with 1-methyl-2-pyrrolidinone (NMP) for 15 min before use. The Fmoc protecting group was removed by treatment with 25% piperidine in NMP (3×5 min). Natural amino acids were coupled for 30 min using 2-(6-chloro-1-H-benzotriazole-1-yl)-1,1,3,3-tetramethylaminium hexafluorophosphate (HCTU) as the activating agent, 10 equivalents of Fmoc-protected amino acid, and 20 equivalents of diisopropyl ethylamine (DIPEA) in NMP. For the coupling of unnatural olefin-bearing amino acids, a reaction time of 2 hours was used with 4 equivalents of amino acid and 8 equivalents of DIPEA. After each coupling or deprotecting reaction, the resin was washed with NMP (3×3 min), CH$_2$Cl$_2$ (5×3 min), and NMP (3×3 min). After the final Fmoc deprotection, the free N-terminus was acetylated by treatment with 30 equivalents of acetic anhydride and 60 equivalents of DIPEA in NMP for 2 hours.

Metathesis and Purification.

Ring closing metathesis of resin-bound N-terminal capped peptides was performed using 20 mol % Grubbs catalyst in degassed 1,2-dichloroethane (DCE) for 2 hours at room temperature. When metathesis was incomplete, the reaction solution was drained and the resin was treated with fresh catalyst for another 2 hours. The resin was washed with DCE (5×3 min), CH$_2$Cl$_2$ (5×3 min), and methanol (3×3 min) and then dried in vacuo overnight. The peptides were cleaved from the resin by treatment with a mixture of trifluoroacetic acid/triisopropylsilane/water (95/2.5/2.5) for 2 hours and precipitated by addition of cold diethyl ether. The precipitate was collected by centrifugation and washed twice with cold diethyl ether. The crude peptides were dissolved in methanol, filtered to remove resin, and purified by reverse phase HPLC to give pure peptide products.

Electrospray Ionization Mass Spectrometry (ESI-MS).

Peptide 9. ESIMS for C$_{75}$H$_{111}$N$_{20}$O$_{21}$ [M+H]$^+$ calcd 1627.8. found 1627.6.

Peptide 4. ESIMS for C$_{91}$H$_{137}$N$_{20}$O$_{19}$ [M+H]$^+$ calcd 1814.0. found 1814.0.

Peptide 6. ESIMS for C$_{82}$H$_{123}$N$_{20}$O$_{19}$ [M+H]$^+$ calcd 1691.9. found 1691.6.

Peptide 5. ESIMS for C$_{85}$H$_{129}$N$_{20}$O$_{19}$ [M+H]$^+$ calcd 1734.0. found 1734.0.

Peptide 8. ESIMS for C$_{88}$H$_{131}$N$_{20}$O$_{19}$ [M+H]$^+$ calcd 1772.0. found 1772.0.

Circular Dichroism.

Peptides were dissolved in water to described concentrations, and the concentrations were determined by absorbance spectroscopy (extinction coefficient for tryptophan, $\epsilon_{280}$=5690 cm$^{-1}$). Circular dichroism spectra were collected on a Jasco J-710 spectropolarimeter equipped with a temperature controller using the following standard measurement parameters: 0.5 nm step resolution, 20 nm/sec speed, 10 accumulations, 1 sec response, 1 nm bandwidth, 0.1 cm path length. All spectra were converted to a uniform scale of molar ellipticity after background subtraction. Temperature-dependent CD spectra of each peptide (94-100 µM) were recorded at varying temperatures (4° C. and every 10° C. from 10° C. to 90° C.) from 260 to 185 nm. CD measurements with varying concentrations (18, 48, 70, and 118 µM) of peptide 4 were performed at 20° C. To generate thermal unfolding curves, the ellipticity at 222 nm for each peptide (94-100 µM) was measured every 1° C. from 4 to 95° C. with temperature slope of 3° C./min. To obtain T$_m$, we analyzed the thermal unfolding curves using a two-state model as previously described with 95% confidence interval (see Favrin, G.; Irbäck, A.; Samuelsson, B.; Wallin, S. *Biophysic. J.* 2003, 85, 1457-1465). Stitched peptides 4 and 8 did not have a cooperative melting transition point in this temperature range, and therefore their T$_m$ could not determined by this method. However, peptide 4 retained more than 50% of their alpha-helicity even at 95° C.

Peptide Digestion Assay.

0.4 mL of trypsin immobilized on agarose (Pierce, catalog #20230) was washed with 0.8 mL of a digestion buffer (0.1 M NH$_4$HCO$_3$ buffer, pH 8.0). The gel was separated from the buffer after each wash by centrifugation. The washed enzyme was suspended in 1.6 mL of the digestion buffer. 350 µL of a peptide solution (24 µM) in the digestion buffer was mixed with 150 µL of the enzyme suspension and the resulting mixture was incubated with rapid shaking at room temperature for 10, 30, 90, 135, 180 minutes. The incubation was quenched by filtering off the enzyme, and the residual substrate in the filtrate was quantified by HPLC-based peak detection at 280 nm. The digestion assay displayed first order kinetics. The half-life, t$_{1/2}$, was determined by linear regression analysis using Kaleida graph (Synergy Software) from a plot of ln [S] versus time (min) (t$_{1/2}$=ln 2/slope, slope: 4.04±0.16×10$^{-5}$ min$^{-1}$ (4); 7.11±0.66×10$^{-5}$ min$^{-1}$ (5)).

Molecular Modeling Study.

A Monte Carlo conformational search was performed to locate all low energy conformations of each linker in the helical state. To generate starting conformations for the MC conformational search, a 15-residue polyalanine peptide was built with a right-handed helical conformation using Macro-Model's Maestro GUI (Macromodel, v.9.1, Schrodinger, LLC, New York, N.Y., 2005). Hydrocarbon cross-links were manually added, and were fully minimized while all non-cross-linker atoms were held frozen. For each isomer, two distinct 10,000 step Monte Carlo conformational searches were run. For all calculations, energies were evaluated using the OPLS2005 force field, as implemented in Macromodel (Macromodel, v.9.1, Schrodinger, LLC, New York, N.Y., 2005). For all minimizations the Polak-Ribiere Conjugate Gradient (PRCG) method was employed, and the convergence criterion for the minimization of gradient norm was set to <0.05 kJ/mol-A. We employed the GB/SA solvation treatment (Still, W. C.; Tempczyk, A.; Hawlely, R. C.; Hendrickson, T. A., A General Treatment of Solvation for Molecular Mechanics. *J. Am. Chem. Soc.* 1990, 112, 6127-6129.), modeling the solvent as chloroform as all metathesis reactions were carried out in 1,2-dichloroethane. Bond dipole cutoffs were employed to truncate the electrostatic and GB terms. Non-bonded cutoffs were as follows: 8 Å in Van der Waals, 99999.0 Å in charge-charge (effectively infinite), 20$^{3/2}$ Å (89.4 Å) in charge-dipole, and 20 Å in dipole-dipole. Harmonic constraints (100 kJ/mol) were placed on each backbone dihedral angle to maintain the helical conformation throughout the search. At each step of the Monte Carlo search, 2-5 cross-linker dihedrals were randomly selected, and their values were adjusted by 0-180°. The C-terminal C—C bond adjacent to each olefin was temporarily broken during each step—allowing for dihedral perturbations along the cross-linker—and then reattached after dihedral modification. After each step up to 500 steps of minimization were performed—if convergence was not achieved in less steps—and conformations within 50 kJ of the global minimum were saved. After the search, all remaining structures were fully minimized, and all conformations within 15 kJ of the global minimum were kept, while redundant structures (RMSD<0.25 Å) were removed. The number of new structures obtained after pooling the conformations obtained from the second run with those obtained from the first run was insignificant, suggesting that conformational space had been fully explored.

Molecular Modeling Study of i,i+4,i+4+7 System (Peptide 4 Versus 3).

Figure 11:
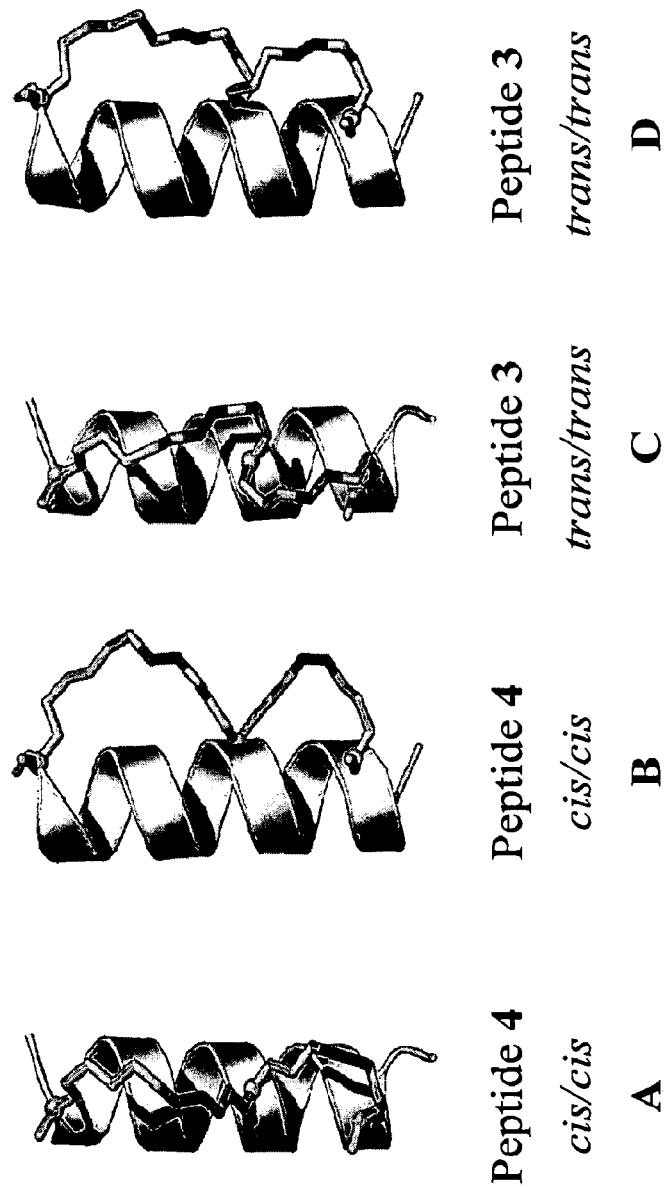
FIG. 11. Graphical representation of the global minimum peptide 4 (A and B) and peptide 3 (C and D). The N-termini lie on the bottom ends of the peptides. Views B and D depict ~90° rotations of A and C, respectively. The alpha-carbons attached to the staple are depicted as spheres, while the olefin moiety is colored red.

Molecular modeling suggests that the lowest energy double bond isomer of product 4 is lower in energy than the most stable isomer of 3 by ~15 kcal/mol (Table 6). This is in part due to three syn-pentane interactions that arise in product 3: two are located at the spiro junction while one is located at the N-terminal attachment of the staple (FIGS. 11, C and D). In the product 4, we also see a preference of ~2.5 kcal/mol for a cis double bond in the i,i+4 staple. Although there is no apparent enthalpic preference for either double bond orientation in the i,i+7 staple, the cis double bond seems to be entropically favored, since there are more low energy states present for this isomer (31 versus 18, Table 6).

TABLE 6

| i, i + 4, i + 4 + 7 | Energy (kcal/mol)$^a$ | | Conformations$^b$ | |
|---|---|---|---|---|
| | Peptide 4 | Peptide 3 | Peptide 4 | Peptide 3 |
| cis/cis | 0.1 (−466.4) | 15.3 (−451.2) | 31 | 25 |
| cis/trans | 0.0 (−466.5) | 15.8 (−450.7) | 18 | 61 |
| trans/cis | 2.5 (−464.0) | 14.9 (−451.6) | 16 | 32 |
| trans/trans | 2.4 (−464.1) | 15.0 (−451.5) | 9 | 45 |

$^a$Energy is that of global minimum relative to global minimum of lowest energy isomer; absolute energies are reported in parenthesis.
$^b$The number of conformations located within 15 kJ/mol (3.59 kcal) of the global minimum of each isomer.

Molecular Modeling Study of i,i+4,i+4+4 System (Peptide 8 Versus 16).

Figure 12:
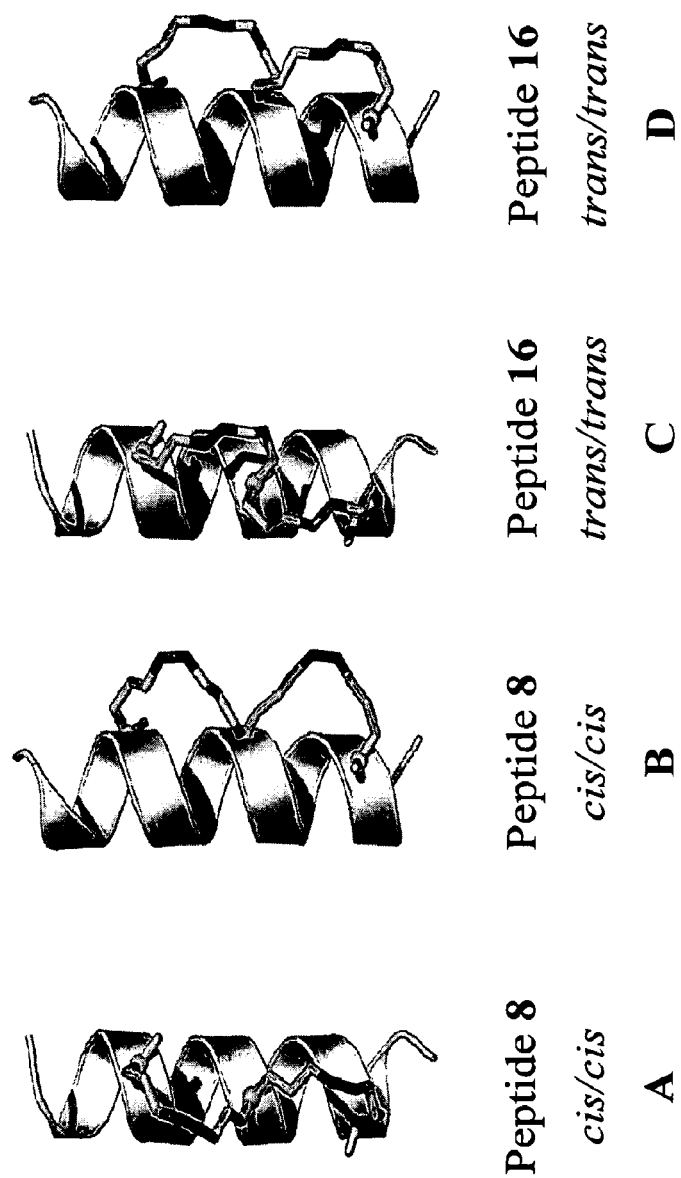
FIG. 12. Graphical representation of the global minimum peptide 8 (A and B) and peptide 16 (C and D) stitched peptides. The N-termini lie on the bottom ends of the peptides. Views B and D depict ~90° rotations of A and C, respectively. The α-carbons attached to the staple are depicted as spheres, while the olefin moiety is colored red.

Molecular modeling suggests that the lowest energy double bond isomer of product 8 is lower in energy than the most stable isomer of 16 by ~14 kcal/mol (Table 7). This is in part due to four syn-pentane interactions that are present in product 16: two are located at the spiro junction while one is located at each of the terminal attachments of the crosslink to the peptide backbone (FIGS. 12, C and D). We see that the cis/cis isomer of product 8 is the most energetically favorable one. The addition of a trans double bond in the i,i+4 linkage is unfavorable by ~2 kcal, while substituting the cis for a trans double bond in the i+4,i+4+4 staple costs ~6 kcal. Interestingly, the lowest energy isomer for the product 16 is the trans/trans isomer. Adding an N-terminal cis bond costs ~0.5 kcal, while making this substitution on the C-terminal linkage is disfavored by ~1.5 kcal.

TABLE 7

| i, i + 4, i + 4 + 4 | Energy (kcal/mol)$^a$ | | Conformations$^b$ | |
|---|---|---|---|---|
| | Peptide 8 | Peptide 16 | Peptide 8 | Peptide 16 |
| cis/cis | 0.0 (−462.0) | 15.6 (−446.3) | 4 | 16 |
| cis/trans | 6.1 (−455.9) | 14.1 (−447.9) | 12 | 8 |
| trans/cis | 2.3 (−459.7) | 15.0 (−446.9) | 8 | 17 |
| trans/trans | 8.0 (−453.9) | 13.5 (−448.5) | 19 | 8 |

$^a$Energy is that of global minimum relative to global minimum of lowest energy isomer; absolute energies are reported in parenthesis.
$^b$The number of conformations located within 15 kJ/mol (3.59 kcal) of the global minimum of each isomer.

Example of Multiple-Stitching.

Figure 13:
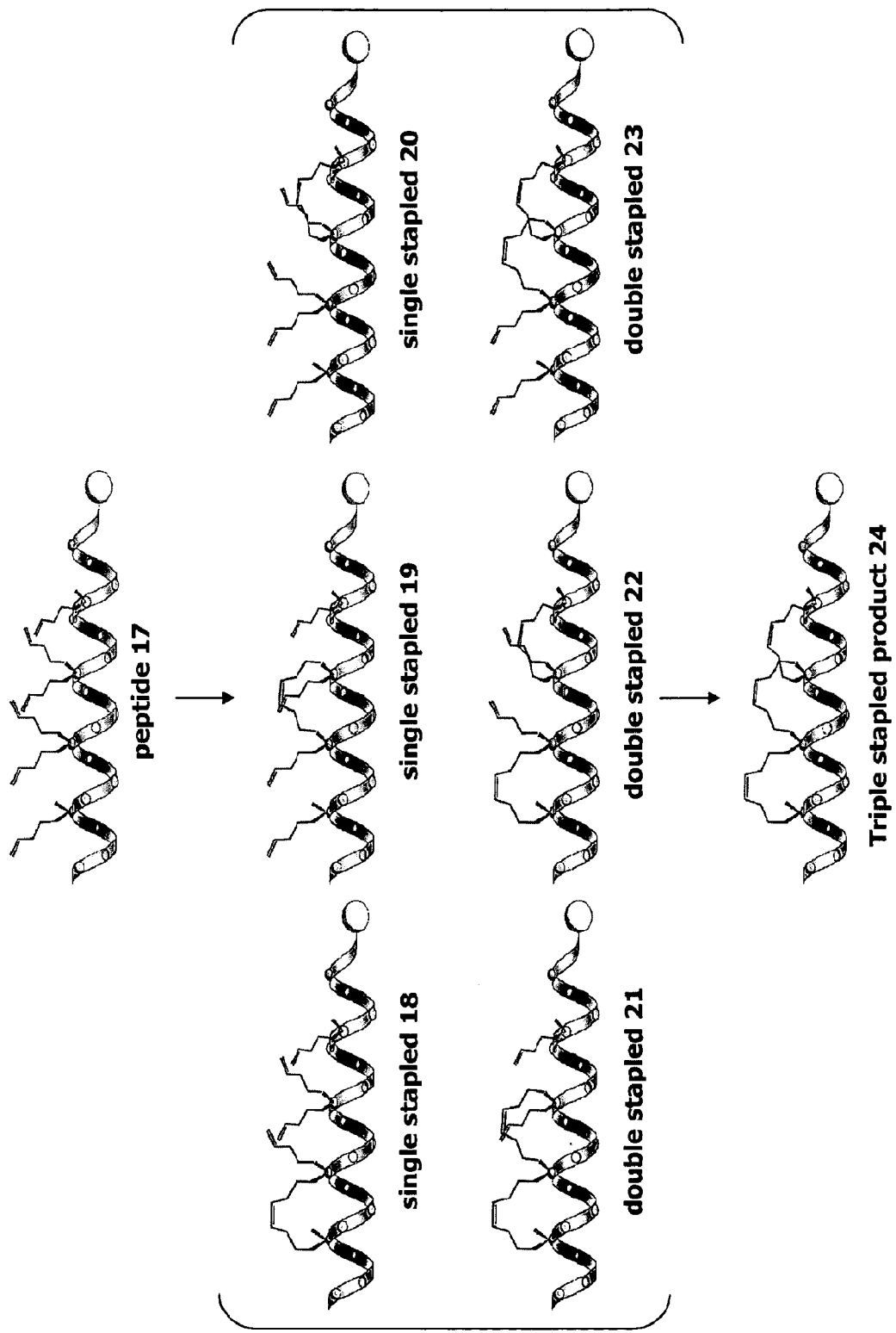
FIG. 13. Triple stitching via tandem ring-closing metathesis of polyalanine-based peptide (S5-Ala-Ala-Ala-B5-Ala-Ala-Ala-B5-Ala-Ala-Ala-S5) on resin.
Figure 14:
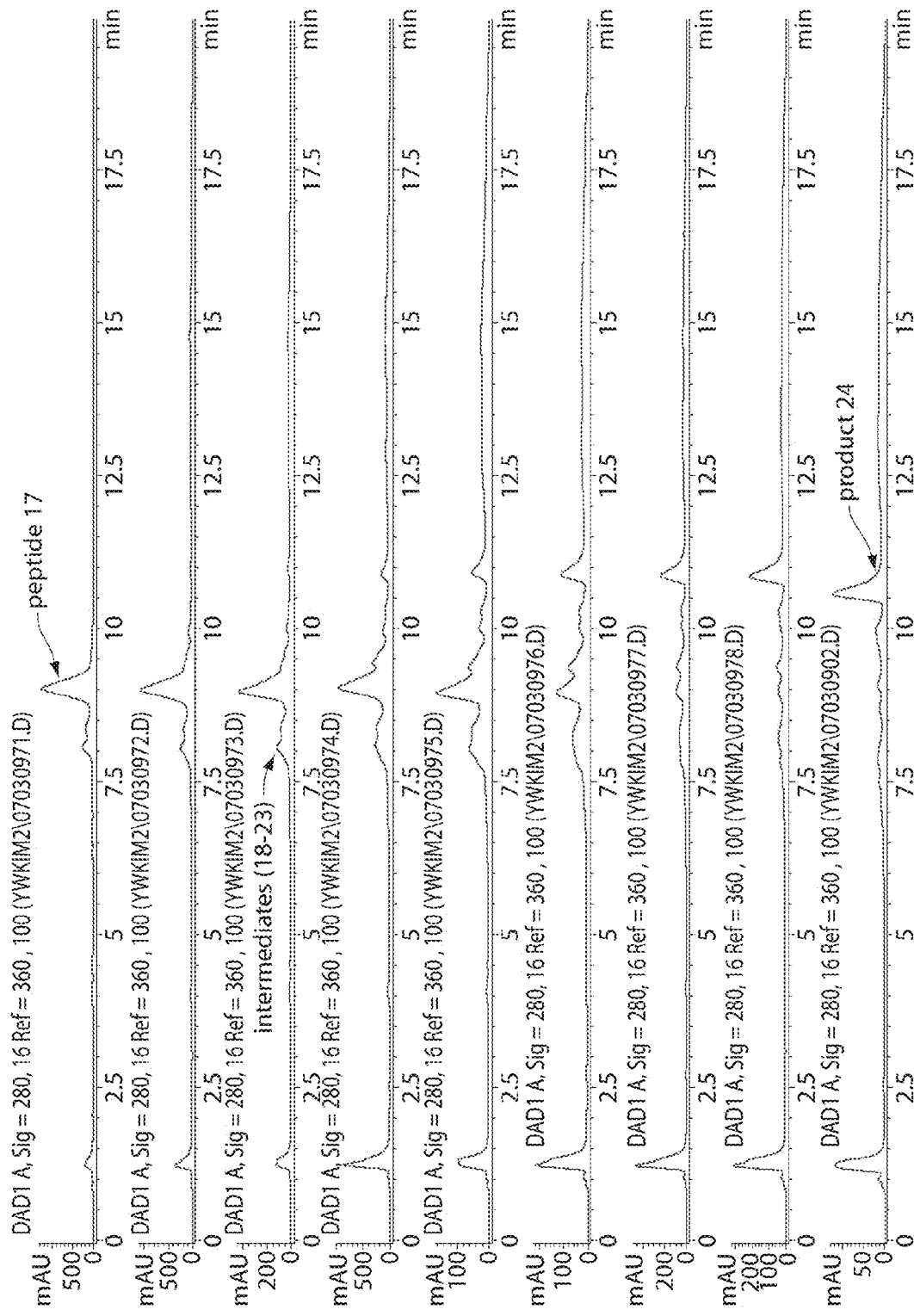
FIG. 14. HPLC chromatogram at 0, 5, 10, 20, 30, 60, 90, 120, 165 minutes of ring-closing metathesis of polyalanine-based peptide using 30% Grubbs catalyst FIG. 15. A model peptide bearing $B_5$ at i and i+4 (peptide 25) did not produce double stitched compound 27, and provided only singly stapled product 26. In addition, a model peptide containing $R_5$ at i and $S_5$ at i+4 position (peptide 28) did not undergo RCM. The results from this model study indicated that peptide 24 of FIG. 13 to be the most likely structure for the triply stitched product. This result suggest that four or more crosslinks also might be introduced to peptide system by rational design.
Figure 15:
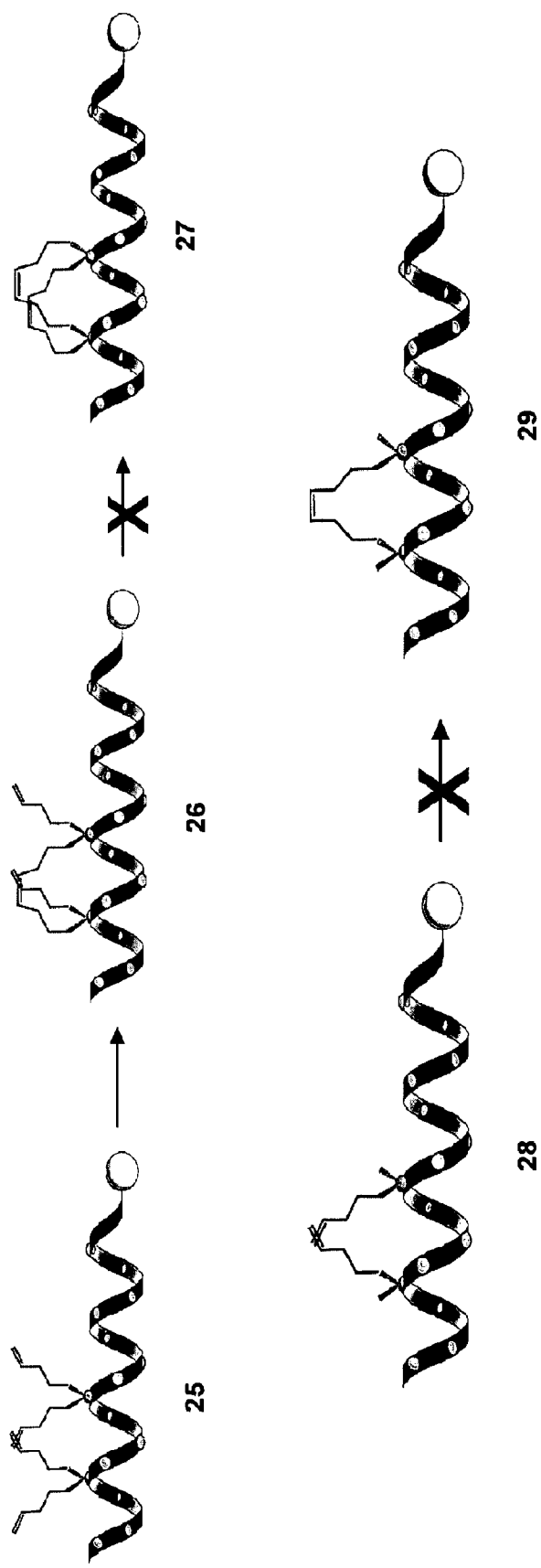
Figure 17:
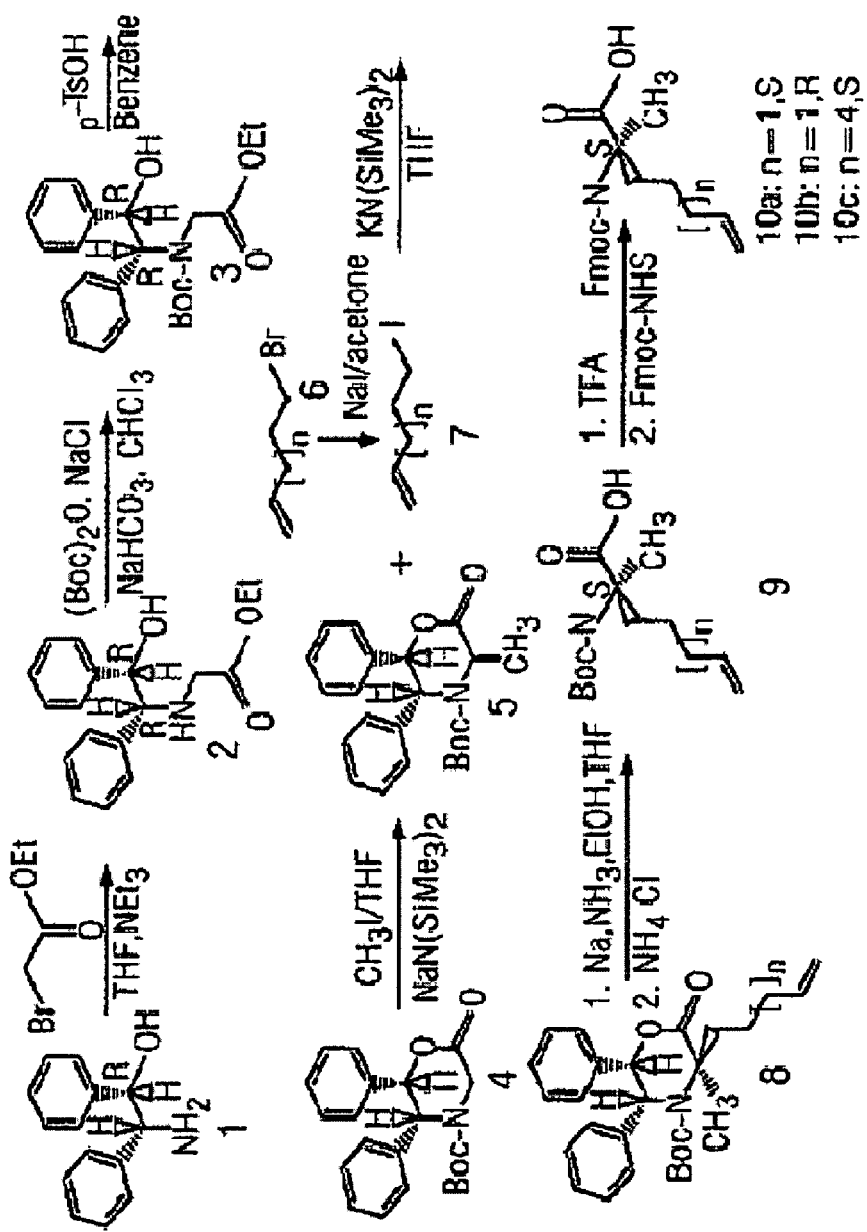
FIG. 17. Depiction of the synthesis of alpha-methyl-alpha-terminally unsaturated amino acids as described by U.S. Patent Application Publication No. 2005/0250680.
Figure 18:
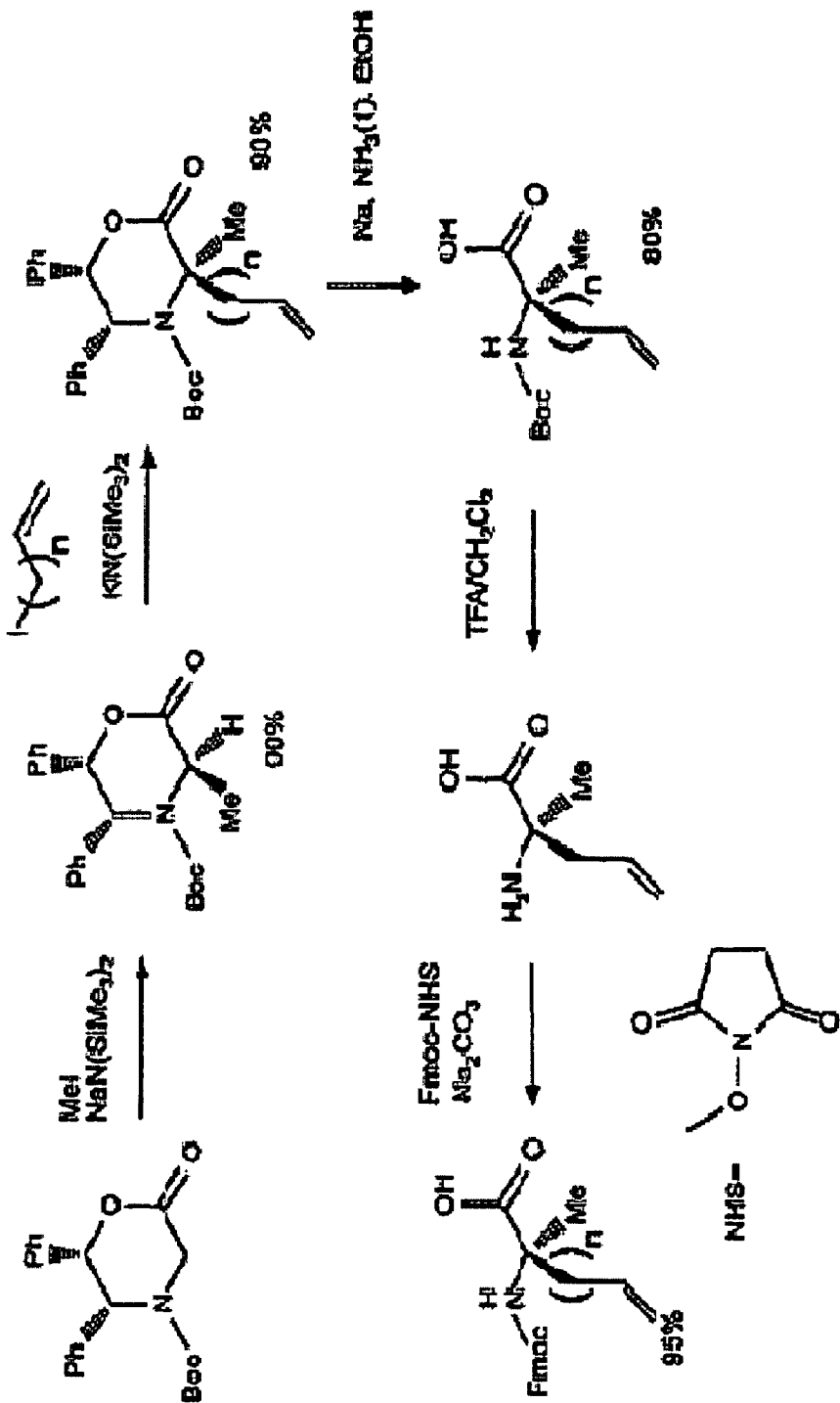
FIG. 18. Depiction of the synthesis of alpha-methyl-alpha-terminally unsaturated amino acids as described by U.S. Patent Application Publication No. 2006/0008848.
Figure 19:
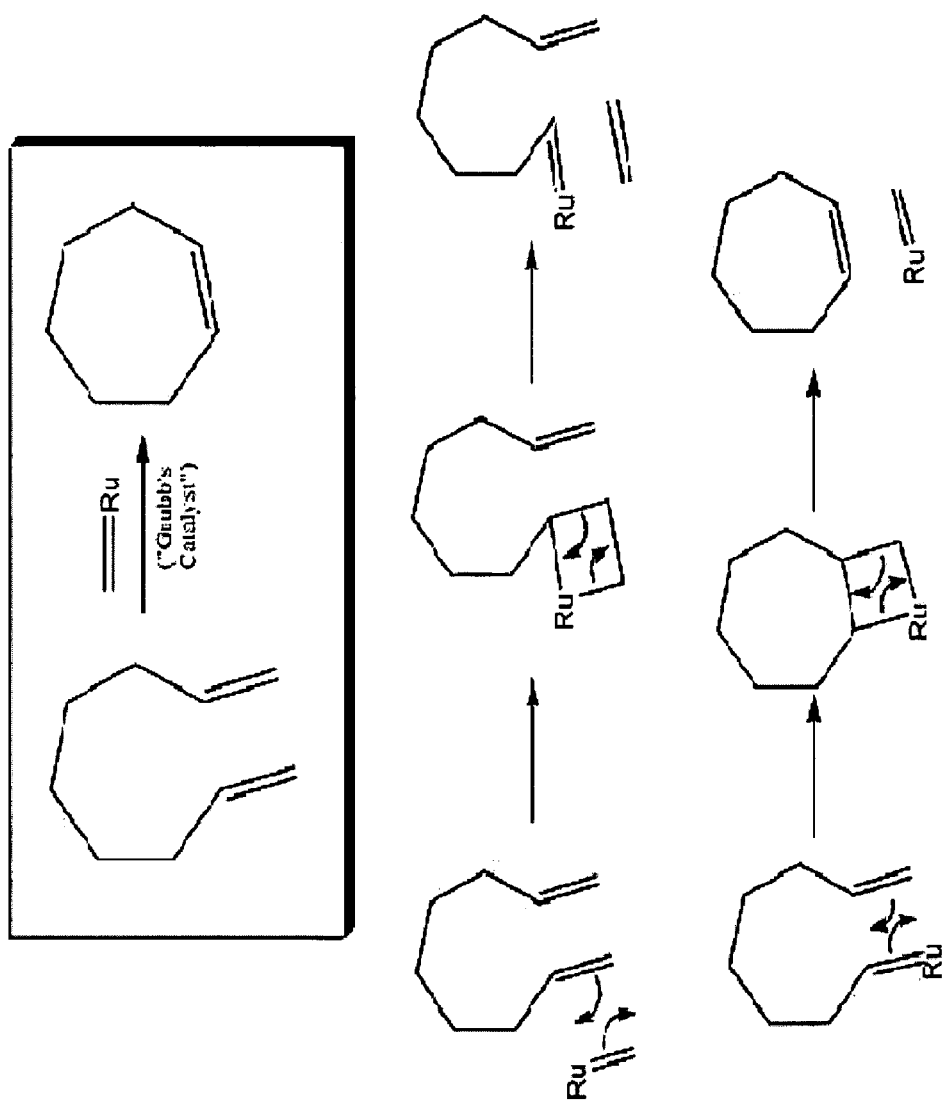
FIG. 19. Exemplary reaction mechanism for a ring closing metathesis (RCM) reaction using a ruthenium (Grubbs) catalyst.
Figure 20:
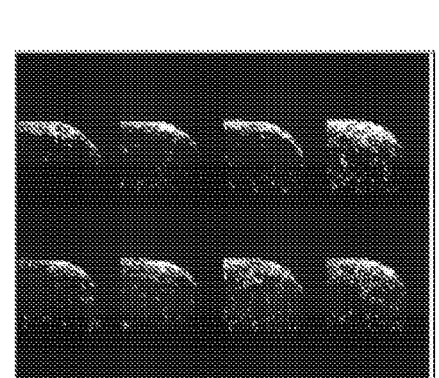
FIG. 20. Uptake of stitched peptides by Jurkat cells in a quantitative immunofluorescence assay. Stitched ("multiply stapled") peptides show compatible cell permeability compared to their singly "stapled" analogs.
Figure 21A:
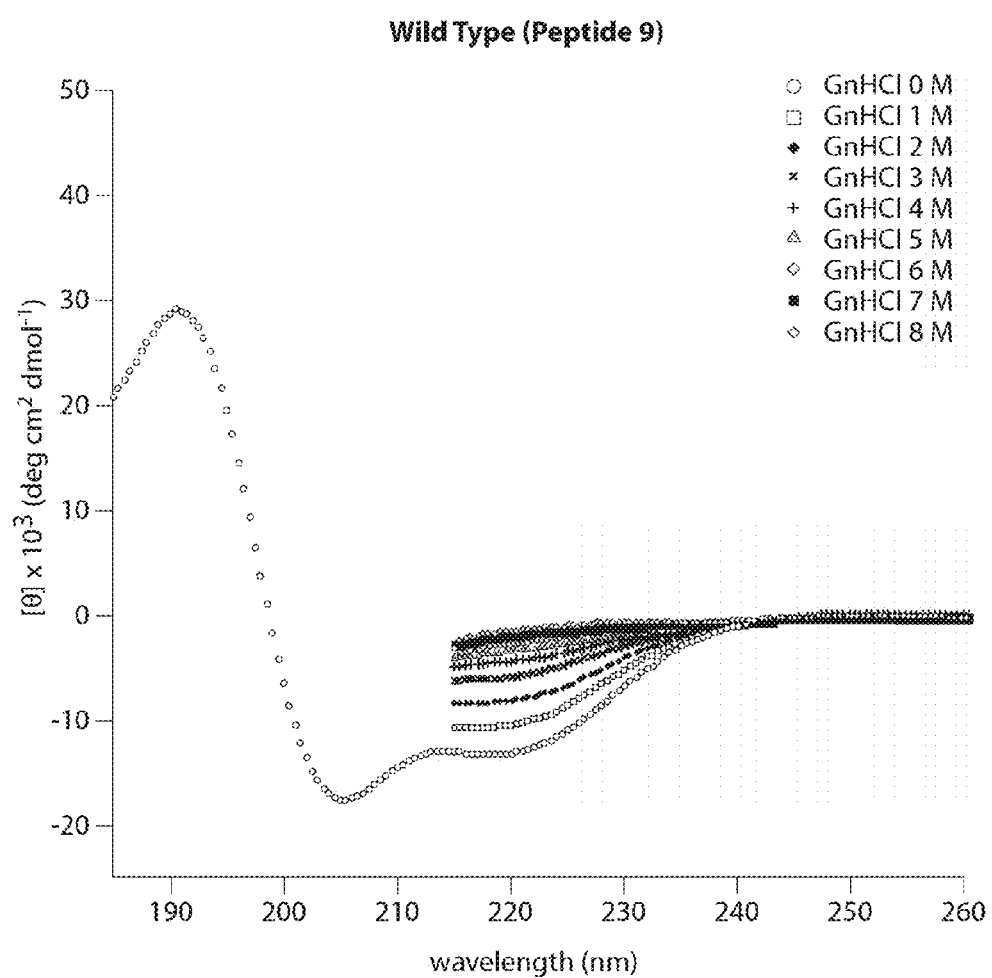
FIGS. 21A-21D. Stabilities of peptides against guanidine hydrochloride. Stitched peptide 4 displays a high level of stability against the denaturing agent as it remains fully helical even at extremely high concentrations of guanidine salt.
Figure 21B:
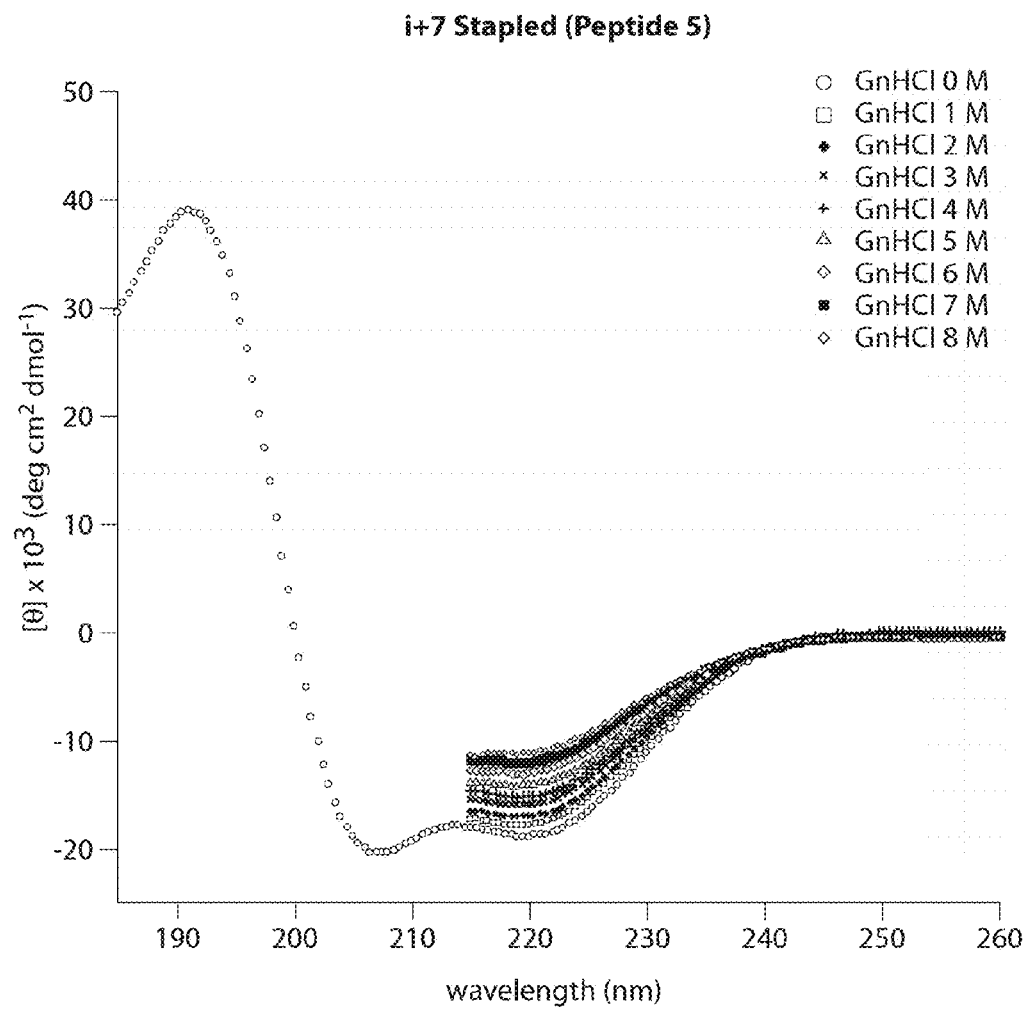
Figure 21C:
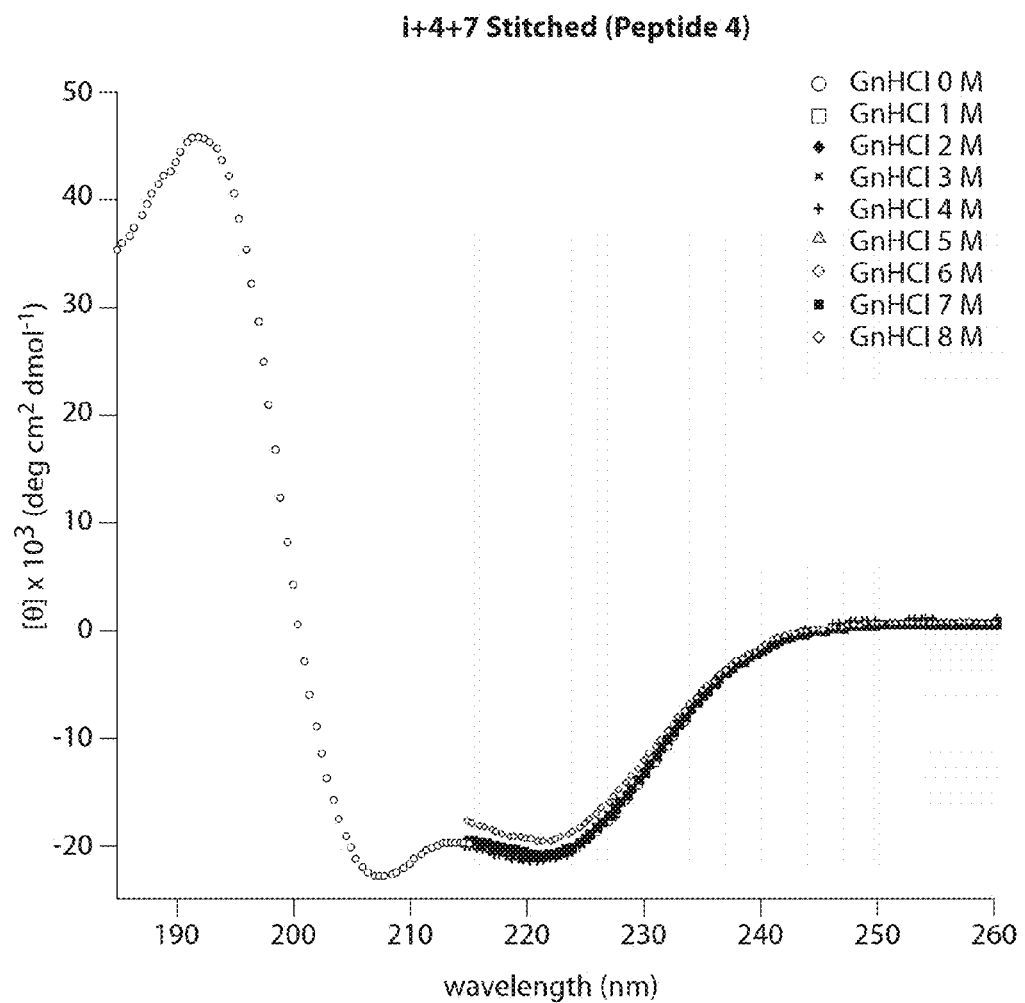
Figure 21D:
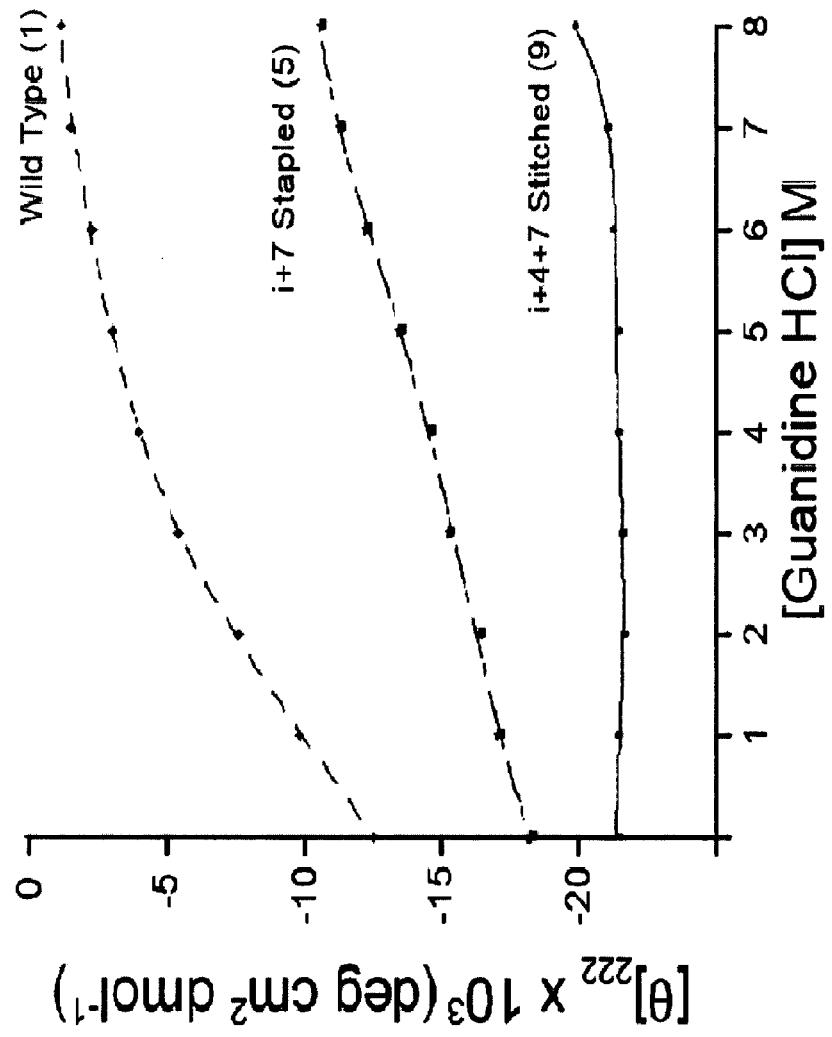
Figure 22A:
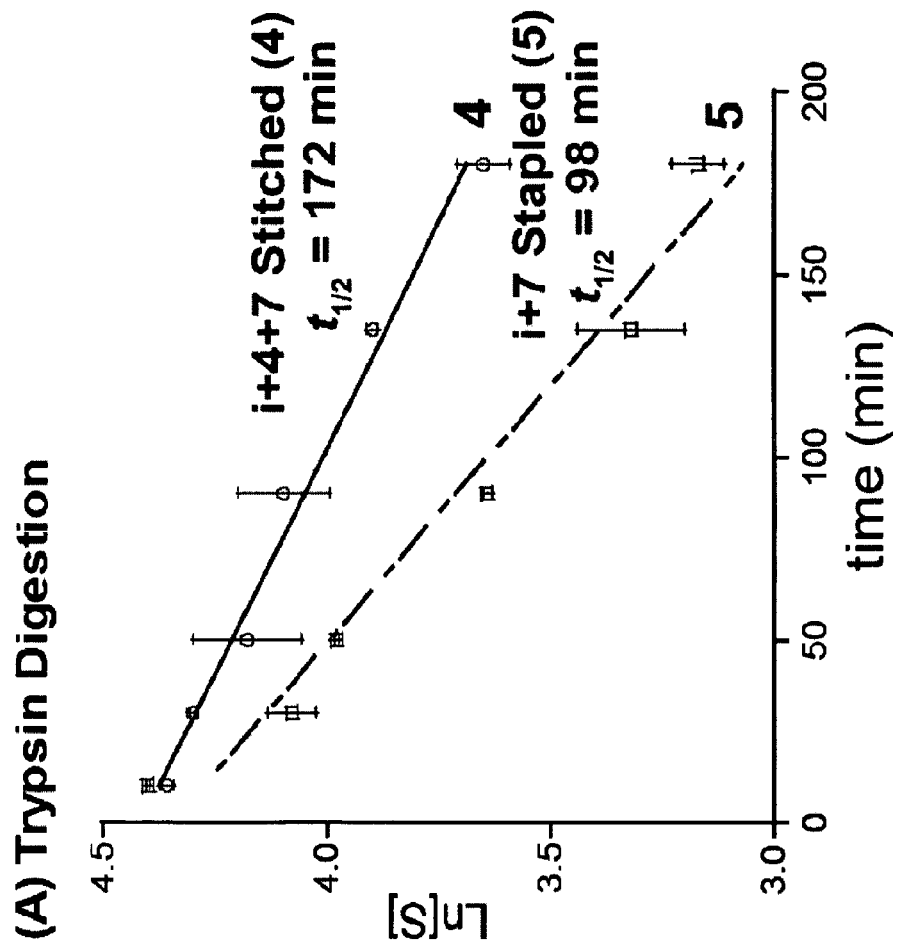
FIGS. 22A-22B. Stabilities of peptides against proteases. Stitched peptide 4 shows a higher level of stability against both trypsin (A) and chymotrypsin (B) than stapled peptide 5.
Figure 22B:
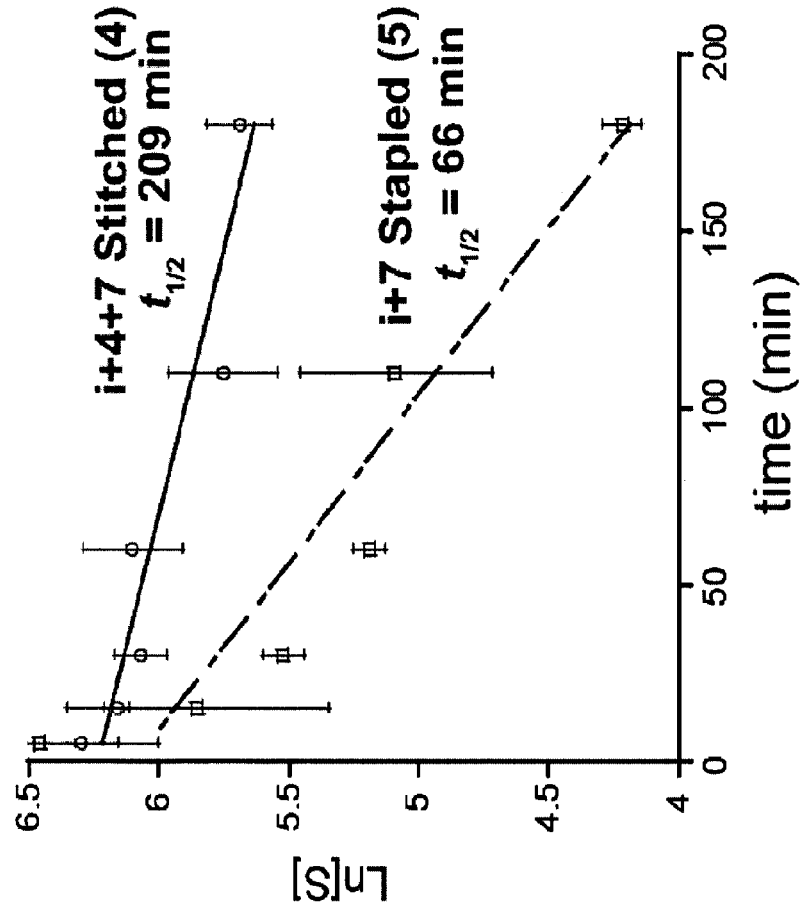
Figure 23A:
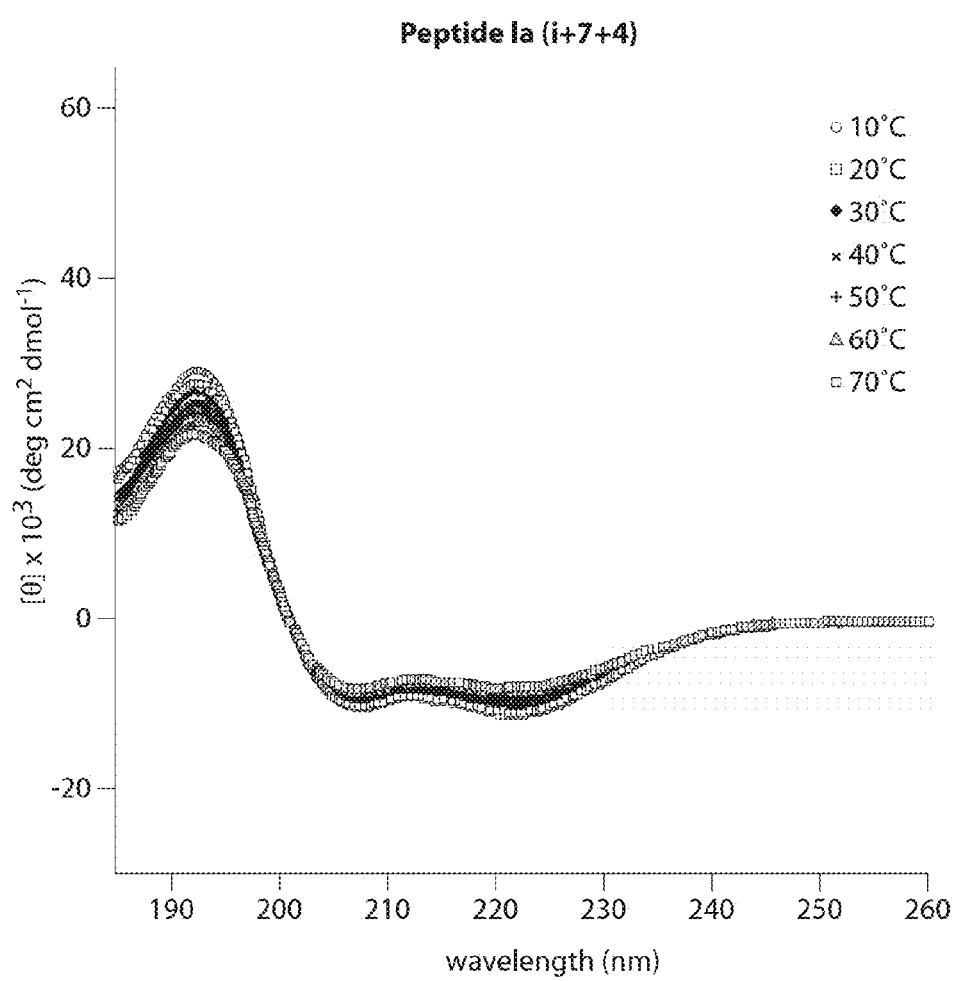
FIGS. 23A-23F. Circular dichroism spectra of stitched peptides with various constitutions. Triple stitched peptide Id shows a high level of thermal stability.
Figure 23B:
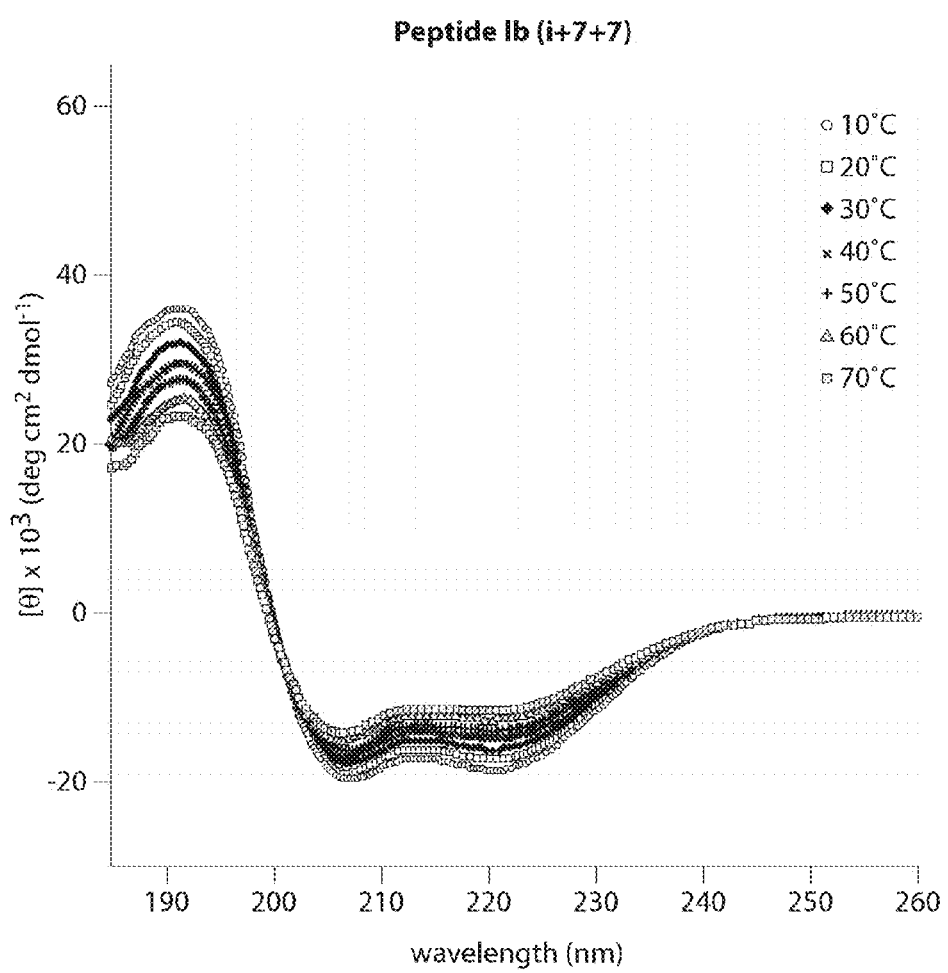
Figure 23C:
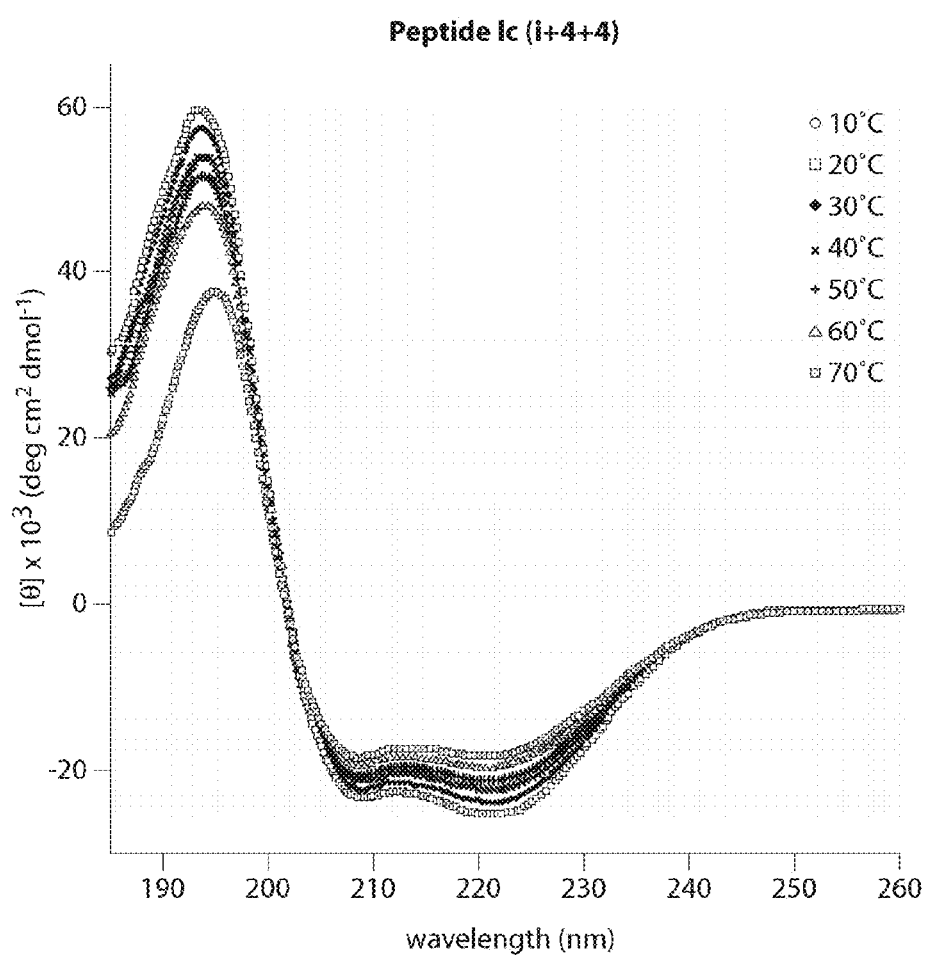
Figure 23D:
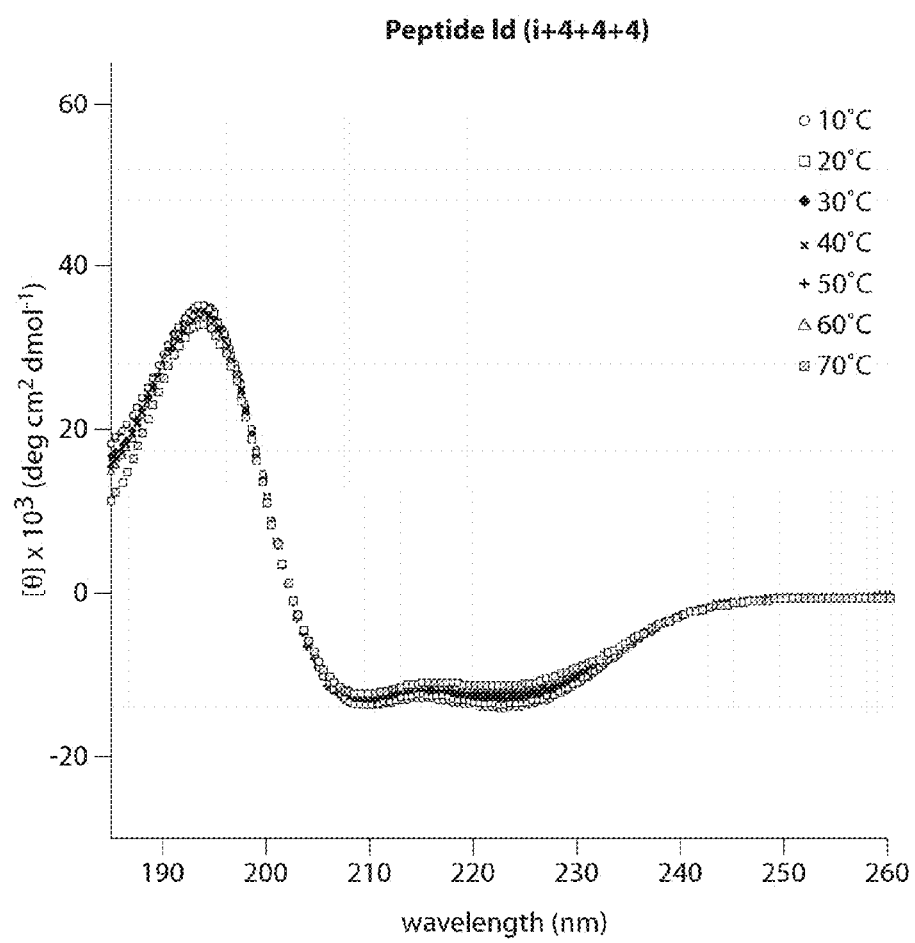
Figure 23E:
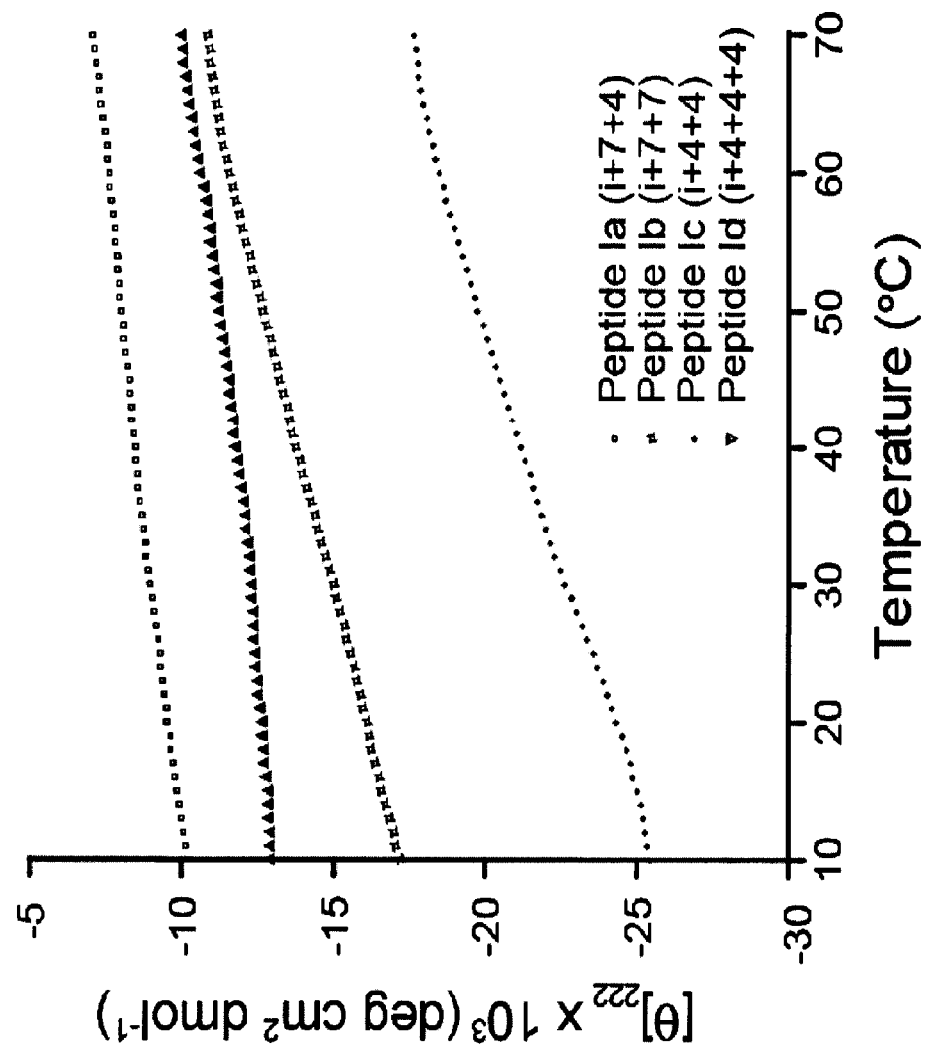
Figure 23F:
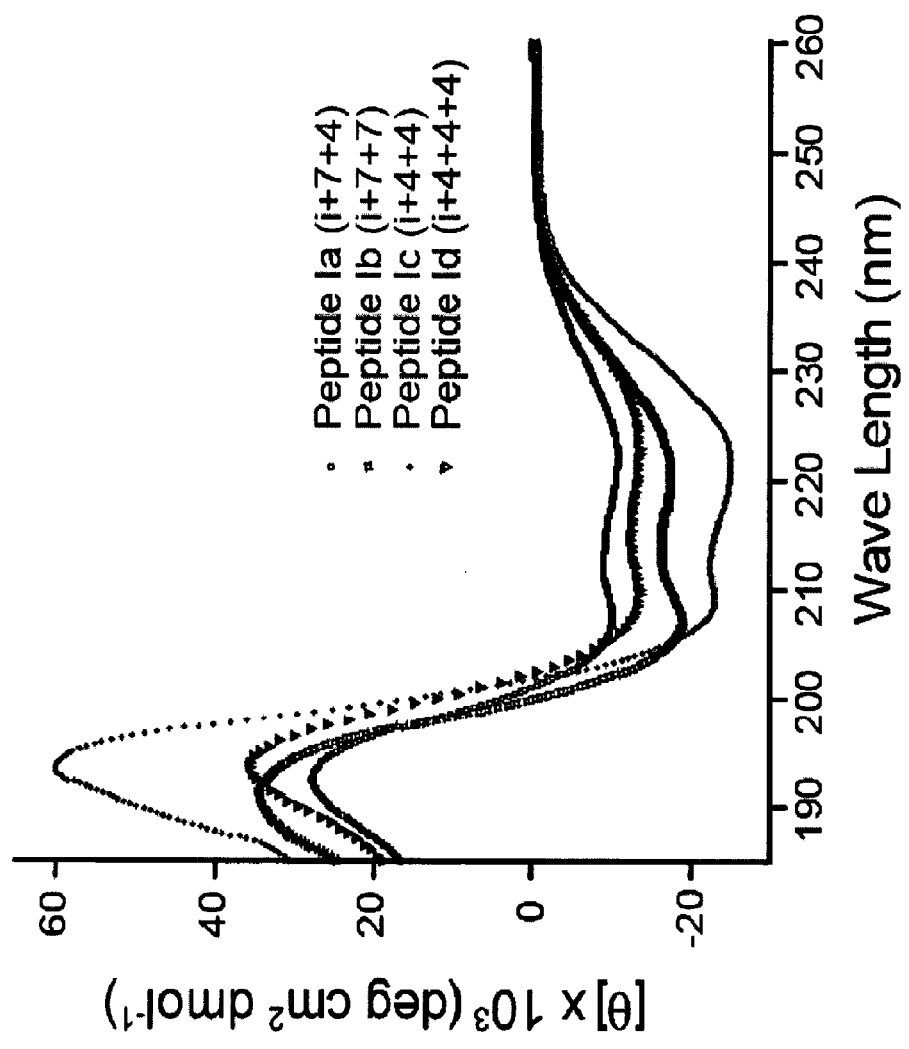
Figure 24A:
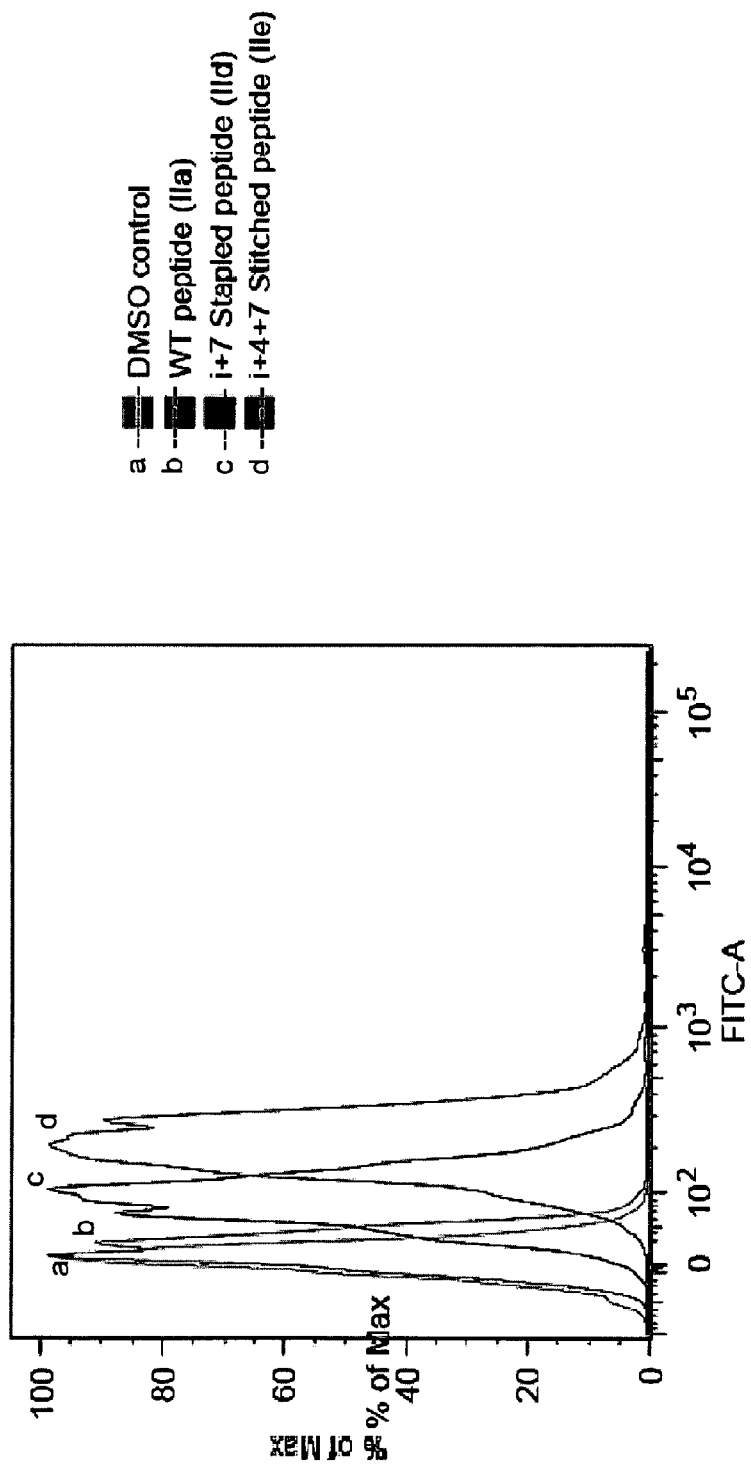
FIGS. 24A-24C. Cell permeabilities of FITC-labeled peptides analyzed by FACS at 37° C.
Figure 24B:
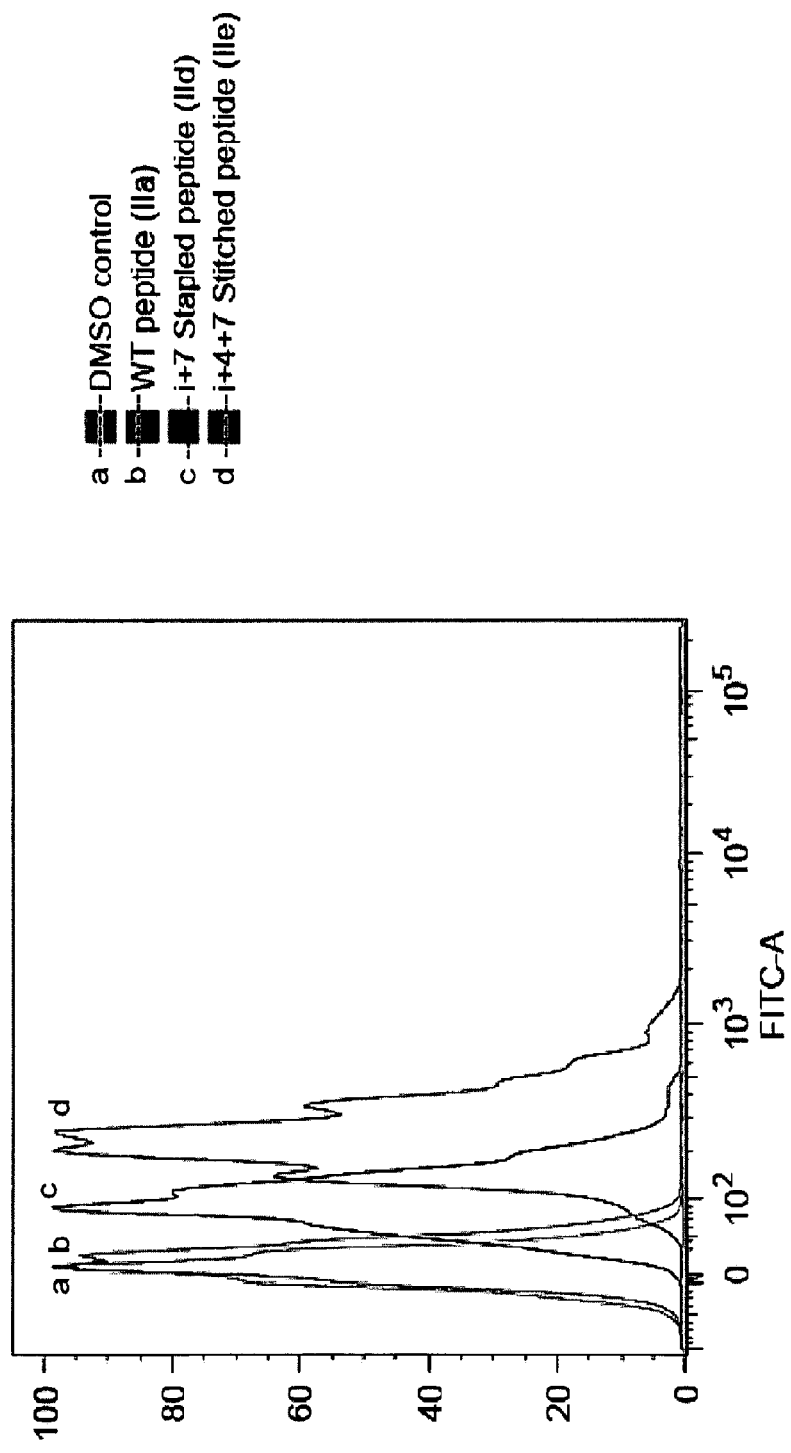
Figure 24C:
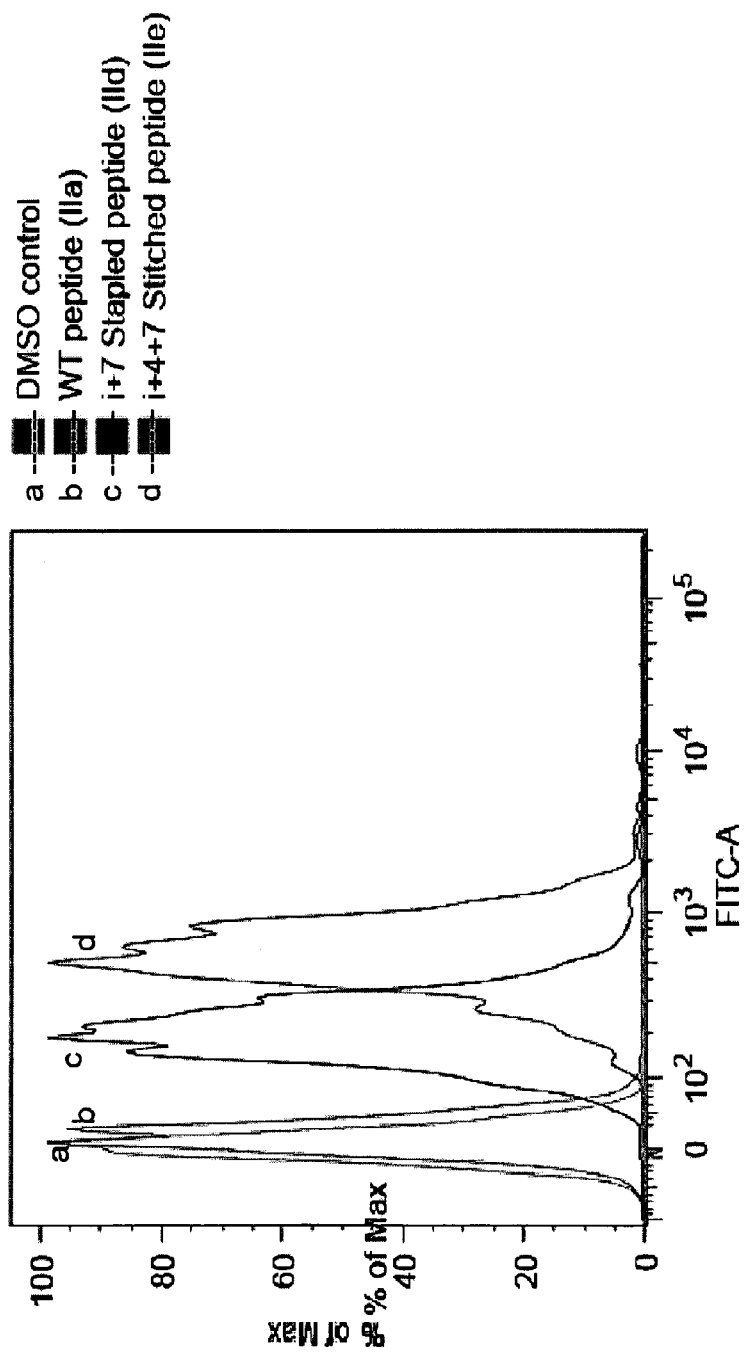
Figure 25A:
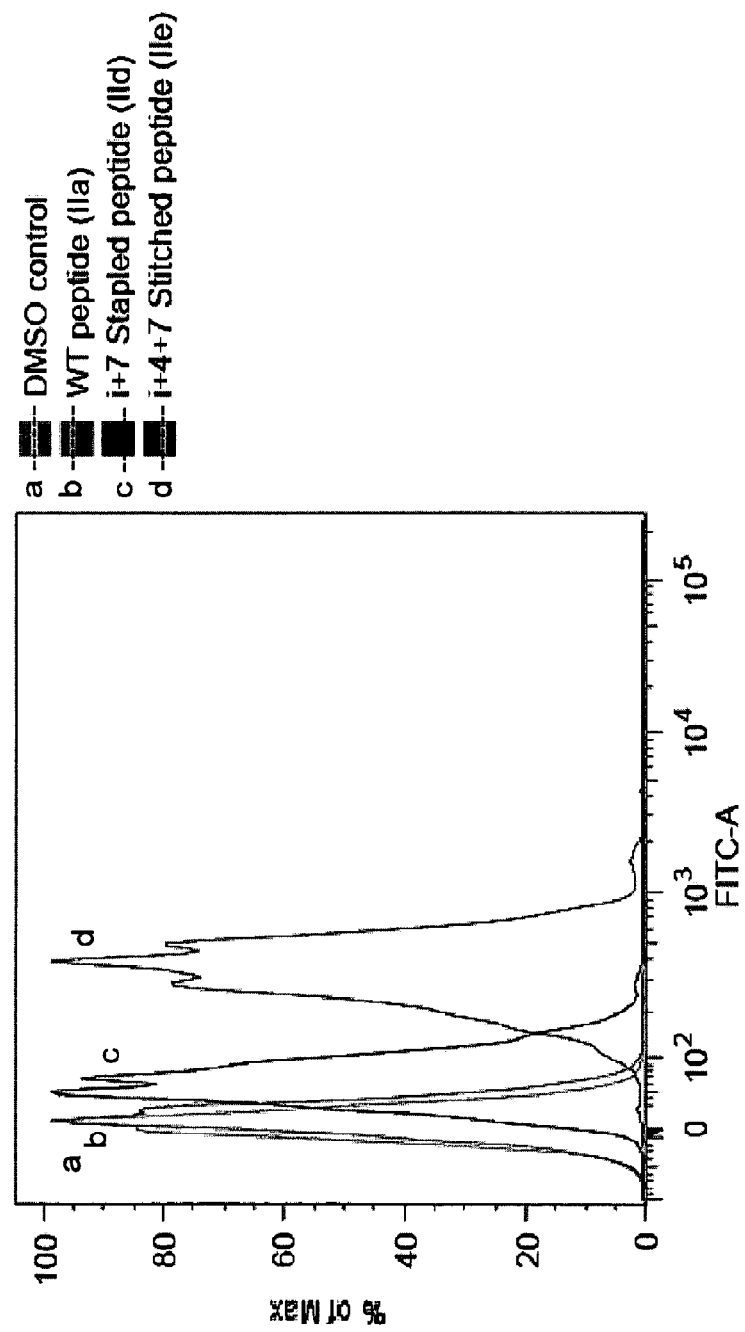
FIGS. 25A-25C. Temperature-dependent cell penetration of peptides. Stitched peptide IIe is less affected by low temperature compared to stapled peptide IId.
Figure 25B:
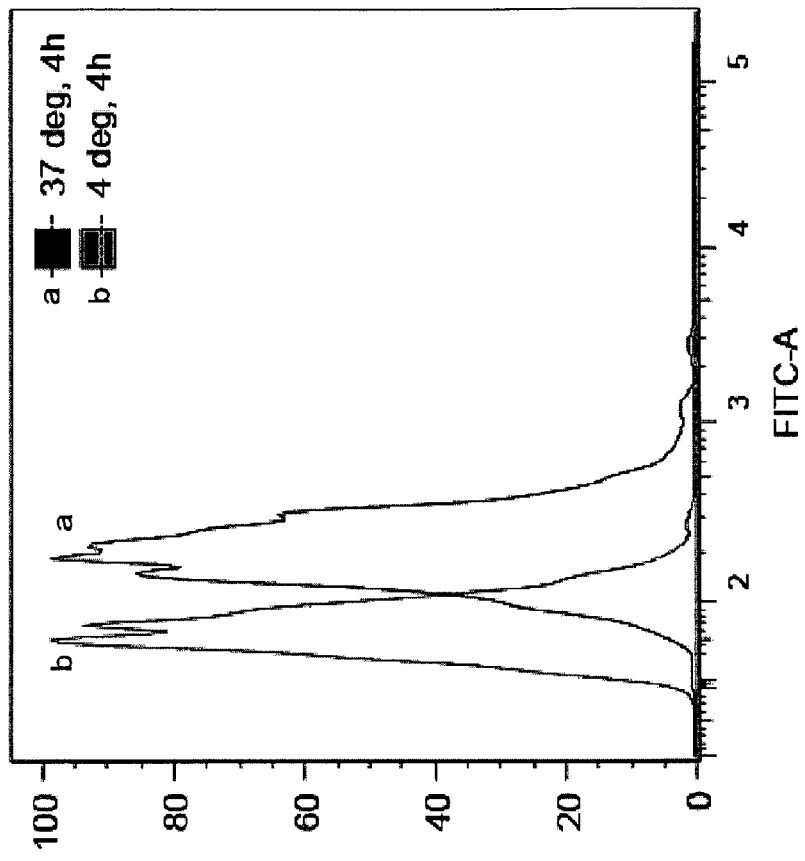
Figure 25C:
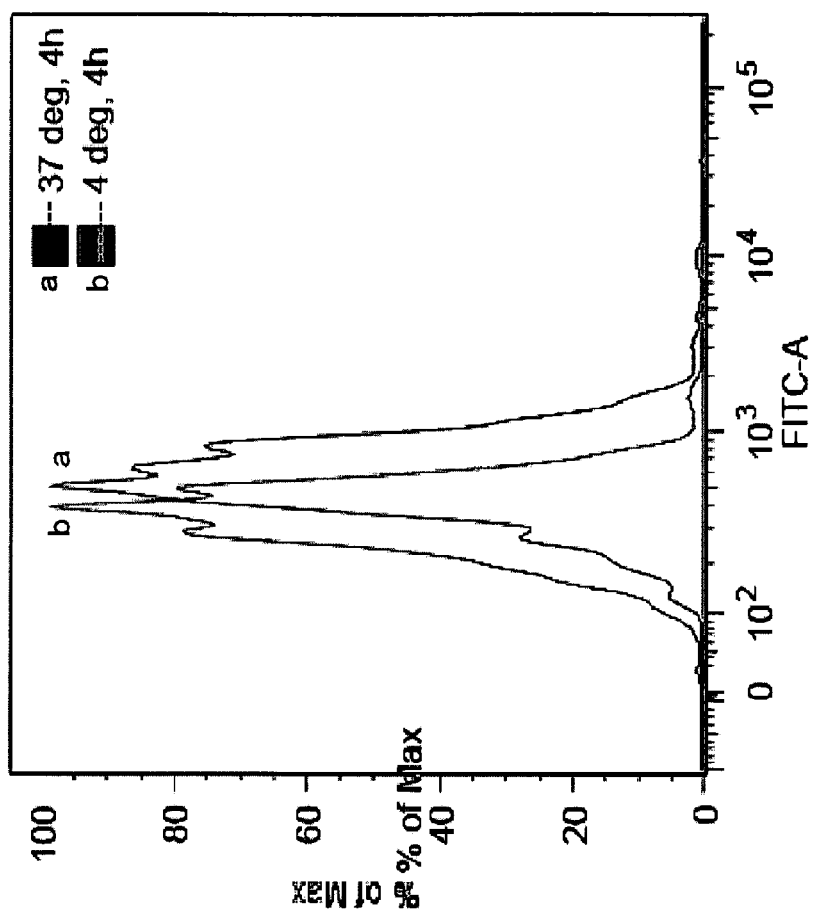

To investigate the possibility of peptides stabilized by three and more crosslinks, peptide 17 (FIG. 13) was designed to contain $S_5$ at i, two $B_5$ at i+4 and i+8, and $S_5$ at i+12 on solid support and subjected it to ring-closing metathesis using 30% Grubbs catalyst in dichloroethane solvent. Small portions of the peptide-containing resin were taken out from the reaction vessel at the time indicated (FIG. 14), and the products were analyzed by LCMS after cleavage. LCMS results clearly show the formation of single- and double-stapled intermediates, most of which were eventually consumed. A single product peak accounted for 90% of product mixture, which had the molecular mass expected of the product of triple crosslinking (peptide 24). A model peptide bearing $B_5$ at i and i+4 (peptide 25 in FIG. 15) did not produce double stapled compound 27 providing only single stapled product 26. In addition, a model peptide containing $R_5$ at i and $S_5$ at i+4 position (peptide 28) did not undergo RCM to produce peptide 29 (FIG. 15). The results from this model study indicated that peptide 24, as depicted in FIG. 13, to be the most likely structure for the triple crosslinked product. This result suggest that four or more crosslinks also might be introduced to peptide system by rational design.

Example 2

Additional Stitched Peptides

Additional Stitched Peptides I: Other RNases A Analogs

TABLE 8

```
Peptide Ia: Ac-R₈WAETAAB₅KFLR₅AHA-NH₂ (SEQ ID 12)
           [ESIMS for C₉₁H₁₃₈N₂₀O₁₉ [M/2 + H]⁺ calcd 907.5, found 907.6]

Peptide Ib: Ac-R₈WAETAAB₅KFLAAHS₈-NH₂ (SEQ ID 13)
           [ESIMS for C₉₄H₁₄₄N₂₀O₁₉ [M/2 + H]⁺ calcd 928.5, found 928.4]

Peptide Ic: Ac-EWAR₅TAAB₅KFLS₅AHA-NH₂ (SEQ ID 14)
           [ESIMS for C₈₈H₁₃₂N₂₀O₁₉ [M/2 + H]⁺ calcd 886.5, found 886.4]

Peptide Id: Ac-S₅EWAB₅TAAB₅KFLS₅AHA-NH₂ (SEQ ID 15)
           [ESIMS for C₉₈H₁₄₇N₂₁O₂₀ [M/2 + H]⁺ calcd 969.1, found 968.8]

Peptide Ie: Ac-linker1-EWAS₅TAAB₅KFLAAHS₈-NH₂ (SEQ ID 16)
           [ESIMS for C₁₀₁H₁₅₆N₂₂O₂₃ [M/2 + H]⁺ calcd 1022.6, found 1022.4]

Peptide If: Ac-linker1-R₈WAETAAB₅KFLAAHS₈-NH₂ (SEQ ID 17)
           [ESIMS for C₁₀₄H₁₆₂N₂₂O₂₃ [M/2 + H]⁺ calcd 1043.6, found 1043.2]

Peptide Ig: Ac-linker1-EWAS₅TAAB₅KFLR₅AHA-NH₂ (SEQ ID 18)
           [ESIMS for C₉₈H₁₅₀N₂₂O₂₃ [M/2 + H]⁺ calcd 1001.6, found 1001.2]
```

TABLE 8-continued

Peptide Ih: FITC-linker1-R$_8$WAETAAB$_5$KFLAAHS$_8$-NH$_2$ (SEQ ID 19)
[ESIMS for C$_{123}$H$_{172}$N$_{23}$O$_{27}$S [M/3 + H]$^+$ calcd 811.7, found 811.6]

Peptide Ii: FITC-linker1-EWAS$_5$TAAB$_5$KFLR$_5$AHA-NH$_2$ (SEQ ID 20)
[ESIMS for C$_{117}$H$_{160}$N$_{23}$O$_{27}$S [M/3 + H]$^+$ calcd 783.7, found 783.6]

Additional Stitched Peptides II: FITC-Labeled RNases A Analogs

TABLE 9

Peptide IIa: FITC-linker1-EWAETAAAKFLAAHA-NH$_2$ (SEQ ID 21)
[ESIMS for C$_{104}$H$_{139}$N$_{23}$O$_{29}$S [M/2 + H]$^+$ calcd 1102.5, found 1102.8]

Peptide IIb  FITC-linker1-EWAR$_5$TAAR$_5$KFLAAHAib-NH$_2$ (SEQ ID 22)
[ESIMS for C$_{111}$H$_{151}$N$_{23}$O$_{27}$S [M/2 + H]$^+$ calcd 1135.0, found 1134.8]

Peptide IIc: FITC-linker1-EWAS$_5$TAAS$_5$KFLAAHAib-NH$_2$ (SEQ ID 23)
[ESIMS for C$_{111}$H$_{151}$N$_{23}$O$_{27}$S [M/2 + H]$^+$ calcd 1135.0, found 1134.8]

Peptide IId: FITC-linker1-EWAAibTAAR$_5$KFLAAHS$_8$-NH$_2$ (SEQ ID 24)
[ESIMS for C$_{114}$H$_{157}$N$_{23}$O$_{27}$S [M/2 + H]$^+$ calcd 1156.1, found 1155.6]

Peptide IIe: FITC-linker1-EWAS$_5$TAAB$_5$KFLAAHS$_8$-NH$_2$ (SEQ ID 25)
[ESIMS for C$_{120}$H$_{165}$N$_{23}$O$_{27}$S [M/2 + H]$^+$ calcd 1196.1, found 1195.6]

Additional Stitched Peptides III: Hydrophilic Stitched Peptide Analogs

TABLE 10

Peptide IIIa: Ac-EWSAibTDNAibKQEADRAib-NH$_2$ (SEQ ID 26)
[ESIMS for C$_{74}$H$_{117}$N$_{23}$O$_{28}$ [M/2 + H]$^+$ calcd 887.4, found 888.0]

Peptide IIIb: Ac-EWSS$_5$TDNB$_5$KQEADRS$_8$-NH$_2$ (SEQ ID 27)
[ESIMS for C$_{89}$H$_{139}$N$_{23}$O$_{28}$ [M/2 + H]$^+$ calcd 989.0, found 989.2]

Peptide IIIc: Ac-EWSS$_5$TDNB$_5$KQER$_5$DRA-NH$_2$ (SEQ ID 28)
[ESIMS for C$_{86}$H$_{133}$N$_{23}$O$_{28}$ [M/2 + H]$^+$ calcd 968.0, found 968.4]

Additional Stitched Peptides IV: Rev-Based Peptides Targeting HIV-RRE

TABLE 11

Peptide IVa: Ac-TRQS$_5$RRNB$_5$RRRWRES$_8$QR-NH$_2$ (SEQ ID 29)
[ESIMS for C$_{111}$H$_{193}$N$_{46}$O$_{24}$ [M/3 + H]$^+$ calcd 851.5, found 852.0]

Peptide IVb: Ac-TRQS$_5$RRNB$_5$WRRR$_5$RERQR-NH$_2$ (SEQ ID 30)
[ESIMS for C$_{108}$H$_{187}$N$_{46}$O$_{24}$ [M/3 + H]$^+$ calcd 837.5, found 837.9]

Peptide IVc: FITC-linker2-TRQS$_5$RRNB$_5$RRRWRES$_8$QR-NH$_2$ (SEQ ID 31)
[ESIMS for C$_{133}$H$_{207}$N$_{48}$O$_{29}$ [M/3 + H]$^+$ calcd 990.9, found 991.2]

Peptide IVd: FITC-linker2-TRQS$_5$RRNB$_5$WRRR$_5$RERQR-NH$_2$ (SEQ ID 32)
[ESIMS for C$_{130}$H$_{201}$N$_{48}$O$_{29}$ [M/3 + H]$^+$ calcd 976.8, found 977.2]

Additional Stitched Peptides V: ARNT-Based Peptides Targeting HIF-1α

TABLE 12

Peptide Va: Ac-ILS$_5$MAVB$_5$HMKSLRS$_8$T-NH$_2$ (SEQ ID 33)
[ESIMS for C$_{90}$H$_{158}$N$_{22}$O$_{18}$S$_2$ [M/2 + H]$^+$ calcd 949.6, found 950.0]

Peptide Vb: Ac-ILRMAVS$_5$HMKB$_5$LRGR$_5$-NH$_2$ (SEQ ID 34)
[ESIMS for C$_{88}$H$_{155}$N$_{25}$O$_{16}$S$_2$ [M/2 + H]$^+$ calcd 941.1, found 941.6]

TABLE 12-continued

Peptide Vc: FITC-linker2-ILS$_5$MAVB$_5$HMKSLRS$_8$T-NH$_2$ (SEQ ID 35)

Peptide Vd: FITC-linker2-ILRMAVS$_5$HMKB$_5$LRGR-NH$_2$ (SEQ ID 36)

Additional Stitched Peptides VI: p53-Based Peptides Targeting hDM-2 and hDMx

TABLE 13

Peptide VIa: Ac-LSS$_5$ETFB$_5$DLWKLLS$_8$EN-NH$_2$ (SEQ ID 37)
[ESIMS for $C_{104}H_{162}N_{20}O_{26}$ [M/2 + H]$^+$ calcd 1053.6, found 1054.0]

Peptide VIb: Ac-LSS$_5$ETAB$_5$DLWKLLS$_8$EN-NH$_2$ (SEQ ID 38)
[ESIMS for $C_{98}H_{158}N_{20}O_{26}$ [M/2 + H]$^+$ calcd 1015.6, found 1016.0]

Peptide VIc: FITC-linker2-LSS$_5$ETFB$_5$DLWKLLS$_8$EN-NH$_2$ (SEQ ID 39)
[ESIMS for $C_{126}H_{176}N_{22}O_{31}S$ [M/2 + H]$^+$ calcd 1262.6, found 1262.8]

Peptide VId: FITC-linker2-LSS$_5$ETAB$_5$DLWKLLS$_8$EN-NH$_2$ (SEQ ID 40)
[ESIMS for $C_{122}H_{172}N_{22}O_{31}S$ [M/2 + H]$^+$ calcd 1224.6, found 1224.8]

Peptide VIe: Biotin-linker1-LSS$_5$ETFB$_5$DLWKLLS$_8$EN-NH$_2$ (SEQ ID 41)
[ESIMS for $C_{122}H_{192}N_{24}O_{31}S$ [M/2 + H]$^+$ calcd 1260.7, found 1261.2]

Peptide VIf: Biotin-linker1-LSS$_5$ETAB$_5$DLWKLLS$_8$EN-NH$_2$ (SEQ ID 42)
[ESIMS for $C_{116}H_{188}N_{24}O_{31}S$ [M/2 + H]$^+$ calcd 1222.7, found 1222.8]

Peptide VIg: FITC-linker2-S$_5$DFSB$_5$YWKR$_5$L-NH$_2$ (SEQ ID 43)
[ESIMS for $C_{96}H_{119}N_{15}O_{20}S$ [M/2 + H]$^+$ calcd 916.9, found 917.2]

Peptide VIh: FITC-linker2-R$_5$DFSB$_5$YWKS$_5$L-NH$_2$ (SEQ ID 44)
[ESIMS for $C_{96}H_{119}N_{15}O_{20}S$ [M/2 + H]$^+$ calcd 916.9, found 917.6]

Additional Stitched Peptides VII: BID-BH3-Based Peptides Targeting BCL-X$_L$

TABLE 14

Peptide VIIa: Ac-EDIIRNIAS$_5$HLAB$_5$VGDWN$_L$DS$_8$SI-NH$_2$ (SEQ ID 45)
[ESIMS for $C_{117}H_{185}N_{29}O_{32}$ [M/2 + H]$^+$ calcd 1324.7, found 1325.2]

Peptide VIIb: Ac-NIAS$_5$HLAB$_5$VGDWN$_L$DS$_8$SI-NH$_2$ (SEQ ID 46)
[ESIMS for $C_{90}H_{139}N_{21}O_{23}$ [M/2 + H]$^+$ calcd 1011.58, found 1012.0]

Peptide VIIc: Ac-NIAS$_5$HLAB$_5$VGDWN$_L$DS$_8$-NH$_2$ (SEQ ID 47)
[ESIMS for $C_{81}H_{121}N_{19}O_{20}$ [M/2 + H]$^+$ calcd 911.5, found 912.0]

Peptide VIId: FITC-linker2-EDIIRNIAS$_5$HLAB$_5$VGDWN$_L$DS$_8$SI-NH$_2$ (SEQ ID 48)
[ESIMS for $C_{139}H_{199}N_{31}O_{37}S$ [M/2 + H]$^+$ calcd 1533.8, found 1534.4]

Peptide VIIe: FITC-linker2-NIAS$_5$HLAB$_5$VGDWN$_L$DS$_8$SI-NH$_2$ (SEQ ID 49)
[ESIMS for $C_{112}H_{153}N_{23}O_{28}S$ [M/2 + H]$^+$ calcd 1220.6, found 1221.2]

Peptide VIIf: FITC-linker2-NIAS$_5$HLAB$_5$VGDWN$_L$DS$_8$-NH$_2$ (SEQ ID 50)
[ESIMS for $C_{103}H_{137}N_{21}O_{25}S$ [M/2 + H]$^+$ calcd 1120.6, found 1120.8]

$N_L$ = norleucine

Additional Stitched Peptides VIII: hE47-Based Peptides Targeting Id Proteins

TABLE 15

Peptide VIIIa: Ac-LS$_5$ILQB$_5$AVQR$_5$ILGLEQQVRER-NH$_2$ (SEQ ID 51)
[ESIMS for $C_{116}H_{199}N_{31}O_{29}$ [M/3 + H]$^+$ calcd 854.9, found 855.2]

Peptide VIIIb: Ac-LS$_5$ILQB$_5$AVQVILS$_8$LEQQVRER-NH$_2$ (SEQ ID 52)
[ESIMS for $C_{122}H_{211}N_{31}O_{29}$ [M/3 + H]$^+$ calcd 882.9, found 883.2]

Peptide VIIIc: Ac-LLILQQAVS$_5$VILB$_5$LEQR$_5$VRER-NH$_2$ (SEQ ID 53)
[ESIMS for $C_{120}H_{211}N_{30}O_{28}$ [M/3 + H]$^+$ calcd 863.9, found 864.0]

Peptide VIIId: Ac-LLILQQAVS$_5$VILB$_5$LEQQVRS$_8$R-NH$_2$ (SEQ ID 54)
[ESIMS for $C_{123}H_{218}N_{31}O_{27}$ [M/3 + H]$^+$ calcd 877.6, found 877.6]

TABLE 15-continued

Peptide VIIIe: Ac-LLILS$_5$QAVB$_5$VILR$_5$LEQQVRER-NH$_2$ (SEQ ID 55)
[ESIMS for C$_{120}$H$_{211}$N$_{30}$O$_{28}$ [M/3 + H]$^+$ calcd 863.9, found 864.4]

Peptide VIIIf: Ac-LLILS$_5$QAVB$_5$VILGLES$_8$QVRER-NH$_2$ (SEQ ID 56)
[ESIMS for C$_{120}$H$_{211}$N$_{29}$O$_{27}$ [M/3 + H]$^+$ calcd 854.2, found 854.4]

Peptide VIIIg: Ac-LLILS$_5$QAVB$_5$VILB$_5$LEQS$_5$VRER-NH$_2$ (SEQ ID 57)
[ESIMS for C$_{125}$H$_{215}$N$_{29}$O$_{27}$ [M/3 + H]$^+$ calcd 876.2, found 876.4]

Peptide VIIIh: FITC-linker2-LS$_5$ILQB$_5$AVQR$_5$ILGLEQQVRER-NH$_2$ (SEQ ID 58)
[ESIMS for C$_{138}$H$_{216}$N$_{33}$O$_{34}$S [M/3 + H]$^+$ calcd 994.2, found 994.5]

Peptide VIIIi: FITC-linker2-LS$_5$ILQB$_5$AVQVILS$_8$LEQQVRER-NH$_2$ (SEQ ID 59)
[ESIMS for C$_{144}$H$_{228}$N$_{33}$O$_{34}$S [M/3 + H]$^+$ calcd 1022.2, found 1022.4]

Peptide VIIIj: FITC-linker2-LLILQQAVS$_5$VILB$_5$LEQR$_5$VRER-NH$_2$ (SEQ ID 60)
[ESIMS for C$_{142}$H$_{225}$N$_{32}$O$_{33}$S [M/3 + H]$^+$ calcd 1003.2, found 1003.6]

Peptide VIIIk: FITC-linker2-LLILQQAVS$_5$VILB$_5$LEQQVRS$_8$R-NH$_2$ (SEQ ID 61)
[ESIMS for C$_{145}$H$_{232}$N$_{33}$O$_{32}$S [M/3 + H]$^+$ calcd 1016.9, found 1017.2]

Peptide VIIIl: FITC-linker2-LLILS$_5$QAVB$_5$VILR$_5$LEQQVRER-NH$_2$ (SEQ ID 62)
[ESIMS for C$_{142}$H$_{225}$N$_{32}$O$_{33}$S [M/3 + H]$^+$ calcd 1003.2, found 1003.6]

Peptide VIIIm: FITC-linker2-LLILS$_5$QAVB$_5$VILGLES$_8$QVRER-NH$_2$ (SEQ ID 63)
[ESIMS for C$_{142}$H$_{226}$N$_{31}$O$_{32}$S [M/3 + H]$^+$ calcd 993.6 found 994.0]

Peptide VIIIn: FITC-linker2-LLILS$_5$QAVB$_5$VILB$_5$LEQS$_5$VRER-NH$_2$ (SEQ ID 64)
[ESIMS for C$_{147}$H$_{232}$N$_{31}$O$_{32}$S [M/3 + H]$^+$ calcd 1024.9, found 1015.6]

Additional Stitched Peptides IX: GLP-1-Based Peptides Targeting GLP-1 Receptor

TABLE 16

Peptide IXa: HAEGTFTSDVSSYS$_5$EGQB$_5$AKEB$_5$IAWS$_5$VKGR-NH$_2$ (SEQ ID 65)
[ESIMS for C$_{159}$H$_{245}$N$_{40}$O$_{45}$ [M/3 + H]$^+$ calcd 1144.94, found 1145.1]

Peptide IXb: HAEGTFTSDVSSYS$_5$EGQB$_5$AKEFIAS$_8$LVKGR-NH$_2$ (SEQ ID 66)
[ESIMS for C$_{156}$H$_{246}$N$_{39}$O$_{45}$ [M/3 + H]$^+$ calcd 1128.6, found 1128.8]

Peptide IXc: HAEGTFTSDVSSYLEGQS$_5$AKEB$_5$IAWLVKS$_8$R-NH$_2$ (SEQ ID 67)
[ESIMS for C$_{162}$H$_{255}$N$_{40}$O$_{45}$ [M/3 + H]$^+$ calcd 1160.3, found 1160.8]

Peptide IXd: HAEGTFTSDVSSYLEGS$_5$AAKB$_5$FIAB$_5$LVKS$_5$R-NH$_2$ (SEQ ID 68)
[ESIMS for C$_{160}$H$_{253}$N$_{38}$O$_{42}$ [M/3 + H]$^+$ calcd 1126.3, found 1126.4]

Peptide IXe: HAEGTFTSDVSSYLEGQAAKS$_5$FIAB$_5$LVKR$_5$R-NH$_2$ (SEQ ID 69)
[ESIMS for C$_{155}$H$_{246}$N$_{39}$O$_{43}$ [M/3 + H]$^+$ calcd 1113.9, found 1114.4]

Peptide IXf: HAEGTFTSDR$_8$SSYLEGB$_5$AAKEFIS$_8$WLVKGR-NH$_2$ (SEQ ID 70)
[ESIMS for C$_{166}$H$_{256}$N$_{39}$O$_{44}$ [M/3 + H]$^+$ calcd 1166.6, found 1166.4]

Peptide IXg: HAEGTFTSDVSSYLES$_5$QAAB$_5$EFIAWLS$_8$KGR-NH$_2$ (SEQ ID 71)
[ESIMS for C$_{163}$H$_{248}$N$_{39}$O$_{45}$ [M/3 + H]$^+$ calcd 1157.2, found 1156.8]

Peptide IXh: HAEGTFTSDVSSR$_8$LEGQAAB$_5$EFIAWLS$_8$KGR-NH$_2$ (SEQ ID 72)
[ESIMS for C$_{159}$H$_{248}$N$_{39}$O$_{44}$ [M/3 + H]$^+$ calcd 1135.9, found 1135.6]

Peptide IXi: HAEGTFTSDVSS$_5$YLEB$_5$QAAKEFS$_8$AWLVKGR-NH$_2$ (SEQ ID 73)
[ESIMS for C$_{165}$H$_{253}$N$_{40}$O$_{44}$ [M/3 + H]$^+$ calcd 1166.3, found 1166.0]

Peptide IXj: HAEGTFTSDS$_5$SSYB$_5$EGQAAKS$_8$FIAWLVKGR-NH$_2$ (SEQ ID 74)
[ESIMS for C$_{160}$H$_{245}$N$_{40}$O$_{43}$ [M/3 + H]$^+$ calcd 1138.3, found 1138.0]

Peptide IXk: HAEGTFTS$_5$DVSB$_5$YLEGQAS$_8$KEFIAWLVKGR-NH$_2$ (SEQ ID 75)
[ESIMS for C$_{167}$H$_{257}$N$_{40}$O$_{43}$ [M/3 + H]$^+$ calcd 1170.3, found 1170.0]

Peptide IXl: HAEGTFTS$_5$DVSB$_5$YLER$_5$QAAKEFIAWLVKGR-NH$_2$ (SEQ ID 76)
[ESIMS for C$_{165}$H$_{253}$N$_{40}$O$_{43}$ [M/3 + H]$^+$ calcd 1161.0, found 1160.8]

Peptide IXm: HAEGTFTS$_5$DVSB$_5$YLEB$_5$QAAS$_5$EFIAWLVKGR-NH$_2$ (SEQ ID 77)
[ESIMS for C$_{169}$H$_{256}$N$_{39}$O$_{43}$ [M/3 + H]$^+$ calcd 1173.3, found 1173.2]

TABLE 16-continued

Peptide IXn: HAEGTFTSDVSS$_5$YLEB$_5$QAAR$_5$EFIAWLVKGR-NH$_2$ (SEQ ID 78)
[ESIMS for C$_{162}$H$_{246}$N$_{39}$O$_{44}$ [M/3 + H]$^+$ calcd 1147.3, found 1146.8]

Additional Stitched Peptides X: NS5A-Based Peptides Targeting Hepatitis C Virus

TABLE 17

Peptide Xa: SGSWLRDS$_5$WDWB$_5$CTVLTDS$_8$KTWLQSKL-NH$_2$ (SEQ ID 79)
[ESIMS for C$_{161}$H$_{245}$N$_{38}$O$_{40}$S [M/3 + H]$^+$ calcd 1127.6, found 1127.6]

Peptide Xb: SGSWLRDVWDWIS$_5$TVLB$_5$DFKB$_5$WLQS$_5$KL-NH$_2$ (SEQ ID 80)
[ESIMS for C$_{174}$H$_{259}$N$_{38}$O$_{37}$ [M/3 + H]$^+$ calcd 1157.7, found 1157.6]

Peptide Xc: SGSWLS$_5$DVWB$_5$WICTVLS$_8$DFKTWLQSKL-NH$_2$ (SEQ ID 81)
[ESIMS for C$_{167}$H$_{250}$N$_{35}$O$_{37}$S [M/3 + H]$^+$ calcd 1123.3, found 1123.6]

Peptide Xd: SGSWLS$_5$DVWB$_5$WICR$_5$VLTDFKTWLQSKL-NH$_2$ (SEQ ID 82)
[ESIMS for C$_{164}$H$_{244}$N$_{35}$O$_{37}$S [M/3 + H]$^+$ calcd 1109.3, found 1109.2]

Peptide Xe: SGSWLS$_5$DVWB$_5$WICB$_5$VLTS$_5$FKTWLQSKL-NH$_2$ (SEQ ID 83)
[ESIMS for C$_{170}$H$_{254}$N$_{35}$O$_{35}$S [M/3 + H]$^+$ calcd 1126.0, found 1126.0]

Peptide Xf: SGSWLRDVWS$_5$WICB$_5$VLTDFKS$_8$WLQSKL-NH$_2$ (SEQ ID 84)
[ESIMS for C$_{169}$H$_{255}$N$_{38}$O$_{36}$S [M/3 + H]$^+$ calcd 1141.7, found 1141.6]

Peptide Xg: SGSWLRDVWS$_5$WICB$_5$VLTR$_5$FKTWLQSKL-NH$_2$ (SEQ ID 85)
[ESIMS for C$_{166}$H$_{248}$N$_{38}$O$_{35}$S [M/3 + H]$^+$ calcd 1123.0, found 1122.8]

Peptide Xh: SGSWLRR$_8$VWDWICB$_5$VLTDFKS$_8$WLQSKL-NH$_2$ (SEQ ID 86)
[ESIMS for C$_{172}$H$_{261}$N$_{38}$O$_{36}$S [M/3 + H]$^+$ calcd 1155.7, found 1155.6]

Peptide Xi: Ac-SGSWLRDS$_5$WDWB$_5$CTVLTDS$_8$KTWLQSKL-NH$_2$ (SEQ ID 87)
[ESIMS for C$_{163}$H$_{247}$N$_{38}$O$_{41}$S [M/3 + H]$^+$ calcd 1141.6, found 1141.6]

Peptide Xj: Ac-SGSWLRDVWDWIS$_5$TVLB$_5$DFKB$_5$WLQS$_5$KL-NH$_2$ (SEQ ID 88)
[ESIMS for C$_{176}$H$_{261}$N$_{38}$O$_{38}$ [M/3 + H]$^+$ calcd 1171.7, found 1171.6]

Peptide Xk: Ac-SGSWLS$_5$DVWB$_5$WICTVLS$_8$DFKTWLQSKL-NH$_2$ (SEQ ID 89)
[ESIMS for C$_{169}$H$_{252}$N$_{35}$O$_{38}$S [M/3 + H]$^+$ calcd 1137.3, found 1137.2]

Peptide Xl: Ac-SGSWLS$_5$DVWB$_5$WICR$_5$VLTDFKTWLQSKL-NH$_2$ (SEQ ID 90)
[ESIMS for C$_{166}$H$_{246}$N$_{35}$O$_{38}$S [M/3 + H]$^+$ calcd 1123.3, found 1123.2]

Peptide Xm: Ac-SGSWLS$_5$DVWB$_5$WICB$_5$VLTS$_5$FKTWLQSKL-NH$_2$ (SEQ ID 91)
[ESIMS for C$_{172}$H$_{256}$N$_{35}$O$_{36}$S [M/3 + H]$^+$ calcd 1140.0, found 1140.0]

Peptide Xn: Ac-SGSWLRDVWS$_5$WICB$_5$VLTDFKS$_8$WLQSKL-NH$_2$ (SEQ ID 92)
[ESIMS for C$_{171}$H$_{257}$N$_{38}$O$_{37}$S [M/3 + H]$^+$ calcd 1155.7, found 1155.6]

Peptide Xo: Ac-SGSWLRDVWS$_5$WICB$_5$VLTR$_5$FKTWLQSKL-NH$_2$ (SEQ ID 93)
[ESIMS for C$_{168}$H$_{253}$N$_{38}$O$_{36}$S [M/3 + H]$^+$ calcd 1137.0, found 1136.8]

Peptide Xp: Ac-SGSWLRR$_8$VWDWICB$_5$VLTDFKS$_8$WLQSKL-NH$_2$ (SEQ ID 94)
[ESIMS for C$_{174}$H$_{263}$N$_{38}$O$_{37}$S [M/3 + H]$^+$ calcd 1169.7, found 1169.6]

Peptide Xq: Ac-linker1-SGSWLRDS$_5$WDWB$_5$CTVLTDS$_8$KTWLQSKL-NH$_2$
(SEQ ID 95)
[ESIMS for C$_{173}$H$_{265}$N$_{40}$O$_{45}$S [M/3 + H]$^+$ calcd 1218.7, found 1218.6]

Peptide Xr: Ac-linker1-SGSWLRDVWDWIS$_5$TVLB$_5$DFKB$_5$WLQS$_5$KL-NH$_2$
(SEQ ID 96)
[ESIMS for C$_{186}$H$_{279}$N$_{40}$O$_{42}$ [M/3 + H]$^+$ calcd 1248.7, found 1248.9]

Peptide Xs: Ac-linker1-SGSWLS$_5$DVWB$_5$WICTVLS$_8$DFKTWLQSKL-NH$_2$
(SEQ ID 97)
[ESIMS for C$_{179}$H$_{270}$N$_{37}$O$_{42}$S [M/3 + H]$^+$ calcd 1214.4, found 1214.4]

Peptide Xt: Ac-linker1-SGSWLS$_5$DVWB$_5$WICR$_5$VLTDFKTWLQSKL-NH$_2$
(SEQ ID 98)
[ESIMS for C$_{176}$H$_{264}$N$_{37}$O$_{42}$S [M/3 + H]$^+$ calcd 1200.3, found 1200.3]

Peptide Xu: Ac-linker1-SGSWLS$_5$DVWB$_5$WICB$_5$VLTS$_5$FKTWLQSKL-NH$_2$
(SEQ ID 99)

TABLE 17-continued

Peptide Xv:   Ac-linker1-SGSWLRDVWS$_5$WICB$_5$VLTDFKS$_8$WLQSKL-NH$_2$
              (SEQ ID 100)
              [ESIMS for C$_{181}$H$_{275}$N$_{40}$O$_{41}$S [M/3 + H]$^+$ calcd 1232.7, found 1232.7]

Peptide Xw:   Ac-linker1-SGSWLRDVWS$_5$WICB$_5$VLTR$_5$FKTWLQSKL-NH$_2$
              (SEQ ID 101)
              [ESIMS for C$_{178}$H$_{271}$N$_{40}$O$_{40}$S [M/3 + H]$^+$ calcd 1214.0, found 1214.1]

Peptide Xx:   Ac-linker1-SGSWLRR$_8$VWDWICB$_5$VLTDFKS$_8$WLQSKL-NH$_2$
              (SEQ ID 102)
              [ESIMS for C$_{184}$H$_{281}$N$_{40}$O$_{41}$S [M/3 + H]$^+$ calcd 1246.7, found 1246.5]

Peptide Xy:   FITC-linker1-SGSWLRDS$_5$WDWB$_5$CTVLTDS$_8$KTWLQSKL-NH$_2$
              (SEQ ID 103)
              [ESIMS for C$_{192}$H$_{274}$N$_{41}$O$_{49}$S$_2$ [M/3 + H]$^+$ calcd 1334.4, found 1334.1]

Peptide Xz:   FITC-linker1-SGSWLRDVWDWIS$_5$TVLB$_5$DFKB$_5$WLQS$_5$KL-NH$_2$
              (SEQ ID 104)
              [ESIMS for C$_{205}$H$_{288}$N$_{41}$O$_{46}$S [M/3 + H]$^+$ calcd 1364.4, found 1364.4]

Peptide Xaa:  FITC-linker1-SGSWLS$_5$DVWB$_5$WICTVLS$_8$DFKTWLQSKL-NH$_2$
              (SEQ ID 105)
              [ESIMS for C$_{198}$H$_{279}$N$_{38}$O$_{46}$S$_2$ [M/3 + H]$^+$ calcd 1330.0, found 1330.2]

Peptide Xab:  FITC-linker1-SGSWLS$_5$DVWB$_5$WICR$_5$VLTDFKTWLQSKL-NH$_2$
              (SEQ ID 106)
              [ESIMS for C$_{195}$H$_{273}$N$_{38}$O$_{46}$S$_2$ [M/3 + H]$^+$ calcd 1316.0, found 1316.1]

Peptide Xac:  FITC-linker1-SGSWLS$_5$DVWB$_5$WICB$_5$VLTS$_5$FKTWLQSKL-NH$_2$
              (SEQ ID 107)

Peptide Xad:  FITC-linker1-SGSWLRDVWS$_5$WICB$_5$VLTDFKS$_8$WLQSKL-NH$_2$
              (SEQ ID 108)
              [ESIMS for C$_{200}$H$_{281}$N$_{41}$O$_{45}$S$_2$ [M/3 + H]$^+$ calcd 1348.4, found 1348.2]

Peptide Xae:  FITC-linker1-SGSWLRDVWS$_5$WICB$_5$VLTR$_5$FKTWLQSKL-NH$_2$
              (SEQ ID 109)
              [ESIMS for C$_{197}$H$_{280}$N$_{41}$O$_{44}$S$_2$ [M/3 + H]$^+$ calcd 1329.7, found 1330.0]

Peptide Xaf:  FITC-linker1-SGSWLRR$_8$VWDWICB$_5$VLTDFKS$_8$WLQSKL-NH$_2$
              (SEQ ID 110)
              [ESIMS for C$_{203}$H$_{290}$N$_{41}$O$_{45}$S$_2$ [M/3 + H]$^+$ calcd 1362.4, found 1362.4]

Peptide Xag:  Biotin-linker1-SGSWLRDS$_5$WDWB$_5$CTVLTDS$_8$KTWLQSKL-NH$_2$
              (SEQ ID 111)
              [ESIMS for C$_{181}$H$_{277}$N$_{42}$O$_{46}$S$_2$ [M/3 + H]$^+$ calcd 1279.7, found 1280.1]

Peptide Xah:  Biotin-linker1-SGSWLRDVWDWIS$_5$TVLB$_5$DFKB$_5$WLQS$_5$KL-NH$_2$
              (SEQ ID 112)
              [ESIMS for C$_{194}$H$_{276}$N$_{42}$O$_{43}$S [M/3 + H]$^+$ calcd 1309.7, found 1310.1]

Peptide Xai:  Biotin-linker1-SGSWLS$_5$DVWB$_5$WICTVLS$_8$DFKTWLQSKL-NH$_2$
              (SEQ ID 113)
              [ESIMS for C$_{187}$H$_{282}$N$_{39}$O$_{43}$S$_2$ [M/3 + H]$^+$ calcd 1275.4, found 1275.6]

Peptide Xaj:  Biotin-linker1-SGSWLS$_5$DVWB$_5$WICR$_5$VLTDFKTWLQSKL-NH$_2$
              (SEQ ID 114)
              [ESIMS for C$_{184}$H$_{276}$N$_{39}$O$_{43}$S$_2$ [M/3 + H]$^+$ calcd 1261.4, found 1261.8]

Peptide Xak:  Biotin-linker1-SGSWLS$_5$DVWB$_5$WICB$_5$VLTS$_5$FKTWLQSKL-NH$_2$
              (SEQ ID 115)

Peptide Xal:  Biotin-linker1-SGSWLRDVWS$_5$WICB$_5$VLTDFKS$_8$WLQSKL-NH$_2$
              (SEQ ID 116)
              [ESIMS for C$_{189}$H$_{287}$N$_{42}$O$_{42}$S$_2$ [M/3 + H]$^+$ calcd 1293.7, found 1294.2]

Peptide Xam:  Biotin-linker1-SGSWLRDVWS$_5$WICB$_5$VLTR$_5$FKTWLQSKL-NH$_2$
              (SEQ ID 117)
              [ESIMS for C$_{186}$H$_{283}$N$_{42}$O$_{41}$S$_2$ [M/3 + H]$^+$ calcd 1275.1, found 1275.3]

Peptide Xan:  Biotin-linker1-SGSWLRR$_8$VWDWICB$_5$VLTDFKS$_8$WLQSKL-NH$_2$
              (SEQ ID 118)
              [ESIMS for C$_{192}$H$_{293}$N$_{42}$O$_{42}$S$_2$ [M/3 + H]$^+$ calcd 1307.7, found 1308.3]

Additional Stitched Peptides XI: Max-Based Peptides Targeting Myc

TABLE 18

Peptide XIa: Ac-KATEYIQYN$_L$S$_5$RKNB$_5$THQQDIS$_8$DL-NH$_2$ (SEQ ID 119)
[ESIMS for C$_{133}$H$_{212}$N$_{35}$O$_{38}$ [M/3 + H]$^+$ calcd 992.6, found 992.6]

Peptide XIb: Ac-KATEYIR$_8$YN$_L$RRKNB$_5$THQQDIS$_8$DL-NH$_2$ (SEQ ID 120)
[ESIMS for C$_{137}$H$_{222}$N$_{37}$O$_{37}$ [M/3 + H]$^+$ calcd 1015.9, found 1016.3]

Additional Stitched Peptides XII: MITF-Based Peptides Targeting MITF

TABLE 19

Peptide XIIa: Ac-TILKASVDYS$_5$RKLB$_5$REQQRAS$_8$EL-NH$_2$ (SEQ ID 121)
[ESIMS for C$_{128}$H$_{220}$N$_{35}$O$_{33}$ [M/3 + H]$^+$ calcd 972.6, found 972.8]

Peptide XIIb: Ac-TILKASR$_8$DYIRKLB$_5$REQQRAS$_8$EL-NH$_2$ (SEQ ID 122)
[ESIMS for C$_{132}$H$_{228}$N$_{35}$O$_{33}$ [M/3 + H]$^+$ calcd 991.3, found 991.4]

Listing of Abbreviations

TABLE 20*

FITC

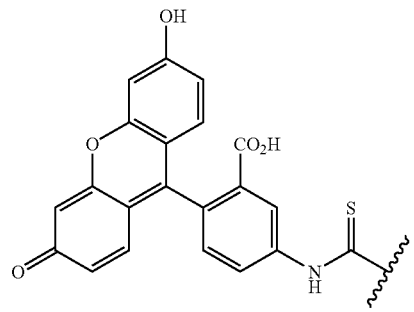 [SMILES: *C(=S)Nc1ccc(-c2c3ccc(=O)cc-3oc3cc(O)ccc23)c(C(=O)O)c1]

Biotin

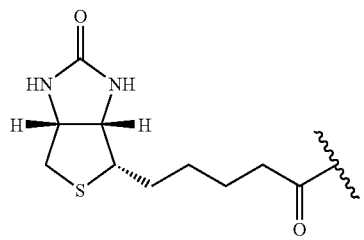 [SMILES: *C(=O)CCCC[C@@H]1SC[C@@H]2NC(=O)N[C@@H]21]

linker1

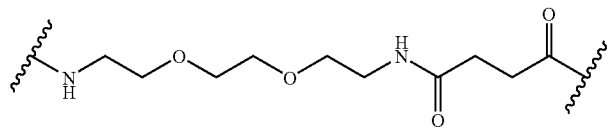 [SMILES: *NCCOCCOCCNC(=O)CCC(*)=O]

linker2

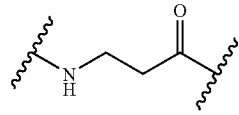 [SMILES: *NCCC(*)=O]

Ac

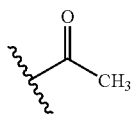 [SMILES: *C(C)=O]

TABLE 20*-continued

R₅

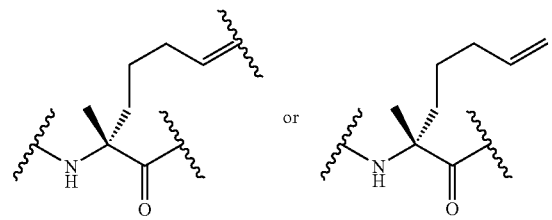 [SMILES: *N[C@](C)(CCCC=*)C(*)=O ; *N[C@](C)(CCCC=C)C(*)=O]

R₈

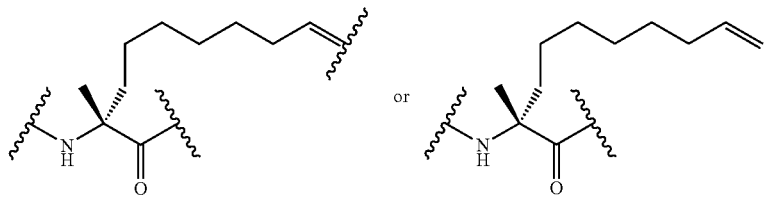 [SMILES: *N[C@](C)(CCCCCCC=*)C(*)=O ; *N[C@](C)(CCCCCCC=C)C(*)=O]

S₅

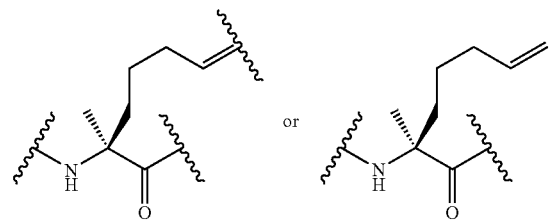 [SMILES: *N[C@@](C)(CCCC=*)C(*)=O ; *N[C@@](C)(CCCC=C)C(*)=O]

S₈

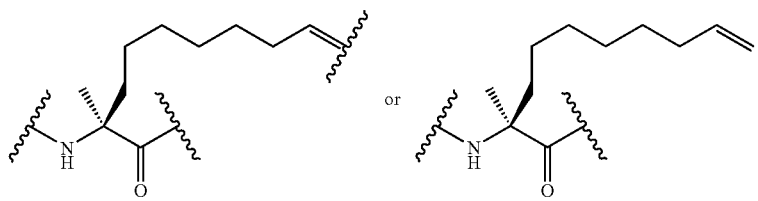 [SMILES: *N[C@@](C)(CCCCCCC=*)C(*)=O ; *N[C@@](C)(CCCCCCC=C)C(*)=O]

B₅

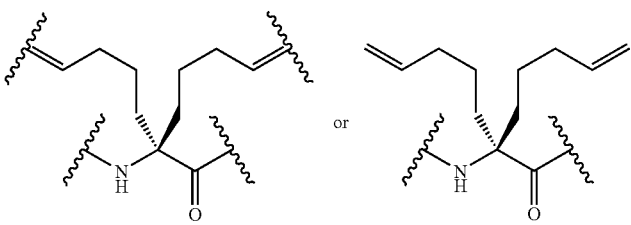

Aib

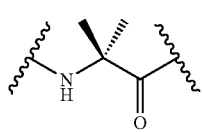

*wherein ⫤ refers to ½ of C——C double bond which is joined to another ½ of another C——C double bond (a "staple" of the stitched peptide).

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

We claim:

1. A substantially alpha-helical polypeptide of the formula:

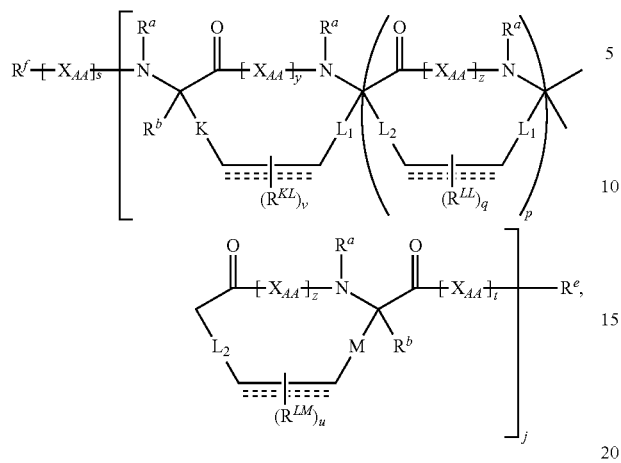

or a pharmaceutically acceptable salt thereof;
wherein:

each instance of K, $L_1$, $L_2$, and M is, independently, a cyclic or acyclic, branched or unbranched, substituted or unsubstituted $C_{1-8}$ alkylene;

each instance of $R^a$ is, independently, hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a cyclic or acyclic, substituted or unsubstituted acyl; or $R^a$ is a suitable amino protecting group;

each instance of $R^b$ is hydrogen or cyclic or acyclic, branched or unbranched, substituted or unsubstituted aliphatic;

each instance of $R^e$ is, independently, $-R^E$, $-OR^E$, $-N(R^E)_2$, or $-SR^E$, wherein each instance of $R^E$ is, independently, hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a substituted or unsubstituted acyl; a resin; a suitable hydroxyl, amino, or thiol protecting group; or two $R^E$ groups together form a 5- to 6-membered heterocyclic or heteroaromatic ring;

each instance of $R^f$ is, independently, hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a 5- to 6-membered heterocyclic or heteroaromatic ring;

each instance of $R^{KL}$, $R^{LL}$, and $R^{LM}$, is, independently, hydrogen; a cyclic or acyclic, branched or unbranched, substituted or unsubstituted aliphatic; a cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; or nitro;

each instance of $X_{AA}$ is, independently, an alpha-amino acid;

each instance of y and z is, independently, an integer from 2 to 6;

each instance of j is, independently, an integer from 1 to 10;

each instance of p is, independently, an integer from 0 to 10;

each instance of s and t is, independently, an integer from 0 and 100;

each instance of u, v, and q, is independently, an integer from 0 to 4; and

========== corresponds to a single, double, or triple bond.

2. The substantially alpha-helical polypeptide or its pharmaceutically acceptable salt of claim 1, wherein all ========== correspond to a single or double bond.

3. The substantially alpha-helical polypeptide or its pharmaceutically acceptable salt of claim 1, wherein all ========== correspond to a single bond.

4. The substantially alpha-helical polypeptide or its pharmaceutically acceptable salt of claim 1, wherein all ========== correspond to a double bond.

5. The substantially alpha-helical polypeptide or its pharmaceutically acceptable salt of claim 1, wherein $R^a$ is hydrogen.

6. The substantially alpha-helical polypeptide or its pharmaceutically acceptable salt of claim 1, wherein $R^b$ is hydrogen.

7. The substantially alpha-helical polypeptide or its pharmaceutically acceptable salt of claim 1, wherein $R^f$ is a label optionally joined by a linker.

8. The substantially alpha-helical polypeptide or its pharmaceutically acceptable salt of claim 7, wherein $R^f$ is a label joined by a heteroalkylene linker.

9. The substantially alpha-helical polypeptide or its pharmaceutically acceptable salt of claim 8, wherein the heteroalkylene linker is selected from the group consisting of:

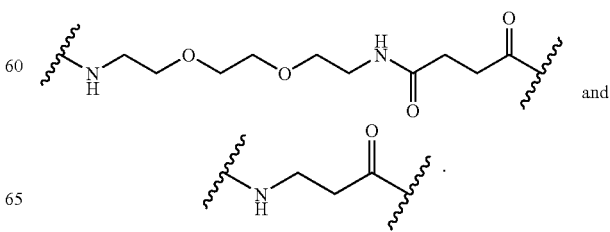

10. The substantially alpha-helical polypeptide or its pharmaceutically acceptable salt of claim 8, wherein the label is selected from the group consisting of:

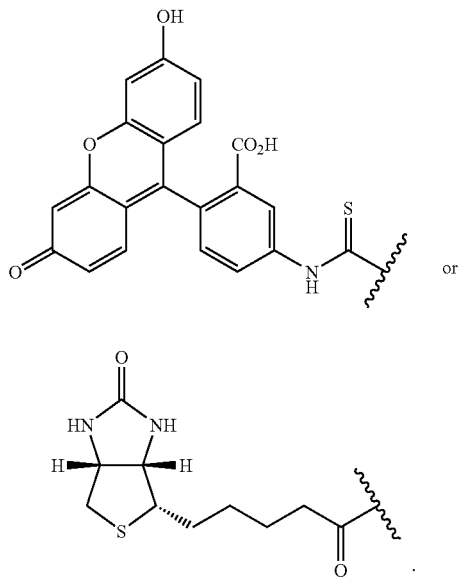

or

11. The substantially alpha-helical polypeptide or its pharmaceutically acceptable salt of claim 1, that is selected from the group consisting of SEQ ID NOs: 1-122.

12. A method of making the alpha-helical polypeptide of claim 1 or its pharmaceutically acceptable salt, comprising:
coupling amino acids of formulae (A), (B), and (C):

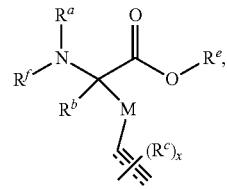

or salts of one of more of these amino acids, with at least one further amino acid or a salt thereof, to form a precursor polypeptide or its salt; and treating the precursor polypeptide or its salt with a catalyst to form the polypeptide or its pharmaceutically acceptable salt;

wherein in the amino acids (A) (B) and (C):

each instance of x is, independently, an integer from 0 to 3;

each instance of $R^c$ is, independently, hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a cyclic or acyclic, substituted or unsubstituted acyl; a substituted or unsubstituted hydroxyl; a substituted or unsubstituted thiol; a substituted or unsubstituted amino; cyano; isocyano; halo; or nitro; and each instance of ══════ independently corresponds to a double or triple bond.

13. The method of claim 12, wherein the catalyst is a ring closing metathesis catalyst.

14. The method of claim 12, wherein the catalyst is a ruthenium catalyst.

15. A pharmaceutical composition comprising at least one of the substantially alpha-helical polypeptide of claim 1, or its pharmaceutically acceptable salt, and a pharmaceutically acceptable excipient.

16. The substantially alpha-helical polypeptide of claim 1, or its pharmaceutically acceptable salt, wherein y is 3, and z is 3.

17. The substantially alpha-helical polypeptide of claim 1, or its pharmaceutically acceptable salt, wherein y is 3, and z is 6.

18. The alpha-helical polypeptide of claim 1, or its pharmaceutically acceptable salt, wherein y is 6, and z is 3.

19. An alpha-helical polypeptide of the formula:

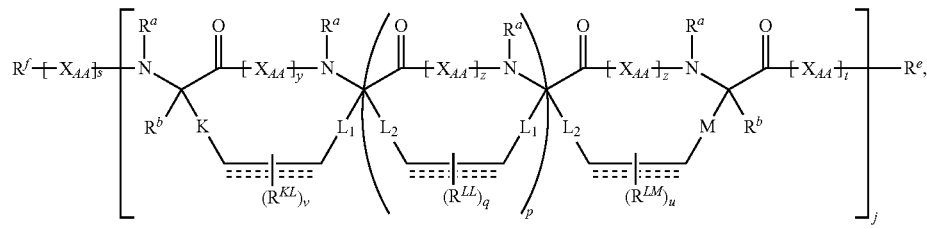

or a pharmaceutically acceptable salt thereof;
wherein:
each instance of $L_1$ and $L_2$ is independently a straight chain alkylene of 3 to 7 carbon atoms;
each instance of K and M is independently, a straight chain alkylene of 1 to 7 carbon atoms;
each instance of $R^a$ is hydrogen or alkyl of 1 to 6 carbon atoms or acyl;
each instance of $R^b$ is hydrogen or cyclic or acyclic, branched or unbranched, substituted or unsubstituted aliphatic;
each instance of $R^e$ is, independently, —$R^E$, —$OR^E$, —$N(R^E)_2$ or —$SR^E$, wherein each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups together form a substituted or unsubstituted 5- to 6-membered heterocyclic or heteroaromatic ring;
each instance of $R^f$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;
each instance of $X_{AA}$ is, independently, an alpha-amino acid;
each instance of y and z is, independently, an integer from 2 to 6;
j is, an integer between 1 to 10;
each instance of p is, independently, an integer between 0 to 10 inclusive;

$R^{KL}$, $R^{LL}$ and $R^{LM}$ are independently hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; or nitro;
each instance of s and t is, independently, an integer from 0 to 100;
u, v, and q, are independently an integer from 0 to 4;

========= corresponds to a single, double or triple bond.

20. The polypeptide or its pharmaceutically acceptable salt of claim 19, wherein $R^a$ is hydrogen.

21. The polypeptide or its pharmaceutically acceptable salt of claim 19, wherein $R^b$ is hydrogen or methyl.

22. The polypeptide or its pharmaceutically acceptable salt of claim 19, wherein y is 2, and z is 2, 3, 5 or 6.

23. The polypeptide or its pharmaceutically acceptable salt of claim 19, wherein y is 3, and z is 2, 3, 5 or 6.

24. The polypeptide or its pharmaceutically acceptable salt of claim 19, wherein y is 5, and z is 2, 3, 5 or 6.

25. The polypeptide or its pharmaceutically acceptable salt of claim 19, wherein y is 6, and z is 2, 3, 5 or 6.

26. The polypeptide or its pharmaceutically acceptable salt of claim 19, wherein ========= corresponds to a double bond.

27. The polypeptide or its pharmaceutically acceptable salt of claim 19, wherein $L_1$ and $L_2$ are both $CH_2CH_2CH_2$.

28. The polypeptide or its pharmaceutically acceptable salt of claim 19, wherein $L_1$ and $L_2$ are both $CH_2CH_2CH_2CH_2$.

29. The polypeptide or its pharmaceutically acceptable salt of claim 19, wherein $L_1$ and $L_2$ are both $CH_2CH_2CH_2CH_2CH_2$.

30. The polypeptide or its pharmaceutically acceptable salt of claim 19, wherein $L_1$ and $L_2$ are both $CH_2CH_2CH_2CH_2CH_2CH_2$.

31. The polypeptide or its pharmaceutically acceptable salt of claim 19, wherein $L_1$ and $L_2$ are both $CH_2CH_2CH_2CH_2CH_2CH_2CH_2$.

32. The polypeptide or its pharmaceutically acceptable salt of claim 19, selected from the group consisting of SEQ ID NO: 10 to SEQ ID No: 20, SEQ ID NO: 25, SEQ ID NO: 27 to 35, SEQ ID NO: 37 to SEQ ID NO: 122, and pharmaceutically acceptable salts thereof.

33. A pharmaceutical composition comprising the polypeptide or its pharmaceutically acceptable salt of claim 19 and a pharmaceutically acceptable carrier.

\* \* \* \* \*

UNITED STATES PATENT AND TRADEMARK OFFICE
CERTIFICATE OF CORRECTION

PATENT NO. : 8,592,377 B2  
APPLICATION NO. : 12/593384  
DATED : November 26, 2013  
INVENTOR(S) : Verdine et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 857 days.

Signed and Sealed this
Fourteenth Day of April, 2015

Michelle K. Lee
*Director of the United States Patent and Trademark Office*

SEQUENCE LISTING

<160> NUMBER OF SEQ ID NOS: 128

<210> SEQ ID NO 1
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis

<400> SEQUENCE: 1

Glu Trp Ala Glu Thr Ala Ala Ala Lys Phe Leu Ala Ala His Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: MISC_FEATURE
<222> LOCATION: (8)..(8)
<223> OTHER INFORMATION: Xaa represents 2-amino-2-(pent-4-enyl)hept-6-
      enoic acid or a stapled derivative

<400> SEQUENCE: 2

Glu Trp Ala Glu Thr Ala Ala Xaa Lys Phe Leu Ala Ala His Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 3

Glu Trp Ala Xaa Thr Ala Ala Ala Lys Phe Leu Ala Ala His Xaa
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents (R)-2-amino-2-methylhept-6-enoic
      acid or a stapled derivative -continued

```
<400> SEQUENCE: 4

Glu Trp Ala Xaa Thr Ala Ala Xaa Lys Phe Leu Ala Ala His Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 5

Glu Trp Ala Glu Thr Ala Ala Xaa Lys Phe Leu Ala Ala His Xaa
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative

<400> SEQUENCE: 6

Glu Trp Ala Xaa Thr Ala Ala Xaa Lys Phe Leu Ala Ala His Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (R)-2-amino-2-methylhept-6-enoic
      acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 7

Glu Trp Ala Glu Thr Ala Ala Xaa Lys Phe Leu Ala Ala His Xaa
1               5                   10                  15

<210> SEQ ID NO 8
<211> LENGTH: 15
```

```
<212> TYPE: PRT
<213> ORGANISM: Artificial Sequence
<220> FEATURE:
<223> OTHER INFORMATION: synthetic peptide synthesized by Fmoc-based
      solid phase peptide
      synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (15)..(15)
<223> OTHER INFORMATION: Xaa represents alpha-methyl-Alanine

<400> SEQUENCE: 8

Glu Trp Ala Xaa Thr Ala Ala Xaa Lys Phe Leu Ala Ala His Xaa
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents alpha-methyl-Alanine
<220> FEATURE:
<221> NAME/KEY: misc_feature
<222> LOCATION: (8)..(8)
<223> OTHER INFORMATION: Xaa represents (R)-2-amino-2-methylhept-6-enoic
      acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 9

Glu Trp Ala Xaa Thr Ala Ala Xaa Lys Phe Leu Ala Ala His Xaa
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 10
```

```
Glu Trp Ala Xaa Thr Ala Ala Xaa Lys Phe Leu Ala Ala His Xaa
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (12)..(12)
<223> OTHER INFORMATION: Xaa represents (R)-2-amino-2-methylhept-6-enoic
      acid or a stapled derivative

<400> SEQUENCE: 11

Glu Trp Ala Xaa Thr Ala Ala Xaa Lys Phe Leu Xaa Ala His Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (1)..(1)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (12)..(12)
<223> OTHER INFORMATION: Xaa represents (R)-2-amino-2-methylhept-6-enoic
      acid or a stapled derivative

<400> SEQUENCE: 12

Xaa Trp Ala Glu Thr Ala Ala Xaa Lys Phe Leu Xaa Ala His Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (1)..(1)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
```

```
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 13

Xaa Trp Ala Glu Thr Ala Ala Xaa Lys Phe Leu Ala Ala His Xaa
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (R)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (12)..(12)
<223> OTHER INFORMATION: Xaa represents (S)-2-amino-2-methylhept-6-enoic
      acid or a stapled derivative

<400> SEQUENCE: 14

Glu Trp Ala Xaa Thr Ala Ala Xaa Lys Phe Leu Xaa Ala His Ala
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (1)..(1)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (5)..(5)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (9)..(9)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents (S)-2-amino-2-methylhept-6-
      enoic acid or a stapled derivative

<400> SEQUENCE: 15

Xaa Glu Trp Ala Xaa Thr Ala Ala Xaa Lys Phe Leu Xaa Ala His Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: synthetic peptide synthesized by Fmoc-based
```

```
    solid phase peptide synthesis -linker1
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 16

Glu Trp Ala Xaa Thr Ala Ala Xaa Lys Phe Leu Ala Ala His Xaa
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis -linker1
<220> FEATURE:
<221> NAME/KEY: misc_feature
<222> LOCATION: (1)..(1)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 17

Xaa Trp Ala Glu Thr Ala Ala Xaa Lys Phe Leu Ala Ala His Xaa
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis -linker1
<220> FEATURE:
<221> NAME/KEY: misc_feature
<222> LOCATION: (4)..(4)
<223> OTHER INFORMATION: Xaa represents (S)-2-amino-2-methylhept-6-
      enoic acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (12)..(12)
<223> OTHER INFORMATION: Xaa represents (R)-2-amino-2-methylhept-6-enoic
      acid or a stapled derivative

<400> SEQUENCE: 18

Glu Trp Ala Xaa Thr Ala Ala Xaa Lys Phe Leu Xaa Ala His Ala
1               5                   10                  15
```

```
<210> SEQ ID NO 19
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (1)..(1)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 19

Xaa Trp Ala Glu Thr Ala Ala Xaa Lys Phe Leu Ala Ala His Xaa
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (12)..(12)
<223> OTHER INFORMATION: Xaa represents (R)-2-amino-2-methylhept-6-
      enoic acid or a stapled derivative

<400> SEQUENCE: 20

Glu Trp Ala Xaa Thr Ala Ala Xaa Lys Phe Leu Xaa Ala His Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis

<400> SEQUENCE: 21

Glu Trp Ala Glu Thr Ala Ala Ala Lys Phe Leu Ala Ala His Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
```

```
<220> FEATURE:
<221> NAME/KEY: misc_feature
<222> LOCATION: (4)..(4)
<223> OTHER INFORMATION: Xaa represents (R)-2-amino-2-methylhept-6-
      enoic acid or a stapled derivative
<220> FEATURE:
<221> NAME/KEY: misc_feature
<222> LOCATION: (8)..(8)
<223> OTHER INFORMATION: Xaa represents (R)-2-amino-2-methylhept-6-
      enoic acid or a stapled derivative
<220> FEATURE:
<221> NAME/KEY: misc_feature
<222> LOCATION: (15)..(15)
<223> OTHER INFORMATION: Xaa represents alpha-methyl-Alanine

<400> SEQUENCE: 22

Glu Trp Ala Xaa Thr Ala Ala Xaa Lys Phe Leu Ala Ala His Xaa
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (15)..(15)
<223> OTHER INFORMATION: Xaa represents alpha-methyl-Alanine

<400> SEQUENCE: 23

Glu Trp Ala Xaa Thr Ala Ala Xaa Lys Phe Leu Ala Ala His Xaa
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents alpha-methyl-Alanine
<220> FEATURE:
<221> NAME/KEY: misc_feature
<222> LOCATION: (8)..(8)
<223> OTHER INFORMATION: Xaa represents (R)-2-amino-2-methylhept-6-enoic
      acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 24

Glu Trp Ala Xaa Thr Ala Ala Xaa Lys Phe Leu Ala Ala His Xaa
1               5                   10                  15

<210> SEQ ID NO 25
<211> LENGTH: 15
<212> TYPE: PRT
```

<213> ORGANISM: Artificial Sequence
<220> FEATURE:
<223> OTHER INFORMATION: synthetic peptide synthesized by Fmoc-based
     solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
     acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
     enoic acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
     acid or a stapled derivative

<400> SEQUENCE: 25

Glu Trp Ala Xaa Thr Ala Ala Xaa Lys Phe Leu Ala Ala His Xaa
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: synthetic peptide synthesized by Fmoc-based
     solid phase peptide synthesis
<220> FEATURE:
<221> NAME/KEY: misc_feature
<222> LOCATION: (4)..(4)
<223> OTHER INFORMATION: Xaa represents alpha-methyl-Alanine
<220> FEATURE:
<221> NAME/KEY: misc_feature
<222> LOCATION: (8)..(8)
<223> OTHER INFORMATION: Xaa represents alpha-methyl-Alanine
<220> FEATURE:
<221> NAME/KEY: misc_feature
<222> LOCATION: (15)..(15)
<223> OTHER INFORMATION: Xaa represents alpha-methyl-Alanine

<400> SEQUENCE: 26

Glu Trp Ser Xaa Thr Asp Asn Xaa Lys Gln Glu Ala Asp Arg Xaa
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: synthetic peptide synthesized by Fmoc-based
     solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
     acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
     enoic acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
     acid or a stapled derivative

<400> SEQUENCE: 27

Glu Trp Ser Xaa Thr Asp Asn Xaa Lys Gln Glu Ala Asp Arg Xaa
1               5                   10                  15

```
<210> SEQ ID NO 28
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (12)..(12)
<223> OTHER INFORMATION: Xaa represents (R)-2-amino-2-methylhept-6-enoic
      acid or a stapled derivative

<400> SEQUENCE: 28

Glu Trp Ser Xaa Thr Asp Asn Xaa Lys Gln Glu Xaa Asp Arg Ala
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 29

Thr Arg Gln Xaa Arg Arg Asn Xaa Arg Arg Trp Arg Glu Xaa Gln
1               5                   10                  15

Arg

<210> SEQ ID NO 30
<211> LENGTH: 17
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
```

```
<222> LOCATION: (12)..(12)
<223> OTHER INFORMATION: Xaa represents (S)-2-amino-2-methylhept-6-enoic
      acid or a stapled derivative

<400> SEQUENCE: 30

Thr Arg Gln Xaa Arg Arg Asn Xaa Trp Arg Arg Xaa Arg Glu Arg Gln
1               5                   10                  15

Arg

<210> SEQ ID NO 31
<211> LENGTH: 17
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 31

Thr Arg Gln Xaa Arg Arg Asn Xaa Arg Arg Arg Trp Arg Glu Xaa Gln
1               5                   10                  15

Arg

<210> SEQ ID NO 32
<211> LENGTH: 17
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (12)..(12)
<223> OTHER INFORMATION: Xaa represents (R)-2-amino-2-methylhept-6-enoic
      acid or a stapled derivative

<400> SEQUENCE: 32

Thr Arg Gln Xaa Arg Arg Asn Xaa Trp Arg Arg Xaa Arg Glu Arg Gln
1               5                   10                  15

Arg

<210> SEQ ID NO 33
<211> LENGTH: 15
<212> TYPE: PRT
<213> ORGANISM: Artificial Sequence
<220> FEATURE:
<223> OTHER INFORMATION: synthetic peptide synthesized by Fmoc-based
```

-continued

```
      solid phase peptide synthesis
<220> FEATURE:
<221> NAME/KEY: misc_feature
<222> LOCATION: (3)..(3)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (7)..(7)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (S)-2-amino-2-methyldec-9-enoic
      acid or a stapled derivative

<400> SEQUENCE: 33

Ile Leu Xaa Met Ala Val Xaa His Met Lys Ser Leu Arg Xaa Thr
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (7)..(7)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (11)..(11)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (15)..(15)
<223> OTHER INFORMATION: Xaa represents (R)-2-amino-2-methylhept-6-enoic
      acid or a stapled derivative

<400> SEQUENCE: 34

Ile Leu Arg Met Ala Val Xaa His Met Lys Xaa Leu Arg Gly Xaa
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (3)..(3)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (7)..(7)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (S)-2-amino-2-methyldec-9-enoic
      acid or a stapled derivative

<400> SEQUENCE: 35

Ile Leu Xaa Met Ala Val Xaa His Met Lys Ser Leu Arg Xaa Thr
1               5                   10                  15
```

```
<210> SEQ ID NO 36
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (7)..(7)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (11)..(11)
<223> OTHER INFORMATION: Xaa represents 2-amino-2-(pent-4-enyl)hept-6-
      enoic acid or a stapled derivative

<400> SEQUENCE: 36

Ile Leu Arg Met Ala Val Xaa His Met Lys Xaa Leu Arg Gly Arg
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (3)..(3)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (7)..(7)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (S)-2-amino-2-methyldec-9-enoic
      acid or a stapled derivative

<400> SEQUENCE: 37

Leu Ser Xaa Glu Thr Phe Xaa Asp Leu Trp Lys Leu Leu Xaa Glu Asn
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (3)..(3)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (7)..(7)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (S)-2-amino-2-methyldec-9-enoic
      acid or a stapled derivative

<400> SEQUENCE: 38

Leu Ser Xaa Glu Thr Ala Xaa Asp Leu Trp Lys Leu Leu Xaa Glu Asn
```

<210> SEQ ID NO 39
<211> LENGTH: 16
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (3)..(3)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (7)..(7)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (S)-2-amino-2-methyldec-9-enoic
      acid or a stapled derivative

<400> SEQUENCE: 39

Leu Ser Xaa Glu Thr Phe Xaa Asp Leu Trp Lys Leu Leu Xaa Glu Asn
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (3)..(3)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (7)..(7)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (S)-2-amino-2-methyldec-9-enoic
      acid or a stapled derivative

<400> SEQUENCE: 40

Leu Ser Xaa Glu Thr Ala Xaa Asp Leu Trp Lys Leu Leu Xaa Glu Asn
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (3)..(3)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (7)..(7)
<223> OTHER INFORMATION: Xaa represents 2-amino-2-(pent-4-enyl)hept-6-
      enoic acid or a stapled derivative
<220> FEATURE:
<221> NAME/KEY: misc_feature

```
<222> LOCATION: (14)..(14)
<223> OTHER INFORMATION: Xaa represents (S)-2-amino-2-methyldec-9-enoic
      acid or a stapled derivative

<400> SEQUENCE: 41

Leu Ser Xaa Glu Thr Phe Xaa Asp Leu Trp Lys Leu Leu Xaa Glu Asn
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (3)..(3)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (7)..(7)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (S)-2-amino-2-methyldec-9-enoic
      acid or a stapled derivative

<400> SEQUENCE: 42

Leu Ser Xaa Glu Thr Ala Xaa Asp Leu Trp Lys Leu Leu Xaa Glu Asn
1               5                   10                  15

<210> SEQ ID NO 43
<211> LENGTH: 10
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (1)..(1)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (5)..(5)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (9)..(9)
<223> OTHER INFORMATION: Xaa represents (R)-2-amino-2-methylhept-6-enoic
      acid or a stapled derivative

<400> SEQUENCE: 43

Xaa Asp Phe Ser Xaa Tyr Trp Lys Xaa Leu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (1)..(1)
<223> OTHER INFORMATION: Xaa represents (R)-2-amino-2-methylhept-6-enoic
      acid or a stapled derivative
```

```
<220> FEATURE:
<221> NAME/KEY: misc_feature
<222> LOCATION: (5)..(5)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (9)..(9)
<223> OTHER INFORMATION: Xaa represents (S)-2-amino-2-methylhept-6-enoic
      acid or a stapled derivative

<400> SEQUENCE: 44

Xaa Asp Phe Ser Xaa Tyr Trp Lys Xaa Leu
1               5                   10

<210> SEQ ID NO 45
<211> LENGTH: 22
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (9)..(9)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (13)..(13)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents Nle (Norleucine)
<220> FEATURE:
<221> NAME/KEY: misc_feature
<222> LOCATION: (20)..(20)
<223> OTHER INFORMATION: Xaa represents (S)-2-amino-2-methyldec-9-enoic
      acid or a stapled derivative

<400> SEQUENCE: 45

Glu Asp Ile Ile Arg Asn Ile Ala Xaa His Leu Ala Xaa Val Gly Asp
1               5                   10                  15

Trp Xaa Asp Xaa Ser Ile
            20

<210> SEQ ID NO 46
<211> LENGTH: 17
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents Nle (Norleucine)
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative
```

-continued

```
<400> SEQUENCE: 46

Asn Ile Ala Xaa His Leu Ala Xaa Val Gly Asp Trp Xaa Asp Xaa Ser
1               5                   10                  15

Ile

<210> SEQ ID NO 47
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents Nle (Norleucine)
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 47

Asn Ile Ala Xaa His Leu Ala Xaa Val Gly Asp Trp Xaa Asp Xaa
1               5                   10                  15

<210> SEQ ID NO 48
<211> LENGTH: 22
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (9)..(9)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (13)..(13)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents Nle (Norleucine)
<220> FEATURE:
<221> NAME/KEY: misc_feature
<222> LOCATION: (20)..(20)
<223> OTHER INFORMATION: Xaa represents (S)-2-amino-2-methyldec-9-enoic
      acid or a stapled derivative

<400> SEQUENCE: 48

Glu Asp Ile Ile Arg Asn Ile Ala Xaa His Leu Ala Xaa Val Gly Asp
1               5                   10                  15

Trp Xaa Asp Xaa Ser Ile
            20

<210> SEQ ID NO 49
<211> LENGTH: 17
<212> TYPE: PRT
```

```
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents Nle (Norleucine)
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 49

Asn Ile Ala Xaa His Leu Ala Xaa Val Gly Asp Trp Xaa Asp Xaa Ser
1               5                   10                  15

Ile

<210> SEQ ID NO 50
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents Nle (Norleucine)
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 50

Asn Ile Ala Xaa His Leu Ala Xaa Val Gly Asp Trp Xaa Asp Xaa
1               5                   10                  15

<210> SEQ ID NO 51
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (2)..(2)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (6)..(6)
```

<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (10)..(10)
<223> OTHER INFORMATION: Xaa represents (R)-2-amino-2-methylhept-6-enoic
      acid or a stapled derivative

<400> SEQUENCE: 51

Leu Xaa Ile Leu Gln Xaa Ala Val Gln Xaa Ile Leu Gly Leu Glu Gln
1               5                   10                  15

Gln Val Arg Glu Arg
            20

<210> SEQ ID NO 52
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (2)..(2)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (6)..(6)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents (S)-2-amino-2-methyldec-9-enoic
      acid or a stapled derivative

<400> SEQUENCE: 52

Leu Xaa Ile Leu Gln Xaa Ala Val Gln Val Ile Leu Xaa Leu Glu Gln
1               5                   10                  15

Gln Val Arg Glu Arg
            20

<210> SEQ ID NO 53
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (9)..(9)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (13)..(13)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (17)..(17)
<223> OTHER INFORMATION: Xaa represents (R)-2-amino-2-methylhept-6-enoic
      acid or a stapled derivative

<400> SEQUENCE: 53

Leu Leu Ile Leu Gln Gln Ala Val Xaa Val Ile Leu Xaa Leu Glu Gln
1               5                   10                  15

Xaa Val Arg Glu Arg
            20

```
<210> SEQ ID NO 54
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (9)..(9)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (13)..(13)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (20)..(20)
<223> OTHER INFORMATION: Xaa represents (S)-2-amino-2-methyldec-9-enoic
      acid or a stapled derivative

<400> SEQUENCE: 54

Leu Leu Ile Leu Gln Gln Ala Val Xaa Val Ile Leu Xaa Leu Glu Gln
1               5                   10                  15

Gln Val Arg Xaa Arg
            20

<210> SEQ ID NO 55
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (5)..(5)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (9)..(9)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents (R)-2-amino-2-methylhept-6-enoic
      acid or a stapled derivative

<400> SEQUENCE: 55

Leu Leu Ile Leu Xaa Gln Ala Val Xaa Val Ile Leu Xaa Leu Glu Gln
1               5                   10                  15

Gln Val Arg Glu Arg
            20

<210> SEQ ID NO 56
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (5)..(5)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (9)..(9)
```

```
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (16)..(16)
<223> OTHER INFORMATION: Xaa represents (S)-2-amino-2-methyldec-9-enoic
      acid or a stapled derivative

<400> SEQUENCE: 56

Leu Leu Ile Leu Xaa Gln Ala Val Xaa Val Ile Leu Gly Leu Glu Xaa
1               5                  10                  15

Gln Val Arg Glu Arg
            20

<210> SEQ ID NO 57
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (5)..(5)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (9)..(9)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (17)..(17)
<223> OTHER INFORMATION: Xaa represents (S)-2-amino-2-methylhept-6-enoic
      acid or a stapled derivative

<400> SEQUENCE: 57

Leu Leu Ile Leu Xaa Gln Ala Val Xaa Val Ile Leu Xaa Leu Glu Gln
1               5                  10                  15

Xaa Val Arg Glu Arg
            20

<210> SEQ ID NO 58
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (2)..(2)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (6)..(6)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (10)..(10)
<223> OTHER INFORMATION: Xaa represents (R)-2-amino-2-methylhept-6-enoic
      acid or a stapled derivative

<400> SEQUENCE: 58

Leu Xaa Ile Leu Gln Xaa Ala Val Gln Xaa Ile Leu Gly Leu Glu Gln
```

```
                1               5                   10                  15

Gln Val Arg Glu Arg
                20

<210> SEQ ID NO 59
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (2)..(2)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (6)..(6)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents (S)-2-amino-2-methyldec-9-enoic
      acid or a stapled derivative

<400> SEQUENCE: 59

Leu Xaa Ile Leu Gln Xaa Ala Val Gln Val Ile Leu Xaa Leu Glu Gln
1               5                   10                  15

Gln Val Arg Glu Arg
                20

<210> SEQ ID NO 60
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (9)..(9)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (13)..(13)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (17)..(17)
<223> OTHER INFORMATION: Xaa represents (R)-2-amino-2-methylhept-6-enoic
      acid or a stapled derivative

<400> SEQUENCE: 60

Leu Leu Ile Leu Gln Gln Ala Val Xaa Val Ile Leu Xaa Leu Glu Gln
1               5                   10                  15

Xaa Val Arg Glu Arg
                20

<210> SEQ ID NO 61
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (9)..(9)
```

```
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (13)..(13)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (20)..(20)
<223> OTHER INFORMATION: Xaa represents (S)-2-amino-2-methyldec-9-enoic
      acid or a stapled derivative

<400> SEQUENCE: 61

Leu Leu Ile Leu Gln Gln Ala Val Xaa Val Ile Leu Xaa Leu Glu Gln
1               5                   10                  15

Gln Val Arg Xaa Arg
            20

<210> SEQ ID NO 62
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (5)..(5)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (9)..(9)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents (R)-2-amino-2-methylhept-6-enoic
      acid or a stapled derivative

<400> SEQUENCE: 62

Leu Leu Ile Leu Xaa Gln Ala Val Xaa Val Ile Leu Xaa Leu Glu Gln
1               5                   10                  15

Gln Val Arg Glu Arg
            20

<210> SEQ ID NO 63
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (5)..(5)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (9)..(9)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (16)..(16)
<223> OTHER INFORMATION: Xaa represents (S)-2-amino-2-methyldec-9-enoic
      acid or a stapled derivative

<400> SEQUENCE: 63

Leu Leu Ile Leu Xaa Gln Ala Val Xaa Val Ile Leu Gly Leu Glu Xaa
```

```
1               5                   10                  15

Gln Val Arg Glu Arg
            20

<210> SEQ ID NO 64
<211> LENGTH: 21
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (5)..(5)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (9)..(9)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (17)..(17)
<223> OTHER INFORMATION: Xaa represents (S)-2-amino-2-methylhept-6-enoic
      acid or a stapled derivative

<400> SEQUENCE: 64

Leu Leu Ile Leu Xaa Gln Ala Val Xaa Val Ile Leu Xaa Leu Glu Gln
1               5                   10                  15

Xaa Val Arg Glu Arg
            20

<210> SEQ ID NO 65
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (14)..(14)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (18)..(18)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (22)..(22)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (26)..(26)
<223> OTHER INFORMATION: Xaa represents (S)-2-amino-2-methylhept-6-enoic
      acid or a stapled derivative

<400> SEQUENCE: 65

His Ala Glu Gly Thr Phe Thr Ser Asp Val Ser Ser Tyr Xaa Glu Gly
1               5                   10                  15

Gln Xaa Ala Lys Glu Xaa Ile Ala Trp Xaa Val Lys Gly Arg
            20                  25                  30
```

```
<210> SEQ ID NO 66
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (14)..(14)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (18)..(18)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (25)..(25)
<223> OTHER INFORMATION: Xaa represents (S)-2-amino-2-methyldec-9-enoic
      acid or a stapled derivative

<400> SEQUENCE: 66

His Ala Glu Gly Thr Phe Thr Ser Asp Val Ser Ser Tyr Xaa Glu Gly
1               5                   10                  15

Gln Xaa Ala Lys Glu Phe Ile Ala Xaa Leu Val Lys Gly Arg
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (18)..(18)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (22)..(22)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (29)..(29)
<223> OTHER INFORMATION: Xaa represents (S)-2-amino-2-methyldec-9-enoic
      acid or a stapled derivative

<400> SEQUENCE: 67

His Ala Glu Gly Thr Phe Thr Ser Asp Val Ser Ser Tyr Leu Glu Gly
1               5                   10                  15

Gln Xaa Ala Lys Glu Xaa Ile Ala Trp Leu Val Lys Xaa Arg
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (17)..(17)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (21)..(21)
<223> OTHER INFORMATION: Xaa represents 2-amino-2-(pent-4-enyl)hept-6-
```

-continued

```
      enoic acid or a stapled derivative
<220> FEATURE:
<221> NAME/KEY: misc_feature
<222> LOCATION: (25)..(25)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (29)..(29)
<223> OTHER INFORMATION: Xaa represents (S)-2-amino-2-methylhept-6-enoic
      acid or a stapled derivative

<400> SEQUENCE: 68

His Ala Glu Gly Thr Phe Thr Ser Asp Val Ser Ser Tyr Leu Glu Gly
1               5                   10                  15

Xaa Ala Ala Lys Xaa Phe Ile Ala Xaa Leu Val Lys Xaa Arg
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (21)..(21)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (25)..(25)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (29)..(29)
<223> OTHER INFORMATION: Xaa represents (R)-2-amino-2-methylhept-6-enoic
      acid or a stapled derivative

<400> SEQUENCE: 69

His Ala Glu Gly Thr Phe Thr Ser Asp Val Ser Ser Tyr Leu Glu Gly
1               5                   10                  15

Gln Ala Ala Lys Xaa Phe Ile Ala Xaa Leu Val Lys Xaa Arg
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (17)..(17)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (24)..(24)
<223> OTHER INFORMATION: Xaa represents (S)-2-amino-2-methyldec-9-enoic
      acid or a stapled derivative

<400> SEQUENCE: 70

His Ala Glu Gly Thr Phe Thr Ser Asp Xaa Ser Ser Tyr Leu Glu Gly
1               5                   10                  15
```

```
Xaa Ala Ala Lys Glu Phe Ile Xaa Trp Leu Val Lys Gly Arg
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (16)..(16)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (20)..(20)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (27)..(27)
<223> OTHER INFORMATION: Xaa represents (S)-2-amino-2-methyldec-9-enoic
      acid or a stapled derivative

<400> SEQUENCE: 71

His Ala Glu Gly Thr Phe Thr Ser Asp Val Ser Ser Tyr Leu Glu Xaa
1               5                   10                  15

Gln Ala Ala Xaa Glu Phe Ile Ala Trp Leu Xaa Lys Gly Arg
            20                  25                  30

<210> SEQ ID NO 72
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (13)..(13)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (20)..(20)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (27)..(27)
<223> OTHER INFORMATION: Xaa represents (S)-2-amino-2-methyldec-9-enoic
      acid or a stapled derivative

<400> SEQUENCE: 72

His Ala Glu Gly Thr Phe Thr Ser Asp Val Ser Ser Xaa Leu Glu Gly
1               5                   10                  15

Gln Ala Ala Xaa Glu Phe Ile Ala Trp Leu Xaa Lys Gly Arg
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (12)..(12)
<223> OTHER INFORMATION: Xaa represents (S)-2-amino-2-methylhept-6-enoic
```

-continued acid or a stapled derivative
<220> FEATURE:
<221> NAME/KEY: misc_feature
<222> LOCATION: (16)..(16)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (23)..(23)
<223> OTHER INFORMATION: Xaa represents (S)-2-amino-2-methyldec-9-enoic
      acid or a stapled derivative

<400> SEQUENCE: 73

His Ala Glu Gly Thr Phe Thr Ser Asp Val Ser Xaa Tyr Leu Glu Xaa
1               5                   10                  15

Gln Ala Ala Lys Glu Phe Xaa Ala Trp Leu Val Lys Gly Arg
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 74

His Ala Glu Gly Thr Phe Thr Ser Asp Xaa Ser Ser Tyr Xaa Glu Gly
1               5                   10                  15

Gln Ala Ala Lys Xaa Phe Ile Ala Trp Leu Val Lys Gly Arg
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (12)..(12)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (19)..(19)
<223> OTHER INFORMATION: Xaa represents (S)-2-amino-2-methyldec-9-enoic
      acid or a stapled derivative

<400> SEQUENCE: 75

His Ala Glu Gly Thr Phe Thr Xaa Asp Val Ser Xaa Tyr Leu Glu Gly
1               5                   10                  15

```
Gln Ala Xaa Lys Glu Phe Ile Ala Trp Leu Val Lys Gly Arg
            20                  25                  30

<210> SEQ ID NO 76
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (12)..(12)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (16)..(16)
<223> OTHER INFORMATION: Xaa represents (R)-2-amino-2-methylhept-6-enoic
      acid or a stapled derivative

<400> SEQUENCE: 76

His Ala Glu Gly Thr Phe Thr Xaa Asp Val Ser Xaa Tyr Leu Glu Xaa
1               5                   10                  15

Gln Ala Ala Lys Glu Phe Ile Ala Trp Leu Val Lys Gly Arg
            20                  25                  30

<210> SEQ ID NO 77
<211> LENGTH: 30
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (12)..(12)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (16)..(16)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (20)..(20)
<223> OTHER INFORMATION: Xaa represents (S)-2-amino-2-methylhept-6-enoic
      acid or a stapled derivative

<400> SEQUENCE: 77

His Ala Glu Gly Thr Phe Thr Xaa Asp Val Ser Xaa Tyr Leu Glu Xaa
1               5                   10                  15

Gln Ala Ala Xaa Glu Phe Ile Ala Trp Leu Val Lys Gly Arg
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: synthetic peptide synthesized by Fmoc-based
```

-continued

```
        solid phase peptide synthesis
<220> FEATURE:
<221> NAME/KEY: misc_feature
<222> LOCATION: (12)..(12)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (16)..(16)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (20)..(20)
<223> OTHER INFORMATION: Xaa represents (R)-2-amino-2-methylhept-6-enoic
      acid or a stapled derivative

<400> SEQUENCE: 78

His Ala Glu Gly Thr Phe Thr Ser Asp Val Ser Xaa Tyr Leu Glu Xaa
1               5                   10                  15

Gln Ala Ala Xaa Glu Phe Ile Ala Trp Leu Val Lys Gly Arg
            20                  25                  30

<210> SEQ ID NO 79
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (12)..(12)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (19)..(19)
<223> OTHER INFORMATION: Xaa represents (S)-2-amino-2-methyldec-9-enoic
      acid or a stapled derivative

<400> SEQUENCE: 79

Ser Gly Ser Trp Leu Arg Asp Xaa Trp Asp Trp Xaa Cys Thr Val Leu
1               5                   10                  15

Thr Asp Xaa Lys Thr Trp Leu Gln Ser Lys Leu
            20                  25

<210> SEQ ID NO 80
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (13)..(13)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (17)..(17)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents 2-amino-2-(pent-4-enyl)hept-6-
      enoic acid or a stapled derivative
```

```
<220> FEATURE:
<221> NAME/KEY: misc_feature
<222> LOCATION: (25)..(25)
<223> OTHER INFORMATION: Xaa represents (S)-2-amino-2-methylhept-6-enoic
      acid or a stapled derivative

<400> SEQUENCE: 80

Ser Gly Ser Trp Leu Arg Asp Val Trp Asp Trp Ile Xaa Thr Val Leu
1               5                   10                  15

Xaa Asp Phe Lys Xaa Trp Leu Gln Xaa Lys Leu
            20                  25

<210> SEQ ID NO 81
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (17)..(17)
<223> OTHER INFORMATION: Xaa represents (S)-2-amino-2-methyldec-9-enoic
      acid or a stapled derivative

<400> SEQUENCE: 81

Ser Gly Ser Trp Leu Xaa Asp Val Trp Xaa Trp Ile Cys Thr Val Leu
1               5                   10                  15

Xaa Asp Phe Lys Thr Trp Leu Gln Ser Lys Leu
            20                  25

<210> SEQ ID NO 82
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-
      enoic acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-
      6-enoic acid or a stapled derivative
<220> FEATURE:
<221> NAME/KEY: misc_feature
<222> LOCATION: (14)..(14)
<223> OTHER INFORMATION: Xaa represents (R)-2-amino-2-methylhept-6-enoic
      acid or a stapled derivative

<400> SEQUENCE: 82

Ser Gly Ser Trp Leu Xaa Asp Val Trp Xaa Trp Ile Cys Xaa Val Leu
1               5                   10                  15

Thr Asp Phe Lys Thr Trp Leu Gln Ser Lys Leu
            20                  25

<210> SEQ ID NO 83
```

```
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (S)-2-amino-2-methylhept-6-enoic
      acid or a stapled derivative

<400> SEQUENCE: 83

Ser Gly Ser Trp Leu Xaa Asp Val Trp Xaa Trp Ile Cys Xaa Val Leu
1               5                   10                  15

Thr Xaa Phe Lys Thr Trp Leu Gln Ser Lys Leu
            20                  25

<210> SEQ ID NO 84
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 84

Ser Gly Ser Trp Leu Arg Asp Val Trp Xaa Trp Ile Cys Xaa Val Leu
1               5                   10                  15

Thr Asp Phe Lys Xaa Trp Leu Gln Ser Lys Leu
            20                  25

<210> SEQ ID NO 85
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
```

```
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (R)-2-amino-2-methylhept-6-enoic
      acid or a stapled derivative

<400> SEQUENCE: 85

Ser Gly Ser Trp Leu Arg Asp Val Trp Xaa Trp Ile Cys Xaa Val Leu
1               5                   10                  15

Thr Xaa Phe Lys Thr Trp Leu Gln Ser Lys Leu
            20                  25

<210> SEQ ID NO 86
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (7)..(7)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 86

Ser Gly Ser Trp Leu Arg Xaa Val Trp Asp Trp Ile Cys Xaa Val Leu
1               5                   10                  15

Thr Asp Phe Lys Xaa Trp Leu Gln Ser Lys Leu
            20                  25

<210> SEQ ID NO 87
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (12)..(12)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (19)..(19)
<223> OTHER INFORMATION: Xaa represents (S)-2-amino-2-methyldec-9-enoic
      acid or a stapled derivative

<400> SEQUENCE: 87

Ser Gly Ser Trp Leu Arg Asp Xaa Trp Asp Trp Xaa Cys Thr Val Leu
1               5                   10                  15
```

```
Thr Asp Xaa Lys Thr Trp Leu Gln Ser Lys Leu
            20                  25
```

<210> SEQ ID NO 88
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (13)..(13)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (17)..(17)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (25)..(25)
<223> OTHER INFORMATION: Xaa represents (S)-2-amino-2-methylhept-6-enoic
      acid or a stapled derivative

<400> SEQUENCE: 88

```
Ser Gly Ser Trp Leu Arg Asp Val Trp Asp Trp Ile Xaa Thr Val Leu
1               5                   10                  15

Xaa Asp Phe Lys Xaa Trp Leu Gln Xaa Lys Leu
            20                  25
```

<210> SEQ ID NO 89
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (17)..(17)
<223> OTHER INFORMATION: Xaa represents (S)-2-amino-2-methyldec-9-enoic
      acid or a stapled derivative

<400> SEQUENCE: 89

```
Ser Gly Ser Trp Leu Xaa Asp Val Trp Xaa Trp Ile Cys Thr Val Leu
1               5                   10                  15

Xaa Asp Phe Lys Thr Trp Leu Gln Ser Lys Leu
            20                  25
```

<210> SEQ ID NO 90
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis

```
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (R)-2-amino-2-methylhept-6-enoic
      acid or a stapled derivative

<400> SEQUENCE: 90

Ser Gly Ser Trp Leu Xaa Asp Val Trp Xaa Trp Ile Cys Xaa Val Leu
1               5                   10                  15

Thr Asp Phe Lys Thr Trp Leu Gln Ser Lys Leu
            20                  25

<210> SEQ ID NO 91
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (S)-2-amino-2-methylhept-6-enoic
      acid or a stapled derivative

<400> SEQUENCE: 91

Ser Gly Ser Trp Leu Xaa Asp Val Trp Xaa Trp Ile Cys Xaa Val Leu
1               5                   10                  15

Thr Xaa Phe Lys Thr Trp Leu Gln Ser Lys Leu
            20                  25

<210> SEQ ID NO 92
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
```

```
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 92

Ser Gly Ser Trp Leu Arg Asp Val Trp Xaa Trp Ile Cys Xaa Val Leu
1               5                   10                  15

Thr Asp Phe Lys Xaa Trp Leu Gln Ser Lys Leu
            20                  25

<210> SEQ ID NO 93
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (R)-2-amino-2-methylhept-6-enoic
      acid or a stapled derivative

<400> SEQUENCE: 93

Ser Gly Ser Trp Leu Arg Asp Val Trp Xaa Trp Ile Cys Xaa Val Leu
1               5                   10                  15

Thr Xaa Phe Lys Thr Trp Leu Gln Ser Lys Leu
            20                  25

<210> SEQ ID NO 94
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (7)..(7)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 94

Ser Gly Ser Trp Leu Arg Xaa Val Trp Asp Trp Ile Cys Xaa Val Leu
1               5                   10                  15

Thr Asp Phe Lys Xaa Trp Leu Gln Ser Lys Leu
            20                  25

<210> SEQ ID NO 95
<211> LENGTH: 27
```

```
<212> TYPE: PRT
<213> ORGANISM: Artificial Sequence
<220> FEATURE:
<223> OTHER INFORMATION: synthetic peptide synthesized by Fmoc-based
      solid phase peptide  synthesis -linker1
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (12)..(12)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (19)..(19)
<223> OTHER INFORMATION: Xaa represents (S)-2-amino-2-methyldec-9-enoic
      acid or a stapled derivative

<400> SEQUENCE: 95

Ser Gly Ser Trp Leu Arg Asp Xaa Trp Asp Trp Xaa Cys Thr Val Leu
1               5                   10                  15

Thr Asp Xaa Lys Thr Trp Leu Gln Ser Lys Leu
            20                  25

<210> SEQ ID NO 96
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis -linker1
<220> FEATURE:
<221> NAME/KEY: misc_feature
<222> LOCATION: (13)..(13)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (17)..(17)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (25)..(25)
<223> OTHER INFORMATION: Xaa represents (S)-2-amino-2-methylhept-6-enoic
      acid or a stapled derivative

<400> SEQUENCE: 96

Ser Gly Ser Trp Leu Arg Asp Val Trp Asp Trp Ile Xaa Thr Val Leu
1               5                   10                  15

Xaa Asp Phe Lys Xaa Trp Leu Gln Xaa Lys Leu
            20                  25

<210> SEQ ID NO 97
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis -linker1
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
```

<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (17)..(17)
<223> OTHER INFORMATION: Xaa represents (S)-2-amino-2-methyldec-9-enoic
      acid or a stapled derivative

<400> SEQUENCE: 97

Ser Gly Ser Trp Leu Xaa Asp Val Trp Xaa Trp Ile Cys Thr Val Leu
1               5                   10                  15

Xaa Asp Phe Lys Thr Trp Leu Gln Ser Lys Leu
            20                  25

<210> SEQ ID NO 98
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis -linker1
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (R)-2-amino-2-methylhept-6-enoic
      acid or a stapled derivative

<400> SEQUENCE: 98

Ser Gly Ser Trp Leu Xaa Asp Val Trp Xaa Trp Ile Cys Xaa Val Leu
1               5                   10                  15

Thr Asp Phe Lys Thr Trp Leu Gln Ser Lys Leu
            20                  25

<210> SEQ ID NO 99
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis -linker1
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (S)-2-amino-2-methylhept-6-enoic
      acid or a stapled derivative

<400> SEQUENCE: 99

```
Ser Gly Ser Trp Leu Xaa Asp Val Trp Xaa Trp Ile Cys Xaa Val Leu
1               5                   10                  15

Thr Xaa Phe Lys Thr Trp Leu Gln Ser Lys Leu
            20                  25

<210> SEQ ID NO 100
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis -linker1
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 100

Ser Gly Ser Trp Leu Arg Asp Val Trp Xaa Trp Ile Cys Xaa Val Leu
1               5                   10                  15

Thr Asp Phe Lys Xaa Trp Leu Gln Ser Lys Leu
            20                  25

<210> SEQ ID NO 101
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis -linker1
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (R)-2-amino-2-methylhept-6-enoic
      acid or a stapled derivative

<400> SEQUENCE: 101

Ser Gly Ser Trp Leu Arg Asp Val Trp Xaa Trp Ile Cys Xaa Val Leu
1               5                   10                  15

Thr Xaa Phe Lys Thr Trp Leu Gln Ser Lys Leu
            20                  25

<210> SEQ ID NO 102
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis -linker1
<220> FEATURE:
```

```
<221> NAME/KEY: misc_feature
<222> LOCATION: (7)..(7)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 102

Ser Gly Ser Trp Leu Arg Xaa Val Trp Asp Trp Ile Cys Xaa Val Leu
1               5                   10                  15

Thr Asp Phe Lys Xaa Trp Leu Gln Ser Lys Leu
                20                  25

<210> SEQ ID NO 103
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (12)..(12)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (19)..(19)
<223> OTHER INFORMATION: Xaa represents (S)-2-amino-2-methyldec-9-enoic
      acid or a stapled derivative

<400> SEQUENCE: 103

Ser Gly Ser Trp Leu Arg Asp Xaa Trp Asp Trp Xaa Cys Thr Val Leu
1               5                   10                  15

Thr Asp Xaa Lys Thr Trp Leu Gln Ser Lys Leu
                20                  25

<210> SEQ ID NO 104
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (13)..(13)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (17)..(17)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents 2-amino-2-(pent-4-enyl)hept-6-
      enoic acid or a stapled derivative
<220> FEATURE:
<221> NAME/KEY: misc_feature
```

```
<222> LOCATION: (25)..(25)
<223> OTHER INFORMATION: Xaa represents (S)-2-amino-2-methylhept-6-enoic
      acid or a stapled derivative

<400> SEQUENCE: 104

Ser Gly Ser Trp Leu Arg Asp Val Trp Asp Trp Ile Xaa Thr Val Leu
1               5                   10                  15

Xaa Asp Phe Lys Xaa Trp Leu Gln Xaa Lys Leu
            20                  25

<210> SEQ ID NO 105
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (17)..(17)
<223> OTHER INFORMATION: Xaa represents (S)-2-amino-2-methyldec-9-enoic
      acid or a stapled derivative

<400> SEQUENCE: 105

Ser Gly Ser Trp Leu Xaa Asp Val Trp Xaa Trp Ile Cys Thr Val Leu
1               5                   10                  15

Xaa Asp Phe Lys Thr Trp Leu Gln Ser Lys Leu
            20                  25

<210> SEQ ID NO 106
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (R)-2-amino-2-methylhept-6-enoic
      acid or a stapled derivative

<400> SEQUENCE: 106

Ser Gly Ser Trp Leu Xaa Asp Val Trp Xaa Trp Ile Cys Xaa Val Leu
1               5                   10                  15

Thr Asp Phe Lys Thr Trp Leu Gln Ser Lys Leu
            20                  25

<210> SEQ ID NO 107
<211> LENGTH: 27
<212> TYPE: PRT
```

```
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (S)-2-amino-2-methylhept-6-enoic
      acid or a stapled derivative

<400> SEQUENCE: 107

Ser Gly Ser Trp Leu Xaa Asp Val Trp Xaa Trp Ile Cys Xaa Val Leu
1               5                   10                  15

Thr Xaa Phe Lys Thr Trp Leu Gln Ser Lys Leu
            20                  25

<210> SEQ ID NO 108
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 108

Ser Gly Ser Trp Leu Arg Asp Val Trp Xaa Trp Ile Cys Xaa Val Leu
1               5                   10                  15

Thr Asp Phe Lys Xaa Trp Leu Gln Ser Lys Leu
            20                  25

<210> SEQ ID NO 109
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
```

```
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (R)-2-amino-2-methylhept-6-enoic
      acid or a stapled derivative

<400> SEQUENCE: 109

Ser Gly Ser Trp Leu Arg Asp Val Trp Xaa Trp Ile Cys Xaa Val Leu
1               5                   10                  15

Thr Xaa Phe Lys Thr Trp Leu Gln Ser Lys Leu
            20                  25

<210> SEQ ID NO 110
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (7)..(7)
<223> OTHER INFORMATION: Xaa represents (R)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 110

Ser Gly Ser Trp Leu Arg Xaa Val Trp Asp Trp Ile Cys Xaa Val Leu
1               5                   10                  15

Thr Asp Phe Lys Xaa Trp Leu Gln Ser Lys Leu
            20                  25

<210> SEQ ID NO 111
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (12)..(12)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (19)..(19)
<223> OTHER INFORMATION: Xaa represents (S)-2-amino-2-methyldec-9-enoic
      acid or a stapled derivative

<400> SEQUENCE: 111

Ser Gly Ser Trp Leu Arg Asp Xaa Trp Asp Trp Xaa Cys Thr Val Leu
1               5                   10                  15

Thr Asp Xaa Lys Thr Trp Leu Gln Ser Lys Leu
            20                  25
```

```
<210> SEQ ID NO 112
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (13)..(13)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (17)..(17)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (25)..(25)
<223> OTHER INFORMATION: Xaa represents (S)-2-amino-2-methylhept-6-enoic
      acid or a stapled derivative

<400> SEQUENCE: 112

Ser Gly Ser Trp Leu Arg Asp Val Trp Asp Trp Ile Xaa Thr Val Leu
1               5                   10                  15

Xaa Asp Phe Lys Xaa Trp Leu Gln Xaa Lys Leu
            20                  25

<210> SEQ ID NO 113
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (17)..(17)
<223> OTHER INFORMATION: Xaa represents (S)-2-amino-2-methyldec-9-enoic
      acid or a stapled derivative

<400> SEQUENCE: 113

Ser Gly Ser Trp Leu Xaa Asp Val Trp Xaa Trp Ile Cys Thr Val Leu
1               5                   10                  15

Xaa Asp Phe Lys Thr Trp Leu Gln Ser Lys Leu
            20                  25

<210> SEQ ID NO 114
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
```

```
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents (R)-2-amino-2-methylhept-6-enoic
      acid or a stapled derivative

<400> SEQUENCE: 114

Ser Gly Ser Trp Leu Xaa Asp Val Trp Xaa Trp Ile Cys Xaa Val Leu
1               5                   10                  15

Thr Asp Phe Lys Thr Trp Leu Gln Ser Lys Leu
            20                  25

<210> SEQ ID NO 115
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (6)..(6)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (10)..(10)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (S)-2-amino-2-methylhept-6-enoic
      acid or a stapled derivative

<400> SEQUENCE: 115

Ser Gly Ser Trp Leu Xaa Asp Val Trp Xaa Trp Ile Cys Xaa Val Leu
1               5                   10                  15

Thr Xaa Phe Lys Thr Trp Leu Gln Ser Lys Leu
            20                  25

<210> SEQ ID NO 116
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
```

```
<223> OTHER INFORMATION: Xaa represents (S)-2-amino-2-methyldec-9-enoic
      acid or a stapled derivative

<400> SEQUENCE: 116

Ser Gly Ser Trp Leu Arg Asp Val Trp Xaa Trp Ile Cys Xaa Val Leu
1               5                   10                  15

Thr Asp Phe Lys Xaa Trp Leu Gln Ser Lys Leu
                20                  25

<210> SEQ ID NO 117
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents (R)-2-amino-2-methylhept-6-enoic
      acid or a stapled derivative

<400> SEQUENCE: 117

Ser Gly Ser Trp Leu Arg Asp Val Trp Xaa Trp Ile Cys Xaa Val Leu
1               5                   10                  15

Thr Xaa Phe Lys Thr Trp Leu Gln Ser Lys Leu
                20                  25

<210> SEQ ID NO 118
<211> LENGTH: 27
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (7)..(7)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 118

Ser Gly Ser Trp Leu Arg Xaa Val Trp Asp Trp Ile Cys Xaa Val Leu
1               5                   10                  15

Thr Asp Phe Lys Xaa Trp Leu Gln Ser Lys Leu
                20                  25

<210> SEQ ID NO 119
<211> LENGTH: 24
<212> TYPE: PRT
<213> ORGANISM: Artificial Sequence
```

```
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (11)..(11)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (15)..(15)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (22)..(22)
<223> OTHER INFORMATION: Xaa represents (S)-2-amino-2-methyldec-9-enoic
      acid or a stapled derivative

<400> SEQUENCE: 119

Lys Ala Thr Glu Tyr Ile Gln Tyr Asn Leu Xaa Arg Lys Asn Xaa Thr
1               5                   10                  15

His Gln Gln Asp Ile Xaa Asp Leu
            20

<210> SEQ ID NO 120
<211> LENGTH: 24
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (7)..(7)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (15)..(15)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (22)..(22)
<223> OTHER INFORMATION: Xaa represents (S)-2-amino-2-methyldec-9-enoic
      acid or a stapled derivative

<400> SEQUENCE: 120

Lys Ala Thr Glu Tyr Ile Xaa Tyr Asn Leu Arg Arg Lys Asn Xaa Thr
1               5                   10                  15

His Gln Gln Asp Ile Xaa Asp Leu
            20

<210> SEQ ID NO 121
<211> LENGTH: 23
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (10)..(10)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
```

```
<223> OTHER INFORMATION: Xaa represents (S)-2-amino-2-methyldec-9-enoic
      acid or a stapled derivative

<400> SEQUENCE: 121

Thr Ile Leu Lys Ala Ser Val Asp Tyr Xaa Arg Lys Leu Xaa Arg Glu
1               5                   10                  15

Gln Gln Arg Ala Xaa Glu Leu
            20

<210> SEQ ID NO 122
<211> LENGTH: 23
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (7)..(7)
<223> OTHER INFORMATION: Xaa represents (R)-2-amino-2-methyldec-9-enoic
      acid or a stapled derivative
<220> FEATURE:
<221> NAME/KEY: misc_feature
<222> LOCATION: (14)..(14)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (21)..(21)
<223> OTHER INFORMATION: Xaa represents (S)-2-amino-2-methyldec-9-enoic
      acid or a stapled derivative

<400> SEQUENCE: 122

Thr Ile Leu Lys Ala Ser Xaa Asp Tyr Ile Arg Lys Leu Xaa Arg Glu
1               5                   10                  15

Gln Gln Arg Ala Xaa Glu Leu
            20

<210> SEQ ID NO 123
<211> LENGTH: 13
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (1)..(1)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (5)..(5)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (9)..(9)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents (S)-2-amino-2-methylhept-6-enoic
      acid or a stapled derivative

<400> SEQUENCE: 123

Xaa Ala Ala Ala Xaa Ala Ala Ala Xaa Ala Ala Ala Xaa
1               5                   10

<210> SEQ ID NO 124
<211> LENGTH: 23
```

```
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (13)..(13)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (18)..(18)
<223> OTHER INFORMATION: Xaa represents Nle (Norleucine)

<400> SEQUENCE: 124

Glu Asp Ile Ile Arg Asn Ile Ala Arg His Leu Ala Xaa Val Gly Asp
1               5                   10                  15

Ser Xaa Asp Arg Ser Ile Trp
            20

<210> SEQ ID NO 125
<211> LENGTH: 18
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (8)..(8)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (13)..(13)
<223> OTHER INFORMATION: Xaa represents Nle (Norleucine)

<400> SEQUENCE: 125

Asn Ile Ala Arg His Leu Ala Xaa Val Gly Asp Ser Xaa Asp Arg Ser
1               5                   10                  15

Ile Trp

<210> SEQ ID NO 126
<211> LENGTH: 22
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (9)..(9)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (13)..(13)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (18)..(18)
<223> OTHER INFORMATION: Xaa represents Nle (Norleucine)
<220> FEATURE:
<221> NAME/KEY: misc_feature
<222> LOCATION: (20)..(20)
<223> OTHER INFORMATION: Xaa represents (S)-2-amino-2-methyldec-9-enoic
      acid or a stapled derivative

<400> SEQUENCE: 126

Glu Asp Ile Ile Arg Asn Ile Ala Xaa His Leu Ala Xaa Val Gly Asp
1               5                   10                  15
```

Ser Xaa Asp Xaa Ser Ile
        20

<210> SEQ ID NO 127
<211> LENGTH: 17
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents Nle (Norleucine)
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 127

Asn Ile Ala Xaa His Leu Ala Xaa Val Gly Asp Ser Xaa Asp Xaa Ser
1               5                   10                  15

Ile

<210> SEQ ID NO 128
<211> LENGTH: 15
<212> TYPE: PRT
<213> ORGANISM: Artificial Sequence
<220> FEATURE:
<223> OTHER INFORMATION: synthetic peptide synthesized by Fmoc-based
      solid phase peptide synthesis
<220> FEATURE:
<221> NAME/KEY: misc_feature
<222> LOCATION: (4)..(4)
<223> OTHER INFORMATION: Xaa represents (S)-2-amino-2-methylhept-6-enoic
      acid or a stapled derivative
<220> FEATURE:
<221> NAME/KEY: misc_feature
<222> LOCATION: (8)..(8)
<223> OTHER INFORMATION: Xaa represents 2-amino-2-(pent-4-enyl)hept-6-
      enoic acid or a stapled derivative
<220> FEATURE:
<221> NAME/KEY: misc_feature
<222> LOCATION: (13)..(13)
<223> OTHER INFORMATION: Xaa represents Nle (Norleucine)
<220> FEATURE:
<221> NAME/KEY: misc_feature
<222> LOCATION: (15)..(15)
<223> OTHER INFORMATION: Xaa represents (S)-2-amino-2-methyldec-9-enoic
      acid or a stapled derivative

<400> SEQUENCE: 128

Asn Ile Ala Xaa His Leu Ala Xaa Val Gly Asp Ser Xaa Asp Xaa
1               5                   10                  15